(12) United States Patent
Kalish et al.

(10) Patent No.: US 11,304,924 B2
(45) Date of Patent: *Apr. 19, 2022

(54) PHARMACEUTICAL COMPOSITIONS COMPRISING NITROXYL DONORS

(71) Applicant: Cardioxyl Pharmaceuticals, Inc., Chapel Hill, NC (US)

(72) Inventors: Vincent Jacob Kalish, Annapolis, MD (US); John Reardon, Chapel Hill, NC (US); Frederick Arthur Brookfield, Oxfordshire (GB); Stephen Martin Courtney, Oxfordshire (GB); Lisa Marie Frost, Oxfordshire (GB); John P. Toscano, Glen Arm, MD (US)

(73) Assignee: Cardioxyl Pharmaceuticals, Inc., Chapel Hill, NC (US)

( * ) Notice: Subject to any disclaimer, the term of this patent is extended or adjusted under 35 U.S.C. 154(b) by 71 days.

This patent is subject to a terminal disclaimer.

(21) Appl. No.: 16/779,015

(22) Filed: Jan. 31, 2020

(65) Prior Publication Data

US 2020/0163929 A1    May 28, 2020

Related U.S. Application Data

(60) Continuation of application No. 16/370,443, filed on Mar. 29, 2019, now Pat. No. 10,548,872, which is a division of application No. 14/761,934, filed as application No. PCT/US2014/012089 on Jan. 17, 2014, now Pat. No. 10,245,249.

(60) Provisional application No. 61/782,781, filed on Mar. 14, 2013, provisional application No. 61/754,237, filed on Jan. 18, 2013.

(51) Int. Cl.
| | |
|---|---|
| *A61K 31/341* | (2006.01) |
| *A61K 31/18* | (2006.01) |
| *A61P 9/04* | (2006.01) |
| *C07C 317/14* | (2006.01) |
| *C07D 307/64* | (2006.01) |
| *A61K 31/255* | (2006.01) |
| *A61K 31/343* | (2006.01) |
| *A61K 31/381* | (2006.01) |
| *A61K 31/404* | (2006.01) |
| *A61K 31/42* | (2006.01) |
| *A61K 31/433* | (2006.01) |
| *A61K 31/4436* | (2006.01) |
| *A61K 31/5377* | (2006.01) |
| *A61K 31/538* | (2006.01) |
| *A61K 47/12* | (2006.01) |
| *A61K 47/40* | (2006.01) |
| *A61K 31/222* | (2006.01) |
| *A61K 31/24* | (2006.01) |
| *A61K 9/00* | (2006.01) |
| *A61K 9/08* | (2006.01) |

(52) U.S. Cl.
CPC .......... *A61K 31/341* (2013.01); *A61K 9/0019* (2013.01); *A61K 9/08* (2013.01); *A61K 31/18* (2013.01); *A61K 31/222* (2013.01); *A61K 31/24* (2013.01); *A61K 31/255* (2013.01); *A61K 31/343* (2013.01); *A61K 31/381* (2013.01); *A61K 31/404* (2013.01); *A61K 31/42* (2013.01); *A61K 31/433* (2013.01); *A61K 31/4436* (2013.01); *A61K 31/538* (2013.01); *A61K 31/5377* (2013.01); *A61K 47/12* (2013.01); *A61K 47/40* (2013.01); *A61P 9/04* (2018.01); *C07C 317/14* (2013.01); *C07D 307/64* (2013.01)

(58) Field of Classification Search
CPC ...... A61K 31/341; A61K 9/0019; A61K 9/08; A61K 31/222; A61K 31/24; A61K 31/255; A61K 31/381; A61K 31/5377; A61K 47/40; A61K 31/18; A61P 9/04; A61P 9/00; C07C 317/14; C07C 307/64
See application file for complete search history.

(56) References Cited

U.S. PATENT DOCUMENTS

| | | |
|---|---|---|
| 3,751,255 A | 8/1973 | Wilson et al. |
| 4,369,174 A | 1/1983 | Nagai et al. |
| 4,539,321 A | 9/1985 | Campbell |
| 4,663,351 A | 5/1987 | Diamond |
| 4,798,824 A | 1/1989 | Belzer et al. |
| 4,842,866 A | 6/1989 | Horder et al. |
| 5,217,720 A | 6/1993 | Sekigawa et al. |
| 5,990,105 A | 11/1999 | Bos et al. |
| 6,156,728 A | 12/2000 | Gao |

(Continued)

FOREIGN PATENT DOCUMENTS

| | | |
|---|---|---|
| CN | 101472576 A | 7/2009 |
| CN | 101874018 A | 10/2010 |

(Continued)

OTHER PUBLICATIONS

Abdellatif, K.R.A. et al., "Synthesis of New 1-[4-Methane(amino)sulfonylphenyl)]-5-[4-(aminophenyl)]-3-trifluoromethyl-1H-pyrazoles", In the Journal of Heterocyclic Chemistry, vol. 45, Nov. 2008, pp. 1707-1710.

Andrewes, C.H. et al., "Experimental Chemotherapy of Typhus: Anti-Rickettsial Action of p-Sulphonamidobenzamidine and Related Compounds", In Proceedings of the Royal Society of London B Biological Sciences, vol. 133, No. 1, Jan. 1946, pp. 20-62.

(Continued)

*Primary Examiner* — Sahar Javanmard
(74) *Attorney, Agent, or Firm* — Byrne Poh LLP; Nina R. Horan

(57) ABSTRACT

The present disclosure provides nitroxyl donating pharmaceutical compositions comprising N-substituted hydroxylamine derivatives. The compositions are highly efficacious in treating cardiovascular diseases (e.g., heart failure), have a suitable toxicological profile, and are sufficiently stable for intravenous or oral administration.

22 Claims, 4 Drawing Sheets

(56) References Cited

U.S. PATENT DOCUMENTS

Figure 1:
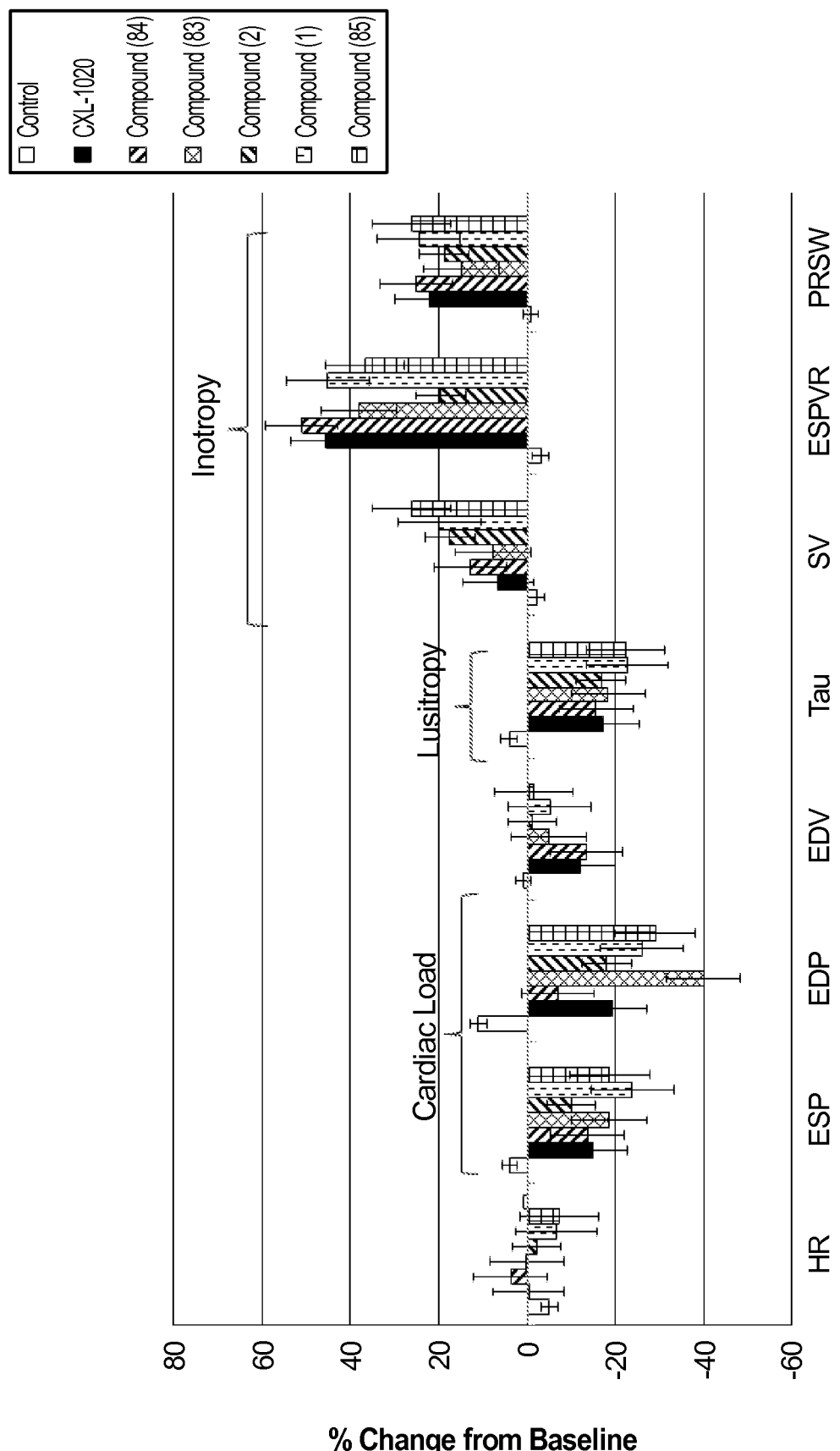

| | | |
|---|---|---|
| 6,525,081 B1 | 2/2003 | Matsumoto et al. |
| 6,569,457 B2 | 5/2003 | Ullah et al. |
| 6,638,534 B1 | 10/2003 | Ishibashi et al. |
| 6,936,639 B2 | 8/2005 | Wink et al. |
| 7,696,373 B2 | 4/2010 | King |
| 7,863,262 B2 | 1/2011 | Wink et al. |
| 7,989,652 B2 | 8/2011 | King |
| 8,030,356 B2 | 10/2011 | Toscano et al. |
| 8,227,639 B2 | 7/2012 | Toscano et al. |
| 8,268,890 B2 | 9/2012 | Wink et al. |
| 8,269,034 B2 | 9/2012 | King |
| 8,318,705 B2 | 11/2012 | Frost et al. |
| 8,569,536 B2 | 10/2013 | King |
| 8,674,132 B2 | 3/2014 | Toscano et al. |
| 8,791,134 B2 | 7/2014 | Frost et al. |
| RE45,314 E | 12/2014 | Toscano et al. |
| 8,987,326 B2 | 3/2015 | Kalish et al. |
| 9,018,411 B2 | 4/2015 | Toscano et al. |
| 9,115,064 B2 | 8/2015 | Toscano et al. |
| 9,156,804 B2 | 10/2015 | Kalish et al. |
| 9,181,213 B2 | 11/2015 | Toscano et al. |
| 9,221,780 B2 | 12/2015 | Toscano et al. |
| 9,458,127 B2 | 10/2016 | Toscano et al. |
| 9,464,061 B2 | 10/2016 | Toscano et al. |
| 9,487,498 B2 | 11/2016 | Toscano et al. |
| 9,586,896 B2 | 3/2017 | Kalish et al. |
| 9,725,410 B2 | 8/2017 | Toscano et al. |
| 9,968,584 B2 | 5/2018 | Kalish et al. |
| 9,969,684 B2 | 5/2018 | Toscano et al. |
| 10,179,765 B2 | 1/2019 | Toscano et al. |
| 10,213,408 B2 | 2/2019 | Kalish et al. |
| 10,245,249 B2 | 4/2019 | Kalish et al. |
| 10,487,049 B2 | 11/2019 | Toscano et al. |
| 10,517,847 B2 | 12/2019 | Kalish et al. |
| 10,548,872 B2 | 2/2020 | Kalish et al. |
| 10,792,273 B2 | 10/2020 | Kalish et al. |
| 10,829,445 B2 | 11/2020 | Toscano et al. |
| 2004/0038947 A1 | 2/2004 | Wink et al. |
| 2005/0153966 A1 | 7/2005 | Gangloff et al. |
| 2009/0118247 A1 | 5/2009 | Hughes et al. |
| 2009/0186045 A1 | 7/2009 | Ray et al. |
| 2009/0281067 A1 | 11/2009 | Toscano et al. |
| 2009/0298795 A1 | 12/2009 | Paolocci et al. |
| 2011/0081427 A1 | 4/2011 | Wink et al. |
| 2011/0144067 A1 | 6/2011 | Toscano et al. |
| 2011/0160200 A1 | 6/2011 | Mazhari et al. |
| 2011/0306614 A1 | 12/2011 | Toscano et al. |
| 2012/0201907 A1 | 8/2012 | Wink et al. |
| 2014/0235636 A1 | 8/2014 | Toscano et al. |
| 2014/0336137 A1 | 11/2014 | Frost et al. |
| 2015/0004259 A1 | 1/2015 | Wink et al. |
| 2015/0141378 A1 | 5/2015 | Toscano et al. |
| 2015/0291519 A1 | 10/2015 | Toscano et al. |
| 2015/0336880 A1 | 11/2015 | Toscano et al. |
| 2016/0031807 A1 | 2/2016 | Kalish et al. |
| 2016/0046569 A1 | 2/2016 | Kalish et al. |
| 2016/0046570 A1 | 2/2016 | Toscano et al. |
| 2016/0052862 A1 | 2/2016 | Frost et al. |
| 2016/0081951 A1 | 3/2016 | Mazhari et al. |
| 2016/0115148 A1 | 4/2016 | Toscano et al. |
| 2016/0166604 A1 | 6/2016 | Paolocci et al. |
| 2016/0228460 A1 | 8/2016 | Wink et al. |
| 2017/0151210 A1 | 6/2017 | Kalish et al. |
| 2021/0053915 A1 | 2/2021 | Toscano et al. |

FOREIGN PATENT DOCUMENTS

| | | |
|---|---|---|
| EA | 200300674 | 12/2000 |
| EP | 1219306 | 7/2002 |
| EP | 2945621 | 11/2015 |
| JP | H 1989-221372 A | 9/1989 |
| JP | 04-321671 A | 11/1992 |
| JP | 10-142729 A | 5/1998 |
| JP | 2002-072459 | 3/2002 |
| JP | 2009530303 | 8/2009 |
| RU | 99101350 | 11/2000 |
| RU | 2448087 | 4/2012 |
| SU | 186456 | 10/1966 |
| WO | WO 2001/010827 | 2/2001 |
| WO | WO 2002/100810 | 12/2002 |
| WO | WO 2005/074598 | 8/2005 |
| WO | WO 2006/086188 | 8/2006 |
| WO | WO 2007/002444 | 1/2007 |
| WO | WO2007109175 | 9/2007 |
| WO | WO2009042970 | 4/2009 |
| WO | WO2011063339 | 5/2011 |
| WO | WO2014113696 | 7/2014 |

OTHER PUBLICATIONS

Backx, P.H. et al., "The Relationship between Contractile Force and Intracellular [Ca2+] in Intact Rat Cardiac Trabeculae", In the Journal of General Physiology, vol. 105, No. 1, Jan. 1995, pp. 1-19.

Badesch, D.B. et al., "Diagnosis and Assessment of Pulmonary Arterial Hypertension", In Journal of the American College of Cardiology, vol. 54, No. 1s1, Jun. 2009, pp. S55-S66.

Baerlocher, F.J. et al., "New and More Potent Antifungal Disulfides", In the Australian Journal of Chemistry, vol. 53, No. 1, Jun. 2000, pp. 1-5.

Baumgarth, M. et al., "(2-Methyl-5-(methylsulfonyl)benzoyl)guanidine Na'/H+ Antiporter Inhibitors", In the Journal of Medicinal Chemistry, vol. 40, No. 13, Jun. 1997, pp. 2017-2034.

Bazylinski, D.A. and Hollocher, T.C., "Metmyoglobin and Methemoglobin as Efficient Traps for Nitrosyl Hydride (Nitroxyl) in Neutral Aqueous Solution", In the Journal of the American Chemical Society, vol. 107, No. 26, Dec. 1985, pp. 7982-7986.

Bhardwaj, A. et al., "A diazen-1-ium-1,2-dioalte analog of 7-anabenzobicyclo[2.2.1] heptanes: Synthesis, nitric oxide and nitroxyl release, in vitro hemodynamic, and anti-hypertensive studies", In Bioorganic & Medicinal Chemistry Letters, vol. 23, Feb. 2013, pp. 2769-2774.

Bonner, F.T. et al., "Kinetic, Istopic, and 15N NMR Study of N-Hydroxybenzenesulfonamide Decomposition: An HNO Source Reaction", In Inorganic Chemistry, vol. 31, Dec. 1992, pp. 2514-2519.

Bouzamondo, A. et al., "Beta-Blocker Treatment in Heart Failure", In Fundamental & Clinical Pharmacology, vol. 15, No. 2, Apr. 2001, pp. 95-109.

Bristow, M.R. et al., "Inotropes and Beta-Blockers: Is there a Need for New Guidelines?", In the Journal of Cardiac Failure, vol. 7, No. 2, Suppl. 1, Jun. 2001, pp. 8-12.

Brynes, S. et al., "Potential Antitumor Agents via Inhibitors of L-Asparagine Synthetase: Substituted Sulfonamides and Sulfonyl Hydrazides Related to Glutamine", In the Journal of Pharmaceutical Sciences, vol. 67, No. 11, Nov. 1978, pp. 1550-1553.

Brynes, S., et al., "Potential Inhibitors of L-Asparagine Biosynthesis. 4. Substituted Sulphonamide and Sulphonylhydrazide Analogues of L-Asparagine", in the Journal of Medicinal Chemistry, vol. 21, No. 1, Jan. 1978, pp. 45-49.

Chowdhury, M.S. et al., "Celecoxib Analogs Possessing a N-(4-nitrooxybutyl)piperidin-4-yl or N-(4-nitroxybutyl)-1,2,3,6-tetrahydropyridin-4-yl Nitric Oxide Donor Moiety: Synthesis, Biological Evaluation and Nitric Oxide Release Studies", Bioorganic Medicine & Chemical Letters, vol. 20, Feb. 2010, pp. 1324-1329.

Crawford, J.H. et al., "Hypoxia, Red Blood Cells, and Nitrite Regulate NO-Dependent Hypoxic Vasodilation", In Blood, vol. 107, No. 2, Jan. 2006, pp. 566-575.

Database CAPlus Abstract Accession No. 1994 :645157, Chemical Abstracts Service, Columbus, Ohio, 1994, pp. 1.

Database CHEMCATS, Chemical Abstracts Service, Kiev, UK, accession No. 2033522701 (XP002509263), Jan. 2008, pp. 1.

Database CHEMCATS, Chemical Abstracts Service, Kiev, UK, accession No. 2033715491 (XP002509261), Jan. 2008, pp. 1.

Database CHEMCATS, Chemical Abstracts Service, San Diego, CA, US, accession No. 2037996565 (XP002509259), Jun. 2008, pp. 1.

Extended Search Report and Written Opinion dated Jul. 13, 2012 in EP Patent Application No. 12155608.8.

(56) References Cited

OTHER PUBLICATIONS

Extended Search Report dated Apr. 5, 2013 in EP Patent Application No. 12195114.9.
Extended Search Report dated Apr. 5, 2013 in EP Patent Application No. 12195118.0.
Extended Search Report dated Apr. 5, 2013 in EP Patent Application No. 12195124.8.
Extended Search Report dated Apr. 5, 2013 in EP Patent Application No. 12195128.9.
Extended Search Report dated Jul. 23, 2012 in EP Patent Application No. 12155608.8.
Fukuto, J.M. et al., "The Physiological Chemistry and Biological Activity of Nitroxyl (HNO): The Neglected, Misunderstood, and Enigmatic Nitrogen Oxide", In Chemical Research in Toxicology, vol. 18, No. 5, May 2005, pp. 790-801.
Gao, W.D. et al., "Calcium Cycling and Contractile Activation in Intact Mouse Cardiac Muscle", In the Journal of Physiology, vol. 507, No. 1, Feb. 1998, pp. 175-184.
Gao, W.D. et al., "Myofilament Ca2+ Sensitivity in Intact Versus Skinned Rat Ventricular Muscle", In Circulation Research, vol. 74, No. 3, Mar. 1994, pp. 408-415.
Hare, J.M. et al., "Nitric Oxide Inhibits the Positive Inotropic Response to Beta-Adrenergic Stimulation in Humans with Left Ventricular Dysfunction", In Circulation, vol. 92, No. 8, Oct. 1995, pp. 2198-2203.
Hare, J.M. et al., "Pertussis Toxin-Sensitive G Proteins Influence Nitric Oxide Synthase III Activity and Protein Levels in Rat Heart", In the Journal of Clinical Investigations, vol. 101, No. 6, Mar. 1998, pp. 1424-1431.
Hart, C.Y.T. et al., "Differential Effects of Natriuretic Peptides and NO on LV Function in Heart Failure and Normal Dogs", In the American Journal of Physiology Heart and Circulatory Physiology, vol. 281, No. 1, Jul. 2001, pp. 146-154.
Ingall, T.J., "Preventing Ischemic Stroke", In Postgraduate Medicine, vol. 107, No. 6, May 2000, pp. 34-50.
International Preliminary Report on Patentability dated Sep. 23, 2008 in International Patent Application No. PCT/US2007/006710.
International Search Report and Written Opinion dated Jan. 23, 2009 in International Patent Application No. PCT/US2008/078024.
International Search Report and Written Opinion dated Mar. 19, 2014 in International Patent Application No. PCT/US2014/012085.
International Search Report and Written Opinion dated Aug. 22, 2007 in International Patent Application No. PCT/US2007/006710.
International Serach Report and Written Opinion dated Mar. 14, 2014 in International Patent Application No. PCT/US2014/012085.
Jackman, G.B. et al., "Studies in the Field of Diuretic Agents", In Journal of Pharmacy and Pharmacology, vol. 15, No. 1, Sep. 1963, pp. 202-211.
Katori, T. et al., "Calcitonin Gene-Related Peptide in Vivo Positive Inotropy is Attributable to Regional Sympatho-Stimulation and is Blunted in Congestive Heart Failure", In Circulation Research, vol. 96, No. 2, Feb. 2005, pp. 234-243.
Lee, M.J.C., et al., "N-Hydroxybenzenecarboximidic Acid Derivatives: A New Class of Nitroxyl-Generating ProDrugs", In Nitric Oxide: Biology and Chemistry, vol. 5, No. 3, May 2001, pp. 278-287.
Lowes, B.D. et al., "Inotropes in the Beta-Blocker Era", In Clinical Cardiology, vol. 23, No. S3, Mar. 2000, pp. III11-III16.
Ma, X.L. et al., "Opposite Effects of Nitric Oxide and Nitroxyl on Postischemic Myocardial Injury", In Proceedings of the National Academy of Sciences of the United States of America, vol. 96, No. 25, Dec. 1999, pp. 14617-14622.
Mincione, F. et al., "Carbonic Anhydrase Inhibitors: Inhibition of Isozymes I, II and IV with N-Hydroxysulfonamides—A Novel Class of Intraocular Pressure Lowering Agents", In the Journal of Enzyme Inhibition and Medicinal Chemistry, vol. 13, No. 4, Jan. 1998, pp. 267-284.
Miranda, K.M. et al., "Donors of HNO", In Current Topics in Medicinal Chemistry, vol. 5, No. 7, Jul. 2005, pp. 649-664.
Miranda, K.M. et al., "Mechanism of Aerobic Decomposition of Angeli's Salt (Sodium Trioxodinitrate) at Physiological pH", In the Journal of the American Chemical Society, vol. 127, No. 2, Jan. 2005, pp. 722-731.
Nagasawa, H.T. et al., "Prodrugs of Nitroxyl as Potential Aldehyde Dehydrogenase Inhibitors vis-a-vis Vascular Smooth Muscle Relaxants", In Journal of Medicinal Chemistry, vol. 38, No. 11, May 1995, pp. 1865-1871.
Nairn, J.G., "Solutions, Emulsions and Extracts", In Remington: The Science and Practice of Pharmacy, 20th Ed. Lippinoctt Williams & Wilkins, Baltimore, MD, 2000, Chapter 39, pp. 721-752.
Notice of Allowance dated Jan. 11, 2018 in U.S. Appl. No. 15/430,946.
Notice of Allowance dated Jun. 23, 2014 in U.S. Appl. No. 14/045,404.
Notice of Allowance dated Aug. 9, 2019 in U.S. Appl. No. 16/242,139.
Notice of Allowance dated Sep. 4, 2014 in U.S. Appl. No. 14/045,404.
Notice of Allowance dated Sep. 15, 2017 in U.S. Appl. No. 15/430,946.
Notice of Allowance dated Oct. 3, 2018 in U.S. Appl. No. 15/960,993.
Notice of Allowance dated Nov. 18, 2014 in U.S. Appl. No. 14/158,456.
Office Action dated Feb. 6, 2017 in AU Patent Application No. 2014207404.
Office Action dated Feb. 11, 2011 in RU Patent Application No. 2008141151/04.
Office Action dated Feb. 13, 2019 in U.S. Appl. No. 16/242,139.
Office Action dated Feb. 14, 2020 in U.S. Appl. No. 16/724,657.
Office Action dated Mar. 6, 2017 in U.S. Appl. No. 15/430,946.
Office Action dated Mar. 20, 2014 in U.S. Appl. No. 14/045,404.
Office Action dated Apr. 9, 2013 in EP Patent Application No. 12155608.8.
Office Action dated Apr. 10, 2013 in CA Patent Application No. 2,645,988.
Office Action dated Apr. 11, 2018 in TW Patent Application No. 103101913.
Office Action dated Apr. 14, 2010 in NZ Patent Application No. 570971.
Office Action dated Apr. 15, 2014 in U.S. Appl. No. 14/158,456.
Office Action dated Apr. 15, 2014 in U.S. Appl. No. 14/641,377.
Office Action dated Apr. 17, 2020 in CA Patent Application No. 2,898,445.
Office Action dated May 11, 2011 in IL Patent Application No. 193839.
Office Action dated May 12, 2010 in CN Patent Application No. 200780011079.6.
Office Action dated May 18, 2012 in CN Patent Application No. 200780011079.6.
Office Action dated May 25, 2018 in U.S. Appl. No. 15/960,993.
Office Action dated Jun. 4, 2013 in JP Patent Application No. 2009-500519.
Office Action dated Jun. 5, 2014 in KR Patent Application No. 10-2014-7006611.
Office Action dated Jun. 10, 2014 in JP Patent Application No. 2013-032658.
Office Action dated Jun. 11, 2014 in CN Patent Application No. 201310086960.X.
Office Action dated Jun. 14, 2011 in AU Patent Application No. 2007227457.
Office Action dated Jun. 14, 2017 in TW Patent Application No. 103101912.
Office Action dated Jun. 16, 2014 in IL Patent Application No. 217739.
Office Action dated Jun. 16, 2017 in AU Patent Application No. 2017200147.
Office Action dated Jul. 6, 2016 in U.S. Appl. No. 14/880,173.
Office Action dated Jul. 13, 2011 in CN Patent Application No. 200780011079.6.
Office Action dated Jul. 17, 2014 in KR Patent Application No. 10-2008-7025245.
Office Action dated Jul. 23, 2014 in KR Patent Application No. 10-2008-7025245.
Office Action dated Aug. 8, 2013 in EP Patent Application No. 12155608.8.

(56) References Cited

OTHER PUBLICATIONS

Office Action dated Aug. 14, 2017 in TW Patent Application No. 103101913.
Office Action dated Aug. 21, 2012 in JP Patent Application No. 2009-500519.
Office Action dated Aug. 23, 2018 in IL Patent Application No. 258882.
Office Action dated Aug. 25, 2011 in NZ Patent Application No. 570971.
Office Action dated Sep. 12, 2013 in KR Patent Application No. 10-2008-7025245.
Office Action dated Sep. 22, 2011 in U.S. Appl. No. 12/239,705.
Office Action dated Sep. 24, 2012 in IL Patent Application No. 217739.
Office Action dated Oct. 1, 2017 in IL Patent Application No. 239906.
Office Action dated Oct. 9, 2018 in IN Patent Appication No. 2672/KOLNP/2015.
Office Action dated Oct. 19, 2016 in AU Patent Application No. 2014207404.
Office Action dated Oct. 21, 2011 in NZ Patent Application No. 595770.
Office Action dated Oct. 31, 2017 in JP Patent Application No. 2017-005276.
Office Action dated Nov. 10, 2015 in U.S. Appl. No. 14/880,173.
Office Action dated Nov. 22, 2010 in EP Patent Application No. 07753345.3.
Office Action dated Nov. 23, 2010 in NZ Patent Applicaiton No. 584036.
Office Action dated Nov. 24, 2015 in RU Patent Application No. 2015134581.
Office Action dated Dec. 19, 2017 in JP Patent Application No. 2015-553856.
Office Action dated Dec. 19, 2017 in RU Patent Application No. 2015134581.
Paolocci, N. et al., "cGMP-Independent Inotropic Effects of Nitric Oxide and Peroxynitrite Donors: Potential Role for Nitrosylation", In the American Journal of Physiology Heart and Circulatory Physiology, vol. 279, No. 4, Oct. 2000, pp. 111982-111988.
Paolocci, N. et al., "Positive Inotropic and Lusitropic Effects of HNO/NO– in Failing Hearts: Independence from Beta-Adrenergic Signaling", In Proceedings of the National Academy of Sciences, vol. 100, No. 9, Apr. 2003, pp. 5537-5542.
Park, C.M. et al., "Discovery of an Orally Bioavailable Small Molecule Inhibitor of Prosurvival B-Cell Lymphoma 2 Proteins", In the Journal of Medicine & Chemistry, vol. 51, No. 21, Nov. 2008, pp. 6902-6915.
Rastaldo, R. et al., "Cytochrome P-450 Metabolite of Arachidonic Acid Mediates Bradykinin-induced Negative Inotropic Effect", In American Journal of Physiology Heart and Circulatory Physiology, vol. 280, No. 6, Jun. 2001, pp. H2823-H2832.
Registry (Apr. 13, 2007) Accession No. 930060-34-7, pp. 1.
Registry (Feb. 13, 2007) Accession No. 920663-30-5, pp. 1.
Registry (Nov. 30, 2004) Accession No. 790725-76-7, pp. 1.
Rehse, K. et al., "New NO Donors with Antithrombotic and Vasodilating Activities, Part 25, Hydroxylamine Derivatives", In Archiv der Pharmazie, vol. 331, Nov. 1998, pp. 365-367.
Sabbah, H.N. et al., "Nitroxyl (HNO) a Novel Approach for the Acute Treatment of Heart Failure", In Circulation: Heart Failure, vol. 6, No. 6, Nov. 2013, pp. 1250-1258.
Scozzafava, A. and Supuran, C.T., "Additions and Corrections", In the Journal of Medicinal Chemistry, vol. 44, Mar. 8, 2001, pp. 1016.
Scozzafava, A. et al., "Carbonic Anhydrase and Matrix Metalloproteinase Inhibitors", In the Journal of Medical Chemistry, vol. 43, Jul. 2000, pp. 3677-3687.
Search Report dated Aug. 30, 2016 in CN Patent Application No. 201480013565.1.
Sha, X. et al., "Hydrolysis of Acyloxy Nitroso Compounds Yields Nitroxyl (HNO)", In the Journal of the American Chemical Society, vol. 128, No. 30, Jul. 2006, pp. 9687-9692.
Shami, P.J. et al., "JS-K, a Glutathione/GlutathioneS-Transferase-activated Nitric Oxide Donor of hte Diazeniumdiolate Class with Potent Antineoplastic Activity", In Molecular Cancer Therapeutics, vol. 2, Apr. 2003, pp. 409-417.
Singapore Search Report and Written Opinion dated Jan. 4, 2010 in Singapore Patent Application No. 200806554-2.
Singapore Search Report and Written Opinion dated Jul. 1, 2011 in Singapore Patent Application No. 201001904-1.
Singapore Search Report and Written Opinion dated Aug. 26, 2011 in Singapore Patent Application No. 201001904-1.
Singapore Search Report and Written Opinion dated Nov. 23, 2009 in Singapore Patent Application No. 200806554-2.
Slotwiner-Nie, P.K. and Brandt, L.J., "Infectious Diarrhea in the Elderly", In Gastroenterology Clinics, vol. 30, No. 3, Sep. 2001, pp. 625-635.
Supplemental European Search Reported dated Jan. 17, 2018 in EP Patent Application No. 17195759.0.
Sutton, A.D. et al., "Optimization of HNO Production from N,O-Bis-Acylated Hydroxylamine Derivatives", In Organic Letters, vol. 14, No. 2, Jan. 20, 2012, pp. 472-475.
Suzuki, T., et al., Novel Inhbitors of the Human Histone Deacetylases: Design, Synthesis, Enzyme Inhibition and Cancer Cell Growth Inhibition of SAHA-based non-hydroxomates, In the Journal of Medicinal Chemistry, vol. 48, No. 4, Jan. 25, 2005, pp. 1019-1032.
Takahira, R. et al., "Dexamethasone Attenuates Neutrophil Infiltration in the Rat Kidney in Ischemia/Reperfusion Injury: The Possible Role of Nitroxyl", In Free Radical Biology & Medicine, vol. 31, No. 6, Sep. 15, 2001, pp. 809-815.
Thevis, M. et al., "High Speed Determination of Beta-Receptor Blocking Agents in Human Urine by Liquid Chromatography/Tandem Mass Spectrometry", In Biomedical Chromatography, vol. 15, No. 6, Oct. 2001, pp. 393-402.
USPTO Official Gazette Notice of Reissue Applications Filed, Dec. 17, 2013, pp. 1-2.
Written Opinion dated Oct. 9, 2017 in Singapore Application No. 11201505567R.
Wrobel, J. et al., "Synthesis of (bis)Sulfonic acid, (bis)Benzamides as follicle-Stimulating hormone (FSH) antagonists", In Bioorganic & Medicinal Chemistry, vol. 10, No. 3, Mar. 2002, pp. 639-656.
Zamora, R. et al., "Oxidative Release of Nitric Oxide Accounts for Guanylyl Cyclase Stimulating, Vasodilator and Anti-Platelet Activity of Piloty's Acid: A Comparison with Angeli's Salt", In the Biochemistry Journal, vol. 312, No. 2, Dec. 1995, pp. 333-339.
Zani, F. et al., "Antimicrobial and Genotoxic Properties of Quinoline Derivatives", In Bollettino Chimico Farmaceutico, vol. 133, No. 5, May 1994, pp. 328-338.
Examination Report dated Dec. 4, 2018 in AU Patent Application No. 2018203240.
Beig, A. et al., "The Use of Captisol (SBE7-Beta-CD) in Oral Solubility-Enabling Formulations: Comparison to HPBetaCD and the Solubility-Permeability Interplay", In the European Journal of Pharmaecutical Sciences, vol. 77, Sep. 18, 2015, pp. 73-38, http://www.sciencedirect.com/science/article/pii/S0928098715002766.
Examination Report dated May 3, 2019 in NZ Patent Application No. 709986.
Examination Report dated Oct. 29, 2018 in IN Patent Application No. 2329/KOLNP/2015.
First Examination Report dated Oct. 9, 2018 in IN Patent Application No. 2672/KOLNP/2015.
Fukuda, M. et al., "Influence of Sulfobutyl Ether Beta-Cyclodextrin (Captisol) on the Dissolution Properties of a Poorly Soluble Drug from Extrudates Prepared by . . . ", International Journal of Pharmacology, vol. 350, No. 1-2, Feb. 28, 2008, pp. 188-196, http://www.sciencedirect.com/science/article/pii/S037851730700734X.
Higashi et al., "Recent Topics of Improvement of Solubility of Poorly-Soluble Drug by the Use of Cyclodextrin", In Farumashia, vol. 42, No. 10, 2006, pp. 1005-1010.
https://zerista.s3.amazonaws.com/item_files/3f69/attachments/25850/original/brochure-a7075472-059c-4470-bd96-52e53e263de3.pdf.
International Search Report and Written Opinion dated Mar. 19, 2014 in International Patent Application No. PCT/US2014/012089.

(56) References Cited

OTHER PUBLICATIONS

Li et al., "Developing Eary Formulations: Practice and Perspective", In the International Journal of Pharmaceuticals, vol. 341, No. 1-2, Jul. 24, 2007, pp. 1-19.
Ligand Pharmaceuticals, Inc. "Captisol Brochure", pp. 1-8, available at: https://zerista.s3.amazonaws.com/item_files/3f69/attachments/25850/original/brochure-a7075472-059c-4470-bd96-52e53e263de3.pdf.
Notice of Allowance dated Sep. 18, 2019 in U.S. Appl. No. 16/370,443.
Notice of Allowance dated Oct. 31, 2018 in U.S. Appl. No. 14/761,934.
Office Action dated Jan. 3, 2019 in IL Patent Application No. 259233.
Office Action dated Jan. 9, 2018 in JP Patent Application No. 2015-553858.
Office Action dated Feb. 5, 2018 in RU Patent Application No. 2015134583.
Office Action dated Feb. 10, 2017 in AU Patent Application No. 2014207408.
Office Action dated Mar. 10, 2017 in U.S. Appl. No. 14/761,934.
Office Action dated Apr. 18, 2017 in AU Patent Application No. AU 2014207408.
Office Action dated May 2, 2019 in U.S. Appl. No. 16/370,443.
Office Action dated May 16, 2018 in U.S. Appl. No. 14/761,934.
Office Action dated Jul. 3, 2018 in MX Patent Application No. MX/a/2015/009269.
Office Action dated Jul. 10, 2018 in JP Patent Application No. 2015-553858.
Office Action dated Aug. 28, 2018 in RU Patent Application No. 2015134583.
Office Action dated Sep. 3, 2019 in BR Patent Application No. 1120150172512.
Office Action dated Sep. 15, 2017 in CN Patent Application No. 201480013223.X.
Office Action dated Sep. 18, 2016 in CN Patent Application No. 201480013565.1.
Office Action dated Sep. 18, 2017 in SG Patent Application No. 11201505568P.
Office Action dated Sep. 29, 2018 in CN Patent Application No. 201480013223.X.
Office Action dated Jan. 3, 2019 in IL Patent Patent Application No. 259233.
Office Action dated Oct. 2, 2017 in IL Patent Application No. 239952.
Office Action dated Oct. 12, 2017 in U.S. Appl. No. 14/761,934.
Office Action dated Oct. 28, 2016 in CN Patent Application No. 201480013223.X.
Office Action dated Nov. 19, 2015 in RU Patent Application No. 2015134583.
Search Report dated Oct. 25, 2018 in EP Patent Application No. 18190818.7.
Sirsalmath, K. et al., "The pH of HNO Donation is Modulated by Ring Substituents in Piloty's Acid Derivatives: Azanone Donors at Biological pH", In the Journal of Inorganic Biochemistry, vol. 118, Jan. 2013, pp. 134-139.
Office Action dated Jul. 9, 2021 in U.S. Appl. No. 17/063,372, pp. 1-27.
Hearing Notice dated Oct. 21, 2021 in IN Patent Application No. 2672/KOLNP/2015, pp. 1-2.
Notice of Allowance dated Oct. 27, 2021 in U.S. Appl. No. 17/063,372, pp. 1-11.

PHARMACEUTICAL COMPOSITIONS COMPRISING NITROXYL DONORS

1. BACKGROUND

Nitroxyl (HNO) has been shown to have positive cardiovascular effects in in vitro and in vivo models of failing hearts. However, at physiological pH, HNO dimerizes to hyponitrous acid, which subsequently dehydrates to nitrous oxide; due to this metastability, HNO for therapeutic use must be generated in situ from donor compounds. A variety of compounds capable of donating nitroxyl have been described and proposed for use in treating disorders known or suspected to be responsive to nitroxyl. See, e.g., U.S. Pat. Nos. 6,936,639; 7,696,373; 8,030,356; 8,268,890; 8,227,639; and 8,318,705 and U.S. pre-grant publication nos. 2009/0281067; 2009/0298795; 2011/0136827; and 2011/0144067. Although all of these compounds are capable of donating nitroxyl, they differ in various physicochemical properties, and there remains a need to identify nitroxyl donors that have physicochemical properties best suited for treating specific clinical conditions via specific routes of administration.

U.S. Pat. No. 8,030,056 describes the synthesis of derivatives of Piloty's acid type compounds that are capable of donating nitroxyl under physiological conditions and are useful in treating heart failure and ischemia/reperfusion injury. The nitroxyl donor CXL-1020 (N-hydroxy-2-methanesulfonylbenzene-1-sulfonamide) has been evaluated in a Phase I safety study in healthy volunteers and in a Phase IIa placebo-controlled, double-blind, dose-escalation study conducted at multiple hospitals. Sabbah et al., "Nitroxyl (HNO) a novel approach for the acute treatment of heart failure", *Circ Heart Fail.*, published online Oct. 9, 2013 (Online ISSN: 1941-3297, Print ISSN: 1941-3289). The studies demonstrated that in patients with systolic heart failure, CXL-1020, when administered intravenously as an aqueous solution at pH=4, reduced both left and right heart filling pressures and systemic vascular resistance, while increasing cardiac and stroke volume index. Hence, the studies demonstrated that CXL-1020 enhances myocardial function in human patients suffering from heart failure. However, at threshold doses of CXL-1020 needed to produce hemodynamic effects, the compound was found to induce side effects, including unacceptable levels of inflammatory irritation at and distal to the intravenous insertion site, and the authors report that because of such side effects, this compound would not be a viable candidate for a human therapeutic.

Accordingly, there is a need to develop new nitroxyl donating compounds (referred to herein as nitroxyl donors) and compositions that are useful for the treatment of heart failure and that have a suitable toxicological profile. Development of such compounds requires an understanding of the pharmacokinetic profile associated with nitroxyl donation and the factors influencing the toxicological profile. Failure to understand these factors has hampered the development of nitroxyl donors for clinical use.

Moreover, formulating nitroxyl donors has proven to be a considerable challenge. Many of the current nitroxyl donors are insoluble in aqueous solutions and/or are insufficiently stable. Solubility and stability problems often preclude the use of such compounds in pharmaceutical compositions for parenteral and/or oral administration. Accordingly, there exists a need to develop compositions containing nitroxyl donors at sufficient concentration for parenteral and/or oral administration that are sufficiently stable and have favorable pharmacological and toxicological profiles.

Citation of any reference in Section 1 of this application is not to be construed as an admission that such reference is prior art to the present application.

2. SUMMARY OF THE DISCLOSURE

The present disclosure relates to the discovery of nitroxyl donating compositions that are highly effective in treating cardiovascular diseases (e.g., heart failure), have a suitable toxicological profile, and are sufficiently stable for intravenous or oral administration.

It has been discovered that the toxicological profile of N-hydroxysulfonamide type nitroxyl donors that have sufficiently long half-lives under physiological conditions is significantly better than the toxicological profile of N-hydroxysulfonamide type nitroxyl donors with shorter half-lives (e.g., CXL-1020). In particular, it has been discovered that N-hydroxysulfonamide type nitroxyl donors with short half-lives (i.e., 10 minutes or less when measured in an aerated phosphate buffered saline (PBS) solution at a pH of 7.4 or in plasma (e.g., human plasma) according to the procedure described in Example 2 (in Section 5.2) have undesirable toxicity when administered parenterally (e.g., intravenously). It will be understood that the term "N-hydroxysulfonamide type nitroxyl donor" includes both compounds with a free sulfonamide hydroxyl group (e.g., compounds depicted in Tables 1 and 2 of Section 4.2) and compounds in which the N-hydroxy group of the sulfonamide is esterified, as depicted below:

(99)

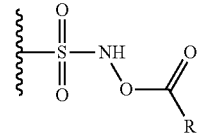

where $\xi$ represents the aromatic, heteroaromatic or polycyclic portion of the compound (see Section 4.2 for definitions of R).

In accordance with the present disclosure, N-hydroxysulfonamide type nitroxyl donors that have half-lives of greater than 10 minutes when measured in PBS or human plasma show significant improvements in the toxicological profile relative to N-hydroxysulfonamide type nitroxyl donors, such as CXL-1020, that have half-lives of less than 10 minutes, while retaining a high level of efficacy in the treatment of cardiovascular diseases (e.g., heart failure).

In certain embodiments, a N-hydroxysulfonamide type nitroxyl donor useful in a pharmaceutical composition (i.e., in a nitroxyl donating composition) of the disclosure has a half-life of greater than 10 minutes when measured in an aerated phosphate buffered saline (PBS) solution at a pH of 7.4 under conditions specified in Example 2. In particular embodiments, a N-hydroxysulfonamide type nitroxyl donor useful in a pharmaceutical composition of the disclosure has a half-life of from about 12 minutes to about 150 minutes when measured in an aerated PBS solution at a pH of 7.4 under conditions specified in Example 2. In specific embodiments, a N-hydroxysulfonamide type nitroxyl donor useful in a pharmaceutical composition of the disclosure has a half-life of from about 15 minutes to about 70 minutes when measured in an aerated PBS solution at a pH of 7.4 under conditions specified in Example 2. Specific examples of such compounds of the disclosure are listed in Tables 1 and 2 (see Section 4.2).

In certain embodiments, a N-hydroxysulfonamide type nitroxyl donor useful in a pharmaceutical composition of the disclosure has a half-life of greater than 10 minutes when measured in human plasma at pH 7.4 in the presence of an anticoagulant (e.g., heparin or sodium citrate), under conditions specified in Example 2. In particular embodiments, a N-hydroxysulfonamide type nitroxyl donor useful in a pharmaceutical composition of the disclosure has a half-life of from greater than 10 minutes to about 85 minutes when measured in human plasma at a pH of 7.4 under conditions specified in Example 2. In some embodiments, a N-hydroxysulfonamide type nitroxyl donor useful in a pharmaceutical composition of the disclosure has a half-life of from about 12 minutes to about 85 minutes when measured in human plasma at a pH of 7.4 under conditions specified in Example 2. In particular embodiments, a N-hydroxysulfonamide type nitroxyl donor useful in a pharmaceutical composition of the disclosure has a half-life of from about 25 minutes to about 75 minutes when measured in human plasma at a pH of 7.4 under conditions specified in Example 2. Specific examples of such compounds of the disclosure are listed in Tables 1 and 2.

In a particular embodiment, a N-hydroxysulfonamide type nitroxyl donor useful in a pharmaceutical composition of the disclosure is a compound of the formula (1):

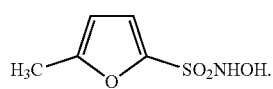

(1)

In another embodiment, a N-hydroxysulfonamide type nitroxyl donor useful in a pharmaceutical composition of the disclosure is a compound of the formula (2):

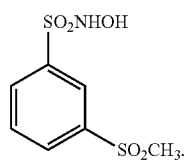

(2)

It has further been discovered that a composition comprising a N-hydroxysulfonamide type nitroxyl donor formulated at a pH of about 5 or greater has a significantly improved toxicological profile relative to compositions comprising the N-hydroxysulfonamide type nitroxyl donor formulated at more acidic pH levels, such as the CXL-1020 compositions evaluated in Phase I and Phase IIa clinical trials. Thus, in various embodiments, a N-hydroxysulfonamide type nitroxyl donor can be formulated for parenteral injection at a pH of from about 5 to about 6 (e.g., a pH of about 5, about 5.5 or about 6). Formulating within this pH range mitigates potential undesirable side effects (e.g., reduced venous irritation) relative to more acidic compositions. Surprisingly, formulating a N-hydroxysulfonamide type nitroxyl donor at a pH within the range of a pH of from about 5 to about 6 can be achieved without a deleterious effect on the stability of the nitroxyl donors.

Additionally, it has been discovered that particular excipients can be used to stabilize and/or solubilize nitroxyl donors useful in compositions of the disclosure. In various embodiments, at least one such pharmaceutically acceptable excipient comprises at least one species of cyclodextrin. In one such embodiment, the excipient is a β-cyclodextrin. One preferred β-cyclodextrin is CAPTISOL®.

In embodiments where a cyclodextrin (e.g., CAPTISOL®) serves an excipient in the disclosed pharmaceutical compositions, the quantity of the cyclodextrin in the composition will depend on the solubility and/or stability of the nitroxyl donor. For example, the molar ratio between the N-hydroxysulfonamide type nitroxyl donor and the cyclodextrin present in the composition can be from about 0.02:1 to about 2:1. In particular embodiments, the molar ratio between the N-hydroxysulfonamide type nitroxyl donor and the cyclodextrin present in the composition can be from about 0.05:1 to about 1.5:1. In certain embodiments, the molar ratio between the N-hydroxysulfonamide type nitroxyl donor and the cyclodextrin present in the composition can be from about 0.1:1 to about 1:1. In certain embodiments, the molar ratio between the N-hydroxysulfonamide type nitroxyl donor and the cyclodextrin present in the composition can be from about 0.5:1 to about 1:1.

Compounds and/or compositions of the disclosure can be used to treat a variety of conditions that are responsive to nitroxyl therapy. For instance, the compounds and/or compositions of the disclosure can be used to treat or prevent the occurrence of cardiovascular diseases. In certain embodiments, a nitroxyl donating composition of the disclosure can be used to treat cardiovascular disease, ischemia/reperfusion injury, pulmonary hypertension or another condition responsive to nitroxyl therapy. In particular embodiments, a nitroxyl donating composition of the disclosure can be used to treat heart failure. In a particular embodiment, a compound and/or composition of the disclosure can be used to treat decompensated heart failure (e.g., acute decompensated heart failure). In certain embodiments, the compounds and/or compositions of the disclosure can be used to treat systolic heart failure. In particular embodiments, the compounds and/or compositions of the disclosure can be used to treat diastolic heart failure.

In one aspect, the compound and/or composition of the disclosure can be administered via parenteral (e.g., subcutaneous, intramuscular, intravenous or intradermal) administration. When administered parenterally (e.g., intravenously) to a human subject, a N-hydroxysulfonamide type nitroxyl donor useful in, for example, a pharmaceutical composition of the disclosure, can be dosed at a rate of from about 5 μg/kg/min to about 100 μg/kg/min. In certain embodiments, a N-hydroxysulfonamide type nitroxyl donor useful in a pharmaceutical composition of the disclosure can be dosed to a human subject at a rate of from about 10 μg/kg/min to about 70 μg/kg/min. In certain embodiments, a N-hydroxysulfonamide type nitroxyl donor useful in a pharmaceutical composition of the disclosure can be dosed to a human subject at a rate of from about 15 μg/kg/min to about 50 μg/kg/min. In certain embodiments, a N-hydroxysulfonamide type nitroxyl donor useful in a pharmaceutical composition of the disclosure can be dosed to a human subject at a rate of from about 20 μg/kg/min to about 30 μg/kg/min. In certain embodiments, a N-hydroxysulfonamide type nitroxyl donor useful in a pharmaceutical composition of the disclosure can be dosed to a human subject at a rate of from about 10 μg/kg/min to about 20 μg/kg/min.

In another embodiment, the compounds and/or compositions of the disclosure can be formulated for oral administration. Compounds for oral administration can be formulated as liquid or solid dosage forms. In particular embodiments where a nitroxyl donor is formulated as an oral liquid dosage form, polyethylene glycol 300 (PEG300) can serve as an exemplary excipient.

3. BRIEF DESCRIPTION OF FIGURES

FIG. 1 shows the hemodynamic profile of CXL-1020 and five compounds useful in pharmaceutical compositions of the disclosure (compounds of formulas (1), (2), (83), (84) and (85)) using a canine tachycardia-pacing model of heart failure (see Example 3). Each compound was administered intravenously at a rate of 100 μg/kg/min. Hemodynamic parameters were obtained 180 minutes after administration of the respective compound.

Figure 2:
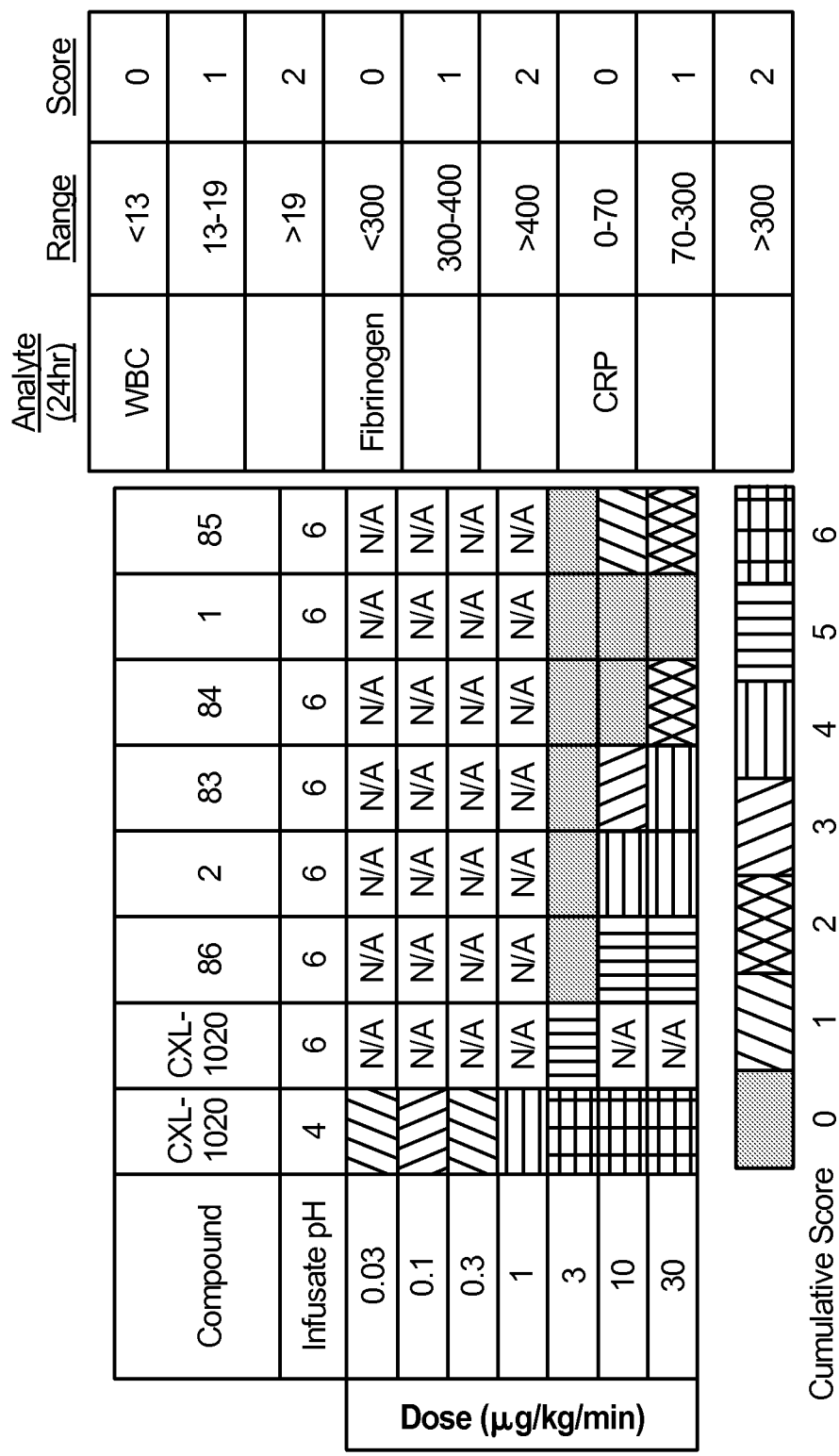

FIG. 2 shows the assessment of the toxicological profile of CXL-1020 and compounds useful in pharmaceutical compositions of the disclosure (compounds of formulas (1), (2), (83), (84), (85) and (86)) following 24 hour infusion at multiple doses using a canine peripheral vein toxicity model (see Example 5). Key inflammatory markers measured include white blood cells (WBC), fibrinogen, and C-reactive protein (CRP).

Figure 3:
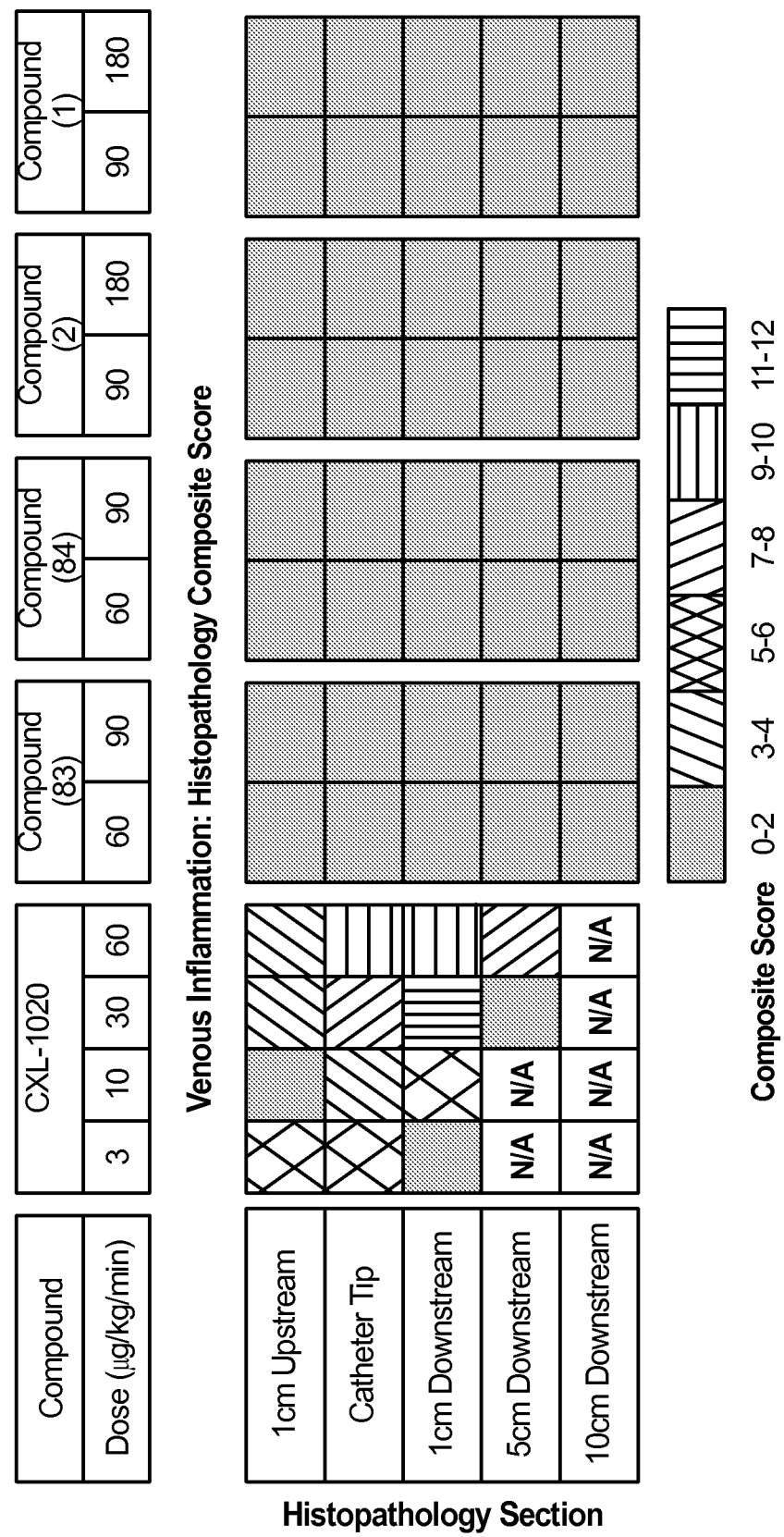

FIG. 3 shows measures of inflammation observed using a canine implanted central catheter 72 hour model using different doses of CXL-1020 and four compounds useful in pharmaceutical compositions of the disclosure (compounds of formulas (1), (2), (83) and (84)) (see Example 5). Scores shown in the table are based on microscopic pathology findings of edema, hemorrhage, vascular inflammation and perivascular inflammation observed at and around the catheter tip and proximal to the catheter tip.

Figure 4:
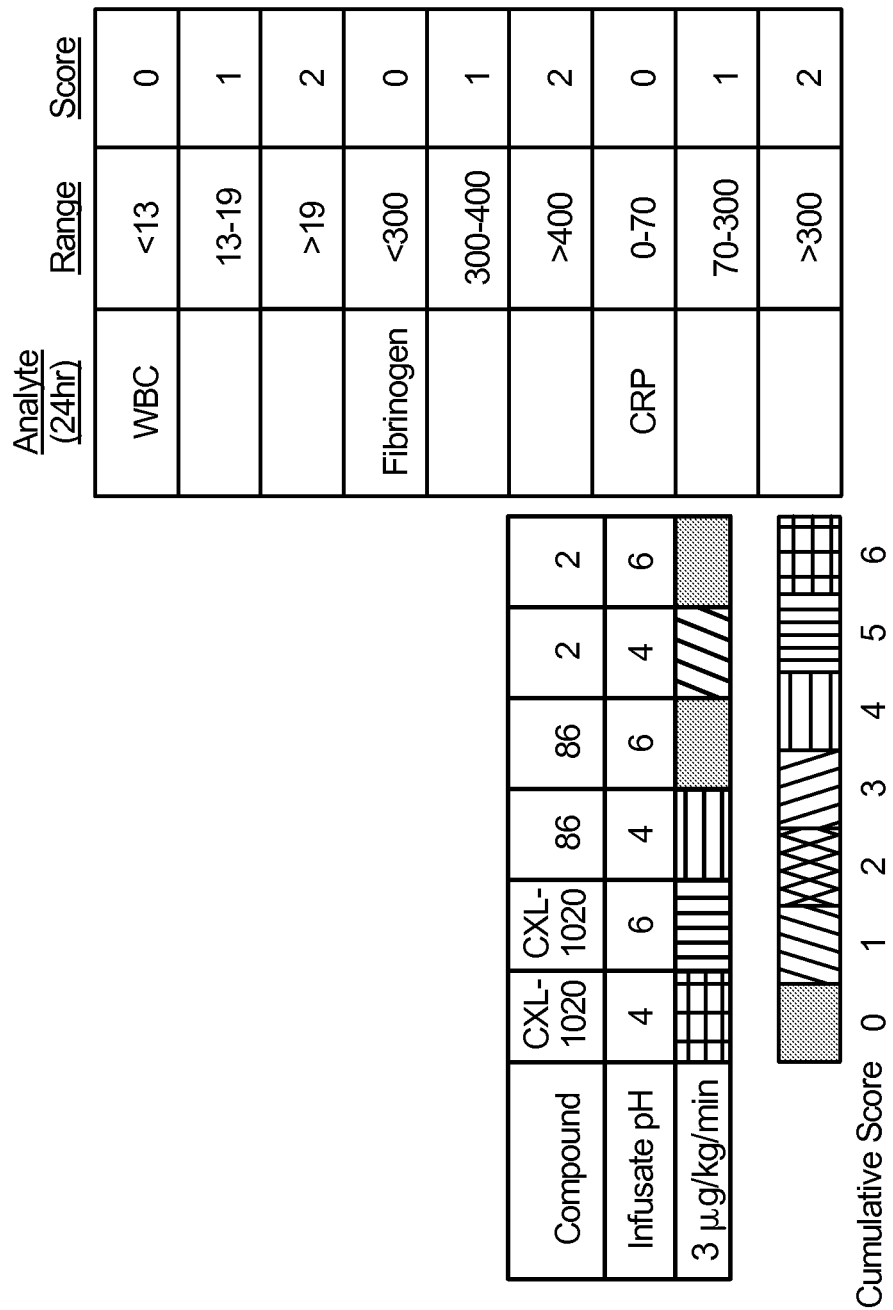

FIG. 4 shows the assessment of the toxicological profile of CXL-1020 and two compounds of the disclosure (compounds of formulas (2) and (86)), formulated at a pH of 4 or 6, following 24 hour infusion at a rate of 3 μg/kg/min (see Examples 4 and 6).

4. DETAILED DESCRIPTION

The invention includes the following:

(1.) A method of treating heart failure, comprising administering to a human patient a nitroxyl donor composition, said composition comprising a N-hydroxysulfonamide type nitroxyl donor that has a half-life of greater than 10 minutes when measured in human plasma at a pH of 7.4 by the procedure described in Example 2 and a cyclodextrin.

(2.) The method of the above (1.), wherein the N-hydroxysulfonamide type nitroxyl donor has a half-life of from about 12 minutes to about 85 minutes when measured in human plasma at a pH of 7.4 under conditions specified in Example 2.

(3.) The method of the above (1.), wherein the N-hydroxysulfonamide type nitroxyl donor has a half-life of from about 25 minutes to about 75 minutes when measured in human plasma at a pH of 7.4 under conditions specified in Example 2.

(4.) The method of the above (1.), wherein the N-hydroxysulfonamide type nitroxyl donor has a half-life of less than 95 minutes when measured in human plasma at a pH of 7.4 under conditions specified in Example 2.

(5.) The method of any one of the above (1.)-(4.), wherein the cyclodextrin is a sulfo-n-butyl ether derivative of β-cyclodextrin having six or seven sulfo-n-butyl ether groups per cyclodextrin molecule.

(6.) The method of any one of the above (1.)-(4.), wherein the cyclodextrin is CAPTISOL®.

(7.) The method of any one of the above (1.)-(6.), wherein the molar ratio between the N-hydroxysulfonamide type nitroxyl donor and the cyclodextrin present in the composition is from about 0.02:1 to about 2:1.

(8.) The method of any one of the above (1.)-(6.), wherein the molar ratio between the N-hydroxysulfonamide type nitroxyl donor and the cyclodextrin present in the composition is from about 0.05:1 to about 1.5:1.

(9.) The method of any one of the above (1.)-(6.), wherein the molar ratio between the N-hydroxysulfonamide type nitroxyl donor and the cyclodextrin present in the composition is from about 0.5:1 to about 1:1.

(10.) The method of any one of the above (1.)-(9.), wherein the composition is suitable for parenteral administration.

(11.) The method of the above (10.), wherein the composition is suitable for intravenous administration.

(12.) The method of the above (10.) or the above (11.), wherein the composition is formulated at a pH of from about 4 to about 6.

(13.) The method of the above (10.) or the above (11.), wherein the composition is formulated at a pH of from about 5 to about 6.

(14.) The method of the above (10.) or the above (11.), wherein the composition is formulated at a pH of from about 5.5 to about 6.

(15.) The method of any one of the above (1.)-(14.), wherein the heart failure is acute decompensated heart failure.

(16.) The method of any one of the above (1.)-(15.), wherein the N-hydroxysulfonamide type nitroxyl donor is a compound of the formula (1):

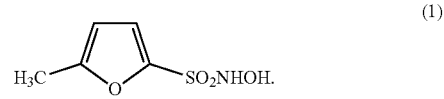

(17.) The method of any one of the above (1.)-(15.), wherein the N-hydroxysulfonamide type nitroxyl donor is a compound of the formula (2):

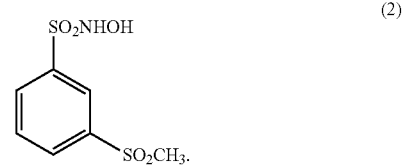

(18.) A method of treating heart failure, comprising administering to a human patient a nitroxyl donor composition comprising a N-hydroxysulfonamide type nitroxyl donor that has a half-life of greater than 10 minutes when measured in human plasma at a pH of 7.4 by the procedure described in Example 2, wherein said composition is administered parenterally at a pH of from about 5 to about 6.5.

(19.) The method of the above (18.), wherein the composition is administered intravenously.

(20.) The method of the above (18.) or the above (19.), wherein the composition is administered at a pH of from about 5.5 to about 6.

(21.) The method of the above (18.) or the above (19.), wherein the composition is administered at a pH of about 6.

(22.) The method of any one of the above (18.)-(21.), wherein the N-hydroxysulfonamide type nitroxyl donor has a half-life of from about 12 minutes to about 85 minutes when measured in human plasma at a pH of 7.4 under conditions specified in Example 2.

(23.) The method of any one of the above (18.)-(21.), wherein the N-hydroxysulfonamide type nitroxyl donor has a half-life of from about 25 minutes to about 75 minutes when measured in human plasma at a pH of 7.4 under conditions specified in Example 2.

(24.) The method of any one of the above (18.)-(21.), wherein the N-hydroxysulfonamide type nitroxyl donor has a half-life of less than 95 minutes when measured in human plasma at a pH of 7.4 under conditions specified in Example 2.

(25.) The method of any one of the above (18.)-(24.), wherein the composition further comprises a stabilizing agent.

(26.) The method of the above (25.), wherein the stabilizing agent is a cyclodextrin.

(27.) The method of the above (26.), wherein the cyclodextrin is a β-cyclodextrin.

(28.) The method of any one of the above (18.)-(27.), wherein the N-hydroxysulfonamide type nitroxyl donor is a compound of the formula (1):

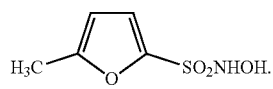

(1)

(29.) The method of any one of the above (18.)-(27.), wherein the N-hydroxysulfonamide type nitroxyl donor is a compound of the formula (2):

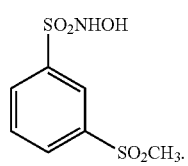

(2)

(30.) A pharmaceutical composition comprising a N-hydroxysulfonamide type nitroxyl donor that has a half-life of greater than 10 minutes when measured in human plasma at a pH of 7.4 by the procedure described in Example 2 and an aqueous buffer, wherein the composition has a pH of from about 5 to about 6.

(31.) The pharmaceutical composition of the above (30.), wherein the aqueous buffer provides a pH to the composition of from about 5.5 to about 6.2.

(32.) The pharmaceutical composition of the above (30.), wherein the aqueous buffer provides a pH to the composition of about 6.

(33.) The pharmaceutical composition of any one of the above (30.)-(32.), wherein the buffer is a phosphate or acetate buffer.

(34.) The pharmaceutical composition of the above (33.), wherein the buffer is a potassium phosphate buffer.

(35.) The pharmaceutical composition of the above (33.), wherein the buffer is a potassium acetate buffer.

(36.) The pharmaceutical composition of any one of the above (30.)-(35.), further comprising a stabilizing agent.

(37.) The pharmaceutical composition of the above (36.), wherein the stabilizing agent is a cyclodextrin.

(38.) The pharmaceutical composition of the above (37.), wherein the cyclodextrin is a sulfo-n-butyl ether derivative of β-cyclodextrin having six or seven sulfo-n-butyl ether groups per cyclodextrin molecule.

(39.) The pharmaceutical composition of the above (37.) or the above (38.), wherein the cyclodextrin is CAPTISOL®.

(40.) The pharmaceutical composition of any one of the above (37.)-(39.), wherein the molar ratio between the N-hydroxysulfonamide type nitroxyl donor and the cyclodextrin present in the composition is from about 0.02:1 to about 2:1.

(41.) The pharmaceutical composition of any one of the above (37.)-(39.), wherein the molar ratio between the N-hydroxysulfonamide type nitroxyl donor and the cyclodextrin present in the composition is from about 0.05:1 to about 1.5:1.

(42.) The pharmaceutical composition of any one of the above (37.)-(39.), wherein the molar ratio between the N-hydroxysulfonamide type nitroxyl donor and the cyclodextrin present in the composition is from about 0.5:1 to about 1:1.

(43.) The pharmaceutical composition of any one of the above (30.)-(42.), wherein the N-hydroxysulfonamide type nitroxyl donor has a half-life of from about 12 minutes to about 85 minutes when measured in human plasma at a pH of 7.4 under conditions specified in Example 2.

(44.) The pharmaceutical composition of any one of the above (30.)-(42.), wherein the N-hydroxysulfonamide type nitroxyl donor has a half-life of from about 25 minutes to about 75 minutes when measured in human plasma at a pH of 7.4 under conditions specified in Example 2.

(45.) The pharmaceutical composition of any one of the above (30.)-(42.), wherein the N-hydroxysulfonamide type nitroxyl donor has a half-life of less than 95 minutes when measured in human plasma at a pH of 7.4 under conditions specified in Example 2.

(46.) The pharmaceutical composition of any one of the above (30.)-(42.), wherein the N-hydroxysulfonamide type nitroxyl donor is a compound of the formula (1)

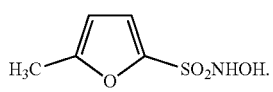

(1)

(47.) The pharmaceutical composition of any one of the above (30.)-(42.), wherein the N-hydroxysulfonamide type nitroxyl donor is a compound of the formula (2):

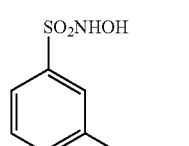

(2)

(48.) A pharmaceutical composition comprising (i) a N-hydroxysulfonamide type nitroxyl donor that has a half-life of greater than 10 minutes when measured in human plasma at a pH of 7.4 by the procedure described in Example 2 and (ii) a cyclodextrin.

(49.) The pharmaceutical composition of the above (48.), wherein the N-hydroxysulfonamide type nitroxyl donor has a half-life of from about 12 minutes to about 85 minutes when measured in human plasma at a pH of 7.4 under conditions specified in Example 2.

(50.) The pharmaceutical composition of the above (48.), wherein the N-hydroxysulfonamide type nitroxyl donor has a half-life of from about 25 minutes to about 75 minutes when measured in human plasma at a pH of 7.4 under conditions specified in Example 2.

(51.) The pharmaceutical composition of the above (48.), wherein the N-hydroxysulfonamide type nitroxyl donor has a half-life of less than 95 minutes when measured in human plasma at a pH of 7.4 under conditions specified in Example 2.

(52.) The pharmaceutical composition of any one of the above (48.)-(51.), wherein the cyclodextrin is a sulfo-n-butyl ether derivative of β-cyclodextrin having six or seven sulfo-n-butyl ether groups per cyclodextrin molecule.

(53.) The pharmaceutical composition of any one of the above (48.)-(51.), wherein the cyclodextrin is CAPTISOL®.

(54.) The pharmaceutical composition of any one of the above (48.)-(53.), wherein the molar ratio between the N-hydroxysulfonamide type nitroxyl donor and the cyclodextrin present in the composition is from about 0.02:1 to about 2:1.

(55.) The pharmaceutical composition of any one of the above (48.)-(53.), wherein the molar ratio between the N-hydroxysulfonamide type nitroxyl donor and the cyclodextrin present in the composition is from about 0.05:1 to about 1.5:1.

(56.) The pharmaceutical composition of any one of the above (48.)-(53.), wherein the molar ratio between the N-hydroxysulfonamide type nitroxyl donor and the cyclodextrin present in the composition is from about 0.5:1 to about 1:1.

(57.) The pharmaceutical composition of any one of the above (48.)-(53.), wherein the N-hydroxysulfonamide type nitroxyl donor is a compound of the formula (1):

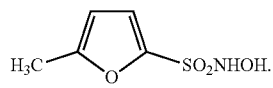

(1)

(58.) The pharmaceutical composition of any one of the above (48.)-(53.), wherein the N-hydroxysulfonamide type nitroxyl donor is a compound of the formula (2):

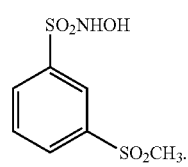

(2)

(59.) An admixture comprising a N-hydroxysulfonamide type nitroxyl donor that has a half-life of greater than 10 minutes when measured in human plasma at a pH of 7.4 by the procedure described in Example 2 and a cyclodextrin, wherein the molar ratio between the N-hydroxysulfonamide type nitroxyl donor and the cyclodextrin present in the composition is from about 0.02:1 to about 2:1.

(60.) The admixture of the above (59.), which is formed by lyophilization.

(61.) The admixture of the above (59.) or the above (60.), wherein the molar ratio between the N-hydroxysulfonamide type nitroxyl donor and the cyclodextrin present in the composition is from about 0.05:1 to about 1.5:1.

(62.) The admixture of the above (61.), wherein the molar ratio between the N-hydroxysulfonamide type nitroxyl donor and the cyclodextrin present in the composition is from about 0.5:1 to about 1:1.

(63.) The admixture of any one of the above (59.)-(62.), further comprising a buffering agent.

(64.) The admixture of the above (63.), wherein the buffering agent is potassium acetate.

(65.) The admixture of any one of the above (59.)-(64.), wherein the N-hydroxysulfonamide type nitroxyl donor is a compound of the formula (1):

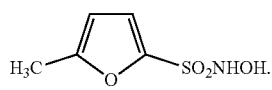

(1)

(66.) The admixture of any one of the above (59.)-(64.), wherein the N-hydroxysulfonamide type nitroxyl donor is a compound of the formula (2):

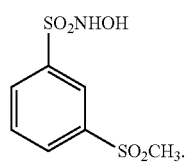

(2)

(67.) Use of a pharmaceutical composition of any one of the above (30.)-(58.) for the manufacture of a medicament useful for treating a cardiovascular disease.

(68.) Use of a pharmaceutical composition of any one of the above (30.)-(58.) for the manufacture of a medicament useful for treating heart failure.

(69.) Use of a pharmaceutical composition of any one of the above (30.)-(58.) for the manufacture of a medicament useful for treating acute decompensated heart failure.

(70.) The pharmaceutical composition of any one of the above (30.)-(58.) for use in the treatment of a cardiovascular disease.

(71.) The pharmaceutical composition of any one of the above (30.)-(58.) for use in the treatment of heart failure.

(72.) The pharmaceutical composition of any one of the above (30.)-(58.) for use in the treatment of acute decompensated heart failure.

4.1 Definitions

Unless clearly indicated otherwise, the following terms as used herein have the meanings indicated below.

A "pharmaceutically acceptable salt" refers to a salt of any therapeutic agent disclosed herein, which salt can include any of a variety of organic and inorganic counter ions known in the art and which salt is pharmaceutically acceptable. When the therapeutic agent contains an acidic functionality, various exemplary embodiments of counter ions are sodium, potassium, calcium, magnesium, ammonium, tetraalkylammonium, and the like. When the therapeutic agent contains a basic functionality, a pharmaceutically acceptable salt can include as a counter ion, by way of example, an organic or inorganic acid, such as hydrochloride, hydrobromide, tartrate, mesylate, acetate, maleate, oxalate, and the like. Illustrative salts include, but are not limited to, sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucaronate, saccharate, formate, benzoate, glutamate, methanesulfonate, ethanesulfonate, benzenesulfonate, and p-toluenesulfonate salts. Accordingly, a salt can be prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl-N-ethylamine; diethylamine; triethylamine; mono-, bis-, or tris-(2-hydroxy-lower-alkyl amines), such as mono-, bis-, or tris-(2-hydroxyethyl)amine, 2-hydroxy-tert-butylamine, or tris-(hydroxymethyl)methylamine, N,N-di-lower-alkyl-N-(hydroxy-lower-alkyl)-amines, such as N,N-dimethyl-N-(2-hydroxyethyl) amine, or tri-(2-hydroxyethyl)amine; N-methyl-D-glucamine; and amino acids such as arginine, lysine, and the like. A salt can also be prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

"Pharmaceutically acceptable excipient" refers to any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or pharmaceutical composition into a unit dosage form for administration. Pharmaceutically acceptable excipients are known in the pharmaceutical arts and are disclosed, for example, in Gennaro, Ed., Remington: The Science and Practice of Pharmacy, 20th Ed. (Lippincott Williams & Wilkins, Baltimore, Md., 2000) and Handbook of Pharmaceutical Excipients, American Pharmaceutical Association, Washington, D.C., (e.g., 1st, 2nd and 3rd Eds., 1986, 1994 and 2000, respectively). As will be known to those in the art, pharmaceutically acceptable excipients can provide a variety of functions and can be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose; (2) starches, such as corn starch and potato starch; (3) cellulose and its derivatives, such as sodium carboxymethyl cellulose, ethyl cellulose, cellulose acetate, hydroxypropylmethylcellulose, and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Unit dosage form" refers to a physically discrete unit suitable as a unitary dosage for a human or an animal. Each unit dosage form can contain a predetermined amount of a therapeutic agent calculated to produce a desired effect.

Unless clearly indicated otherwise, a "patient" refers to an animal, such as a mammal, including but not limited to, a human. Hence, the methods disclosed herein can be useful in human therapy and veterinary applications. In particular embodiments, the patient is a mammal. In certain embodiments, the patient is a human.

"Effective amount" refers to such amount of a therapeutic agent or a pharmaceutically acceptable salt thereof, which in combination with its parameters of efficacy and potential for toxicity, as well as based on the knowledge of the practicing specialist, should be effective in a given therapeutic form. As is understood in the art, an effective amount can be administered in one or more doses.

"Treatment", "treating" and the like is an approach for obtaining a beneficial or desired result, including clinical results. For purposes of this disclosure, beneficial or desired results include but are not limited to inhibiting and/or suppressing the onset and/or development of a condition or reducing the severity of such condition, such as reducing the number and/or severity of symptoms associated with the condition, increasing the quality of life of those suffering from the condition, decreasing the dose of other medications required to treat the condition, enhancing the effect of another medication a patient is taking for the condition, and/or prolonging survival of patients having the condition.

"Prevent", "preventing" and the like refers to reducing the probability of developing a condition in a patient who does not have, but is at risk of developing a condition. A patient "at risk" may or may not have a detectable condition, and may or may not have displayed a detectable condition prior to the treatment methods disclosed herein. "At risk" denotes that a patient has one or more so-called risk factors, which are measurable parameters that correlate with development of a condition and are known in the art. A patient having one or more of these risk factors has a higher probability of developing the condition than a patient without such risk factor(s).

"Positive inotrope" refers to an agent that causes an increase in myocardial contractile function. Exemplary positive inotropes are a beta-adrenergic receptor agonist, an inhibitor of phosphodiesterase activity, and calcium-sensitizers. Beta-adrenergic receptor agonists include, among others, dopamine, dobutamine, terbutaline, and isoproterenol. Analogs and derivatives of such compounds are also intended. For example, U.S. Pat. No. 4,663,351 discloses a dobutamine prodrug that can be administered orally.

A condition that is "responsive to nitroxyl therapy" includes any condition in which administration of a compound that donates an effective amount of nitroxyl under physiological conditions treats and/or prevents the condition, as those terms are defined herein. A condition whose symptoms are suppressed or diminished upon administration of nitroxyl donor is a condition responsive to nitroxyl therapy.

"Pulmonary hypertension" or "PH" refers to a condition in which the pulmonary arterial pressure is elevated. The current hemodynamic definition of PH is a mean pulmonary arterial pressure (MPAP) at rest of greater than or equal to 25 mmHg. Badesch et al., *J. Amer. Coll. Cardiol.* 54(Suppl.): S55-S66 (2009).

"N/A" means not assessed.

"$(C_1-C_6)$alkyl" refers to saturated linear and branched hydrocarbon structures having 1, 2, 3, 4, 5, or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_1-C_6)$alkyl groups include methyl, ethyl, n-propyl, iso-propyl, n-butyl, tert-butyl, n-hexyl, and the like.

"$(C_1-C_4)$alkyl" refers to saturated linear and branched hydrocarbon structures having 1, 2, 3, or 4 carbon atoms. Examples of $(C_1-C_4)$alkyl groups include methyl, ethyl, n-propyl, iso-propyl, n-butyl and tert-butyl.

"$(C_3-C_5)$alkyl" refers to saturated linear and branched hydrocarbon structures having 3, 4, or 5 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_3-C_5)$alkyl groups include n-propyl, iso-propyl, n-butyl, tert-butyl, n-pentyl, and the like.

"$(C_2-C_4)$alkenyl" refers to a straight-chain or branched unsaturated hydrocarbon radical having 2, 3, or 4 carbon atoms and a double bond in any position, e.g., ethenyl, 1-propenyl, 2-propenyl (allyl), 1-butenyl, 2-butenyl, 3-butenyl, 1-methylethenyl, 1-methyl-1-propenyl, 2-methyl-2-propenyl, 2-methyl-1-propenyl, 1-methyl-2-propenyl, and the like.

"$(C_2-C_3)$alkynyl" refers to a straight chain non-cyclic hydrocarbon having 2 or 3 carbon atoms and including at least one carbon-carbon double bond. Examples of $(C_2-C_3)$ alkenyls include -vinyl, -allyl, and 1-prop-1-enyl.

"$(C_5-C_7)$heterocycloalkyl" refers to a 5-, 6-, or 7-membered, saturated or unsaturated, bridged, mono- or bicyclic-heterocycle containing 1, 2, 3, or 4 ring heteroatoms each independently selected from nitrogen, oxygen, and sulfur. Examples of $(C_5-C_7)$heterocycloalkyl groups include pyrazolyl, pyrrolidinyl, piperidinyl, piperazinyl, tetrahydrooxazinyl, tetrahydrofuran, thiolane, dithiolane, pyrroline, pyrrolidine, pyrazoline, pyrazolidine, imidazoline, imidazolidine, tetrazole, piperidine, pyridazine, pyrimidine, pyrazine, tetrahydrofuranone, γ-butyrolactone, α-pyran, γ-pyran, dioxolane, tetrahydropyran, dioxane, dihydrothiophene, piperazine, triazine, tetrazine, morpholine, thiomorpholine, diazepan, oxazine, tetrahydro-oxazinyl, isothiazole, pyrazolidine, and the like.

"(5- or 6-membered)heteroaryl" refers to a monocyclic aromatic heterocycle ring of 5 or 6 members, i.e., a monocyclic aromatic ring comprising at least one ring heteroatom, e.g., 1, 2, 3, or 4 ring heteroatoms, each independently selected from nitrogen, oxygen, and sulfur. Examples of -(5- or 6-membered)heteroaryls include pyridyl, pyrrolyl, furyl, imidazolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

"Halo" refers to —F, —Cl, —Br or —I.

"Sulfo-n-butyl ether derivative of β-cyclodextrin" refers to β-cyclodextrin having at least one —OH group that is derivatized by replacing the hydrogen atom thereof with —$(CH_2)_4$—$S(O)_2$—OH or —$(CH_2)_4$—$S(O)_2$—$O^-Z^+$ to provide a —O—$(CH_2)_4$—$S(O)_2$—OH or —O—$(CH_2)_4$—$S(O)_2O^-Z^+$ group, respectively, where $Z^+$ is a cation such as sodium, potassium, ammonium, tetramethylammonium, and the like. In one embodiment, each Z is sodium.

4.2 N-Hydroxysulfonamide Type Nitroxyl Donors

It has been discovered that N-hydroxysulfonamide type nitroxyl donors that have sufficiently long half-lives under physiological conditions have significantly better toxicological profiles as compared to N-hydroxysulfonamide type nitroxyl donors that have shorter half-lives (e.g., CXL-1020). These longer half-life nitroxyl donors provide efficacy levels similar to CXL-1020 when administered intravenously but show significantly reduced side effects (e.g., irritation and/or inflammation) (see Examples 4-6). Moreover, these nitroxyl donors provide an onset of hemodynamic effects in 1 hour or less, which is clinically desirable.

Without being bound by theory, the experiments reported in the Examples of this disclosure suggest that nitroxyl donors with half-lives substantially shorter than 10 minutes when measured in PBS or human plasma (see Example 2), such as CXL-1020, produce high local concentrations of nitroxyl upon administration, and that the high local concentration of nitroxyl is a cause of the observed side effects. Nitroxyl at high concentration dimerizes, resulting in the formation of hyponitrous acid, which is capable of producing hydroxyl radicals. Alternatively, or in addition, peroxide emanating from white blood cells can react with nitroxyl to form hydroxyl radicals. Hydroxyl radicals can be toxic to endothelial cells, resulting in inflammation or intolerance. While nitroxyl compounds with longer half-lives could, in theory, produce hydroxyl radicals through similar mechanisms, formation of such radicals would be expected to be reduced by virtue of the low concentrations of nitroxyl, thus reducing the ability of nitroxyl to dimerize or react with peroxide. Compounds with very long half-lives (e.g., greater than 95 minutes when measured in human plasma in accordance with the method described in Example 2) would therefore be expected to have a favorable toxicological profile; however, because these compounds would be expected to be cleared from the circulation and/or diluted prior to substantial nitroxyl formation, such compounds are expected to have low efficacy.

Accordingly, the disclosure provides pharmaceutical compositions comprising N-hydroxysulfonamide type nitroxyl donors with half-lives greater than about 10 minutes when measured in an aerated phosphate buffered saline (PBS) solution at pH 7.4, or in human plasma in the presence of an anticoagulant (e.g., heparin or sodium citrate) at pH 7.4, each in accordance with the procedure described in Example 2. In particular embodiments, the disclosure provides pharmaceutical compositions comprising N-hydroxysulfonamide type nitroxyl donors with half-lives greater than about 17 minutes when measured in an aerated phosphate buffered saline (PBS) solution at pH 7.4, or in human plasma in the presence of an anticoagulant (e.g., heparin or sodium citrate) at pH 7.4, each in accordance with the procedure described in Example 2.

N-hydroxysulfonamide type nitroxyl donors with half-lives within the range of from about 12 minutes to about 85 minutes when measured in an aerated phosphate buffered saline (PBS) solution at pH 7.4, or in human plasma in the presence of an anticoagulant (e.g., heparin or sodium citrate) at pH 7.4, each in accordance with the procedure described in Example 2, have been found to have favorable efficacy and an improved toxicological profile relative to compounds with shorter half-lives. In certain embodiments, a N-hydroxysulfonamide type nitroxyl donor useful in a pharmaceutical composition of the disclosure has a half-life of from about 15 minutes to about 80 minutes when measured in an aerated phosphate buffered saline (PBS) solution at pH 7.4, or in human plasma in the presence of an anticoagulant (e.g., heparin or sodium citrate) at pH 7.4, each in accordance with the procedure described in Example 2. In particular embodiments, a nitroxyl donor useful in a pharmaceutical composition of the disclosure has a half-life of from about 25 minutes to about 75 minutes when measured in an aerated phosphate buffered saline (PBS) solution at pH 7.4, or in human plasma in the presence of an anticoagulant (e.g., heparin or sodium citrate) at pH 7.4, each in accordance with the procedure described in Example 2. In particular embodiments, a nitroxyl donor useful in a pharmaceutical composition of the disclosure has a half-life of from about 25 minutes to about 60 minutes when measured in an aerated phosphate buffered saline (PBS) solution at pH 7.4, or in human plasma in the presence of an anticoagulant (e.g., heparin or sodium citrate) at pH 7.4, each in accordance with the procedure described in Example 2. In particular embodiments, a nitroxyl donor useful in a pharmaceutical composition of the disclosure has a half-life of from about 35 minutes to about 60 minutes when measured in an aerated phosphate buffered saline (PBS) solution at pH 7.4, or in human plasma in the presence of an anticoagulant (e.g., heparin or sodium citrate) at pH 7.4, each in accordance with the procedure described in Example 2. In particular embodiments, a nitroxyl donor useful in a pharmaceutical composition of the disclosure has a half-life of from about 35 minutes to about 50 minutes when measured in an aerated phosphate buffered saline (PBS) solution at pH 7.4, or in human plasma in the presence of an anticoagulant (e.g., heparin or sodium citrate) at pH 7.4, each in accordance with the procedure described in Example 2. In particular embodiments, a nitroxyl donor useful in a pharmaceutical composition of the disclosure has a half-life of from about 40 minutes to about 50 minutes an aerated phosphate buffered saline (PBS) solution at pH 7.4, or in human plasma in the presence of an anticoagulant (e.g., heparin or sodium citrate) at pH 7.4, each in accordance with the procedure described in Example 2.

N-hydroxysulfonamide type nitroxyl donors useful in pharmaceutical compositions of the disclosure are capable of donating nitroxyl at physiological pH (i.e., a pH of about 7.4) and physiological temperature (i.e., a temperature of about 37° C.) (together, "physiological conditions"). The level of nitroxyl donating ability can be expressed as a percentage of a N-hydroxysulfonamide type nitroxyl donor's theoretical stoichiometric maximum. A compound that donates a "significant level of nitroxyl" means, in various embodiments, a N-hydroxysulfonamide type nitroxyl donor useful in a pharmaceutical composition of the disclosure that donates about 40% or more, about 50% or more, about 60% or more, about 70% or more, about 80% or more, about 90% or more, or about 95% or more of its theoretical maximum amount of nitroxyl under physiological conditions. In particular embodiments, a N-hydroxysulfonamide type nitroxyl donor useful in a pharmaceutical composition donates from about 70% to about 90% of its theoretical maximum amount of nitroxyl. In particular embodiments, a N-hydroxysulfonamide type nitroxyl donor useful in a pharmaceutical composition of the disclosure donates from about 85% to about 95% of its theoretical maximum amount of nitroxyl. In particular embodiments, a N-hydroxysulfonamide type nitroxyl donor useful in a pharmaceutical composition donates from about 90% to about 95% of its theoretical maximum amount of nitroxyl. Compounds that donate less than about 40%, or less than about 50%, of their theoretical maximum amount of nitroxyl are still nitroxyl donors and can be used in the methods disclosed. A N-hydroxysulfonamide type nitroxyl donor that donates less than about 50% of its theoretical amount of nitroxyl can be used in the methods disclosed, but may require higher dosing levels as compared to a N-hydroxysulfonamide type nitroxyl donor that donates a higher level of nitroxyl.

It will be understood that a N-hydroxysulfonamide type nitroxyl donor useful in a pharmaceutical composition of the disclosure can also donate a limited amount of nitric oxide, so long as the amount of nitroxyl donation exceeds the amount of nitric oxide donation. In certain embodiments, a N-hydroxysulfonamide type nitroxyl donor useful in a pharmaceutical composition of the disclosure can donate about 25 mole % or less of nitric oxide under physiological conditions. In particular embodiments, a N-hydroxysulfonamide type nitroxyl donor useful in a pharmaceutical composition of the disclosure can donate about 20 mole % or less of nitric oxide under physiological conditions. In particular embodiments, a N-hydroxysulfonamide type nitroxyl donor useful in a pharmaceutical composition of the disclosure can donate about 15 mole % or less of nitric oxide under physiological conditions. In particular embodiments, a N-hydroxysulfonamide type nitroxyl donor useful in a pharmaceutical composition of the disclosure donating compound can donate about 10 mole % or less of nitric oxide under physiological conditions. In particular embodiments, a N-hydroxysulfonamide type nitroxyl donor useful in a pharmaceutical composition of the disclosure can donate about 5 mole % or less of nitric oxide under physiological conditions. In particular embodiments, a N-hydroxysulfonamide type nitroxyl donor useful in a pharmaceutical composition of the disclosure can donate about 2 mole % or less of nitric oxide under physiological conditions. In a particular embodiment, a N-hydroxysulfonamide type nitroxyl donor useful in a pharmaceutical composition of the disclosure can donate an insignificant amount (e.g., about 1 mole % or less) of nitric oxide under physiological conditions.

Particular embodiments of N-hydroxysulfonamide type nitroxyl donors useful in pharmaceutical compositions of the disclosure are provided in Table 1 and Table 2. The compounds listed in Table 1 have been developed to optimize the half-life and toxicological profile of the nitroxyl donor, in accordance with one of the goals of the present disclosure. Compounds listed in Table 2 have previously been described (see, e.g., U.S. Pat. No. 8,030,356, the contents of which are hereby incorporated by reference in their entirety). The compounds listed in Table 1 and Table 2 generally have half-lives of greater than 10 minutes when measured in an aerated phosphate buffered saline (PBS) solution and/or in plasma (see Table 4 in Section 5.2).

TABLE 1

Representative Novel N-Hydroxysulfonamide Compounds of the Disclosure

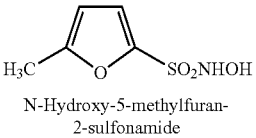
(1) N-Hydroxy-5-methylfuran-2-sulfonamide

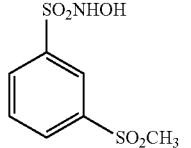
(2) N-Hydroxy-3-methanesulfonylbenzene-1-sulfonamide

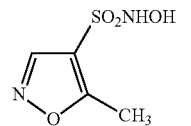
(3) N-Hydroxy-5-methyl-1,2-oxazole-4-sulfonamide

(4) N-Hydroxy-1-benzofuran-7-sulfonamide

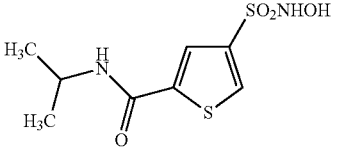
(5) 4-(Hydroxysulfamoyl)-N-(propan-2-yl)thiophene-2-carboxamide

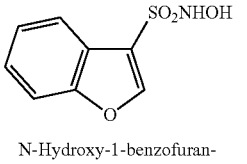
(6) N-Hydroxy-1-benzofuran-3-sulfonamide

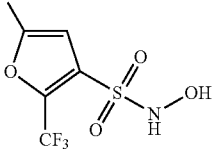
(7) N-Hydroxy-5-methyl-2-(trifluoromethyl)furan-3-sulfonamide

TABLE 1-continued

Representative Novel N-Hydroxysulfonamide Compounds of the Disclosure

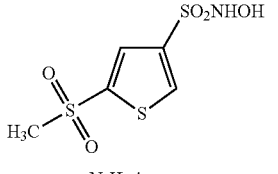
(8) N-Hydroxy-5-methanesulfonylthiophene-3-sulfonamide

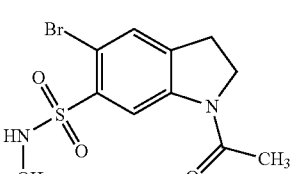
(9) 1-Acetyl-5-bromo-N-hydroxy-2,3-dihydro-1H-indole-6-sulfonamide

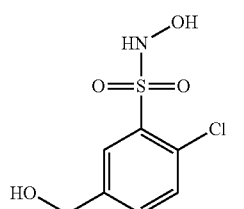
(10) 2-Chloro-N-hydroxy-5-(hydroxymethyl)benzene-1-sulfonamide

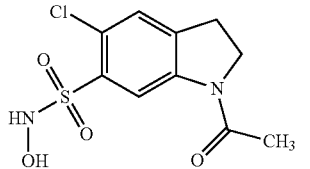
(11) 1-Acetyl-5-chloro-N-hydroxy-2,3-dihydro-1H-indole-6-sulfonamide

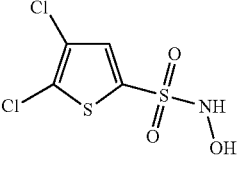
(12) 4,5-Dichloro-N-hydroxythiophene-2-sulfonamide

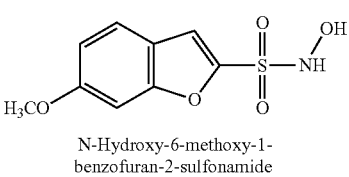 [SMILES: COc1ccc2cc(S(=O)(=O)NO)oc2c1]
(13) N-Hydroxy-6-methoxy-1-benzofuran-2-sulfonamide

TABLE 1-continued

Representative Novel N-Hydroxysulfonamide Compounds of the Disclosure

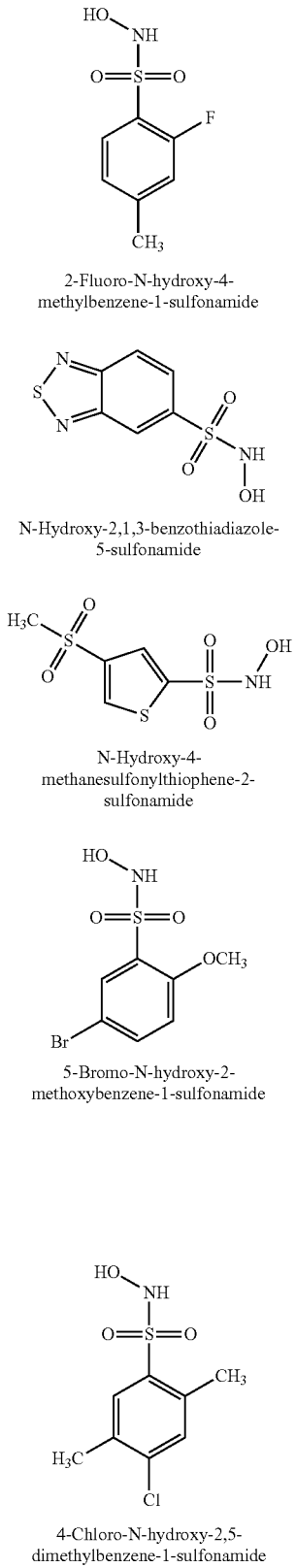

(14) 2-Fluoro-N-hydroxy-4-methylbenzene-1-sulfonamide

(15) N-Hydroxy-2,1,3-benzothiadiazole-5-sulfonamide

(16) N-Hydroxy-4-methanesulfonylthiophene-2-sulfonamide

(17) 5-Bromo-N-hydroxy-2-methoxybenzene-1-sulfonamide

(18) 4-Chloro-N-hydroxy-2,5-dimethylbenzene-1-sulfonamide

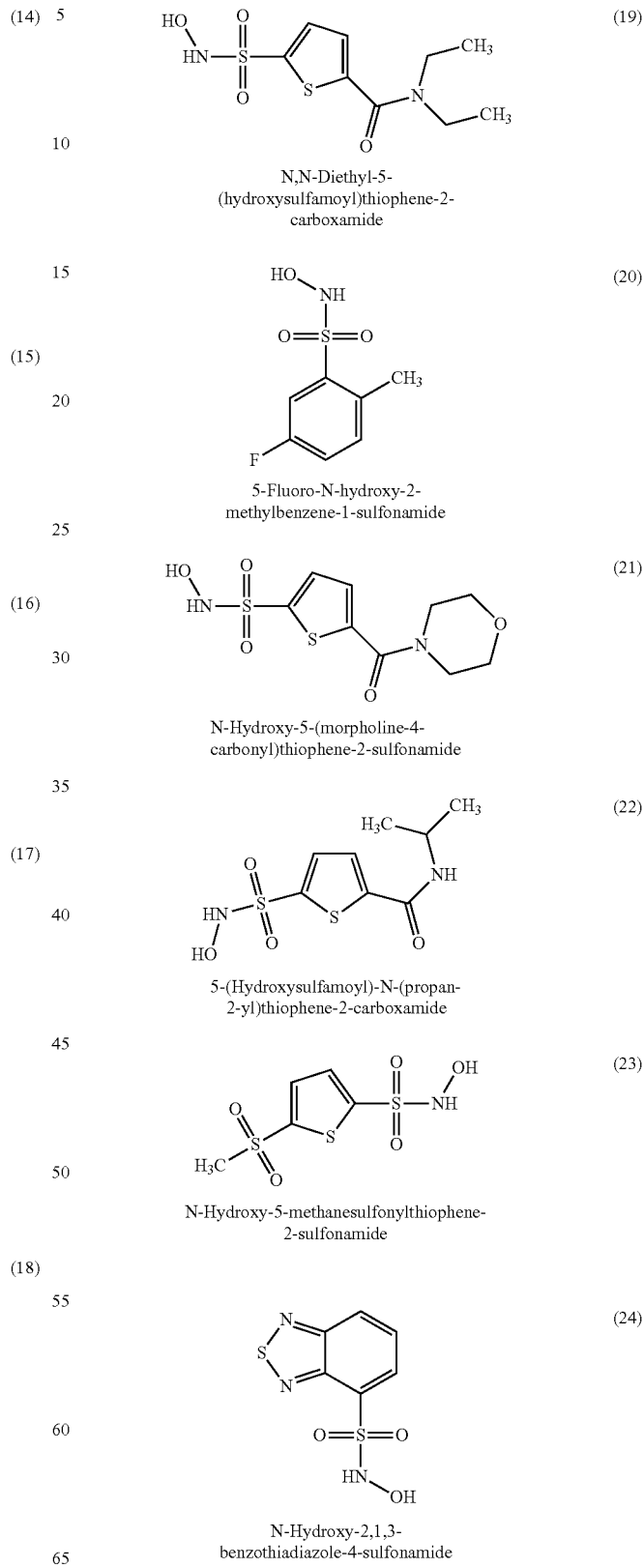

(19) N,N-Diethyl-5-(hydroxysulfamoyl)thiophene-2-carboxamide

(20) 5-Fluoro-N-hydroxy-2-methylbenzene-1-sulfonamide

(21) N-Hydroxy-5-(morpholine-4-carbonyl)thiophene-2-sulfonamide

(22) 5-(Hydroxysulfamoyl)-N-(propan-2-yl)thiophene-2-carboxamide

(23) N-Hydroxy-5-methanesulfonylthiophene-2-sulfonamide

(24) N-Hydroxy-2,1,3-benzothiadiazole-4-sulfonamide

TABLE 1-continued

Representative Novel N-Hydroxysulfonamide Compounds of the Disclosure

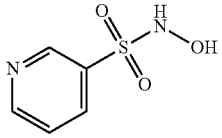
(26) N-Hydroxypyridine-3-sulfonamide

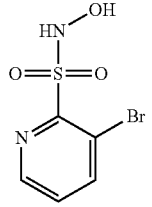
(28) N-Hydroxy-5-(morpholine-4-carbonyl)thiophene-3-sulfonamide

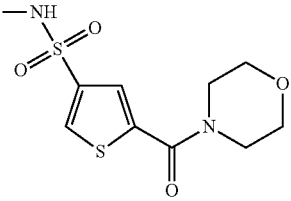
(29) 1-N-Hydroxy-2-N-(propan-2-yl)benzene-1,2-disulfonamide

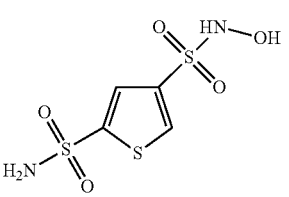
(30) 5-Chloro-N-hydroxy-1,3-dimethyl-1H-pyrazole-4-sulfonamide

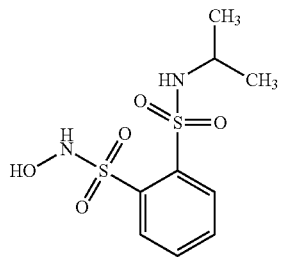
(31) N-Hydroxy-1-methyl-1H-pyrazole-4-sulfonamide

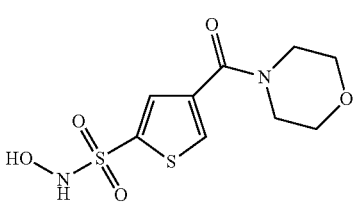
(32) N-Hydroxypyridine-2-sulfonamide

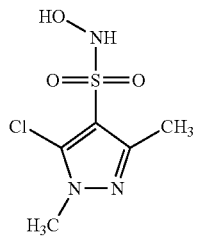
(33) 3-Bromo-N-hydroxypyridine-2-sulfonamide

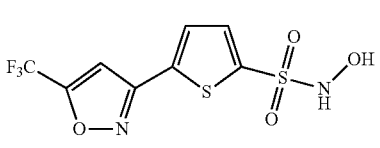
(34) 4-N-Hydroxythiophene-2,4-disulfonamide

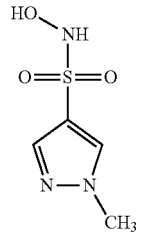
(35) N-Hydroxy-4-(morpholine-4-carbonyl)thiophene-2-sulfonamide

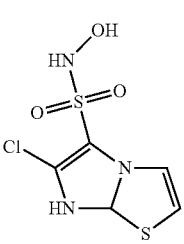
(36) N-Hydroxy-5-[5-(trifluoromethyl)-1,2-oxazol-3-yl]thiophene-2-sulfonamide

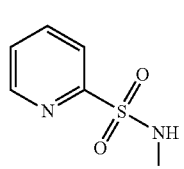
(37) 6-Chloro-N-hydroxy-7H,7aH-imidazol[2,1-b][1,3]thiazole-5-sulfonamide

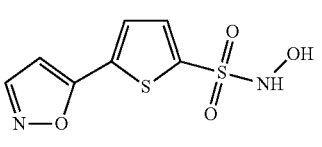
(38) N-Hydroxy-5-(1,2-oxazol-5-yl)thiophene-2-sulfonamide

TABLE 1-continued

Representative Novel N-Hydroxysulfonamide Compounds of the Disclosure

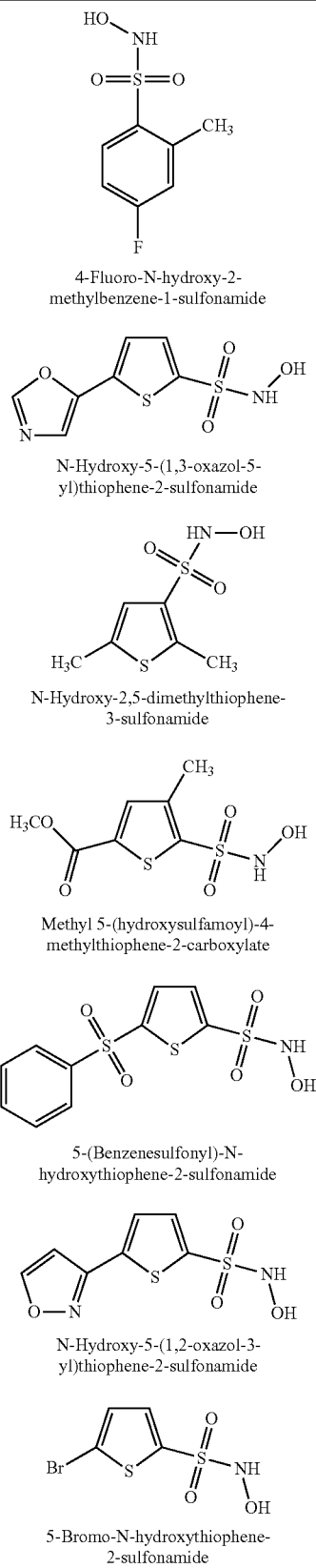

(39) 4-Fluoro-N-hydroxy-2-methylbenzene-1-sulfonamide

(40) N-Hydroxy-5-(1,3-oxazol-5-yl)thiophene-2-sulfonamide

(41) N-Hydroxy-2,5-dimethylthiophene-3-sulfonamide

(42) Methyl 5-(hydroxysulfamoyl)-4-methylthiophene-2-carboxylate

(43) 5-(Benzenesulfonyl)-N-hydroxythiophene-2-sulfonamide

(44) N-Hydroxy-5-(1,2-oxazol-3-yl)thiophene-2-sulfonamide

(45) 5-Bromo-N-hydroxythiophene-2-sulfonamide

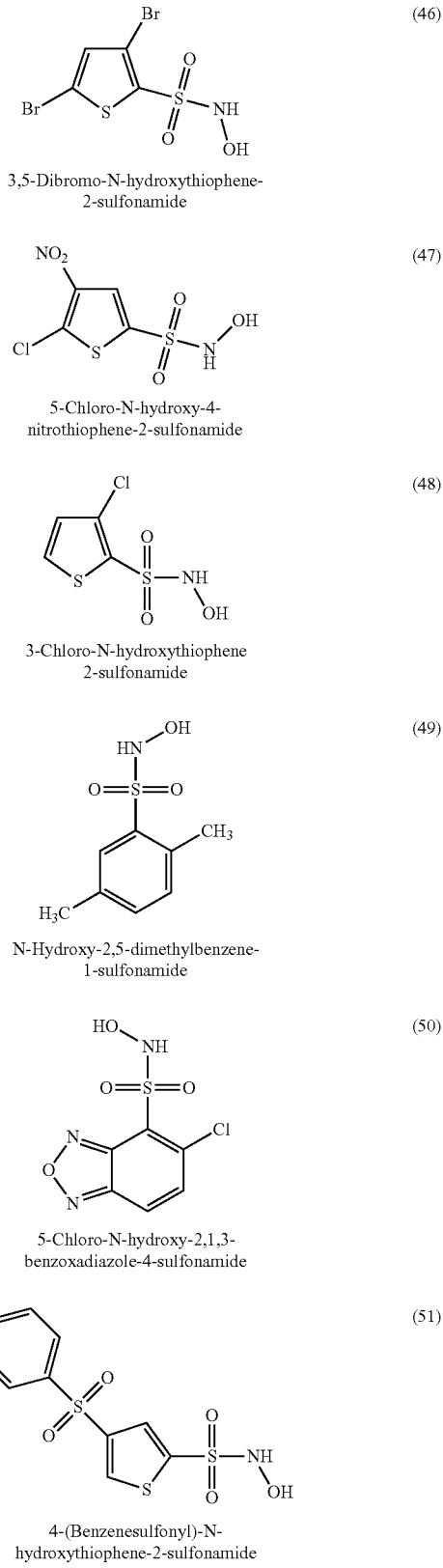

(46) 3,5-Dibromo-N-hydroxythiophene-2-sulfonamide

(47) 5-Chloro-N-hydroxy-4-nitrothiophene-2-sulfonamide

(48) 3-Chloro-N-hydroxythiophene-2-sulfonamide

(49) N-Hydroxy-2,5-dimethylbenzene-1-sulfonamide

(50) 5-Chloro-N-hydroxy-2,1,3-benzoxadiazole-4-sulfonamide

(51) 4-(Benzenesulfonyl)-N-hydroxythiophene-2-sulfonamide

TABLE 1-continued

Representative Novel N-Hydroxysulfonamide Compounds of the Disclosure

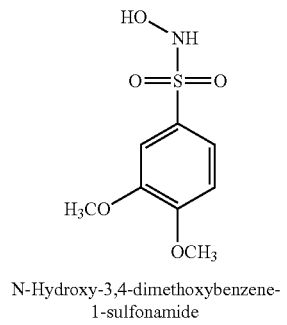 [SMILES: COc1ccc(S(=O)(=O)NO)cc1OC]

(52)

N-Hydroxy-3,4-dimethoxybenzene-
1-sulfonamide

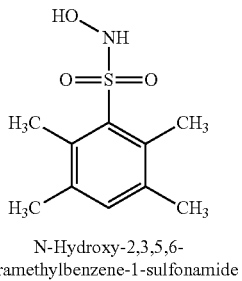

(53)

N-Hydroxy-2,3,5,6-
tetramethylbenzene-1-sulfonamide

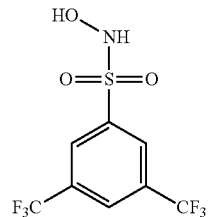

(54)

N-Hydroxy-3,5-
bis(trifluoromethyl)benzene-
1-sulfonamide

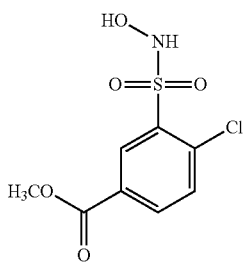

(55)

Methyl 4-chloro-3-
(hydroxysulfamoyl)benzoate

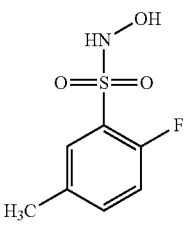

(56)

2-Fluoro-N-hydroxy-5-
methylbenzene-1-sulfonamide

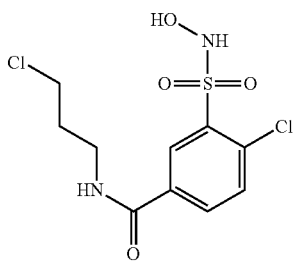

(57)

4-Chloro-N-(3-chloropropyl)-3-
(hydroxysulfamoyl)-benzamide

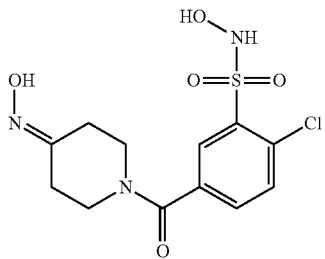

(58)

2-Chloro-N-hydroxy-5-[4-
(hydroxyimino)piperidine-1-
carbonyl]benzene-1-sulfonamide

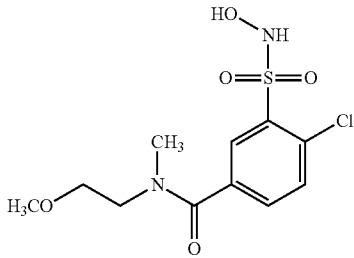 [SMILES: COCCN(C)C(=O)c1ccc(Cl)c(S(=O)(=O)NO)c1]

(59)

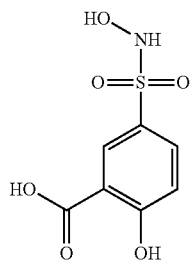

(60)

2-Hydroxy-5-
(hydroxysulfamoyl)benzoic acid

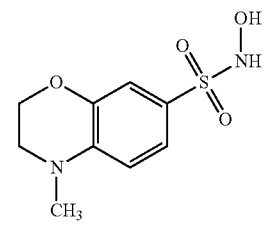

(61)

N-Hydroxy-4-methyl-3,4-dihydro-
2H-1,4-benzoxazine-7-sulfonamide

TABLE 1-continued

Representative Novel N-Hydroxysulfonamide Compounds of the Disclosure

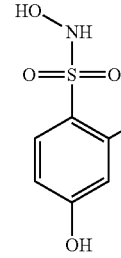
(62) 2-Chloro-N,4-dihydroxybenzene-1-sulfonamide

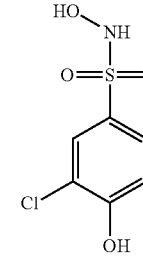
(63) 3,5-Dichloro-N,4-dihydroxybenzene-1-sulfonamide

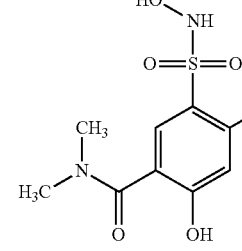
(64) 4-Chloro-2-hydroxy-5-(hydroxysulfamoyl)-N,N-dimethylbenzamide

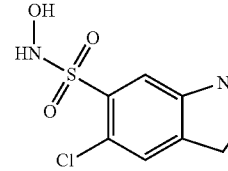
(65) 5-Chloro-N-hydroxy-1-methyl-2,3-dihydro-1H-indole-6-sulfonamide

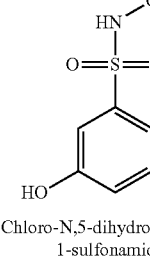
(66) 2-Chloro-N,5-dihydroxybenzene-1-sulfonamide

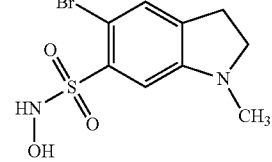
(67) 5-Bromo-N-hydroxy-1-methyl-2,3-dihydro-1H-indole-6-sulfonamide

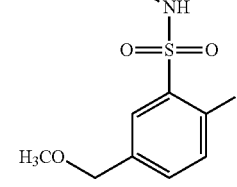
(68) 2-Chloro-N-hydroxy-5-(methoxymethyl)benzene-1-sulfonamide

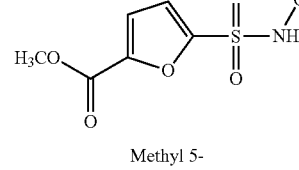
(69) Methyl 5-(hydroxysulfamoyl)furan-2-carboxylate

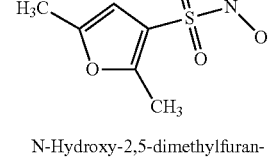
(70) N-Hydroxy-2,5-dimethylfuran-3-sulfonamide

(71) N-Hydroxy-8-oxatricyclo[7.4.0.0]trideca-1(9),2(7),3,5,10,12-hexaene-4-sulfonamide

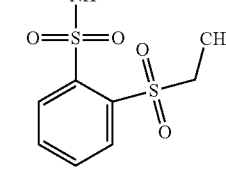
(72) 2-(Ethanesulfonyl)-N-hydroxybenzene-1-sulfonamide

TABLE 1-continued

Representative Novel N-Hydroxysulfonamide Compounds of the Disclosure

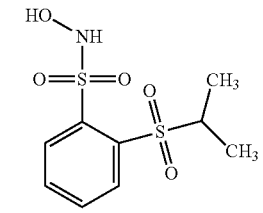

(73) N-Hydroxy-2-(propane-2-sulfonyl)benzene-1-sulfonamide

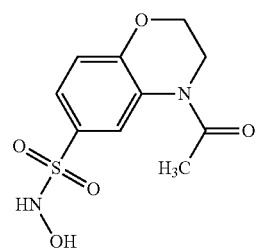

(74) 4-Acetyl-N-hydroxy-3,4-dihydro-2H-1,4-benzoxazine-6-sulfonamide

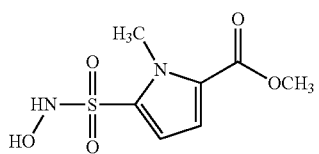

(75) Methyl 5-(hydroxysulfamoyl)-1-methyl-1H-pyrrole-2-carboxylate

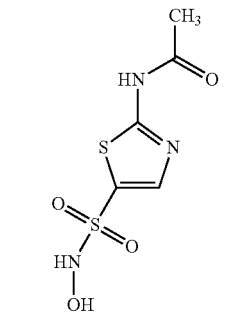

(76) N-[5-(Hydroxysulfamoyl)-1,3-thiazol-2-yl]acetamide

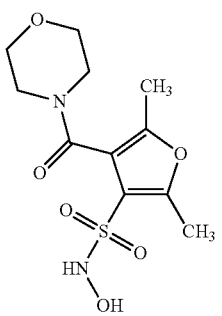

(77) N-Hydroxy-2,5-dimethyl-4-(morpholine-4-carbonyl)furan-3-sulfonamide

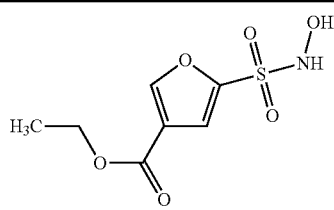

(78) Ethyl 5-(hydroxysulfamoyl)furan-3-carboxylate

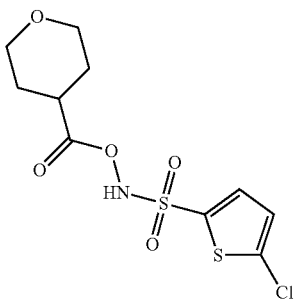

(79) 5-Chlorothiophene-2-sulfonamidooxane-4-carboxylate

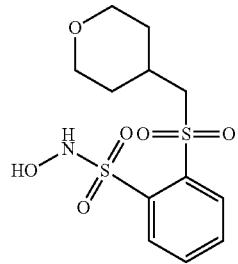

(80) N-Hydroxy-2-(oxan-4-ylmethanesulfonyl)benzene-1-sulfonamide

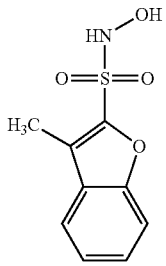

(81) N-Hydroxy-3-methyl-1-benzofuran-2-sulfonamide

TABLE 1-continued

Representative Novel N-Hydroxysulfonamide Compounds of the Disclosure

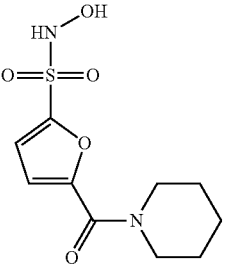 (82)

N-Hydroxy-5-(piperidine-1-carbonyl)furan-2-sulfonamide

TABLE 2

Additional N-Hydroxysulfonamide Donors with Desired Half-Lives (83)

N-Hydroxyfuran-2-sulfonamide (84)

N-Hydroxy-5-methylthiophene-2-sulfonamide (85)

N-Hydroxy-1-methyl-1H-pyrazole-3-sulfonamide (86)

5-Chloro-N-hydroxythiophene-2-sulfonamide (87)

3-Chloro-4-fluoro-N-hydroxybenzene-1-sulfonamide (88)

1-N,3-N-Dihydroxybenzene-1,3-disulfonamide

TABLE 2-continued

Additional N-Hydroxysulfonamide Donors with Desired Half-Lives (89)

3-Bromo-N-hydroxybenzene-1-sulfonamide (90)

5-Fluoro-N-hydroxy-2-methylbenzene-1-sulfonamide (91)

N-Hydroxy-3,5-dimethyl-1,2-oxazole-4-sulfonamide (92)

N-Hydroxy-3-(trifluoromethoxy)benzene-1-sulfonamide (93)

N-Hydroxy-4-methanesulfonylbenzene-1-sulfonamide

TABLE 2-continued

Additional N-Hydroxysulfonamide Donors with Desired Half-Lives

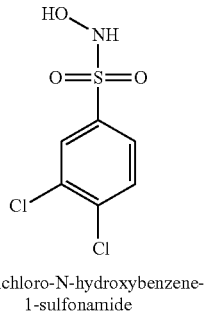

3,4-Dichloro-N-hydroxybenzene-
1-sulfonamide
(95)

In certain embodiments, the nitroxyl donors listed in Table 1 and Table 2 can be converted into a pharmaceutically acceptable salt thereof. Representative salts include, but are not limited, to oxalate, chloride, bromide, iodide, sulfate, citrate, acetate, trifluoroacetate, nitrate, bisulfate, phosphate, acid phosphate, isonicotinate, lactate, glutamate, salicylate, acid citrate, tartrate, oleate, tannate, pantothenate, bitartrate, ascorbate, succinate, maleate, gentisinate, fumarate, gluconate, glucoronate, saccharate, formate, benzoate, methanesulfonate, ethanesulfonate, benzenesulfonate, p-toluenesulfonate, and pamoate salts.

In some embodiments, the N-hydroxyl group of the compounds listed in Tables 1 and 2 can be esterified to produce compounds of the general formula (99), indicated below:

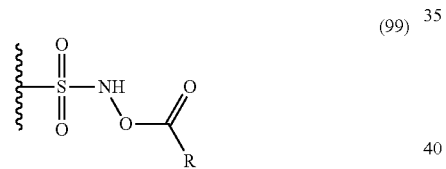
(99)

where ⦃ represents the aromatic, heteroaromatic or polycyclic portion of the compounds depicted in Tables 1 and 2—including the substituents(s) depicted in Tables 1 and 2, if any—and where R is hydrogen, —($C_1$-$C_6$)alkyl, —($C_2$-$C_4$)alkenyl, phenyl, benzyl, cyclopentyl, cyclohexyl, —($C_5$-$C_7$)heterocycloalkyl, benzyloxy, —O—($C_1$-$C_6$)alkyl, —$NH_2$, —NH—($C_1$-$C_4$)alkyl, or —N(($C_1$-$C_4$)alkyl)$_2$, wherein said —($C_1$-$C_6$)alkyl, —($C_2$-$C_4$)alkenyl, phenyl, benzyl, cyclopentyl, cyclohexyl, —($C_5$-$C_7$)heterocycloalkyl, benzyloxy, —O—($C_1$-$C_6$)alkyl, —NH—($C_1$-$C_4$)alkyl, or —N(($C_1$-$C_4$)alkyl)$_2$ can be unsubstituted or substituted with one or more substituents selected from halo, —($C_1$-$C_6$)alkyl, —($C_2$-$C_4$)alkenyl, —($C_2$-$C_3$)alkynyl, -(5- or 6-membered)heteroaryl, —O—($C_1$-$C_6$)alkyl, —S—($C_1$-$C_6$) alkyl, —C(halo)$_3$, —CH(halo)$_2$, —$CH_2$(halo), —CN, —$NO_2$, —$NH_2$, —NH—($C_1$-$C_4$)alkyl, —N(—($C_1$-$C_4$)alkyl)$_2$, —C(=O)($C_1$-$C_4$)alkyl, —C(=O)O($C_1$-$C_4$)alkyl, —OC(=O)($C_1$-$C_4$)alkyl, —OC(=O)$NH_2$, —S(=O)($C_1$-$C_4$)alkyl, or —S(=O)$_2$($C_1$-$C_4$)alkyl. In particular embodiments, R is methyl, ethyl, benzyl, or phenyl. In particular embodiments, R is methyl or ethyl. In particular embodiments, R is methyl. In particular embodiments, R is ethyl. In particular embodiments, R is benzyl or phenyl. In particular embodiments, R is benzyl. In particular embodiments, R is phenyl.

4.3 Measuring Nitroxyl Donating Ability

Compounds are easily tested for nitroxyl donation by routine experiments. Because it is typically impractical to directly measure whether nitroxyl is donated, several analytical approaches are accepted as suitable proxies for determining whether a compound donates nitroxyl. For example, the compound of interest can be placed in solution, for example in phosphate buffered saline (PBS) or in a phosphate buffered solution at a pH of about 7.4, in a sealed container. After sufficient time for disassociation has elapsed, such as from several minutes to several hours, the headspace gas is withdrawn and analyzed to determine its composition, such as by gas chromatography and/or mass spectrometry. If the gas $N_2O$ is formed (which occurs by HNO dimerization), the test is positive for nitroxyl donation and the compound is deemed to be a nitroxyl donor.

For compounds in which the N-hydroxyl group of a N-hydroxysulfonamide type nitroxyl donor is esterified, porcine liver esterase (PLE) can be added to the stock solution used to perform the headspace analysis.

If desired, nitroxyl donation also can be detected by exposing the test compound to metmyoglobin ($Mb^{3+}$). See Bazylinski et al., J. Amer. Chem. Soc. 107(26):7982-7986 (1985). Nitroxyl reacts with $Mb^{3+}$ to form a $Mb^{2+}$—NO complex, which can be detected by changes in the ultraviolet/visible spectrum or by electron paramagnetic resonance (EPR). The $Mb^{2+}$—NO complex has an EPR signal centered around a g-value of about 2. Nitric oxide, on the other hand, reacts with Mb' to form an $Mb^{3+}$—NO complex that has a negligible, if any, EPR signal. Accordingly, if a compound reacts with Mb' to form a complex detectable by common methods, such as ultraviolet/visible or EPR, then the test is positive for nitroxyl donation.

4.4 Pharmaceutical Compositions

The disclosure encompasses pharmaceutical compositions comprising a nitroxyl donor and at least one pharmaceutically acceptable excipient. Examples of pharmaceutically acceptable excipients include those described above, such as carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and any combination thereof. The selection and use of pharmaceutically acceptable excipients is taught, e.g., in Troy, Ed., Remington: The Science and Practice of Pharmacy, 21$^{st}$ Ed. (Lippincott Williams & Wilkins, Baltimore, Md., 2005).

The pharmaceutical compositions can be formulated for administration in solid or liquid form, including those adapted for the following: (1) oral administration, for example, as drenches (for example, aqueous or non-aqueous solutions or suspensions), tablets (for example, those targeted for buccal, sublingual and systemic absorption), caplets, boluses, powders, granules, pastes for application to the tongue, hard gelatin capsules, soft gelatin capsules, mouth sprays, troches, lozenges, pellets, syrups, suspensions, elixirs, liquids, emulsions and microemulsions; or (2) parenteral administration by, for example, subcutaneous, intramuscular, intravenous or epidural injection as, for example, a sterile solution or suspension. The pharmaceutical compositions can be for immediate, sustained or controlled release.

The compounds and pharmaceutical compositions disclosed herein can be prepared as any appropriate unit dosage form, such as capsules, sachets, tablets, powder, granules, solution, suspension in an aqueous liquid, suspension in a non-aqueous liquid, oil-in-water liquid emulsion, water-in-oil liquid emulsion, liposomes or bolus.

4.4.1 Compositions for Parenteral Administration

The disclosure provides nitroxyl donating compositions for parenteral (e.g., intravenous) administration. In one embodiment, the pharmaceutical composition is formulated for intravenous administration by continuous infusion.

Various embodiments of pharmaceutical compositions suitable for parenteral administration include, without limitation, either aqueous sterile injection solutions or non-aqueous sterile injection solutions, each containing, for example, anti-oxidants, buffers, bacteriostats and solutes that render the formulation isotonic with the blood of the intended recipient; and aqueous sterile suspensions and non-aqueous sterile suspensions, each containing, for example, suspending agents and thickening agents. The formulations can be presented in unit-dose or multi-dose containers, for example, sealed ampules or vials, and can be stored in a freeze dried (lyophilized) condition requiring only the addition of a sterile liquid carrier, such as water, immediately prior to use. Alternately, the formulation can be in the form of a liquid.

Pharmaceutical compositions administered parenterally can be administered in an acidic, neutral or basic solution. In one embodiment, pharmaceutical compositions comprising a nitroxyl donor can be formulated in an acidic solution having a pH of from about 4 to about 5, for instance, a pH of about 4, about 4.5, about 4.8, or about 5, including values there between. While a pH of about 4 has generally been considered optimal for formulating N-hydroxysulfonamide type nitroxyl donors in order to achieve adequate stability of the donor, it has been discovered that formulating under such acidic conditions can potentially cause or exacerbate venous irritation following parenteral administration. The amount of irritation can be attenuated by formulating the N-hydroxysulfonamide type nitroxyl donors in a less acidic medium (see Example 6 and FIG. 4).

Accordingly, in certain embodiments, a N-hydroxysulfonamide type nitroxyl donor useful in a pharmaceutical composition of the disclosure is formulated for parenteral injection at a pH of from about 5 to about 6.5 in some embodiments, from about 5 to about 6 in some embodiments, from about 5.5 to about 6 in some embodiments, from about 5 to about 5.5 in some embodiments, from about 5.2 to about 6.2 in some embodiments, from about 5.5 to about 6.2 in some embodiments, from about 5.8 to about 6.2 in some embodiments, and at a pH of about 6 in particular embodiments. In another embodiment, a N-hydroxysulfonamide type nitroxyl donor useful in a pharmaceutical composition of the disclosure is formulated for parenteral injection at a pH of about 5.

To achieve the desired pH of the pharmaceutical composition, a N-hydroxysulfonamide type nitroxyl donor can be formulated in an aqueous buffer. For example, a N-hydroxysulfonamide type nitroxyl donor can be formulated in a phosphate or acetate buffer. In particular embodiments, a N-hydroxysulfonamide type nitroxyl donor is formulated in a potassium phosphate or sodium phosphate buffer. In other embodiments, a N-hydroxysulfonamide type nitroxyl donor is formulated in a potassium phosphate buffer or sodium phosphate buffer. In other embodiments, a N-hydroxysulfonamide type nitroxyl donor is formulated in a potassium citrate buffer or sodium citrate buffer.

The aqueous buffer can also include an appropriate sugar in order to maintain an appropriate osmolality. For instance, the pharmaceutical composition can include an appropriate amount of dextrose. The pharmaceutical compositions exemplified in the Examples of the disclosure were generally prepared by diluting a concentrate comprising a N-hydroxysulfonamide type nitroxyl donor, optionally a cyclodextrin (see Section 4.4.3) and an appropriate buffer into an aqueous solution comprising 5% dextrose (D5W) or 2.5% dextrose (D2.5W).

4.4.2 Compositions for Oral Administration

Pharmaceutical compositions comprising N-hydroxysulfonamide type nitroxyl donors can be formulated for oral administration. Compounds for oral administration can be formulated as liquid or solid dosage forms. In particular embodiments where the nitroxyl donors are formulated as oral liquid dosage forms, polyethylene glycol 300 (PEG300) can usefully serve as an excipient.

Tablets for oral administration can be made by compression or molding, optionally with one or more accessory ingredients. Compressed tablets can be prepared by compressing in a suitable machine the therapeutic agent or agents in a free-flowing form such as a powder or granules, optionally mixed with a binder, lubricant, inert diluent, preservative, surface-active or dispersing agent. Molded tablets can be made by molding in a suitable machine a mixture of the powdered compound moistened with an inert liquid diluent. The tablets can be optionally coated or scored and can be formulated so as to provide slow or controlled release of the active ingredient therein. Methods of formulating such slow or controlled release compositions of pharmaceutically active ingredients, such as the therapeutic agents herein and other compounds known in the art, are known in the art and disclosed in issued U.S. patents, some of which include, but are not limited to, U.S. Pat. Nos. 4,369,174, 4,842,866, and the references cited therein. Coatings can be used for delivery of compounds to the intestine (see, e.g., U.S. Pat. Nos. 6,638,534, 5,217,720, 6,569,457, and the references cited therein). An artisan will recognize that in addition to tablets, other dosage forms can be formulated to provide slow or controlled release of the active ingredient. Such dosage forms include, but are not limited to, capsules, granulations and gel-caps.

4.4.3 Stabilizing and Solubility Enhancing Agents

It has been discovered that N-hydroxysulfonamide type nitroxyl donors can suffer from stability problems when formulated for parenteral and oral administration. In particular, the N-hydroxysulfonamide type nitroxyl donors gradually release nitroxyl and at least one byproduct in the pharmaceutical composition, which can compromise the efficacy and safety of the composition. For instance, compounds of formula (1) and formula (2) release nitroxyl and sulfinic acid byproducts (respectively, compounds of formula (100) and formula (101)) according to the following schemes.

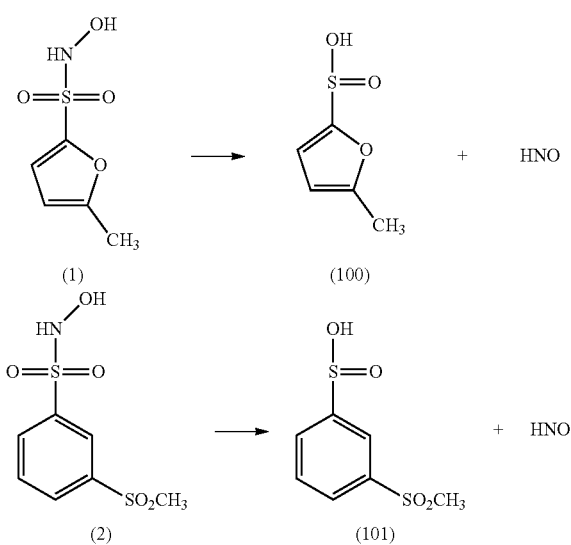

Moreover, N-hydroxysulfonamide type nitroxyl donors can also have solubility problems that limit or preclude their use in an oral or parenteral dosage form. Accordingly, increasing the stability and solubility of N-hydroxysulfonamide type nitroxyl donors can be important before the donors can be used in therapeutic applications.

In accordance with one aspect of the disclosure, it has been found that cyclodextrins can be used to dramatically enhance the stability and/or solubility of N-hydroxysulfonamide type nitroxyl donors. Specifically, the cyclodextrins can mitigate or eliminate the formation of nitroxyl and sulfinic acid byproducts (e.g., compounds of formula (100) and (101)) in a pharmaceutical composition during storage prior to administration to a patient. The presence of the cyclodextrin also allows some of the N-hydroxysulfonamide type nitroxyl donors to be stabilized at a higher pH (e.g. pH of between 5 and 6), which, for reasons discussed in Section 4.4.2, results in the production of a composition with an improved toxicological profile.

In various embodiments, the at least one pharmaceutically acceptable excipient comprises at least one species of cyclodextrin. In a particular embodiment, the cyclodextrin is a cyclic structure having glucose units linked by α(1-4) linkages. In another embodiment, the cyclodextrin is a β-cyclodextrin, i.e., a cyclic structure having seven glucose units linked by α(1-4) linkages. In another embodiment, the cyclodextrin is chemically modified by derivatizing any combination of the three available hydroxyl groups on each glucopyranose unit thereof.

In some embodiments where the pharmaceutically acceptable excipient comprises at least one species of cyclodextrin, the cyclodextrin is a sulfo($C_1$-$C_6$)alkyl ether derivative of 3-cyclodextrin. In certain of these embodiments, the cyclodextrin is a sulfo($C_1$-$C_6$)alkyl ether derivative of β-cyclodextrin having from about six to about seven sulfo($C_1$-$C_6$) alkyl ether groups per cyclodextrin molecule. In various embodiments, the cyclodextrin is a sulfo($C_1$-$C_6$)alkyl ether derivative of β-cyclodextrin having an average of from about six to about seven sulfo($C_1$-$C_6$)alkyl ether groups per cyclodextrin molecule. In another such embodiment, the cyclodextrin is a sulfo($C_1$-$C_6$)alkyl ether derivative of β-cyclodextrin having six or seven sulfo($C_1$-$C_6$)alkyl ether groups per cyclodextrin molecule.

In a particular series of embodiments where the pharmaceutically acceptable excipient comprises at least one species of cyclodextrin, the cyclodextrin is a sulfo($C_3$-$C_5$)alkyl ether derivative of β-cyclodextrin. In one such embodiment, the cyclodextrin is a sulfo($C_3$-$C_5$)alkyl ether derivative of β-cyclodextrin having from about six to about seven sulfo($C_3$-$C_5$)alkyl ether groups per cyclodextrin molecule. In various such embodiments, the cyclodextrin is a sulfo($C_3$-$C_5$)alkyl ether derivative of β-cyclodextrin having an average of from about six to about seven sulfo($C_3$-$C_5$)alkyl ether groups per cyclodextrin molecule. In another such embodiment, the cyclodextrin is a sulfo($C_3$-$C_5$)alkyl ether derivative of β-cyclodextrin having six or seven sulfo($C_3$-$C_5$)alkyl ether groups per cyclodextrin molecule.

In particular embodiments where the pharmaceutically acceptable excipient comprises at least one species of cyclodextrin, the cyclodextrin is a sulfobutyl ether derivative of 3-cyclodextrin. In certain of these embodiments, the cyclodextrin is a sulfobutyl ether derivative of β-cyclodextrin having from about six to about seven sulfobutyl ether groups per cyclodextrin molecule. In another such embodiment, the cyclodextrin is a sulfobutyl ether derivative of β-cyclodextrin having an average of from about six to about seven sulfobutyl ether groups per cyclodextrin molecule. In another such embodiment, the cyclodextrin is a sulfobutyl ether derivative of β-cyclodextrin having six or seven sulfobutyl ether groups per cyclodextrin molecule.

In certain embodiments where the pharmaceutically acceptable excipient comprises at least one species of cyclodextrin, the cyclodextrin is a sulfo-n-butyl ether derivative of 3-cyclodextrin. In one such embodiment, the cyclodextrin is a sulfo-n-butyl ether derivative of 3-cyclodextrin having from about six to about seven sulfo-n-butyl ether groups per cyclodextrin molecule. In another such embodiment, the cyclodextrin is a sulfo-n-butyl ether derivative of β-cyclodextrin having an average of from about six to about seven sulfo-n-butyl ether groups per cyclodextrin molecule. In another such embodiment, the cyclodextrin is a sulfo-n-butyl ether derivative of β-cyclodextrin having six or seven sulfo-n-butyl ether groups per cyclodextrin molecule.

In various particular embodiments where the pharmaceutically acceptable excipient comprises at least one species of cyclodextrin, the cyclodextrin comprises a plurality of negative charges at physiologically compatible pH values, e.g., at a pH of from about 5.0 to about 6.8 in some embodiments, from about 5.5 to about 6.5 in some embodiments, from about 5.7 to about 6.3 in some embodiments, from about 5.8 to about 6.2 in some embodiments, from about 5.9 to about 6.1 in some embodiments, and about 6.0 in particular embodiments. In one such embodiment, the at least one pharmaceutically acceptable excipient comprises CAPTISOL® cyclodextrin (Ligand Pharmaceuticals, La Jolla, Calif.).

The molar ratio between the N-hydroxysulfonamide type nitroxyl donor and the cyclodextrin present in the composition can be from about 0.02:1 to about 2:1. In certain embodiments, the molar ratio between the N-hydroxysulfonamide type nitroxyl donor and the cyclodextrin present in the composition can be from about 0.05:1 to about 1.5:1. In certain embodiments, the molar ratio between the N-hydroxysulfonamide type nitroxyl donor and the cyclodextrin present in the composition can be from about 0.1:1 to about 1:1. In certain embodiments, the molar ratio between the N-hydroxysulfonamide type nitroxyl donor and the cyclodextrin present in the composition can be from about 0.5:1 to about 1:1. In certain embodiments, the molar ratio between the N-hydroxysulfonamide type nitroxyl donor and the cyclodextrin present in the composition can be in from about 0.7:1 to about 1:1. In certain embodiments, the molar ratio between the N-hydroxysulfonamide type nitroxyl donor and the cyclodextrin present in the composition can be from about 0.1:1 to about 0.8:1. In certain embodiments, the molar ratio between the N-hydroxysulfonamide type nitroxyl donor and the cyclodextrin present in the composition can be from about 0.1:1 to about 0.6:1. In certain embodiments, the molar ratio between the N-hydroxysulfonamide type nitroxyl donor and the cyclodextrin present in the composition can be from about 0.2:1 to about 1:1. In certain embodiments, the molar ratio between the N-hydroxysulfonamide type nitroxyl donor and the cyclodextrin present in the composition can be from about 0.2:1 to about 0.8:1. In certain embodiments, the molar ratio between the N-hydroxysulfonamide type nitroxyl donor and the cyclodextrin present in the composition can be from about 0.4:1 to about 0.8:1. In certain embodiments, the molar ratio between the N-hydroxysulfonamide type nitroxyl donor and the cyclodextrin present in the composition can be from about 0.4:1 to about 0.6:1. In particular embodiments, the cyclodextrin is CAPTISOL®. For the purposes of calculating molar amounts, it will be assumed that CAPTISOL® has an average molecular weight (MW) of 2163 g/mol.

In embodiments where a N-hydroxysulfonamide type nitroxyl donor is administered parenterally (e.g., intravenously) as an aqueous composition, the cyclodextrin can be present in the composition within the range of from about 0.001% cyclodextrin (w/v) to about 10% cyclodextrin (w/v). In some embodiments, the cyclodextrin can be present in the composition within the range of from about 0.005% cyclodextrin (w/v) to about 8% cyclodextrin (w/v). In certain embodiments, the cyclodextrin can be present in the composition within the range of from about 0.010% cyclodextrin (w/v) to about 6% cyclodextrin (w/v). In certain embodiments, the cyclodextrin can be present in the composition within the range of from about 0.5% cyclodextrin (w/v) to about 8% cyclodextrin (w/v). In certain embodiments, the cyclodextrin can be present in the composition within the range of from about 1% cyclodextrin (w/v) to about 8% cyclodextrin (w/v). In certain embodiments, the cyclodextrin can be present in the composition within the range of from about 2% cyclodextrin (w/v) to about 8% cyclodextrin (w/v). In certain embodiments, the cyclodextrin can be present in the composition within the range of from about 2% cyclodextrin (w/v) to about 6% cyclodextrin (w/v). In particular embodiments, the cyclodextrin is CAPTISOL®.

As described in Example 7, compositions comprising a nitroxyl donor and a cyclodextrin can be prepared as a concentrate at a particular pH. Such a concentrate can be prepared by adding the nitroxyl donor to an aqueous solution of the cyclodextrin at a particular pH (e.g., pH of 4). The concentrate can then be diluted into an appropriate aqueous solution (e.g., buffer) and administered to a patient. Alternatively, the concentrate comprising the nitroxyl donor and the cyclodextrin can be lyophilized to form a powder. The lyophilized powder can be reconstituted in the appropriate aqueous vehicle prior to administration.

4.5 Methods of Using the Compounds and Pharmaceutical Compositions of the Disclosure In one aspect, the disclosure provides a method of increasing in vivo nitroxyl levels, comprising administering to a patient in need thereof an effective amount of a compound or a pharmaceutical composition as disclosed herein. In various embodiments, the patient has, is suspected of having, or is at risk of having or developing a condition that is responsive to nitroxyl therapy.

In particular embodiments, the disclosure provides a method of treating, preventing or delaying the onset and/or development of a condition, comprising administering to a patient (including a patient identified as in need of such treatment, prevention or delay) an effective amount of a compound or a pharmaceutical composition as disclosed herein. Identifying a patient in need thereof can be in the judgment of a physician, clinical staff, emergency response personnel or other health care professional and can be subjective (e.g., opinion) or objective (e.g., measurable by a test or diagnostic method).

Particular conditions embraced by the methods disclosed herein include, without limitation, cardiovascular diseases, ischemia/reperfusion injury, and pulmonary hypertension (PH).

4.5.1 Cardiovascular Diseases

In one embodiment, the disclosure provides a method of treating a cardiovascular disease, comprising administering an effective amount of a compound or a pharmaceutical composition as disclosed herein to a patient in need thereof.

Examples of cardiovascular diseases and symptoms that can usefully be treated with the compounds and compositions disclosed herein include cardiovascular diseases that are responsive to nitroxyl therapy, coronary obstructions, coronary artery disease (CAD), angina, heart attack, myocardial infarction, high blood pressure, ischemic cardiomyopathy and infarction, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, diastolic heart failure, systolic heart failure, congestive heart failure, acute congestive heart failure, acute decompensated heart failure, and cardiac hypertrophy.

4.5.1.1 Heart Failure

The nitroxyl donating compositions of the disclosure can be used to treat patients suffering from heart failure. The heart failure can be of any type or form, including any of the heart failures disclosed herein. Nonlimiting examples of heart failure include early stage heart failure, Class I, II, III and IV heart failure, acute heart failure, congestive heart failure (CHF) and acute congestive heart failure. In one embodiment, the compounds and compositions of the disclosure can be used to treat acute decompensated heart failure.

In embodiments where the nitroxyl donating compositions of the disclosure are used to treat patients suffering from heart failure, another active agent that treats heart failure can also be administered. In one such embodiment, the nitroxyl donor can be administered in conjunction with a positive inotrope such as a beta-agonist. Examples of beta-agonists include, without limitation, dopamine, dobutamine, isoproterenol, analogs of such compounds and derivatives of such compounds. In another embodiment, nitroxyl donor can be administered in conjunction with a beta-adrenergic receptor antagonist (also referred to herein as beta-antagonist or beta-blocker). Examples of beta-antagonists include, without limitation, propranolol, metoprolol, bisoprolol, bucindolol, and carvedilol.

As described in Example 3, a heart failure model was used to evaluate the hemodynamic profiles of compositions comprising several of the longer half-life nitroxyl donors. As shown in FIG. 1, which are discussed in Example 3, the compositions of the disclosure produced significant enhancement of inotropy and lusitropy, and modest reductions in blood pressure without tachycardia. Moreover, the onset of significant hemodynamic effects was rapid (e.g., within 1 hour) and for all compositions near-maximal effect was achieved within 2 hours.

While the hemodynamic activity of compositions of the disclosure are similar to compositions comprising the nitroxyl donor CXL-1020 when administered intravenously, the toxicological profile of the N-hydroxysulfonamide type nitroxyl donors, which have longer half-lives than CXL-1020, is significantly improved as compared to compositions comprising CXL-1020 (see Examples 5 and 6 and FIGS. 2-4). For example, the "No Observed Adverse Effect Levels" (NOAEL) of nitroxyl donors useful in compositions of the disclosure were substantially higher than the NOAEL for CXL-1020 (see Example 5 for description of NOAEL determination). In particular, the compound of formula (1) has the most favorable toxicological profile of all N-hydroxysulfonamide type nitroxyl donors tested thus far and shows no adverse effects on clinical markers of inflammation when administered intravenously at concentrations at least as high as 30 µg/kg/min (FIG. 2). In contrast, CXL-1020 begins to show undesirable side effects at concentrations as low as 0.3 µg/kg/min.

4.5.1.2 Ischemia/Reperfusion Injury

In another embodiment, the disclosed subject matter provides a method of treating, preventing or delaying the onset and/or development of ischemia/reperfusion injury, comprising administering an effective amount of a compound or pharmaceutical composition as disclosed herein to a subject in need thereof.

In a particular embodiment, the method is for preventing ischemia/reperfusion injury. In a particular embodiment, a pharmaceutical composition of the disclosure is administered prior to the onset of ischemia. In a particular embodiment, a pharmaceutical composition of the disclosure is administered prior to procedures in which myocardial ischemia can occur, for example an angioplasty or surgery, such as a coronary artery bypass graft surgery. In a particular embodiment, a pharmaceutical composition of the disclosure is administered after ischemia but before reperfusion. In a particular embodiment, a pharmaceutical composition of the disclosure is administered after ischemia and reperfusion.

In a another embodiment, a pharmaceutical composition of the disclosure can be administered to a patient who is at risk for an ischemic event. In a particular embodiment, a pharmaceutical composition of the disclosure is administered to a patient at risk for a future ischemic event, but who has no present evidence of ischemia. The determination of whether a patient is at risk for an ischemic event can be performed by any method known in the art, such as by examining the patient or the patient's medical history. In a particular embodiment, the patient has had a prior ischemic event. Thus, the patient can be at risk of a first or subsequent ischemic event. Examples of patients at risk for an ischemic event include patients with known hypercholesterolemia, EKG changes associated with ischemia (e.g., peaked or inverted T-waves or ST segment elevations or depression in an appropriate clinical context), abnormal EKG not associated with active ischemia, elevated CKMB, clinical evidence of ischemia (e.g., crushing sub-sternal chest pain or arm pain, shortness of breath and/or diaphoresis), prior history of myocardial infarction, elevated serum cholesterol, sedentary lifestyle, angiographic evidence of partial coronary artery obstruction, echocardiographic evidence of myocardial damage, or any other evidence of a risk for a future ischemic event. Examples of ischemic events include, without limitation, myocardial infarction (MI) and neurovascular ischemia, such as a cerebrovascular accident (CVA).

In another embodiment, the subject of treatment is an organ that is to be transplanted. In a particular embodiment, a pharmaceutical composition of the disclosure can be administered prior to reperfusion of the organ in a transplant recipient. In a particular embodiment, a pharmaceutical composition of the disclosure can be administered prior to removal of the organ from the donor, for example through the perfusion cannulas used in the organ removal process. If the organ donor is a live donor, for example a kidney donor, the compounds or pharmaceutical compositions of the disclosure can be administered to the organ donor. In a particular embodiment, the compounds or pharmaceutical compositions of the disclosure are administered by storing the organ in a solution comprising the compound or pharmaceutical composition. For example, a compound or pharmaceutical composition of the disclosure can be included in the organ preservation solution, such as the University of Wisconsin "UW" solution, which is a solution comprising hydroxyethyl starch substantially free of ethylene glycol, ethylene chlorohydrin and acetone (see U.S. Pat. No. 4,798,824). In a particular embodiment, a pharmaceutical composition of the disclosure that is administered is such that ischemia/reperfusion injury to the tissues of the organ is reduced upon reperfusion in the recipient of transplanted organ. In a particular embodiment, the method reduces tissue necrosis (the size of infarct) in at-risk tissues.

Ischemia/reperfusion injury can damage tissues other than those of the myocardium and the disclosed subject matter embraces methods of treating or preventing such damage. In various embodiments, the ischemia/reperfusion injury is non-myocardial. In particular embodiments, the method reduces injury from ischemia/reperfusion in the tissue of the brain, liver, gut, kidney, bowel, or any part of the body other than the myocardium. In another embodiment, the patient is at risk for such injury. Selecting a person at risk for non-myocardial ischemia could include a determination of the indicators used to assess risk for myocardial ischemia. However, other factors can indicate a risk for ischemia/reperfusion in other tissues. For example, surgery patients often experience surgery related ischemia. Thus, patients scheduled for surgery could be considered at risk for an ischemic event. The following risk factors for stroke (or a subset of these risk factors) could demonstrate a patient's risk for ischemia of brain tissue: hypertension, cigarette smoking, carotid artery stenosis, physical inactivity, diabetes mellitus, hyperlipidemia, transient ischemic attack, atrial fibrillation, coronary artery disease, congestive heart failure, past myocardial infarction, left ventricular dysfunction with mural thrombus, and mitral stenosis. Ingall, Postgrad. Med. 107(6):34-50 (2000). Further, complications of untreated infectious diarrhea in the elderly can include myocardial, renal, cerebrovascular and intestinal ischemia. Slotwiner-Nie et al., Gastroenterol. Clin. N. Amer. 30(3):625-635 (2001). Alternatively, patients could be selected based on risk factors for ischemic bowel, kidney and/or liver disease. For example, treatment would be initiated in elderly patients at risk of hypotensive episodes (such as surgical blood loss). Thus, patients presenting with such an indication would be considered at risk for an ischemic event. In another embodiment, the patient has any one or more of the conditions listed herein, such as diabetes mellitus and hypertension. Other conditions that can result in ischemia, such as cerebral arteriovenous malformation, could demonstrate a patient's risk for an ischemic event.

4.5.2 Pulmonary Hypertension

In another embodiment, a pharmaceutical composition of the disclosure can be used to prevent or delay the onset and/or development of pulmonary hypertension. In one such embodiment, a pharmaceutical composition of the disclosure can be used to prevent or delay the onset and/or development of pulmonary arterial hypertension (PAH).

In another embodiment, the disclosure provides a method of reducing mean pulmonary arterial pressure (MPAP), comprising administering an effective amount of a compound or a pharmaceutical composition disclosed herein to a patient in need thereof. In another embodiment, the MPAP is reduced by up to about 50%. In another embodiment, the MPAP is reduced by up to about 25%. In another embodiment, the MPAP is reduced by up to about 20%. In another embodiment, the MPAP is reduced by up to about 15%. In another embodiment, the MPAP is reduced by up to about 10%. In another embodiment, the MPAP is reduced by up to about 5%. In another embodiment, the MPAP is reduced to be from about 12 mmHg to about 16 mmHg. In another embodiment, the MPAP is reduced to be about 15 mmHg.

4.6 Administration Modes, Regimens and Dose Levels

The compounds and pharmaceutical compositions of the disclosure can be administered via parenteral (e.g., subcutaneous, intramuscular, intravenous or intradermal) administration. In certain embodiments, the N-hydroxysulfonamide type nitroxyl donor useful in a pharmaceutical composition of the disclosure is administered by intravenous infusion. In other embodiments, the compounds and pharmaceutical compositions of the disclosure can be administered by oral administration.

When a pharmaceutical composition comprising a compound of the present disclosure is administered, dosages are expressed based on the amount of active pharmaceutical ingredient, i.e., the amount of nitroxyl donor compound(s) of the disclosure present in the pharmaceutical composition.

For intravenous administration, the dose can usefully be expressed per unit time, either as a fixed amount per unit time or as a weight-based amount per unit time.

In various embodiments, a N-hydroxysulfonamide type nitroxyl donor useful in a pharmaceutical composition of the disclosure is administered intravenously in an amount of at least about 0.1 µg/kg/min, at least about 0.2 µg/kg/min, at least about 0.3 µg/kg/min, at least about 0.4 µg/kg/min, at least about 0.5 µg/kg/min, at least about 1 µg/kg/min, at least about 2.5 µg/kg/min, at least about 5 µg/kg/min, at least about 7.5 µg/kg/min, at least about 10 µg/kg/min, at least about 11 µg/kg/min, at least about 12 µg/kg/min, at least about 13 µg/kg/min, at least about 14 µg/kg/min, at least about 15 µg/kg/min, at least about 16 µg/kg/min, at least about 17 µg/kg/min, at least about 18 µg/kg/min, at least about 19 µg/kg/min, at least about 20 µg/kg/min, at least about 21 µg/kg/min, at least about 22 µg/kg/min, at least about 23 µg/kg/min, at least about 24 µg/kg/min, at least about 25 µg/kg/min, at least about 26 µg/kg/min, at least about 27 µg/kg/min, at least about 28 µg/kg/min, at least about 29 µg/kg/min, at least about 30 µg/kg/min, at least about 31 µg/kg/min, at least about 32 µg/kg/min, at least about 33 µg/kg/min, at least about 34 µg/kg/min, at least about 35 µg/kg/min, at least about 36 µg/kg/min, at least about 37 µg/kg/min, at least about 38 µg/kg/min, at least about 39 µg/kg/min, or at least about 40 µg/kg/min.

In various embodiments, the N-hydroxysulfonamide type nitroxyl donor useful in a pharmaceutical composition of the disclosure is administered intravenously in an amount of no more than about 100 µg/kg/min, no more than about 90 µg/kg/min, no more than about 80 µg/kg/min, no more than about 70 µg/kg/min, no more than about 60 µg/kg/min, no more than about 50 µg/kg/min, no more than about 49 µg/kg/min, no more than about 48 µg/kg/min, no more than about 47 µg/kg/min, no more than about 46 µg/kg/min, no more than about 45 µg/kg/min, no more than about 44 µg/kg/min, no more than about 43 µg/kg/min, no more than about 42 µg/kg/min, no more than about 41 µg/kg/min, no more than about 40 µg/kg/min, no more than about 39 µg/kg/min, no more than about 38 µg/kg/min, no more than about 37 µg/kg/min, no more than about 36 µg/kg/min, no more than about 35 µg/kg/min, no more than about 34 µg/kg/min, no more than about 33 µg/kg/min, no more than about 32 µg/kg/min, no more than about 31 µg/kg/min, or no more than about 30 µg/kg/min In some embodiments, the N-hydroxysulfonamide type nitroxyl donor useful in a pharmaceutical composition of the disclosure is administered intravenously in an amount ranging from about 0.1 µg/kg/min to about 100 µg/kg/min, about 1 µg/kg/min to about 100 µg/kg/min, about 2.5 µg/kg/min to about 100 µg/kg/min, about 5 µg/kg/min to about 100 µg/kg/min, about 10 µg/kg/min to about 100 µg/kg/min, about 1.0 µg/kg/min to about 80 µg/kg/min, from about 10.0 µg/kg/min to about 70 µg/kg/min, from about 20 µg/kg/min to about 60 µg/kg/min, from about 15 µg/kg/min to about 50 µg/kg/min, from about 0.01 µg/kg/min to about 1.0 µg/kg/min, from about 0.01 µg/kg/min to about 10 µg/kg/min, from about 0.1 µg/kg/min to about 1.0 µg/kg/min, from about 0.1 µg/kg/min to about 10 µg/kg/min, from about 1.0 µg/kg/min to about 5 µg/kg/min, from about 70 µg/kg/min to about 100 µg/kg/min, or from about 80 µg/kg/min to about 90 µg/kg/min.

In particular embodiments, the N-hydroxysulfonamide type nitroxyl donor useful in a pharmaceutical composition of the disclosure is administered intravenously in an amount ranging from about 10 µg/kg/min to about 50 µg/kg/min, about 20 µg/kg/min to about 40 µg/kg/min, about 25 µg/kg/min to about 35 µg/kg/min, or about 30 µg/kg/min to about 40 µg/kg/min. In particular embodiments, a N-hydroxysulfonamide type nitroxyl donor useful in a pharmaceutical composition of the disclosure is administered intravenously in an amount of from about 20 µg/kg/min to about 30 µg/kg/min.

In a variety of embodiments, including various oral administration embodiments, the compounds or pharmaceutical compositions of the disclosure are administered according to a weight-based daily dosing regimen, either as a single daily dose (QD) or in multiple divided doses administered, e.g., twice a day (BID), three times a day (TID), or four times a day (QID).

In certain embodiments, the nitroxyl donating N-hydroxysulfonamide type nitroxyl donor useful in a pharmaceutical composition of the disclosure is administered in a dose of at least about 0.5 mg/kg/d, at least about 0.75 mg/kg/d, at least about 1.0 mg/kg/d, at least about 1.5 mg/kg/d, at least about 2 mg/kg/d, at least about 2.5 mg/kg/d, at least about 3 mg/kg/d, at least about 4 mg/kg/d, at least about 5 mg/kg/d, at least about 7.5 mg/kg/d, at least about 10 mg/kg/d, at least about 12.5 mg/kg/d, at least about 15 mg/kg/d, at least about 17.5 mg/kg/d, at least about 20 mg/kg/d, at least about 25 mg/kg/d, at least about 30 mg/kg/d, at least about 35 mg/kg/d, at least about 40 mg/kg/d, at least about 45 mg/kg/d, at least about 50 mg/kg/d, at least about 60 mg/kg/d, at least about 70 mg/kg/d, at least about 80 mg/kg/d, at least about 90 mg/kg/d, or at least about 100 mg/kg/d.

In certain embodiments, the nitroxyl donating N-hydroxysulfonamide type nitroxyl donor useful in a pharmaceutical composition of the disclosure is administered at a dose of no more than about 100 mg/kg/d, no more than about 100 mg/kg/d, no more than about 90 mg/kg/d, no more than about 80 mg/kg/d, no more than about 80 mg/kg/d, no more than about 75 mg/kg/d, no more than about 70 mg/kg/d, no more than about 60 mg/kg/d, no more than about 50 mg/kg/d, no more than about 45 mg/kg/d, no more than about 40 mg/kg/d, no more than about 35 mg/kg/d, no more than about 30 mg/kg/d.

In a variety of embodiments, the dose is from about 0.001 mg/kg/d to about 10,000 mg/kg/d. In certain embodiments, the dose is from about 0.01 mg/kg/d to about 1,000 mg/kg/d. In certain embodiments, the dose is from about 0.01 mg/kg/d to about 100 mg/kg/d. In certain embodiments, the dose is from about 0.01 mg/kg/d to about 10 mg/kg/d. In certain embodiments, the dose is from about 0.1 mg/kg/d to about 1 mg/kg/d. In certain embodiments, the dose is less than about 1 g/kg/d.

In certain embodiments, a N-hydroxysulfonamide type nitroxyl donor useful in a pharmaceutical composition of the disclosure is administered in a dose range in which the low end of the range is any amount from about 0.1 mg/kg/day to about 90 mg/kg/day and the high end of the range is any amount from about 1 mg/kg/day to about 100 mg/kg/day (e.g., from about 0.5 mg/kg/day to about 2 mg/kg/day in one series of embodiments and from about 5 mg/kg/day to about 20 mg/kg/day in another series of embodiment).

In particular embodiments, the N-hydroxysulfonamide type nitroxyl donor useful in a pharmaceutical composition of the disclosure is administered in a dose range of about 3 to about 30 mg/kg, administered from once a day (QD) to three times a day (TID).

In certain embodiments, compounds or pharmaceutical compositions of the disclosure are administered according to a flat (i.e., non-weight-based) dosing regimen, either as a single daily dose (QD) or in multiple divided doses administered, e.g., twice a day (BID), three times a day (TID), or four times a day (QID).

In various embodiments, the N-hydroxysulfonamide type nitroxyl donor useful in a pharmaceutical composition of the disclosure is administered at a dose of at least about 0.01 grams/day (g/d), at least about 0.05 g/d, at least about 0.1 g/d, at least about 0.5 g/d, at least about 1 g/d, at least about 1.5 g/d, at least about 2.0 g/d, at least about 2.5 g/d, at least about 3.0 g/d, or at least about 3.5 g/d.

In various embodiments, the N-hydroxysulfonamide type nitroxyl donor useful in a pharmaceutical composition of the disclosure is administered at a dose of no more than about 5 g/d, no more than about 4.5 g/d, no more than about 4 g/d, no more than about 3.5 g/d, no more than about 3 g/d, no more than about 2.5 g/d, or no more than about 2 g/d.

In certain embodiments, the N-hydroxysulfonamide type nitroxyl donor useful in a pharmaceutical composition of the disclosure is administered in a dose of about 0.01 grams per day to about 4.0 grams per day. In certain embodiments, a N-hydroxysulfonamide type nitroxyl donor useful in a pharmaceutical composition of the disclosure can be administered at a dose in which the low end of the range is any amount from about 0.1 mg/day to about 400 mg/day and the high end of the range is any amount from about 1 mg/day to about 4000 mg/day. In certain embodiments, the N-hydroxysulfonamide type nitroxyl donor useful in a pharmaceutical composition of the disclosure is administered in a dose of about 5 mg/day to about 100 mg/day. In various embodiments, the N-hydroxysulfonamide type nitroxyl donor useful in a pharmaceutical composition of the disclosure is administered at a dose of from about 150 mg/day to about 500 mg/day.

The dosing interval for parenteral or oral administration can be adjusted according to the needs of the patient. For longer intervals between administrations, extended release or depot formulations can be used.

A N-hydroxysulfonamide type nitroxyl donor useful in a pharmaceutical composition of the disclosure as disclosed herein can be administered prior to, at substantially the same time with, or after administration of an additional therapeutic agent. The administration regimen can include pretreatment and/or co-administration with the additional therapeutic agent. In such case, the N-hydroxysulfonamide type nitroxyl donor useful in a pharmaceutical composition of the disclosure and the additional therapeutic agent can be administered simultaneously, separately, or sequentially.

Examples of administration regimens include without limitation: administration of each compound, pharmaceutical composition or therapeutic agent in a sequential manner; and co-administration of each compound, pharmaceutical composition or therapeutic agent in a substantially simultaneous manner (e.g., as in a single unit dosage form) or in multiple, separate unit dosage forms for each compound, pharmaceutical composition or therapeutic agent.

It will be appreciated by those in the art that the "effective amount" or "dose" ("dose level") will depend on various factors such as the particular administration mode, administration regimen, compound, and pharmaceutical composition selected, as well as the particular condition and patient being treated. For example, the appropriate dose level can vary depending upon the activity, rate of excretion and potential for toxicity of the specific N-hydroxysulfonamide type nitroxyl donor useful in a pharmaceutical composition of the disclosure employed; the age, body weight, general health, gender and diet of the patient being treated; the frequency of administration; the other therapeutic agent(s) being co-administered; and the type and severity of the condition.

4.7 Kits Comprising the Compounds or Pharmaceutical Compositions

The disclosure provides kits comprising a compound or a pharmaceutical composition disclosed herein. In a particular embodiment, the kit comprises a compound or a pharmaceutical composition disclosed herein, each in dry form, and a pharmaceutically acceptable liquid diluent.

Either a compound in dry form or a pharmaceutical composition in dry form contains about 2.0% or less water by weight, about 1.5% or less water by weight, about 1.0% or less water by weight, about 0.5% or less water by weight, about 0.3% or less water by weight, about 0.2% or less water by weight, about 0.1% or less water by weight, about 0.05% or less water by weight, about 0.03% or less water by weight, or about 0.01% or less water by weight.

Pharmaceutically acceptable liquid diluents are known in the art and include but are not limited to sterile water, saline solutions, aqueous dextrose, glycerol, glycerol solutions, and the like. Other examples of suitable liquid diluents are disclosed by Nairn, "Solutions, Emulsions, Suspensions and Extracts," pp. 721-752 in Gennaro, Ed., *Remington: The Science and Practice of Pharmacy,* 20th Ed. (Lippincott Williams & Wilkins, Baltimore, Md., 2000).

In one embodiment, the kit further comprises instructions for using the compound or pharmaceutical composition. The instructions can be in any appropriate form, such as written or electronic form. In another embodiment, the instructions can be written instructions. In another embodiment, the instructions are contained in an electronic storage medium (e.g., magnetic diskette or optical disk). In another embodiment, the instructions include information as to the compound or pharmaceutical composition and the manner of administering the compound or pharmaceutical composition to a patient. In another embodiment, the instructions relate to a method of use disclosed herein (e.g., treating, preventing and/or delaying onset and/or development of a condition selected from cardiovascular diseases, ischemia/reperfusion injury, pulmonary hypertension and other conditions responsive to nitroxyl therapy).

In another embodiment, the kit further comprises suitable packaging. Where the kit comprises more than one compound or pharmaceutical composition, the compounds or pharmaceutical compositions can be packaged patiently in separate containers, or combined in one container when cross-reactivity and shelf life permit.

5. EXAMPLES

The following examples are presented for illustrative purposes and should not serve to limit the scope of the disclosed subject matter.

5.1 Example 1: HNO Production as Determined Via $N_2O$ Quantification

Nitrous oxide ($N_2O$) is produced via the dimerization and dehydration of HNO, and is the most common marker for nitroxyl production (Fukuto et al., *Chem. Res. Toxicol.* 18:790-801 (2005)). Nitroxyl, however, can also be partially quenched by oxygen to provide a product that does not produce $N_2O$ (see Mincione et al., *J. Enzyme Inhibition* 13:267-284 (1998); and Scozzafava et al., *J. Med. Chem.* 43:3677-3687 (2000)). Using either nitrous oxide gas or Angeli's salt (AS) as a standard, the relative amounts of $N_2O$ released from compounds of the disclosure was examined via gas chromatography (GC) headspace analysis.

A procedure for determining the relative amounts of $N_2O$ released from compounds of the disclosure is as follows. GC was performed on an Agilent gas chromatograph equipped with a split injector (10:1 splitting), microelectron capture detector, and a HP-MOLSIV 30 m×0.32 mm×25 μm molecular sieve capillary column. Helium was used as the carrier (4 mL/min) gas and nitrogen was used as the make-up (20 mL/min) gas. The injector oven and the detector oven were kept at 200° C. and 325° C., respectively. All nitrous oxide analyses were performed with the column oven held at a constant temperature of 200° C.

All gas injections were made using an automated headspace analyzer. Vial pressurization was 15 psi. The analyzer's sample oven, sampling valve, and transfer line were kept at 40° C., 45° C., and 50° C., respectively. The oven stabilization, vial pressurization, loop fill, loop equilibration, and sample injection times were 1.00 min., 0.20 min., 0.20 min., 0.05 min., and 1.00 min., respectively.

All determinations used a batch of nominal 20 mL headspace vials with volumes pre-measured for sample uniformity (actual vial volume varied by <2.0% relative standard deviation (n=6)). The average vial volume for the batch was determined from six randomly-selected vials by calculating the weight difference between the capped and sealed empty (i.e., air-filled) vial and the capped and sealed deionized water-filled vial using the known density of deionized water, then averaging. Blanks were prepared by sealing and capping two vials then purging each for 20 seconds with a gentle argon stream. Nitroxyl standards were prepared by sealing and capping four vials then purging each for 1 minute with a gentle stream, from a gas cylinder, of a 3000 ppm nitroxyl standard.

CXL-1020 (N-hydroxy-2-methanesulfonylbenzene-1-sulfonamide) "standards" were prepared by, in duplicate, accurately weighing 10±0.5 mg of CXL-1020 and adding it to each 4 mL vial. Using an auto pipette, 1 mL of argon-purged anhydrous DMF (Sigma-Aldrich) was added to each 4 mL vial to form a CXL-1020 stock solution for each sample and the vials were capped and shaken and/or sonicated to insure complete dissolution upon visual observation. Using an auto pipette, 20 mL vials were charged with 5 mL of PBS (purged for at least 30 min. with argon prior to use), purged with argon for at least 20 sec., and sealed with a rubber septum. Using a 50 μL syringe, 50 μL of the CXL-1020 stock solution was injected into each 20 mL vial containing the PBS.

Samples were prepared as follows. In duplicate, 18±1 mg of each sample was accurately weighed into each 4 mL vial. Using an auto pipette, 1 mL of argon-purged anhydrous DMF was added to each 4 mL vial to form a sample stock solution for each sample and the vials were capped and shaken and/or sonicated to insure complete sample dissolution upon visual observation. Using an auto pipette, 20 mL vials were charged with 5 mL of PBS (purged for at least 30 min. with argon prior to use), purged with argon for at least 20 sec., and sealed with a rubber septum. The vials were equilibrated for at least 10 min. at 37° C. in a dry block heater. Thereafter, using a 50 μL syringe, 50 μL of a sample stock solution was injected into each 20 mL vial containing the PBS. The vials were then held at 37° C. in the dry block heater for a time period such that the sum of the time spent in the dry block heater plus the time spent in the automated headspace analyzer oven before sample injection equaled the desired incubation time.

The sequence for auto-injection was as follows: blank replicate 1, blank replicate 2, $N_2O$ standard replicate 1, $N_2O$ standard replicate 2, CXL-1020 standard replicate 1, CXL-1020 standard replicate 2, sample 1 replicate 1, sample 1 replicate 2, sample 2 replicate 1, sample 2 replicate 2, etc., concluding with $N_2O$ standard replicate 3, and $N_2O$ standard replicate 4. An EXCEL spreadsheet is used for inputting data thus determined and calculating, for each sample, the relative $N_2O$ yield in percent for each incubation time. The results obtained are provided in Table 3. "-" indicates that results were not determined.

TABLE 3

Results of N₂O Headspace Analysis

| Compound No. | Compound | Relative N$_2$O Yield (90 minutes incubation) | Relative N$_2$O Yield (360 minutes incubation) |
|---|---|---|---|
| 1 | N-Hydroxy-5-methylfuran-2-sulfonamide | 52% | — |
| 2 | N-Hydroxy-3-methanesulfonylbenzene-1-sulfonamide | 82% | 94% |
| 3 | N-Hydroxy-5-methyl-1,2-oxazole-4-sulfonamide | 45% | 56% |
| 4 | N-Hydroxy-1-benzofuran-7 sulfonamide | 64% | — |
| 5 | 4-(Hydroxysulfamoyl)-N-(propan-2-yl)thiophene-2-carboxamide | 48% | 72% |
| 6 | N-Hydroxy-1-benzofuran-3-sulfonamide | 85% | — |
| 7 | N-Hydroxy-5-methyl-2-(trifluoromethyl)furan-3-sulfonamide | 51% | — |
| 8 | N-Hydroxy-5-methanesulfonylthiophene-3-sulfonamide | 77% | — |
| 9 | 1-Acetyl-5-bromo-N-hydroxy-2,3-dihyrdo-1H-indole-6-sulfonamide | 53% | 71% |
| 10 | 2-Chloro-N-hydroxy-5-(hydroxymethyl)benzene-1-sulfonamide | 91% | — |
| 11 | 1-Acetyl-5-chloro-N-hydroxy-2,3-dihydro-1H-indole-6-sulfonamide | 55% | 81% |
| 12 | 4,5-Dichloro-N-hydroxythiophene-2-sulfonamide | 29% | — |
| 13 | N-Hydroxy-6-methoxy-1-benzofuran-2-sulfonamide | 86% | — |
| 14 | 2-Fluoro-N-hydroxy-4-methylbenzene-1-sulfonamide | 48% | 70% |
| 15 | N-Hydroxy-2,1,3-benzothiadiazole-5-sulfonamide | 59% | 71% |
| 16 | N-Hydroxy-4-methanesulfonylthiophene-2-sulfonamide | 86% | — |
| 17 | 5-Bromo-N-hydroxy-2-methoxybenzene-1-sulfonamide | 53% | 77% |
| 18 | 4-Chloro-N-hydroxy-2,5-dimethylbenzene-1-sulfonamide | 56% | 73% |
| 19 | N,N-Diethyl-5-(hydroxysulfamoyl)thiophene-2-carboxamide | 77% | — |
| 20 | 5-Fluoro-N-hydroxy-2-methylbenzene-1-sulfonamide | 90% | — |
| 21 | N-Hydroxy-5-(morpholine-4-carbonyl)thiophene-2-sulfonamide | 73.5% | — |
| 22 | 5-(Hydroxysulfamoyl)-N-(propan-2-yl)thiophene-2-carboxamide | 85% | — |
| 24 | N-Hydroxy-2,1,3-benzothiadiazole-4-sulfonamide | 60% | 69% |
| 25 | N-Hydroxy-2-methoxybenzene-1-sulfonamide | 7% | 28% |
| 26 | N-Hydroxypyridine-3-sulfonamide | 73.5% | — |
| 27 | N-Hydroxy-3,5-dimethyl-1,2-oxazole-4-sulfonamide | 35.5% | 66% |
| 28 | N-Hydroxy-5-(morpholine-4-carbonyl)thiophene-3-sulfonamide | 74% | — |
| 30 | 5-Chloro-N-hydroxy-1,3-dimethyl-1H-pyrazole-4-sulfonamide | 27% | — |
| 32 | N-Hydroxypyridine-2-sulfonamide | 71% | — |
| 33 | 3-Bromo-N-hydroxypyridine-2-sulfonamide | 85.5% | — |
| 34 | 4-N-Hydroxythiophene-2,4-disulfonamide | 100% | — |
| 35 | N-Hydroxy-4-(morpholine-4-carbonyl)thiophene-2-sulfonamide | 100% | — |
| 36 | N-Hydroxy-5-[5-(trifluoromethyl)-1,2-oxazol-3-yl]thiophene-2-sulfonamide | 51% | — |
| 37 | 6-Chloro-N-hydroxy-7H,7aH-imidazo[2,1-b][1,3]thiazole-5-sulfonamide | 51% | — |
| 38 | N-Hydroxy-5-(1,2-oxazol-5-yl)thiophene-2-sulfonamide | 25% | — |
| 39 | 4-Fluoro-N-hydroxy-2-methylbenzene-1-sulfonamide | 60% | 75% |
| 40 | N-Hydroxy-5-(1,3-oxazol-5-yl)thiophene-2-sulfonamide | 50% | — |
| 41 | N-Hydroxy-2,5-dimethylthiophene-3-sulfonamide | 13% | — |
| 42 | Methyl 5-(hydroxysulfamoyl)-4-methylthiophene-2-carboxylate | 91% | — |
| 43 | 5-(Benzenesulfonyl)-N-hydroxythiophene-2-sulfonamide | 82% | — |

TABLE 3-continued

Results of N$_2$O Headspace Analysis

| Compound No. | Compound | Relative N$_2$O Yield (90 minutes incubation) | Relative N$_2$O Yield (360 minutes incubation) |
|---|---|---|---|
| 44 | N-Hydroxy-5-(1,2-oxazol-3-yl)thiophene-2-sulfonamide | 81% | — |
| 45 | 5-Bromo-N-hydroxythiophene-2-sulfonamide | 76% | — |
| 46 | 3,5-Dibromo-N-hydroxythiophene-2-sulfonamide | 95% | — |
| 47 | 5-Chloro-N-hydroxy-4-nitrothiophene-2-sulfonamide | 58% | 70% |
| 48 | 3-Chloro-N-hydroxythiophene-2-sulfonamide | 82% | — |
| 49 | N-Hydroxy-2,5-dimethylbenzene-1-sulfonamide | 42% | 68% |
| 50 | 5-Chloro-N-hydroxy-2,1,3-benzoxadiazole-4-sulfonamide | 31% | — |
| 51 | 4-(Benzenesulfonyl)-N-hydroxythiophene-2-sulfonamide | 96% | — |
| 52 | N-Hydroxy-3,4-dimethoxybenzene-1-sulfonamide | 11% | — |
| 53 | N-Hydroxy-2,3,5,6-tetramethylbenzene-1-sulfonamide | 70% | — |
| 54 | N-Hydroxy-3,5-bis(trifluoromethyl)benzene-1-sulfonamide | 2% | — |
| 55 | Methyl 4-chloro-3-(hydroxysulfamoyl)benzoate | 87% | — |
| 56 | 2-Fluoro-N-hydroxy-5-methylbenzene-1-sulfonamide | 72% | 78% |
| 58 | 2-Chloro-N-hydroxy-5-[4-(hydroxyimino)piperidine-1-carbonyl]benzene-1-sulfonamide | 92% | — |
| 59 | 4-Chloro-3-(hydroxysulfamoyl)-N-(2-methoxyethyl)-N-methylbenzamide | 82% | — |
| 60 | 2-Hydroxy-5-(hydroxysulfamoyl)benzoic acid | 9% | — |
| 61 | N-Hydroxy-4-methyl-3,4-dihydro-2H-1,4-benzoxazine-7-sulfonamide | 11% | — |
| 62 | 2-Chloro-N,4-dihydroxybenzene-1-sulfonamide | 28% | — |
| 64 | 4-Chloro-2-hydroxy-5-(hydroxysulfamoyl)-N,N-dimethylbenzamide | 36% | — |
| 65 | 5-Chloro-N-hydroxy-1-methyl-2,3-dihydro-1H-indole-6-sulfonamide | 71% | — |
| 66 | 2-Chloro-N,5-dihydroxybenzene-1-sulfonamide | 80% | — |
| 67 | 5-Bromo-N-hydroxy-1-methyl-2,3-dihydro-1H-indole-6-sulfonamide | 59% | — |
| 68 | 2-Chloro-N-hydroxy-5-(methoxymethyl)benzene-1-sulfonamide | 86% | — |
| 69 | Methyl 5-(hydroxysulfamoyl)furan-2-carboxylate | 100% | — |
| 70 | N-Hydroxy-2,5-dimethylfuran-3-sulfonamide | 6% | — |
| 72 | 2-(Ethanesulfonyl)-N-hydroxybenzene-1-sulfonamide | 97% | — |
| 73 | N-Hydroxy-2-(propane-2-sulfonyl)benzene-1-sulfonamide | 97% | — |
| 74 | 4-Acetyl-N-hydroxy-3,4-dihydro-2H-1,4-benzoxazine-6-sulfonamide | 17% | — |
| 75 | Methyl 5-(hydroxysulfamoyl)-1-methyl-1H-pyrrole-2-carboxylate | 4% | — |
| 76 | N-[5-(Hydroxysulfamoyl)-1,3-thiazol-2-yl]acetamide | 76% | — |
| 77 | N-Hydroxy-2,5-dimethyl-4-(morpholine-4-carbonyl)furan-3-sulfonamide | 14% | — |
| 78 | Ethyl 5-(hydroxysulfamoyl)furan-3-carboxylate | 86% | — |
| 83 | N-Hydroxyfuran-2-sulfonamide | 42% | 86% |
| 84 | N-Hydroxy-5-methylthiophene-2-sulfonamide | 52% | 67% |
| 85 | N-Hydroxy-1-methyl-1H-pyrazole-3-sulfonamide | 33.5% | — |
| 87 | 3-Chloro-4-fluoro-N-hydroxybenzene-1-sulfonamide | 53% | 79% |
| 88 | 1-N,3-N-Dihydroxybenzene-1,3-disulfonamide | 53% | 100% |
| 90 | 5-Fluoro-N-hydroxy-2-methylbenzene-1-sulfonamide | 90% | — |
| 92 | N-Hydroxy-3-(trifluoromethoxy)benzene-1-sulfonamide | 59% | — |
| 93 | N-Hydroxy-4-methanesulfonylbenzene-1-sulfonamide | 86% | — |

For compounds of formula (99), determinations are as described above except enzyme activated samples are also prepared as follows: (i) accurately weigh 50 mg of porcine liver esterase (PLE, E3019-20KU, crude, Sigma-Aldrich) into a 20 mL headspace vial; (ii) using an auto pipette, 5 mL of argon-purged anhydrous PBS is added to form a PLE stock solution; (iii) the vial is capped and shaken to insure complete dissolution upon visual observation; (iv) samples of nitroxyl donors are prepared as disclosed above except 4.75 mL of PBS is added instead of 5 mL; and (v) using an auto pipette, the 20 mL vials are then charged with 250 μmL of PLE stock solution prior to sample addition. The sequence for auto-injection is as follows: blank replicate 1, blank replicate 2, $N_2O$ standard replicate 1, $N_2O$ standard replicate 2, CXL-1020 standard replicate 1, CXL-1020 standard replicate 2, sample 1 (no PLE) replicate 1, sample 1 (no PLE) replicate 2, sample 1 (with PLE) replicate 1, sample 1 (with PLE) replicate 2, sample 2 (no PLE) replicate 1, sample 2 (no PLE) replicate 2, sample 2 (with PLE) replicate 1, sample 2 (with PLE) replicate 2, etc., concluding with $N_2O$ standard replicate 3, and $N_2O$ standard replicate 4.

Another procedure for determining the relative amounts of $N_2O$ released from compounds of the disclosure is as follows. GC is performed on a Varian CP-3800 instrument equipped with a 1041 manual injector, electron capture detector, and a 25 m 5 Å molecular sieve capillary column. Grade 5.0 nitrogen is used as both the carrier (8 mL/min) and the make-up (22 mL/min) gas. The injector oven and the detector oven are kept at 200° C. and 300° C., respectively. All nitrous oxide analyses are performed with the column oven held at a constant temperature of 150° C. All gas injections are made using a 100 μL gas-tight syringe with a sample-lock. Samples are prepared in 15 mL amber headspace vials with volumes pre-measured for sample uniformity (actual vial volume ranges from 15.19 to 15.20 mL). Vials are charged with 5 mL of PBS containing diethylenetriamine pentaacetic anhydride (DTPA), purged with argon, and sealed with a rubber septum. The vials are equilibrated for at least 10 minutes at 37° C. in a dry block heater. A 10 mM stock solution of AS is prepared in 10 mM sodium hydroxide, and solutions of the nitroxyl donors are prepared in either acetonitrile or methanol and used immediately after preparation. From these stock solutions, 50 μL is introduced into individual thermally-equilibrated headspace vials using a 100 μL gas-tight syringe with a sample-lock to provide final substrate concentrations of 0.1 mM. Substrates are then incubated for 90 minutes or 360 minutes. The headspace (60 μL) is then sampled and injected five successive times into the GC apparatus using the gas-tight syringe with a sample lock. This procedure is repeated for two or more vials per donor.

5.2 Example 2: In Vitro Stability of Nitroxyl Donors in Plasma

Certain compounds from Tables 1 and 2 and CXL-1020 were tested for their stability in phosphate buffered saline (PBS) and plasma. The assay system comprised (i) PBS, or plasma from rat, dog or human (at least 3 donors, male, pooled) at pH 7.4, and (ii) for tests conducted in plasma, an anticoagulant (sodium heparin or sodium citrate). Each test compound (5 μM) was incubated in PBS or plasma at 37° C. on a THERMOMIXER® with shaking. Three samples (n=3) were taken at each of seven sampling time points: 0, 10, 30, 60, 90, 180 and 360 minutes. The samples were immediately combined with 3 volumes (i.e., 3 times the volume of PBS or plasma) of acetonitrile containing 1% formic acid and an internal standard to terminate the reaction. AB SCIEX API 3000 LC-MS/MS analysis of the test compounds was performed without a standard curve. Half-lives ($T_{1/2}$) of the test compounds were determined from graphs of the percent remaining values using the peak area response ratio. The half-lives determined are provided in Table 4. For compounds tested multiple times, the value provided in the Table represents an average of the replicate assays.

TABLE 4

Half-lives ($T_{1/2}$) of Nitroxyl Donors

| Compound No. | Compound | $T_{1/2}$ (minutes) PBS | $T_{1/2}$ (minutes) Rat | $T_{1/2}$ (minutes) Dog | $T_{1/2}$ (minutes) Human |
|---|---|---|---|---|---|
| CXL-1020 | N-Hydroxy-2-methanesulfonylbenzene-1-sulfonamide | 2 | | | 2 |
| 1 | N-Hydroxy-5-methylfuran-2-sulfonamide | 68 | 40 | 25 | 65 |
| 2 | N-Hydroxy-3-methanesulfonylbenzene-1-sulfonamide | 50 | 20 | 33 | 37 |
| 3 | N-Hydroxy-5-methyl-1,2-oxazole-4-sulfonamide | 98 | 37 | 38 | 71 |
| 4 | N-Hydroxy-1-benzofuran-7-sulfonamide | 149 | | | |
| 5 | 4-(Hydroxysulfamoyl)-N-(propan-2-yl)thiophene-2-carboxamide | 136 | 104 | 28 | 24 |
| 7 | N-Hydroxy-5-methyl-2-(trifluoromethyl)furan-3-sulfonamide | 224 | | 56 | |
| 8 | N-Hydroxy-5-methanesulfonylthiophene-3-sulfonamide | 42 | | 27 | |
| 9 | 1-Acetyl-5-bromo-N-hydroxy-2,3-dihydro-1H-indole-6-sulfonamide | 2 | >360 | | |

TABLE 4-continued

Half-lives (T$_{1/2}$) of Nitroxyl Donors

| Compound No. | Compound | T$_{1/2}$ (minutes) PBS | T$_{1/2}$ (minutes) Rat | T$_{1/2}$ (minutes) Dog | T$_{1/2}$ (minutes) Human |
|---|---|---|---|---|---|
| 10 | 2-Chloro-N-hydroxy-5-(hydroxymethyl)benzene-1-sulfonamide | 5 | | | |
| 11 | 1-Acetyl-5-chloro-N-hydroxy-2,3-dihydro-1H-indole-6-sulfonamide | 5 | <5 | | |
| 12 | 4,5-Dichloro-N-hydroxythiophene-2-sulfonamide | 20 | | | |
| 13 | N-Hydroxy-6-methoxy-1-benzofuran-2-sulfonamide | 42 | | | |
| 14 | 2-Fluoro-N-hydroxy-4-methylbenzene-1-sulfonamide | 75 | 13 | | |
| 15 | N-Hydroxy-2,1,3-benzothiadiazole-5-sulfonamide | 63 | | | |
| 16 | N-Hydroxy-4-methanesulfonylthiophene-2-sulfonamide | 20 | | | |
| 17 | 5-Bromo-N-hydroxy-2-methoxybenzene-1-sulfonamide | 59 | >360 | | |
| 18 | 4-Chloro-N-hydroxy-2,5-dimethylbenzene-1-sulfonamide | 56 | >360 | | |
| 19 | N,N-Diethyl-5-(hydroxysulfamoyl)thiophene-2-carboxamide | 44 | | | |
| 20 | 5-Fluoro-N-hydroxy-2-methylbenzene-1-sulfonamide | 25 | 7 | | |
| 21 | N-Hydroxy-5-(morpholine-4-carbonyl)thiophene-2-sulfonamide | 39 | 36 | | |
| 22 | 5-(Hydroxysulfamoyl)-N-(propan-2-yl)thiophene-2-carboxamide | 33 | 23 | | |
| 23 | N-Hydroxy-5-methanesulfonylthiophene-2-sulfonamide | 66 | | | |
| 24 | N-Hydroxy-2,1,3-benzothiadiazole-4-sulfonamide | 37 | 14 | | |
| 25 | N-Hydroxy-2-methoxybenzene-1-sulfonamide | 86 | | | |
| 26 | N-Hydroxypyridine-3-sulfonamide | 53 | 29 | | 45 |
| 27 | N-Hydroxy-3,5-dimethyl-1,2-oxazole-4-sulfonamide | 225 | 75 | | 99 |
| 28 | N-Hydroxy-5-(morpholine-4-carbonyl)thiophene-3-sulfonamide | 136 | | | |
| 30 | 5-Chloro-N-hydroxy-1,3-dimethyl-1H-pyrazole-4-sulfonamide | 385 | | | |
| 31 | N-Hydroxy-1-methyl-1H-pyrazole-4-sulfonamide | 745 | | | |
| 32 | N-Hydroxypyridine-2-sulfonamide | 61 | 32 | | |
| 35 | N-Hydroxy-4-(morpholine-4-carbonyl)thiophene-2-sulfonamide | 58 | 19 | | |
| 39 | 4-Fluoro-N-hydroxy-2-methylbenzene-1-sulfonamide | 30 | 29 | | |
| 47 | 5-Chloro-N-hydroxy-4-nitrothiophene-2-sulfonamide | 11 | <5 | | |
| 49 | N-Hydroxy-2,5-dimethylbenzene-1-sulfonamide | 87 | 13 | | |
| 51 | 4-(Benzenesulfonyl)-N-hydroxythiophene-2-sulfonamide | 15 | 7 | | |
| 56 | 2-Fluoro-N-hydroxy-5-methylbenzene-1-sulfonamide | 34 | 8 | | |
| 83 | N-Hydroxyfuran-2-sulfonamide | 37 | 43 | 38 | 16 |
| 84 | N-Hydroxy-5-methylthiophene-2-sulfonamide | 125 | 65 | 55 | 60 |
| 85 | N-Hydroxy-1-methyl-1H-pyrazole-3-sulfonamide | 59 | | 72 | |

TABLE 4-continued

Half-lives ($T_{1/2}$) of Nitroxyl Donors

| Compound No. | Compound | $T_{1/2}$ (minutes) PBS | $T_{1/2}$ (minutes) Rat | $T_{1/2}$ (minutes) Dog | $T_{1/2}$ (minutes) Human |
|---|---|---|---|---|---|
| 86 | 5-Chloro-N-hydroxythiophene-2-sulfonamide | 38 | | 12 | 18 |
| 87 | 3-Chloro-4-fluoro-N-hydroxybenzene-1-sulfonamide | 101 | 49 | 24 | |
| 88 | 1-N,3-N-Dihydroxybenzene-1,3-disulfonamide | 38 | | 16 | |
| 89 | 3-Bromo-N-hydroxybenzene-1-sulfonamide | 76 | 38.4 | 34 | |
| 90 | 5-Fluoro-N-hydroxy-2-methylbenzene-1-sulfonamide | 25.1 | 6.8 | 21 | |
| 91 | N-Hydroxy-3,5-dimethyl-1,2,-oxazole-4-sulfonamide | 211 | 176 | 54.4 | |
| 92 | N-Hydroxy-3-(trifluoromethoxy)benzene-1-sulfonamide | 58 | 35 | 19 | 40 |
| 92 | N-Hydroxy-3-(trifluoromethoxy)benzene-1-sulfonamide | 57.9 | 35.1 | 18.5 | |
| 93 | N-Hydroxy-4-methanesulfonylbenzene-1-sulfonamide | 68 | 38 | | 35 |
| 95 | 3,4-Dichloro-N-hydroxybenzene-1-sulfonamide | >360 | >360 | | |
| 95 | 3,4-Dichloro-N-hydroxybenzene-1-sulfonamide | >360 | >360 | | |

For measuring half-lives of a compound of formula (99), a stock solution of pig liver esterase (PLE) is added to the PBS or plasma prior to addition of said compound.

5.3 Example 3: Hemodynamic Efficacy of Nitroxyl Donors in Normal and Heart Failure Canines (Tachycardia-Pacing Model)

5.3.1 Materials and Methods

The cardiovascular effects of nitroxyl donors were examined by means of pressure-volume (PV) curve (loops) analysis in conscious, sling-restrained beagle dogs. Animals were allowed free access to drinking water and a commercial canine diet under standard laboratory conditions. Fluorescent lighting was provided via an automatic timer for approximately 12 hours per day. On occasion, the dark cycle was interrupted intermittently due to study-related activities. Temperature and humidity were monitored and recorded daily and maintained to the maximum extent possible between 64° F. and 84° F. and 30% to 70%, respectively. The dogs were acclimated for a period of at least 1 week prior to surgery. Following surgery and recovery the animals were acclimated to sling restraint for a period up to 4.5 hours. Animals were fasted overnight prior to surgery.

Surgical Procedure

Anesthesia

An indwelling venous catheter was placed in peripheral vein (e.g., cephalic) for administration of anesthetic. General anesthesia was induced intravenously (bolus) with buprenorphine (about 0.015 mg/kg) followed by an intravenous bolus of propofol (about 6 mg/kg). Additionally, a prophylactic antibiotic (cefazolin 20 to 50 mg/kg via i.v.) was given upon induction. A cuffed tracheal tube was placed and used to ventilate mechanically the lungs with 100% O2 via a volume-cycled animal ventilator (about 12 breaths/minute with a tidal volume of about 12.5 mL/kg) in order to sustain PaCO$_2$ values within the physiological range. Anesthesia was maintained with inhaled isoflurane (1% to 3%).

Cardiovascular Instrumentation

Once a stable (surgical) plane of anesthesia had been established, a left-thoracotomy was performed (under strict aseptic conditions) and each animal was chronically instrumented with sono-micrometry crystals providing left-ventricular (LV) dimensions/volume. Additionally, a fluid-filled catheter and a solid-state monometer were placed in the left ventricle for pressure monitoring. A fluid-filled catheters was placed in the right ventricle (RV) and the aorta (Ao) for pressure monitoring/test article administration. A hydraulic (In-Vivo Metrics) occluder was placed/secured around the inferior vena cava (IVC), in order to allow its controlled constriction for the generation of LV pressure-volume curves during heterometric auto-regulation. The catheters/wires were aseptically tunneled and externalized between the scapulae. Over the course of the study, fluid-filled catheters were regularly (at least once weekly) flushed with a locking-solution in order to prevent both clotting and bacterial growth (2-3 mL of Taurolidine-Citrate solution, TCS-04; Access Technologies).

Pacemaker Implantation

Following the cardiovascular instrumentation, the right jugular vein was carefully exposed and cannulated with a bipolar pacing lead/catheter (CAPSUREFIX® Novus; Medtronic). Under fluoroscopic guidance, this pacing lead was advanced normograde into the right ventricle and actively affixed (screwed in) to the apical endocardium. The proximal end of the lead was secured to the pacing device (Kappa 900; Medtronic). Subsequently, the pacemaker was placed/secured in a subcutaneous pocket in the neck.

Considering that the heart was exposed via a thoracotomy, a bipolar pacing wire was secured in the right ventricular mid-myocardium. This pacing lead was tunneled/externalized between the scapulae, and used in conjunction with an external impulse generator/pacemaker. The implanted endocardial pacemaker was used as a back-up to the external/epicardial pacemaker.

Recovery

Prior to closure of the chest from the thoracotomy, a chest tube was placed for drainage of any fluid and/or gas that accumulated from the surgical procedure. The tube was aspirated twice daily until the amount of fluid removed was less than 35 mL per aspiration in an approximately 24 hour period. The chest tube was then removed.

All animals were administered a prophylactic antibiotic (cefazolin 20 to 50 mg/kg via i.v.) and pain medication (meloxicam at about 0.2 mg/kg via i.v.). If necessary, an additional analgesic was also administered which included a fentanyl patch (25 to 50 mcg/hour). All surgical incisions were closed in layers; the underlying musculature was closed with absorbable sutures and the skin was closed with staples.

Following surgery, the animals were allowed to recover for at least 14 days. Cephalexin (20 to 50 mg/kg) was administered orally BID for at least 7 days and meloxicam (0.1 mg/kg) was administered SID orally or subcutaneously for at least 2 days after surgery. Throughout the recovery phase, the animals were observed daily for routine signs of recovery and the wound sites were observed for any signs of potential infections. Animals experiencing pain, distress and/or infections were brought to the attention of the attending veterinarian and the study director. The skin incision staples were not removed for at least 7 days after surgery.

Induction of Heart Failure

Following a recovery from surgery and/or sufficient washout period from dosing with a nitroxyl donor, animals were subjected to a 3-week overdrive pacing (210 ppm) protocol aimed to trigger left-ventricular dysfunction/remodeling consistent with the heart failure syndrome. In short, via the implanted pacemaker/right-ventricular lead, the ventricle(s) was asynchronously and continuously paced at 210 beats per minute (bpm). Left-ventricular remodeling (and heart failure induction) were confirmed by both echocardiographic (e.g., ejection fraction EF decrease from about 60% to a target of about 35%, left ventricular LV dilatation) and neuro-humoral (e.g., N-terminal pro-brain natriuretic peptide (NT proBNP) elevation to greater than 1800 pM/L from a baseline of about 300 pM/L) changes after approximately 3 weeks of pacing. Echocardiographs and blood samples were collected in the absence of pacing (for at least 15 min).

5.3.2 Results

Hemodynamic Efficacy Assessments

The animals (normal or heart failure) were studied during treatment with both vehicle (control) and a nitroxyl donor (either CXL-1020 or a compound of formula (1), (2) (83), (84) or (85)). At each dosing period, conscious sling-restrained animals were continuously monitored for up to two to three hours. Following hemodynamic stabilization, infusion of the vehicle was started. Shortly thereafter, left-ventricular pre-load was acutely reduced by means of brief vena cava occlusions (via transient inflation of the vessel occluder) in order to generate a family of pressure-volume curves/loops; up to three occlusions were performed, allowing for hemodynamic recovery between tests. Infusion of the vehicle was continued and after 30 min another (baseline) set of hemodynamic data was collected. Following collection of baseline hemodynamic data, infusion of the nitroxyl donor compound being tested was initiated and type hemodynamic/functional parameters were obtained/performed at up to four (4) time points selected from the following: at 30, 60, 90, 120, and 180 minutes after the onset of vehicle/test compound infusion. For the placebo or time-control treatment group, each animal was administered an infusion of an appropriate placebo for up to 180 minutes. In all cases, the test compound was delivered at a constant intravenous infusion rate of 1 mL/kg/hr and was compared at a molar equivalent or approximate two-thirds of a molar equivalent dose rate.

The resulting left-ventricular pressure and volume data were analyzed in order to generate relationships representing the contractile and energetic state of the myocardium. Systolic arterial pressure (SAP), diastolic arterial pressure (DAP), and mean arterial pressure (MAP) were collected. Left-ventricular mechanical and/or geometrical indices were obtained from the pressure (ESP, EDP, dP/dt max/min, time-constant of relaxation-tau [based on mono-exponential decay with non-zero asymptote]) and volume (end-systolic volume (ESV), end diastolic volume (EDV), stroke volume (SV)) signal. In addition, the following measurements were type from left-ventricular pressure-volume data (PV loops) generated during brief periods of preload reduction: pressure volume area (PVA) and stroke work (SW), end-systolic (ESPVR) and end-diastolic (EDPVR) pressure volume relationships, and end systolic pressure and stroke volume relationship (arterial elastance (Ea)). Representative data obtained from studies in normal dogs and heart failure dogs are shown in Table 5 and Table 6. Representative data for heart failure dogs are also shown in FIG. 1. An SVR (systemic vascular resistance) decrease correlates with vasodilation.

TABLE 5

Hemodynamic Parameters for Nitroxyl Donors in Normal Canines
(% Change from Baseline)

| | | | Compound | | | |
|---|---|---|---|---|---|---|
| | Control | CXL-1020 | (1) | (2) | (83) | (84) |
| Dose Rate (μmol/kg/min) | 0 | 100 | 50 | 100 | 65 | 77 |
| Number of Animals | 3 | 6 | 8 | 4 | 4 | 4 |
| HR | −2.21 ± 1.51 | 6.71 ± 4.72 | −4 ± 2 | −6.17 ± 5.58 | 2.89 ± 2.94 | 4.31 ± 2.98 |
| ESP | −1.8 ± 0.58 | −17.79 ± 3.09 | −18 ± 2 | −15.22 ± 2.39 | −21.99 ± 3.32 | −16.85 ± 2.33 |
| EDV | 2.62 ± 0.42 | −20.51 ± 7.63 | −6 ± 2 | −17.41 ± 1.58 | −16.88 ± 1.69 | −10.99 ± 2.33 |
| Tau | 11.14 ± 1.15 | −6.58 ± 4.53 | −6 ± 1 | −6.40 ± 7.11 | −10.10 ± 1.56 | −9.60 ± 6.06 |
| SW | −2.80 ± 1.26 | −13.96 ± 5.51 | −11 ± 4 | −17.56 ± 2.66 | −19.18 ± 6.70 | −13.98 ± 1.14 |

TABLE 5-continued

Hemodynamic Parameters for Nitroxyl Donors in Normal Canines
(% Change from Baseline)

| | Compound | | | | | |
|---|---|---|---|---|---|---|
| | Control | CXL-1020 | (1) | (2) | (83) | (84) |
| ESPVR | −3.20 ± 1.15 | 28.25 ± 8.69 | 19 ± 1 | 25.87 ± 5.04 | 29.33 ± 8.36 | 50.71 ± 8.14 |
| PRSW | −0.78 ± 0.38 | 12.60 ± 2.96 | 12 ± 1 | 12.88 ± 1.12 | 19.79 ± 3.39 | 17.70 ± 2.35 |

Abbreviations:
HR: Heart rate. Increased HR, either due to reflex response to low blood pressure or due to a primary drug effect on the heart, is bad.
ESP: End systolic pressure-similar to MAP below.
EDP or LVEDP: End diastolic pressure (left ventricular). Correlates with pulmonary pressures. A decrease indicates a reduction of pulmonary congestion (a key objective of acute heart failure therapy).
Tau: An index of lusitropy, or relaxation of the heart during diastole. Decrease is positive and indicates improved diastolic performance.
SW: Stroke work. Measure of how much work the heart exerts to create a given amount of forward flow.
ESPVR: End systolic pressure volume relationship. A measure of inotropy/contractility (a key objective of acute heart failure therapy). Increases indicate improved cardiac performance and efficiency.
PRSW: Preload recruitable stroke work-similar to ESPVR above.
SV: Stroke volume. The amount of blood ejected from the left ventricle with each beat of the heart. An inotrope should increase this, given identical loading conditions.
MAP OR MBP: Mean arterial pressure or mean blood pressure. Small drops are positive and evidence of vasodilation.
EDV or LVEDV: End diastolic volume (left ventricular). Index of the degree of filling in diastole. A decrease indicates a reduction in volume overload.

TABLE 6

Hemodynamic Parameters for Nitroxyl Donors in Heart Failure Canines
(% Change from Baseline)

| Compound | Control | CXL-1020 | (1) | (2) | (83) | (84) |
|---|---|---|---|---|---|---|
| Dose Rate (μmol/kg/min) | 0 | 100 | 75 | 100 | 65 | 77 |
| Number of Animals | 3 | 6 | 6 | 4 | 4 | 4 |
| ESP | 3.89 ± 2.11 | −14.78 ± 3.24 | −17 ± 1 | −13.83 ± 3.30 | −18.52 ± 2.59 | −13.72 ± 2.83 |
| HR | −5.08 ± 5.83 | −0.23 ± 2.25 | −6 ± 2 | −1.36 ± 2.06 | 0.05 ± 1.25 | 3.72 ± 2.45 |
| EDV | 0.86 ± 0.86 | −12.03 ± 3.72 | −9 ± 2 | −3.26 ± 1.05 | −4.91 ± 0.57 | −13.43 ± 4.63 |
| SW | 1.83 ± 1.87 | −12.01 ± 4.24 | 10 ± 5 | −9.41 ± 2.84 | −9.63 ± 1.70 | −5.96 ± 1.58 |
| Tau | 4.05 ± 4.72 | −17.27 ± 1.39 | −16 ± 4 | −12.51 ± 2.72 | −18.32 ± 3.06 | 15.61 ± 1.58 |
| ESPVR | −3.14 ± 0.87 | 45.42 ± 16.48 | 29 ± 1 | 22.84 ± 5.69 | 38.06 ± 8.79 | 51.01 ± 5.85 |
| PRSW | −0.88 ± 0.68 | 21.97 ± 3.79 | 22 ± 1 | 17.91 ± 1.47 | 14.90 ± 2.27 | 25.03 ± 2.52 |

Abbreviations: HR, heart rate; ESP, end systolic pressure; EDV, end diastolic volume; Tau, time constant for relaxation; SW, stroke work; ESPVR, end systolic pressure volume relationship; PRSW, preload recruitable stroke work.

The results, e.g., in FIG. 1, demonstrate that compounds of formulas (1), (2), (83), (84) and (85) have comparable hemodynamic activity to CXL-1020 in both normal and failing canine models.

5.4 Toxicology Studies with Nitroxyl Donors

5.4.1 Example 4: In Vivo Trials with CXL-1020

During in vivo trials of the nitroxyl donor CXL-1020 (N-hydroxy-2-methanesulfonylbenzene-1-sulfonamide), a 14-day study was conducted to evaluate tolerance in dogs treated with continuous infusions of CXL-1020 at dose rates of up to 90 μg/kg/min. This first study found that CXL-1020 was tolerated when administered at a dose rate of 60 μg/kg/min. Unexpectedly, however, clinical pathology changes consistent with an inflammation process, as reflected in changes in clinical pathology markers of inflammation, were observed at the 60 μg/kg/min dose rate. To further investigate this undesirable side-effect, a follow-up 14-day study in dogs was initiated. The follow-up study needed to be terminated after only 4 days due to the appearance of other undesirable side-effects: the unexpected occurrence of significant swelling and inflammation in the dogs' hind limbs where infusion catheters had been surgically implanted, which occasionally interfered with normal limb function; skin discoloration in the inguinal region; decreased activity; inappetance; and in the highest-dosage group, skin cold to the touch.

To determine the cause of the inflammation and hind limb swelling, a series of 72-hour continuous infusion investigative studies were conducted over the following 6 months. The results of those studies showed that CXL-1020, when administered in a pH 4 formulation of a 1:1 molar ratio of CXL-1020:CAPTISOL®, diluted into a solution of 5% dextrose in water, caused clinical pathology changes consistent with an inflammatory process at dose rates greater than or equal to 0.03 μg/kg/min in dogs. Vascular inflammation was observed around the site of insertion of the catheter into the femoral vein (15 cm upstream from the catheter tip), at the catheter tip, and downstream from the catheter tip. The first site of inflammation, the catheter insertion site, caused the dog hind limb swelling and inflammation observed in the early-terminated follow-up study. Increasing infusate pH from 4 to 6 decreased inflammation, improving the inflammatory profile by approximately 3-fold (see FIG. 4). However, significant undesirable side effects were still demonstrated when CXL-1020 was administered at dose rates greater than or equal to 3 μg/kg/min in the dogs.

To avoid the catheter insertion site-associated side effects and to assess whether the vascular inflammation was due to the design of the implanted catheter, a 24-hour continuous infusion study was conducted in dogs using a percutaneous catheter placed in a peripheral (cephalic) vein. After 6 hours of infusion, significant edema was observed in the upper forelimb, downstream from the catheter tip. After 24 hours of infusion, clinical pathology changes similar to those observed in previous studies using an implanted central catheter were detected. Also detected was microscopic pathology demonstrating a severe thrombophlebitis at the catheter tip and progressing with a gradient of lessening severity downstream from the catheter tip.

To determine whether a local phlebitis would occur in humans upon longer duration dosing, a longer duration study was conducted in healthy volunteers. The longer duration study included a dose escalation study in which cohorts of 10 volunteers were to be sequentially administered a 24-hour continuous infusion of CXL-1020 at the dose rates of 10, 20, and 30 µg/kg/min with a safety assessment between each cohort. Each cohort consisted of 2 placebo and 8 active treatments with a sentinel pair of 1 active and 1 placebo followed by the main group of 1 placebo and 7 active treatments. The infusion was via a percutaneous catheter inserted into a forearm vein. The catheter was switched to the contralateral arm after 12 hours of infusion. The dose rate of 10 µg/kg/min for 24-hours was found to be well tolerated. In the second cohort, administered a dose of 20 µg/kg/min for 24-hours, there were no adverse findings in the 2 placebo-treated volunteers but there were mild findings (either clinical signs and/or changes in clinical pathology) in all 8 subjects consistent with infusion site phlebitis. Based on these results, the longer duration safety study was halted.

Exploratory studies were continued to determine the cause of the undesirable side effects of CXL-1020 at the higher, but still clinically desirable, doses. Studies conducted with the byproduct of CXL-1020, the moiety that remains after nitroxyl donation, was negative, indicating that the CXL-1020's side effects were attributable to either the parent compound, CXL-1020, or to the HNO produced therefrom. Studies were conducted with alternative Nitroxyl donors that were structurally unrelated to CXL-1020 but had similar half-lives for nitroxyl donation (half-lives of about 2 minutes). In all instances, local vascular side effects at the catheter tip were observed. These results suggested that the inflammation was caused by nitroxyl that was rapidly released from the short half-life nitroxyl donors.

5.4.2 Example 5: Longer Half-Life N-Hydroxysulfonamide Type Nitroxyl Donors Have an Improved Toxicological Profile Relative to CXL-1020

Studies were conducted in male and female beagle dogs. Animals were allowed free access to drinking water and a commercial canine diet under standard laboratory conditions. Animals were fasted prior to blood sample collections when indicated by the study protocol. Fluorescent lighting was provided via an automatic timer for approximately 12 hours per day. On occasion, the dark cycle was interrupted intermittently due to study-related activities. Temperature and humidity were monitored and recorded daily and maintained to the maximum extent possible between 64° F. to 84° F. and 30% to 70%, respectively. The dogs were acclimated for a period of at least 1 week. During this period, the animals were weighed weekly and observed with respect to general health and any signs of disease. The animals were acclimated to wearing a jacket for at least three days prior to dose administration. Additionally, the animals were also acclimated to wearing an Elizabethan collar (e-collar) during the jacket acclimation.

Surgical Procedure and Dosing Procedure

Animals were catheterized the day prior to dose administration. A percutaneous catheter was placed (using aseptic technique and sterile bandaging) in the cephalic vein distal to the elbow. The animals were free-moving in their cages during continuous infusion dose administration. To facilitate continuous infusion dose administration, the peripheral catheter was attached to an extension set routed underneath a canine jacket and then attached to a tether infusion system. To prevent the animals from accessing/removing the peripherally placed percutaneous catheter, the catheterization site was bandaged using Vet Wrap and an e-collar was placed on the animals for the duration of the treatment (i.e., the catheterized period). During the pretreatment period, the venous catheter was infused continuously at a rate of approximately 2-4 mL/hr with 0.9% sodium chloride for injection, USP (saline) to maintain catheter patency. Prior to dosing, the infusion system was pre-filled (slow bolus infusion) with the respective dosing solution to ensure that dosing began as soon as the infusion pump was started. The infusion line was connected to a reservoir containing the control or test compound and the infusion was started. Test compositions were infused continuously, at a predetermined constant infusion rate (1 or 2 mL/kg/hr), for 24 hours and were compared at molar equivalent dose rates.

Clinical Observations, Clinical Pathology, and Microscopic Pathology

A detailed clinical examination of each animal was performed twice daily and body temperature measurements and blood samples for clinical pathology were collected from all animals pre-dose and 6 hours, 12 hours, 24 hours and 72 hours post start of composition infusion. At the termination of the study, all animals were euthanized at their scheduled necropsy and complete necropsy examinations were performed. Selected tissues were collected, fixed and stored for potential future microscopic examination. The cephalic vein containing the infusion catheter was dissected intact along with the brachial vein and examined along its entire length. The location of the catheter tip was marked on the unfixed specimen. After fixation, the specimen was trimmed and processed to slide to provide transverse histologic sections representing the catheter tip and surrounding tissues both proximal and distal to the catheter tip (i.e., 1 cm distal to the catheter tip, at the catheter tip, and 1, 5, 10, 15, and 20 cm proximal to the catheter tip). Relative to the catheter tip, "proximal" was defined as closer to the heart and "distal" was defined as further from the heart.

Safety Assessment

Clinical pathology changes consistent with an inflammatory syndrome were observed at some dose rates of compounds of formulas (1), (2) (83), (84), (85), (86) and CXL-1020. Each compound was formulated with CAPTISOL® (7% w/v) in sterile water at a pH of 4. The most sensitive biomarkers of the inflammation were: (1) white cell count (WBC, obtained as (number of white blood cells)/µL by multiplying the values in the rightmost portion of FIG. 2 by 103), (2) fibrinogen concentration (given in mg/dL in the rightmost portion of FIG. 2), and (3) C-Reactive Protein (CRP) concentration (given in mg/L in the rightmost portion of FIG. 2). The severity of the changes was dependent on the identity of the compound and the dose rate at which the compound was administered (FIG. 2). In FIG. 2, a score ranging from 0 (low severity) to 2 (high severity) was assigned to each of these biomarkers of inflammation according to the rightmost portion in that figure. A cumulative score was calculated from the sum of these marker scores. The NOAELs, determined based on these clinical pathology markers and expressed in molar equivalent dose rates (µg/kg/min) to CXL-1020, are provided in Table 7.

TABLE 7

No Observed Adverse Effect Levels (NOAEL) of Nitroxyl Donors

| Compound | NOAEL (µg/kg/min) (actual) |
|---|---|
| N-Hydroxy-2-methanesulfonylbenzene-1-sulfonamide (CXL-1020) | <0.03 |
| N-Hydroxy-5-methylfuran-2-sulfonamide (1) | >20 |
| N-Hydroxy-3-methanesulfonylbenzene-1-sulfonamide (2) | 3 |
| N-Hydroxyfuran-2-sulfonamide (83) | 3 |
| N-Hydroxy-5-methylthiophene-2-sulfonamide (84) | 10 |
| N-Hydroxy-1-methyl-1H-pyrazole-3-sulfonamide (85) | 3 |
| 5-Chloro-N-hydroxythiophene-2-sulfonamide (86) | 3 |

For CXL-1020, significant elevations in WBC, fibrinogen and CRP were observed, even at concentrations as low as 0.03 µg/kg/min. The longer half-life compounds of formulas of formulas (1), (2) (83), (84), (85) and (86) all have a NOAEL at doses significantly higher than that of CXL-1020. The compound of formula (1) has the most favorable toxicological profile, showing no adverse effects at doses at least as high as 20 µg/kg/min. This represents a greater than 660-fold improvement of the compound of formula (1) relative to CXL-1020.

Collectively, these findings suggest that CXL-1020 infusion causes an inflammatory syndrome, which is substantially reduced with the longer half-life nitroxyl donors of the disclosure.

The findings suggested that the vascular toxicity associated with CXL-1020 at the catheter tip, downstream of the catheter tip and in certain circumstances, upstream of the catheter tip, were due to local inflammation caused by nitroxyl release. Moreover, it was postulated that inflammation can be significantly mitigated at these sites using longer half-life nitroxyl donors. Confirmation of this was obtained through evaluating the nitroxyl donors through detailed histopathology of the vasculature at the site of insertion of into the femoral vein (15 cm distal to the catheter tip), along the catheter track to the catheter tip, and past the tip downstream 20 cm. Microscopic pathology findings of edema, hemorrhage, vascular inflammation and perivascular inflammation were determined at particular dose rates of the nitroxyl donors.

FIG. 3 depicts a "heat-map" showing a composite score of the microscopic pathology findings in which the severity of vascular inflammation, hemorrhage, thrombus and vascular degeneration/regeneration was scored in sections of the vasculature as described above. Findings of (1) edema, (2) vascular and perivascular inflammation, and (3) hemorrhage were scored (each assigned a value selected from: 0=within normal limits; 1=minimal; 2=mild; 3=moderate; 4=severe) in sections of the vessel beginning 1 cm distal (upstream) from the catheter tip progressing 20 cm proximal (downstream) from the catheter tip. A composite score was calculated from the sum of these findings scores. In FIG. 3, the cumulative histology composite score ranges from 0-2 (low severity) to 11-12 (high severity). The severity of the microscopic changes and the distance from the catheter tip in which they were detected was observed to be dependent on the identity of the nitroxyl donor and the dose rate at which the nitroxyl donor was administered. The NOAEL values determined based on these microscopic pathology markers for a series of nitroxyl donors, expressed in molar equivalent dose rates (µg/kg/min) to CXL-1020, are provided in Table 8.

TABLE 8

No Observed Adverse Effect Levels (NOAEL) of Nitroxyl Donors

| Compound | NOAEL (µg/kg/min) (molar equivalent to CXL-1020) |
|---|---|
| N-Hydroxy-2-methanesulfonylbenzene-1-sulfonamide (CXL-1020) | <3 |
| N-Hydroxy-5-methylfuran-2-sulfonamide (1) | ≥180 |
| N-Hydroxy-3-methanesulfonylbenzene-1-sulfonamide (2) | ≥180 |
| N-Hydroxyfuran-2-sulfonamide (83) | ≥90 |
| N-Hydroxy-5-methylthiophene-2-sulfonamide (84) | ≥60 |
| N-Hydroxy-1-methyl-1H-pyrazole-3-sulfonamide (85) | ≥180 |
| 5-Chloro-N-hydroxythiophene-2-sulfonamide (86) | ≥180 |

The findings presented in Table 8 that the longer half-life nitroxyl donors (e.g., compounds of formulas (83), (84), (85) and (86)) have a substantially improved toxicological profile relative to CXL-1020. The side effect profile at any dose decreased in severity as a function of distance from the catheter tip, and the severity of vascular side effects decreased with decreasing dose. These findings confirmed a large safety margin for compounds of formulas compounds of formulas (83), (84), (85) and (86), which can translate into a substantially improved therapeutic index in humans, and suitability for intravenous administration at therapeutically effective doses and dosage rates.

5.5 Example 6: Increasing pH Improves Toxicological Profile

Three nitroxyl donors (CXL-1020, compound (2), and compound (86)) were formulated at a pH of 4 and at a pH of 6 (in a potassium acetate buffer) and the toxicological profiles of the compositions were assessed. For samples at a pH of 4, the compositions were prepared by admixing a 1:1 molar ratio of the nitroxyl donor:CAPTISOL®, lyophilizing the admixture, then diluting the lyophilized admixture into D5W. For samples at a pH of 6, the compositions were prepared by admixing a 1:1 molar ratio of the nitroxyl donor:CAPTISOL®, lyophilizing the admixture, then diluting the lyophilized admixture into D5W with 5 mM potassium phosphate. Compounds were infused at a rate of 3 µg/kg/min. As shown in FIG. 4, increasing the infusate pH from approximately 4 to approximately 6 improved the toxicology of the three compounds.

5.6 Concentrate Stability Assessment

5.6.1 Example 7: Compound of Formula (1)

The stability of liquid concentrates of the compound of formula (1) and CAPTISOL® was evaluated. Three concentrations of the compound of formula (1) were assessed: 21.2 mg/mL, 50 mg/mL and 100 mg/mL. Samples were prepared to the three target concentrations in four aqueous vehicles comprising different percentages of CAPTISOL®, as summarized in Table 9. The appropriate amounts of solid and vehicle were combined, and upon complete dissolution, the pH of each sample was adjusted to 4.0 by adding 1 N NaOH. The samples were prepared on a 1.5-mL scale. Aliquots were stored at 2° C.-8° C. and 25° C.

TABLE 9

Samples Prepared for Assessment of the Compound of Formula (1) Concentrate Stability

| Sample # | Compound of Formula (1) Concentration (mg/mL) | % CAPTISOL ® (w/v) |
|---|---|---|
| C1 | 21.2 | 0 |
| C2 | | 30 |
| C3 | 50 | 0 |
| C4 | | 10 |
| C5 | | 20 |
| C6 | | 30 |
| C7 | 100 | 0 |
| C8 | | 10 |
| C9 | | 20 |
| C10 | | 30 |

Upon preparation and after 1, 3, and 7 days of storage, samples were removed from their respective temperature conditions and their visual appearances noted. Samples were analyzed by HPLC (XBridge Phenyl Column (Waters); UV absorbance detector at 272 nm; mobile phase a step gradient of aqueous acetonitrile containing 0.1% (v/v) formic acid), and the pH of each sample was measured. The results are summarized in Table 10 and Table 11. The recovery values are normalized to the concentrations observed right after preparation of the concentrate (t=0). Complete recovery (within the accuracy of the method) was achieved in all samples stored at 2° C.-8° C. over the 7 days but not in all samples stored at 25° C.

Correspondingly, the decrease in pH and increase in intensity of yellow color were less pronounced in the refrigerated samples than in the samples stored at a temperature of 25° C. Complete recovery was observed after 7 days in the 21.2 and 50 mg/mL samples prepared in 30% CAPTISOL® and after 3 days in the 100 mg/mL sample prepared in the same vehicle. Recovery of greater than 90% was also observed after three days in the 50 mg/mL sample prepared in 20% CAPTISOL®. The stability was greatest at lower concentrations, higher percentages of CAPTISOL®, and lower temperature.

TABLE 10

Visual Appearance of Concentrate Stability Samples

| Sample # | % CAPTISOL ® (w/v) | Compound of Formula (1) Concentration (mg/mL) | Storage Temperature (° C.) | Visual Appearance t = 0 | t = 1 d | t = 3 d | t = 7 d |
|---|---|---|---|---|---|---|---|
| C1 | 0 | 21.2 | 2-8 | A | A | A | A |
| | | | 25 | | A | B | C |
| C2 | 30 | 21.2 | 2-8 | A | A | A | A |
| | | | 25 | | A | A | A |
| C3 | 0 | 50 | 2-8 | B | B | B | B |
| | | | 25 | | B | C | D |
| C4 | 10 | 50 | 2-8 | B | B | B | B |
| | | | 25 | | B | C | D |
| C5 | 20 | 50 | 2-8 | B | B | B | B |
| | | | 25 | | B | B | C |
| C6 | 30 | 50 | 2-8 | B | B | B | B |
| | | | 25 | | B | B | B |
| C7 | 0 | 100 | 2-8 | B | B | B | B |
| | | | 25 | | C | D | D |
| C8 | 10 | 100 | 2-8 | B | B | B | B |
| | | | 25 | | C | D | D |
| C9 | 20 | 100 | 2-8 | B | B | B | B |
| | | | 25 | | C | D | D |
| C10 | 30 | 100 | 2-8 | B | B | B | B |
| | | | 25 | | C | C | C |

A = clear, colorless
B = clear, very pale yellow
C = clear, pale yellow
D = clear, yellow

TABLE 11

Results of Analysis of Concentrate Stability Samples

| Sample # | % CAPTISOL ® (w/v) | Concentration Compound of Formula (1) (mg/mL) | Storage Temp. (° C.) | Recovery from t0, % t = 1 d | t = 3 d | t = 7 d | pH t = 0 | t = 1 d | t = 3 d | t = 7 d |
|---|---|---|---|---|---|---|---|---|---|---|
| C1 | 0 | 21.2 | 2-8 | 101% | 100% | 99% | 4.03 | 3.41 | 3.03 | 2.81 |
| | | | 25 | 103% | 82% | 38% | | 3.50 | 1.73 | 1.29 |
| C2 | 30 | 21.2 | 2-8 | 99% | 101% | 98% | 4.02 | 3.93 | 3.82 | 3.72 |
| | | | 25 | 100% | 101% | 98% | | 3.65 | 3.44 | 3.23 |
| C3 | 0 | 50 | 2-8 | 100% | 99% | 99% | 4.02 | 3.38 | 3.25 | 3.00 |
| | | | 25 | 100% | 79% | 50% | | 2.93 | 1.38 | 1.13 |
| C4 | 10 | 50 | 2-8 | 98% | 96% | 97% | 4.00 | 3.35 | 3.29 | 3.22 |
| | | | 25 | 99% | 82% | 55% | | 3.03 | 1.66 | 1.29 |
| C5 | 20 | 50 | 2-8 | 99% | 97% | 97% | 4.00 | 3.14 | 3.13 | 3.04 |
| | | | 25 | 100% | 92% | 69% | | 2.87 | 2.05 | 1.42 |
| C6 | 30 | 50 | 2-8 | 100% | 100% | 98% | 3.98 | 3.61 | 3.61 | 3.40 |
| | | | 25 | 100% | 101% | 98% | | 3.21 | 2.95 | 2.84 |
| C7 | 0 | 100 | 2-8 | 100% | 97% | 98% | 3.96 | 2.96 | 2.86 | 2.75 |
| | | | 25 | 98% | 70% | 68% | | 2.13 | 1.14 | 1.07 |

TABLE 11-continued

Results of Analysis of Concentrate Stability Samples

| Sample # | % CAPTISOL® (w/v) | Concentration Compound of Formula (1) (mg/mL) | Storage Temp. (°C.) | Recovery from t0, % | | | pH | | | |
|---|---|---|---|---|---|---|---|---|---|---|
| | | | | t = 1 d | t = 3 d | t = 7 d | t = 0 | t = 1 d | t = 3 d | t = 7 d |
| C8 | 10 | 100 | 2-8 | 101% | 100% | 99% | 4.02 | 2.51 | 2.41 | 2.18 |
| | | | 25 | 91% | 78% | 71% | | 1.67 | 1.21 | 1.12 |
| C9 | 20 | 100 | 2-8 | 99% | 99% | 99% | 3.96 | 3.30 | 3.20 | 3.03 |
| | | | 25 | 100% | 84% | 70% | | 2.57 | 1.42 | 1.14 |
| C10 | 30 | 100 | 2-8 | 102% | 102% | 102% | 3.99 | 3.39 | 3.27 | 3.11 |
| | | | 25 | 103% | 101% | 80% | | 2.90 | 2.20 | 1.31 |

5.6.2 Example 8: Compound of Formula (2)

The storage stability of a liquid concentrate of the Compound of formula (2) (30 mg/mL) in the vehicle 30% CAPTISOL® (w/v) at pH 4.0, was assessed at 4° C. and 25° C. over 7 days, with time points after 1, 3 and 7 days. At each time point samples were assessed for visual appearance, pH, and concentration and purity by HPLC (XBridge Phenyl Column (Waters); UV absorbance detector at 272 nm; mobile phase a step gradient of aqueous acetonitrile containing 0.1% (v/v) formic acid).

The selected vehicle, CAPTISOL® (30% w/v) in water with pH adjusted to 4.0, was prepared by accurately weighing 30 grams of CAPTISOL® into a 150 mL beaker and dissolved with 45 mL of water. The pH was adjusted to pH 4.0 by addition of 0.1N HCl. Subsequently, the vehicle was transferred to a volumetric flask and brought to 100 mL final volume by addition of water. After incubation at a temperature of about 25° C. for 30 minutes, the pH of the vehicle was re-adjusted to pH 4.0 by addition of 0.1N HCl. The vehicle formed a clear, colorless solution.

A concentrated solution of the compound of formula (2) was prepared as follows. A stir bar and 30 mL of vehicle were added to a 150 mL beaker. Approximately 1.8 g of the compound of formula (2) was dispensed and transferred to the beaker under low to medium stirring. After 45 minutes of stirring at a temperature of about 25° C. (protected from light), the concentrate formed a clear, colorless solution with some small, white clumps of the compound of formula (2) floating in solution. The remaining clumps were gently broken-up using a spatula. Following an additional 45 minutes of stirring, the concentrate formed a clear, colorless solution without any visible solids. The concentrate was then filtered (0.2 µm) through a 0.22 µm PVDF syringe filter.

For t=0 h testing, aliquots were distributed into vials and analyzed by HPLC (XBridge Phenyl Column (Waters); UV absorbance detector at 272 nm; mobile phase a step gradient of aqueous acetonitrile containing 0.1% (v/v) formic acid) and the sample pH was determined. Twelve aliquots of 1 mL of the concentrate were distributed into microcentrifuge tubes for storage at 4° C. and 25° C. After approximately 24, 72 and 168 hours of storage, two aliquots were removed from each storage condition and assessed for visual appearance, pH, and concentration and purity by HPLC. All samples were clear, colorless solutions. The pH of the samples stored at 4° C. and 25° C. decreased from 3.7 to 3.6 and 3.3, respectively, over the 7 days. Both vehicles sustained the compound of formula (2) at a concentration of 30 mg/mL over 7 days, as summarized in Table 12. In Table 12, the term "c/c" refers to clear and colorless. No detectable levels of the known degradant (compound of formula (101)) were observed.

TABLE 12

Summary of Observed Properties of a Concentrate Solution of the Compound of Formula (2) During Storage Over 7 Days

| Storage Condition | Parameter | Sample | Time Point | | | |
|---|---|---|---|---|---|---|
| | | | 0 h | 24 h | 72 h | 168 h |
| 4° C. | Concentration, mg/mL | 1 | 30.3 | 30.6 | 29.6 | 29.7 |
| | | 2 | | 30.2 | 29.4 | 29.9 |
| | pH | 1 | 3.71 | 3.70 | 3.66 | 3.58 |
| | | 2 | | 3.70 | 3.66 | 3.61 |
| | Appearance | 1 | c/c | c/c | c/c | c/c |
| | | 2 | | c/c | c/c | c/c |
| | Observed Degradant Compound of Formula (101), mg/mL | 1 | No | No | No | No |
| | | 2 | | No | No | No |
| 25° C. | Concentration, mg/mL | 1 | 30.3 | 30.2 | 29.4 | 29.5 |
| | | 2 | | 30.2 | 29.8 | 29.4 |
| | pH | 1 | 3.71 | 3.47 | 3.34 | 3.32 |
| | | 2 | | 3.48 | 3.34 | 3.30 |
| | Appearance | 1 | c/c | c/c | c/c | c/c |
| | | 2 | | c/c | c/c | c/c |
| | Observed Degradant, Compound of Formula (101), mg/mL | 1 | No | No | No | No |
| | | 2 | | No | No | No |

5.7 Stability of Intravenous Dosing Solutions 5.7.1 Example 9: Compound of Formula (1)—Dosing Solution Stored at 25° C.

The stability of dosing solutions of the compound of formula (1) prepared from a CAPTISOL® concentrate diluted into commercially-available IV diluents was assessed at 25° C. over 48 hours, with analysis points at 0, 8, 12, 16, 24, and 48 hours after dilution. Due to the analysis points required, two studies were executed with separate sets of dosing solutions. The first (group A) encompassed all time points except that at 16 hours. The second (group B) entailed analysis at 0 and 16 hours only. The concentrates used to prepare the two sets of dosing solutions were prepared from two separate vials of the same lot of lyophilized drug product (24 mg/mL Compound of formula (1)/30% CAPTISOL®).

Concentrate Preparation

One vial of lyophilized drug product (24 mg/mL Compound of formula (1)/30% CAPTISOL®, pH 4) was reconstituted with 10 mL of water for injection quality water (WFI) to prepare each concentrate (for dosing solution groups A and B). The pH values of the resultant solutions were measured, and were determined to be approximately 3.9 for both vials. No pH adjustment was performed. The concentrates were diluted and analyzed by HPLC (XBridge Phenyl Column (Waters); UV absorbance detector at 272 nm; mobile phase a step gradient of aqueous acetonitrile containing 0.1% (v/v) formic acid), and both were determined to contain 20-21 mg/mL of the compound of formula (1), rather than the nominal value of 24 mg/mL, ostensibly due to contribution of the dissolved API and CAPTISOL® to the total solution volume.

Diluent Preparation

Commercially-available potassium acetate and potassium phosphate solutions were selected for evaluation. Potassium acetate was obtained commercially, and a USP potassium phosphate solution was prepared according to the Hospira product insert for the commercial product. Each solution was diluted to 10 mM in 5% dextrose (D5W) and 2.5% dextrose (D2.5W). Commercially-available D5W was diluted 2-fold with WFI quality water to produce the D2.5W solution. The pH of each concentrated and diluted solution was measured; the results are presented in Table 13.

TABLE 13

Results of pH Measurement of Selected Diluents

| Diluent | Concentration | pH |
|---|---|---|
| Acetate | 10 mM in D2.5W | 6.2 |
|  | 10 mM in D5W | 6.0 |
|  | Initial (2 M) | 6.7 |
| Phosphate | 10 mM in D2.5W | 6.8 |
|  | 10 mM in D5W | 6.7 |
|  | Initial (3 M) | 6.5 |

Dosing Solution Preparation

The compound of formula (1) concentrate was diluted volumetrically on a 5 mL scale into the 10 mM diluent solutions to achieve concentrations of 8, 1, and 0.1 mg/mL of the compound of formula (1), as summarized in Table 14. Each sample was prepared in duplicate. The dextrose content in the 10% CAPTISOL® solution was reduced to ensure that the dosing solutions were substantially isotonic. Each solution was stored at 25° C.

TABLE 14

Preparation of Dosing Solutions for Stability Evaluation

| Compound of Formula (1) (mg/mL) | Diluent | Dilution factor | CAPTISOL ® (% w/v) |
|---|---|---|---|
| 8.0 | 10 mM acetate or phosphate in D2.5W | 3 | 10% |
| 1.0 | 10 mM acetate or phosphate | 24 | 1.3% |
| 0.1 | in D5W | 240 | 0.1% |

Sample Analysis

Samples were analyzed upon preparation and after 8, 12, 16, 24, and 48 hours of storage at 25° C. The visual appearance of each sample was noted, the pH was measured, and each sample was analyzed by HPLC for concentration and presence of the major degradant, the compound of formula (100).

Results

The results of the stability evaluation are presented in Table 15, Table 16, and Table 17. In Table 17, the presence of a peak corresponding to the degradant (the compound of formula (100)) in a sample is denoted by an "X".

The results were generally consistent for each duplicate within a pair and between corresponding dosing solutions prepared in groups A and B. A difference in recovery was observed between duplicates at the 24 and 48 hour time points for the samples prepared to contain 0.1 mg/mL of the compound of formula (1) in phosphate.

Complete recovery (within the accuracy of the HPLC method) and absence of a detectable degradant (compound of formula (100)) peak was maintained over 48 hours for the samples prepared to 8 mg/mL of the compound of formula (1) in acetate- and phosphate-based diluents. These samples actually contained approximately 7 mg/mL of the compound of formula (1), consistent with the concentration of 20-21 mg/mL compound of formula (1) in the concentrate. In both diluents, stability was superior in the samples prepared to 8 mg/mL compound of formula (1) than in the samples prepared to lower concentrations. Without being bound by theory, the better stability of these samples compared to those prepared to lower concentrations of the compound of formula (1) might be attributed to the higher CAPTISOL® concentration (10% in the diluted solutions).

All samples remained clear and colorless over the 48 hours of storage. The pH of all samples decreased over time. The known degradant (compound of formula (100)) was observed upon preparation (at t0) in all samples prepared to contain 0.1 mg/mL of the compound of formula (1) and at all subsequent time points in all samples prepared to contain 0.1 mg/mL and 1 mg/mL of the compound of formula (1).

In general, stability decreased with decreasing concentration of the compound of formula (1). Without being bound by theory, the decreased stability was likely due to the lower percent CAPTISOL® in the dosing solutions. The initial extent of degradation (through 16 hours) was similar in the samples prepared to contain 0.1 mg/mL of the compound of formula (1) in the acetate- and phosphate-based diluents. However, the stability of the samples prepared to contain 1 mg/mL demonstrated significantly better stability in acetate than in phosphate.

TABLE 15

Results of Dosing Solution Stability Evaluation at 25° C., Percent Recovery

| Dosing Solution | Duplicate | Diluent | Compound of Formula (1) mg/mL | Compound of Formula (1) mg/mL t0 (group A) | t0 (group | 8 h (A) | 12 h (A) | 16 h (B) | 24 h (A) | 48 h (A) |
|---|---|---|---|---|---|---|---|---|---|---|
| 1 | a | 10 mM acetate | 8.0 | 6.94 | 7.06 | 101% | 102% | 101% | 102% | 101% |
|  | b | in D2.5W |  | 6.95 | 7.06 | 101% | 102% | 101% | 102% | 103% |
| 2 | a | 10 mM acetate | 1.0 | 0.86 | 0.85 | 97% | 97% | 97% | 94% | 92% |
|  | b | in D5W |  | 0.87 | 0.84 | 98% | 98% | 98% | 96% | 95% |

TABLE 15-continued

Results of Dosing Solution Stability Evaluation at 25° C., Percent Recovery

| Dosing Solution | Duplicate | Diluent | Compound of Formula (1) mg/mL | Compound of Formula (1) mg/mL t0 (group A) | t0 (group B) | 8 h (A) | 12 h (A) | 16 h (B) | 24 h (A) | 48 h (A) |
|---|---|---|---|---|---|---|---|---|---|---|
| 3 | a | 10 mM acetate in D5W | 0.1 | 0.10 | 0.09 | 81% | 78% | 66% | 67% | 55% |
|   | b |   |   | 0.10 | 0.09 | 80% | 75% | 68% | 63% | 51% |
| 4 | a | 10 mM phosphate in D2.5W | 8.0 | 6.98 | 6.79 | 98% | 99% | 102% | 99% | 100% |
|   | b |   |   | 7.00 | 6.93 | 99% | 94% | 100% | 100% | 100% |
| 5 | a | 10 mM phosphate in D5W | 1.0 | 0.87 | 0.85 | 89% | 86% | 86% | 78% | 71% |
|   | b |   |   | 0.88 | 0.85 | 90% | 83% | 82% | 79% | 72% |
| 6 | a | 10 mM phosphate in D5W | 0.1 | 0.10 | 0.10 | 83% | 78% | 72% | 62% | 41% |
|   | b |   |   | 0.10 | 0.10 | 79% | 72% | 68% | 50% | 32% |

TABLE 16

Results of Dosing Solution Stability Evaluation at 25° C., pH

| Dosing Solution | Duplicate | Diluent | Compound of Formula (1) mg/mL | pH t0 (group A) | t0 (group B) | 8 h (A) | 12 h (A) | 16 h (B) | 24 h (A) | 48 h (A) |
|---|---|---|---|---|---|---|---|---|---|---|
| 1 | a | 10 mM acetate in D2.5W | 8.0 | 5.6 | 5.5 | 5.4 | 5.4 | 5.4 | 5.4 | 5.3 |
|   | b |   |   | 5.6 | 5.5 | 5.5 | 5.4 | 5.4 | 5.3 | 5.3 |
| 2 | a | 10 mM acetate in D5W | 1.0 | 5.7 | 5.7 | 5.6 | 5.7 | 5.5 | 5.5 | 5.3 |
|   | b |   |   | 5.9 | 5.7 | 5.7 | 5.8 | 5.5 | 5.5 | 5.4 |
| 3 | a | 10 mM acetate in D5W | 0.1 | 6.1 | 5.9 | 5.9 | 5.9 | 5.4 | 5.7 | 5.7 |
|   | b |   |   | 5.8 | 5.9 | 5.9 | 5.9 | 5.3 | 5.7 | 5.5 |
| 4 | a | 10 mM phosphate in D2.5W | 8.0 | 6.3 | 6.1 | 5.9 | 5.9 | 5.6 | 5.5 | 5.0 |
|   | b |   |   | 6.3 | 6.2 | 5.9 | 5.8 | 5.6 | 5.5 | 4.7 |
| 5 | a | 10 mM phosphate in D5W | 1.0 | 6.5 | 6.6 | 6.3 | 6.4 | 6.2 | 6.1 | 5.8 |
|   | b |   |   | 6.6 | 6.5 | 6.3 | 6.4 | 6.1 | 6.3 | 6.0 |
| 6 | a | 10 mM phosphate in D5W | 0.1 | 6.8 | 6.7 | 6.6 | 6.6 | 6.3 | 6.5 | 6.4 |
|   | b |   |   | 6.8 | 6.8 | 6.5 | 6.5 | 6.2 | 6.5 | 6.4 |

TABLE 17

Results of Dosing Solution Stability Evaluation at 25° C.-Measuring Appearance of Compound of Formula (100)

| Dosing Solution | Duplicate | Diluent | Compound of Formula (1) mg/mL | Compound of Formula (100) t0 (group A) | t0 (group B) | 8 h (A) | 12 h (A) | 16 h (B) | 24 h (A) | 48 h (A) |
|---|---|---|---|---|---|---|---|---|---|---|
| 1 | a | 10 mM acetate in D2.5W | 8.0 |   |   |   |   |   |   |   |
|   | b |   |   |   |   |   |   |   |   |   |
| 2 | a | 10 mM acetate in D5W | 1.0 |   |   | X | X | X | X | X |
|   | b |   |   |   |   | X | X | X | X | X |
| 3 | a | 10 mM acetate in D5W | 0.1 | X | X | X | X | X | X | X |
|   | b |   |   | X | X | X | X | X | X | X |
| 4 | a | 10 mM phosphate in D2.5W | 8.0 |   |   |   |   |   |   |   |
|   | b |   |   |   |   |   |   |   |   |   |
| 5 | a | 10 mM phosphate in D5W | 1.0 |   |   | X | X | X | X | X |
|   | b |   |   |   |   | X | X | X | X | X |
| 6 | a | 10 mM phosphate in D5W | 0.1 | X | X | X | X | X | X | X |
|   | b |   |   | X | X | X | X | X | X | X |

5.7.2 Example 10: Compound of Formula (1)—Dosing Solution Stored at 2° C.-8° C. Followed by Storage at 25° C.

The stability of dosing solutions of the compound of formula (1) prepared from a CAPTISOL® concentrate diluted into commercially available IV diluents was prepared as described in Example 9. The solutions were assessed at 2° C.-8° C. over 24 hours followed by storage at 25° C. over 48 hours. As shown in Table 18, recoveries of the compound of formula (1) were generally higher than for the corresponding samples stored at 25° C. for all dosing solutions (see Table 16 from previous example), suggesting improved stability for dosing solutions prepared and stored at 2° C.-8° C. prior to storage at a temperature of 25° C.

TABLE 18

Results of Dosing Solution Stability Evaluation at 2° C.-8° C. and 25° C., Percent Recovery

| Sample # | Diluent | Compound of Formula (1) mg/mL | Compound of Formula (1) mg/mL t0 (group A) 2-8° C. | t0 (group B) 2-8° C. | 24 h (A) 2-8° C. | 24 h (B) 2-8° C. | 32 h (A) 8 h at 25° C. | 36 h (A) 12 h at 25° C. | 40 h (B) 16 h at 25° C. | 48 h (A) 24 h at 25° C. | 72 h (A) 48 h at 25° C. |
|---|---|---|---|---|---|---|---|---|---|---|---|
| 1 | 10 mM acetate in D2.5W | 8.0 | 7.13 | 6.91 | 99% | 103% | 101% | 99% | 103% | 97% | 99% |
| 2 | 10 mM acetate in D5W | 1.0 | 0.89 | 0.89 | 99% | 100% | 98% | 98% | 93% | 95% | 92% |
| 3 | 10 mM acetate in D5W | 0.1 | 0.10 | 0.10 | 97% | 97% | 92% | 89% | 67% | 82% | 73% |
| 4 | 10 mM phosphate in D2.5W | 8.0 | 7.18 | 7.08 | 100% | 102% | 99% | 99% | 100% | 97% | 97% |
| 5 | 10 mM phosphate in D5W | 1.0 | 0.89 | 0.88 | 99% | 101% | 95% | 93% | 90% | 87% | 81% |
| 6 | 10 mM phosphate in D5W | 0.1 | 0.11 | 0.10 | 97% | 97% | 89% | 86% | 76% | 76% | 63% |

5.7.3 Example 11: Compound of Formula (2)—Dosing Solution Stored at 25° C.

A series of dosing solutions of the compound of formula (2) for IV administration was assessed. The selected concentrate of compound of formula (2), prepared at 30 mg/mL in a vehicle of 30% CAPTISOL® at pH 4.0, was evaluated at low, mid, and high concentrations (0.1, 1 and 5 mg/mL, respectively) upon dilution into various dosing solutions. For dilution of the compound of formula (2) to 0.1 and 1 mg/mL, three dosing solutions were evaluated; 1) D5W, 2) D5W with 5 mM K-phosphate (pH=6), and 3) D5W with 20 mM K-phosphate (pH=6). To maintain iso-osmolality for dilutions of the compound of formula (2) to 5 mg/mL, the concentration of dextrose in the dosing solutions was reduced to 2.5% (w/v). Thus, the dosing solutions evaluated were; (1) D2.5W, (2) D2.5W with 5 mM K-phosphate (pH=6), and (3) D2.5W with 20 mM K-phosphate (pH=6).

The potential dosing solutions were assessed for visual appearance, pH, osmolality, and concentration and purity by HPLC (XBridge Phenyl Column (Waters); UV absorbance detector at 272 nm; mobile phase a step gradient of aqueous acetonitrile containing 0.1% (v/v) formic acid) after approximately 0, 16, 24, and 48 hours of storage at 25° C. All samples were clear, colorless solutions—with the sole exception of 5 mg/mL of the compound of formula (2) in D2.5W with 5 mM phosphate which had a clear, light yellow appearance after 48 hours at 25° C. All solutions were iso-osmotic (290+/−50 mOsm/kg)—with the sole exception of 1 mg/mL of the compound of formula (2) in D5W with 20 mM phosphate which had an osmolality of approximately 350 mOsm/kg. Furthermore, with the exception of 5 mg/mL of the compound of formula (2) in D2.5W with 5 mM phosphate, all other dosing solutions sustained the compound of formula (2) at the target concentrations of 0.1, 1 and 5 mg/mL over 48 hours. In addition, the known degradant, the compound of formula (101), formed by release of the active HNO group, was observed after 16 hours at 25° C. in small quantities by HPLC in the dosing solutions containing phosphate buffer. The observed amount of the compound of formula (101) was on the order of the limit of detection of the method.

The stability of 5 mg/mL of the compound of formula (2) dosing solutions was further evaluated as a function of pH and buffer. A concentrated solution of the compound of formula (2), prepared at 30 mg/mL in a vehicle of 30% CAPTISOL® at pH 4.0, was diluted to 5 mg/mL into four potential dosing solutions. The four dosing solutions were evaluated: 1) D2.5W, 5 mM K-phosphate (pH=6.0), 2) D2.5W with 5 mM K-citrate (pH=6.0), 3) D2.5W, 5 mM K-citrate (pH=5.0), and 4) D2.5W, 5 mM K-acetate (pH=5.0). All dosing solutions of the compound of formula (2) were iso-osmotic (290+/−50 mOsm/kg). After approximately 24 and 48 hours of storage at 25° C., the dosing solutions were assessed for visual appearance, pH, and concentration and purity by HPLC. The non-phosphate dosing solutions were clear, colorless and sustained the compound of formula (2) at the target concentration of 5 mg/mL over 48 hours; while consistent with the dosing solution screen, the 5 mg/mL compound of formula (2) in D2.5W with 5 mM phosphate (pH 6.0) dosing solution was clear, light yellow in appearance with only 60% recovery of the compound of formula (2) after 48 hours. Furthermore, the known degradant, the compound of formula (101), was observed in small quantities by HPLC in all samples except 5 mg/mL of the compound of formula (2) in D2.5W, 5 mM citrate (pH 5.0).

After 7 days of storage at 25° C. the non-phosphate dosing solutions were still clear and colorless in appearance. The smallest increase in acidity over the 7 days was measured for the 5 mg/mL of the compound of formula (2) in D2.5W, 5 mM citrate pH 6.0 dosing solution, while the D2.5W, 5 mM citrate pH 5.0 dosing solution had the smallest change in pH over the initial 24-48 h. Furthermore, after 14 days of storage at 25° C. the samples with dosing solution containing 5 mM citrate pH 6.0 were still clear, colorless solutions, while the dosing solutions containing either 5 mM citrate or 5 mM acetate at pH 5.0 were clear, yellow solutions. The results are summarized in Table 19.

TABLE 19

Recovery of the Compound of Formula (2) from 5 mg/mL Dosing Solutions

| Dosing Solution | Sample | Time Point | | |
|---|---|---|---|---|
| | | 0 h | 24 h | 48 h |
| (1). D2.5W, 5 mM phosphate, pH 6.0 | 1 | 101% | 100% | 60.7% |
| | 2 | 100% | 100% | 62.8% |
| (2). D2.5W, 5 mM citrate, pH 6.0 | 1 | 101% | 98.6% | 96.7% |
| | 2 | 101% | 98.8% | 96.5% |
| (3). D2.5W, 5 mM citrate, pH 5.0 | 1 | 101% | 100% | 99.1% |
| | 2 | 100% | 102% | 99.3% |
| (4). D2.5W, 5 mM acetate, pH 5.0 | 1 | 95.6% | 95.4% | 95.4% |
| | 2 | 96.0% | 96.8% | 94.8% |

5.8 Example 12: Evaluation of CAPTISOL®/Nitroxyl Donor Ratios

The compound of formula (1) was chosen as a model nitroxyl donor. A stability assessment was performed with concentrate solutions containing molar ratios of CAPTISOL® (MW 2163 g/mol) to the compound of formula (1) (MW 177.18 g/mol) selected based on projected toxicology studies. The concentrates evaluated are summarized in Table 20. Concentrate samples were prepared by combining the appropriate amounts of solid and vehicle, and upon complete dissolution, the pH of each sample was adjusted to 4.0 by adding 1 N NaOH. The samples were prepared on a 1.8-mL scale. Aliquots of each solution were stored at 25° C.

TABLE 20

Summary of Concentrate Samples Evaluated

| Sample # | % CAPTISOL® (w/v) | Compound of Formula (1), mg/mL | Target pH | Molar Ratio, CAPTISOL®:Compound of Formula (1) |
|---|---|---|---|---|
| C11 | 10% | 40 | 4.0 | 0.20 |
| C12 | 20% | 40 | 4.0 | 0.41 |
| C13 | 30% | 40 | 4.0 | 0.61 |

Each concentrate solution was additionally diluted into IV diluents to the highest and lowest concentrations expected to be administered during toxicology studies (8 mg/mL and 0.02 mg/mL of the compound of formula (1), respectively). The dosing solutions evaluated are summarized in Table 21. The vehicles were selected to produce administrable formulations approximately isoosmotic with human blood (about 290 mOsm/kg water). The dilutions were performed volumetrically, on a 5-mL scale for the higher concentration samples and on a 25-mL scale for the lower concentration samples. Aliquots of each solution were stored at 25° C.

TABLE 21

Summary of Dosing Solutions Evaluated

| Sample # | Concentrate # | Vehicle | Compound of Formula (1), mg/mL | Dilution Factor | Final % CAPTISOL® (about w/v) |
|---|---|---|---|---|---|
| D7 | C11 | D5W | 8 | 5 | 2% |
| D8 | C12 | D5W | 8 | 5 | 4% |
| D9 | C13 | D2.5W | 8 | 5 | 6% |
| D10 | C11 | D5W | 0.02 | 2000 | .005% |
| D11 | C12 | D5W | 0.02 | 2000 | .010% |
| D12 | C13 | D5W | 0.02 | 2000 | .015% |

Upon preparation (t0) and after 1 day (24 hours) and 2 days (48 hours) of storage, samples were removed from storage and their visual appearances noted. All concentrate samples remained clear and pale yellow over the 48 hours. Dosing solutions D7-D9 were clear and very pale at each time point and dosing solutions D10-D12 remained clear and colorless. At each time point, samples were analyzed by HPLC (XBridge Phenyl Column (Waters); UV absorbance detector at 272 nm; mobile phase a step gradient of aqueous acetonitrile containing 0.1% (v/v) formic acid). The results of the HPLC analysis of the concentrates are summarized in Table 22. The results of the HPLC analysis of the dosing solutions are summarized in Table 23. Complete recovery (within the accuracy of the method) was achieved over 48 hours in all concentrates and dosing solutions. The major degradation product of the compound of formula (1) (i.e., the compound of formula (100)) was observed at low concentrations in the dosing solutions prepared to 0.02 mg/mL. The degradant concentration did not increase over time and did not affect recovery of the compound of formula (1).

TABLE 22

Results of HPLC Analysis of Concentrate Samples

| Sample # | % CAPTISOL® (w/v) | Compound of formula (1), mg/mL | | | Recovery from t0, % | |
|---|---|---|---|---|---|---|
| | | t = 0 | t = 1 d | t = 2 d | t = 1 d | t = 2 d |
| C11 | 10 | 39.4 | 39.9 | 38.2 | 101% | 97% |
| C12 | 20 | 40.9 | 39.9 | 40.6 | 97% | 99% |
| C13 | 30 | 40.6 | 40.2 | 40.1 | 99% | 99% |

TABLE 23

Results of HPLC Analysis of Dosing Solutions

| Sample # | Concentrate # | Concentration of Compound of Formula (1) mg/mL | Compound of Formula (1), mg/mL | | | Recovery from t0, % | |
|---|---|---|---|---|---|---|---|
| | | | t = 0 | t = 1 d | t = 2 d | t = 1 d | t = 2 d |
| D7 | C11 | 8.00 | 7.96 | 8.07 | 7.99 | 101% | 100% |
| D8 | C12 | 8.00 | 8.06 | 8.06 | 7.85 | 100% | 97% |
| D9 | C13 | 8.00 | 8.20 | 8.17 | 8.06 | 100% | 98% |
| D10 | C11 | 0.02 | 0.018 | 0.019 | 0.019 | 106% | 105% |

TABLE 23-continued

Results of HPLC Analysis of Dosing Solutions

| Sample # | Concentrate # | Concentration of Compound of Formula (1) mg/mL | Compound of Formula (1), mg/mL | | | Recovery from t0, % | |
|---|---|---|---|---|---|---|---|
| | | | t = 0 | t = 1 d | t = 2 d | t = 1 d | t = 2 d |
| D11 | C12 | 0.02 | 0.020 | 0.020 | 0.020 | 100% | 100% |
| D12 | C13 | 0.02 | 0.019 | 0.021 | 0.020 | 108% | 105% |

5.9 Synthesis of Compounds

The compounds disclosed herein can be made according to the methods disclosed below or by procedures known in the art. Starting materials for the reactions can be commercially available or can be prepared by known procedures or obvious modifications thereof. For example, some of the starting materials are available from commercial suppliers such as Sigma-Aldrich (St. Louis, Mo.). Others can be prepared by procedures or obvious modifications thereof disclosed in standard reference texts such as *March's Advanced Organic Chemistry* (John Wiley and Sons) and *Larock's Comprehensive Organic Transformations* (VCH Publishers).

Example 13: Preparation of N-Hydroxy-5-methylfuran-2-sulfonamide (1)

To a solution of hydroxylamine (0.92 mL of a 50% aqueous solution; 13.8 mmol) in THF (6 mL) and water (2 mL) cooled to 0° C. was added 5-methylfuran-2-sulfonyl chloride (1 g, 5.5 mmol) as a solution in THF (6 mL) dropwise so as to maintain the temperature below 10° C. The reaction was stirred for 5 minutes, after which time TLC (1:1 hexane:ethyl acetate (H:EA)) showed substantially complete consumption of the sulfonyl chloride. The reaction was diluted twice with 50 mL dichloromethane (DCM) and the organic portion was separated and washed with water (10 mL). The organic portion was dried over sodium sulfate, filtered and concentrated under reduced pressure. The product was chromatographed with a silica gel column eluting with heptanes:EtOAc followed by trituration with heptane to provide the title compound as a yellow solid (0.59 g, 61% yield). LC-MS $t_R$=0.91 min; $^1$H NMR (DMSO, 500 MHz) δ ppm 9.82 (1H, d, J=3.1 Hz), 9.64 (1H, d, J=3.2 Hz), 7.10 (1H, d, J=3.4 Hz), 6.36 (1H, d, J=3.4 Hz), 2.36 (3H, s).

Example 14: Preparation of N-Hydroxy-3-methanesulfonylbenzene-1-sulfonamide (2)

3-Methanesulfonylbenzene-1-sulfonyl chloride

The intermediate 3-methanesulfonylbenzene-1-sulfonyl chloride was synthesized according to the methods disclosed in Park et al., J Med. Chem. 51(21):6902-6915 (2008). Specifically, methyl sulfonyl benzene (110 g, 0.7 mol) was heated for 18 hours at 90° C. in chlorosulfonic acid (450 mL, 6.7 mol) after which time the reaction mixture was allowed to cool to a temperature of about 21° C. before slowly being poured onto crushed ice. The resulting slurry was twice extracted into EtOAc (2 L for each extraction). The organic portions were combined and washed with brine (50 mL) before being dried over sodium sulfate, filtered and concentrated under reduced pressure to provide the intermediate sulfonyl chloride as an off white solid (125 g, 75% yield). $^1$H NMR (400 MHz, CDCl$_3$) δ ppm 8.61 (1 h, t, J=1.7 Hz), 8.35-8.31 (2H, m), 7.90 (1H, t, J=7.9 Hz), 3.15 (3H, s).

N-Hydroxy-3-methanesulfonylbenzene-1-sulfonamide

To a solution of aqueous hydroxylamine (16 mL of a 50% aqueous solution, 245 mmol) in THF (150 mL) and water (25 mL) cooled to −5° C. was slowly added 3-methanesulfonylbenzene-1-sulfonyl chloride (25 g, 98 mmol) while maintaining a reaction temperature of less than 10° C. The reaction was maintained at this temperature until substantially complete consumption of the sulfonyl chloride was observed (about 5 min), after which time the reaction was diluted with DCM (250 mL), the organic portion was separated and washed twice with 50 mL of water. The aqueous extracts were combined and rewashed twice with DCM (250 mL for each wash). All of the organic portions were combined, dried over sodium sulfate, filtered and concentrated under reduced pressure to provide the title compound as a beige solid. Trituration was carried out using heptanes:EtOAc (1:1; v:v) to provide the title compound as a beige solid (14 g, 56% yield). LC-MS $t_R$=0.90 min; High Resolution Mass Spectroscopy (HRMS): theoretical (C$_7$H$_9$NO$_5$S$_2$)=249.9844, measured=249.9833; $^1$H NMR (500 MHz, DMSO-d$_6$) δ ppm 9.85 (2H, q, J=3.3 Hz), 8.31 (1H, t, J=1.6 Hz), 8.28 (1H, dt, J=7.8, 1.3 Hz), 8.14-8.19 (1H, m), 7.93 (1H, t, J=7.9 Hz), 3.32 (3H, s).

Example 15: Preparation of N-Hydroxy-5-methyl-1,2-oxazole-4-sulfonamide (3)

To a solution of hydroxylamine (0.45 mL of a 50% aqueous solution; 13.7 mmol) in THF (6 mL) and water (1 mL) cooled to 0° C. was added 5-methyl-1,2-oxazole-4-sulfonyl chloride (1.0 g, 5.5 mmol) portionwise so as to maintain the temperature below 10° C. The reaction was stirred for 10 minutes, after which time LC-MS showed complete consumption of the sulfonyl chloride. The reaction was diluted with DCM (50 mL) and the organic portion was separated and washed with water (10 mL). The organic portion was dried over sodium sulfate, filtered and concentrated under reduced pressure. The product was triturated with diethyl ether to provide the title compound as a off white solid (0.45 g, 46% yield). LC-MS $t_R$=0.66 min; HRMS: theoretical (C$_4$H$_6$N$_2$O$_4$S)=176.997, measured=176.9972; $^1$H NMR (500 MHz, DMSO-d$_6$) δ ppm 9.83 (1H, s), 9.68 (1H, br. s.), 8.77 (1H, s), 2.64 (3H, s).

Example 16: Preparation of N-Hydroxy-1-benzofuran-7-sulfonamide (4)

To a solution of hydroxylamine (0.76 mL of a 50% aqueous solution; 11.5 mmol) in THF (12 mL) and water (2 mL) cooled to 0° C. was added 1-benzofuran-7-sulfonyl chloride (1 g, 4.6 mmol) portionwise so as to maintain the temperature below 10° C. The reaction was stirred for 10 minutes, after which time TLC (heptane:EtOAc) showed substantially complete consumption of the sulfonyl chloride. The reaction was diluted with DCM (25 mL) and the organic portion was separated and washed with water (10 mL). The organic portion was dried over sodium sulfate, filtered and concentrated under reduced pressure. Trituration with heptane provided the title compound as an off white solid (0.63 g, 64% yield). LC-MS $t_R$=1.32; $^1$H NMR (500 MHz, DMSO) δ 9.75 (d, J=3.0 Hz, 1H), 9.66 (1H, d, J=3.1 Hz), 8.18 (1H, d, J=2.2 Hz), 8.01 (1H, d, J=6.8 Hz), 7.72 (1H, d, J=7.7 Hz), 7.45 (1H, t, J=7.7 Hz), 7.14 (1H, d, J=2.2 Hz).

Example 17: Preparation of 4-(Hydroxysulfamoyl)-N-(propan-2-yl)thiophene-2-carboxamide (5)

N-(Propan-2-yl)thiophene-2-carboxamide

A solution of propan-2-amine (9.7 mL, 112.6 mmol) in DCM (150 mL) was cooled at 0° C. with stirring under nitrogen. Thiophene-2-carbonyl chloride (11.0 mL, 102.3 mmol) was added dropwise and then ethyl diisopropylamine (19.5 mL, 112.6 mmol) was added. The reaction mixture was left to warm to a temperature of about 21° C. and stirring was continued for 18 hours after which time the reaction mixture was further diluted with DCM (100 mL) and washed with 1M HCl solution (2×50 mL), water (1×50 mL), saturated NaHCO$_3$ solution (1×25 mL) and brine (2×25 mL) before the organic layer was dried over magnesium sulfate, filtered and concentrated under reduced pressure to provide N-(propan-2-yl)thiophene-2-carboxamide as a white solid (18.1 g, 99.2% yield). LC-MS $t_R$=1.43 min; $^1$H NMR (500 MHz, chloroform-d) δ ppm 7.54-7.46 (1H, m), 7.43 (1H, d, J=5.0 Hz), 7.04 (1H, t, J=4.3 Hz), 6.00 (1H, br s), 4.31-4.16 (1H, m, J=6.6 Hz), 1.24 (6H, d, J=6.7 Hz).

5-[(Propan-2-yl)carbamoyl]thiophene-3-sulfonyl chloride

A solution of N-(propan-2-yl)thiophene-2-carboxamide (17.3 g, 102.3 mmol) in chlorosulfonic acid (68.1 mL, 1023.2 mmol) was heated at 100° C. for 2 hours, after which time the solution was allowed to cool to a temperature of about 21° C. and was carefully poured onto ice (500 mL). The aqueous solution was extracted into DCM (2×250 mL) and the combined organic portions were dried over magnesium sulfate, filtered and concentrated under reduced pressure to provide the desired compound as a mixture with 5-[(propan-2-yl)carbamoyl]thiophene-2-sulfonyl chloride which was separated with a silica gel column eluting with heptanes:EtOAc to provide the product as a white solid (9.9 g, 36.1% yield). LC-MS $t_R$=1.85 min; $^1$H NMR (250 MHz, chloroform-d) δ ppm 8.33 (1H, d, J=1.4 Hz), 7.82 (1H, d, J=1.4 Hz), 6.24 (1H, d, J=6.5 Hz), 4.27 (1H, qd, J=6.6, 14.4 Hz), 1.30 (6H, d, J=6.7 Hz).

4-(Hydroxysulfamoyl)-N-(propan-2-yl)thiophene-2-carboxamide

To a solution of hydroxylamine (6.1 mL of a 50% aqueous solution; 95.3 mmol) in THF (30 mL) and water (10 mL) cooled to 0° C. was added 5-[(propan-2-yl)carbamoyl]thiophene-3-sulfonyl chloride (9.9 g, 36.9 mmol) as a solution in THF (30 mL) dropwise so as to maintain the temperature below 10° C. The reaction was stirred for 10 minutes, after which time LC-MS showed complete consumption of the sulfonyl chloride. The reaction was diluted with DCM (100 mL) and the organic portion was separated and washed with water (50 mL). The aqueous layer was re-extracted with DCM (2×50 mL) and EtOAc (50 mL). All the organic portions were combined, dried over sodium sulfate, filtered and concentrated under reduced pressure. Trituration with heptanes:EtOAc provided the title compound as a white solid (6.4 g, 65.4% yield). LC-MS $t_R$=1.22 min; HRMS: theoretical ($C_8H_{12}N_2O_4S_2$)=263.0160, measured=263.j0164; $^1$H NMR (500 MHz, DMSO-d$_6$) δ ppm 9.69 (1H, d, J=3.2 Hz), 9.59 (1H, d, J=3.2 Hz), 8.61 (1H, d, J=7.6 Hz), 8.34 (1H, d, J=1.4 Hz), 8.10 (1H, d, J=1.1 Hz), 3.92-4.16 (1H, m), 1.15 (6H, d, J=6.6 Hz).

Example 18: Preparation of N-Hydroxy-1-benzofuran-3-sulfonamide (6)

1-Benzofuran-3-sulfonyl chloride

1-Benzofuran-3-sulfonyl chloride was synthesized according to the methods disclosed in Park et al., *Bioorg. Med. Chem. Letters* 18(14):3844-3847 (2008). Benzofuran (4.2 g, 35.6 mmol) was added to a solution of sulfuryl chloride (4.9 mL, 60.4 mmol) in DMF (13 mL) at 0° C. and the reaction was heated to 85° C. for 3 hours. After the reaction was substantially complete, as determined by TLC (heptanes:EtOAc), the reaction was cooled to a temperature of about 21° C. and poured onto ice. The product was extracted into EtOAc (2×50 mL) and dried over sodium sulfate, filtered and concentrated under reduced pressure. The product was chromatographed with a silica gel column eluting with heptanes:EtOAc to provide the sulfonyl chloride as a yellow oil (0.27 g, 3.5% yield). LC-MS $t_R$=2.06 min; $^1$H NMR (500 MHz, DMSO-d$_6$) δ ppm 7.93 (1H, s), 7.68-7.81 (1H, m), 7.54 (1H, dd, 0.9 Hz), 7.17-7.38 (2H, m).

N-Hydroxy-1-benzofuran-3-sulfonamide

To a solution of hydroxylamine (0.1 mL of a 50% aqueous solution; 3.0 mmol) in THF (1.25 mL) and water (0.25 mL) cooled to 0° C. was added 1-benzofuran-3-sulfonyl chloride (0.26 g, 1.2 mmol) portionwise so as to maintain the temperature below 10° C. The reaction was stirred for 10 minutes, after which time LC-MS showed complete consumption of the sulfonyl chloride. The reaction was diluted with DCM (10 mL) and the organic portion was separated and washed with water (5 mL). The organic portion was dried over sodium sulfate, filtered and concentrated under reduced pressure. The product was chromatographed with a silica gel column eluting with heptanes:EtOAc followed by trituration with heptanes:DCM to provide the title compound as a yellow solid (0.03 g, 12% yield). LC-MS $t_R$=1.45; $^1$H NMR (500 MHz, DMSO-d$_6$) δ ppm 9.75 (2H, s), 8.68 (1H, s), 7.86 (1H, d, J=7.7 Hz), 7.76 (1H, d, J=8.2 Hz), 7.36-7.57 (2H, m).

Example 19: Preparation of N-Hydroxy-5-methyl-2-(trifluoromethyl)furan-3-sulfonamide (7)

To a solution of hydroxylamine (0.66 mL of a 50% aqueous solution; 10.1 mmol) in THF (6 mL) and water (1 mL) cooled to 0° C. was added 5-methyl-2-(trifluoromethyl)furan-3-sulfonyl chloride (1 g, 4.0 mmol) portionwise so as to maintain the temperature below 10° C. The reaction was stirred for 5 minutes, after which time LC-MS showed complete consumption of the sulfonyl chloride. The reaction was diluted with DCM (25 mL) and the organic portion was separated and washed with water (10 mL). The organic portion was dried over sodium sulfate, filtered and concentrated under reduced pressure. The product was triturated with heptane to provide the title compound as an off white solid (0.7 g, 71% yield). LC-MS $t_R$=1.64 min; $^1$H NMR (500 MHz, DMSO-d$_6$) δ ppm 9.81 (1H, d, J=3.3 Hz), 9.68 (1H, d, J=3.2 Hz), 7.37 (1H, s), 2.60 (3H, s).

Example 20: Preparation of N-Hydroxy-5-methanesulfonylthiophene-3-sulfonamide (8)

5-Methanesulfonylthiophene-3-sulfonyl chloride and 5-methanesulfonylthiophene-2-sulfonyl chloride A solution of 2-methanesulfonylthiophene (1.0 g, 6.2 mmol) in chlorosulfonic acid (2.9 mL, 43.2 mmol) was heated at 90° C. for 1 hour, after which time the solution was allowed to cool to a temperature of about 21° C. and was carefully poured onto ice (20 mL). The aqueous solution was extracted into DCM (2×25 mL). The organic portions were combined, dried over sodium sulfate, filtered and concentrated under reduced pressure to provide the sulfonyl chloride as a mixture with 5-methanesulfonylthiophene-2-sulfonyl chloride. The mixture was chromatographed with a silica gel column eluting with heptanes:EtOAc only partially separated the two isomers and the sulfonyl chloride was taken on to the next step (0.5 g, 31% yield as a 85:15 mixture with the other isomer). LC-MS $t_R$=1.67 min; $^1$H NMR (500 MHz, DMSO-$d_6$) δ ppm 7.99 (1H, d, J=1.6 Hz), 7.69 (1H, d, J=1.6 Hz), 3.36 (3H, s).

N-Hydroxy-5-methanesulfonylthiophene-3-sulfonamide

To a solution of hydroxylamine (0.3 mL of a 50% aqueous solution; 4.8 mmol) in THF (6 mL) and water (1 mL) cooled to 0° C. was added a mixture of 5-methanesulfonylthiophene-3-sulfonyl chloride and 5-methanesulfonylthiophene-2-sulfonyl chloride (85:15 by LC-MS) (0.5 g, 1.9 mmol) portionwise so as to maintain the temperature below 10° C. The reaction was stirred for 5 minutes, after which time LC-MS showed complete consumption of the sulfonyl chloride. The reaction was diluted with DCM (10 mL) and the organic portion was separated and washed with water (5 mL). The organic portion was dried over sodium sulfate, filtered and concentrated under reduced pressure. The product was chromatographed by reverse phase neutral preparative HPLC to provide the title compound as a white solid (0.07 g, 14% yield). LC-MS $t_R$=0.94; $^1$H NMR (500 MHz, DMSO-$d_6$) δ ppm 9.85 (1H, d, J=2.8 Hz), 9.78 (1H, d, J=2.8 Hz), 8.65 (1H, d, J=1.6 Hz), 7.98 (1H, d, J=1.4 Hz), 3.46 (3H, s).

Example 21: 1-Acetyl-5-bromo-N-hydroxy-2,3-dihydro-1H-indole-6-sulfonamide (9)

1-(5-Bromo-2,3-dihydro-1H-indol-1-yl)ethan-1-one

To a solution of 5-bromo-2,3-dihydro-1H-indole (1.5 g, 7.5 mmol) in acetic acid (12 mL) was added acetyl chloride (3.57 g, 45.4 mmol). The reaction was heated to 90° C. until consumption of the starting material was substantially complete (c.a. 1 h) and the solvents removed under reduced pressure. The organic portion was diluted in ethyl acetate and washed with sodium bicarbonate solution. The combined organics were dried over sodium sulfate, filtered and concentrated under reduced pressure to provide the title compound as a brown solid (1.76 g, 99.99% yield). $^1$H NMR (250 MHz, DMSO-$d_6$) δ ppm 7.96 (1H, d, 8.7 Hz), 7.40 (1H, d, 0.8 Hz), 7.30 (1H, dd, 8.5, 2.0 Hz), 4.09 (2H, t, 8.6 Hz), 3.14 (2H, t, 8.5 Hz), 2.14 (3H, s).

1-Acetyl-5-bromo-2,3-dihydro-1H-indole-6-sulfonyl chloride 1-(5-Bromo-2,3-dihydro-1H-indol-1-yl)ethan-1-one (1.2 g, 5.0 mmol) and chlorosulfonic acid (3.5 mL, 30 mmol) were heated in a sealed tube to 80° C. for 18 hours. The reaction was quenched by pouring onto ice and the resulting solid was filtered and dried under reduced pressure then chromatographed with a silica gel column eluting with 40% heptane:ethyl acetate to provide the title compound as an off white solid (0.95 g, 56% yield). $^1$H NMR (250 MHz, DMSO-$d_6$) δ ppm 8.60 (1H, s), 7.37 (1H, s), 4.09 (2H, t, 8.6 Hz), 3.11 (2H, t, 8.5 Hz), 2.14 (3H, s).

1-Acetyl-5-bromo-N-hydroxy-2,3-dihydro-1H-indole-6-sulfonamide

To a solution of aqueous hydroxylamine (1.6 mL, 3.7 mmol, 50% aqueous), in THF (2.5 mL) and water (0.5 mL) at −10° C. was added 1-acetyl-5-bromo-2,3-dihydro-1H-indole-6-sulfonyl chloride (0.5 g, 1.48 mmol) portion wise maintaining and internal temperature of −5° C. Stirring was continued at low temperature until complete consumption of the sulfonyl chloride was observed by LC-MS. Diethyl ether was added and the reaction was washed with a 10% citric acid solution. The organics were dried over Na$_2$SO$_4$, filtered and concentrated under reduced pressure to provide 1-acetyl-5-bromo-N-hydroxy-2,3-dihydro-1H-indole-6-sulfonamide as an off white solid (0.32 g, 66% yield). $^1$H NMR (250 MHz, DMSO-$d_6$) δ ppm 9.44-9.76 (2H, m), 8.72 (1H, s), 7.68 (1H, s), 4.16 (2H, t, 8.6 Hz), 3.22 (2H, t, 8.8 Hz), 2.17 (3H, s); predicted [M−H]$^-$=332.9545; observed [M−H]$^-$=332.9553.

Example 22: 2-Chloro-N-hydroxy-5-(hydroxymethyl)benzene-1-sulfonamide (10)

2-Chloro-5-(hydroxymethyl)aniline

To a solution of 1-chloro-4-(hydroxymethyl)-2-nitrobenzene (4.5 g, 24 mmol) in EtOH (23 mL) and water (4.5 mL) was added iron (3.45 g, 84 mmol) and HCl (9 drops). The reaction was heated to 85° C. for 4 hours. The cooled reaction mixture was filtered through CELITE, washed with EtOAc and concentrated under reduced pressure and used directly in the next step (3.5 g, 95% yield). $^1$H NMR (250 MHz, DMSO-$d_6$) δ 7.09 (1H, d, 8.1 Hz), 6.76 (1H, d, 2.0 Hz), 6.47 (1H, dd, 8.1, 1.9 Hz), 5.10 (1H, t, 5.7 Hz), 4.34 (2H, d, 5.8 Hz).

2-Chloro-5-(hydroxymethyl)benzene-1-sulfonyl chloride

To a solution of 2-chloro-5-(hydroxymethyl)aniline (0.5 g, 3.1 mmol) in acetic acid (3.2 mL) and HCl (0.8 mL) cooled to 0° C. was added sodium nitrite (0.24 g, 3.5 mmol) portion wise maintaining an internal temperature <5° C. The reaction mixture was allowed to stir at 0° C. for 1 hour. Simultaneously, CuCl$_2$.H$_2$O (0.5 g, 3.1 mmol) was suspended in AcOH:water (3.2 mL:1.6 mL) at 0° C. and stirred at 0° C. until all CuCl$_2$ was in solution. SO$_2$ gas was condensed into a flask at −78° C. via the aid of a cold finger and the diazo compound and CuCl$_2$ solution added and the reaction warmed to 0° C. The reaction was allowed to warm to a temperature of about 25° C. over 2 hours. The reaction was quenched by addition to ice and extracted into DCM (2×10 mL). The organics were dried over sodium sulfate, filtered and concentrated under reduced pressure to provide the title compound as a yellow oil. The sulfonyl chloride was chromatographed with a silica gel column eluting with DCM to provide the sulfonyl chloride as a yellow oil (0.2 g, 26% yield). ¹H NMR (250 MHz, chloroform-d) δ 8.14 (1H, d, 1.2 Hz), 7.41-7.83 (2H, m), 4.79 (2H, s).

2-Chloro-N-hydroxy-5-(hydroxymethyl)benzene-1-sulfonamide

To a solution of hydroxylamine (0.45 mL of a 50% aqueous solution; 15.5 mmol) in tetrahydrofuran (5 mL) and water (1 mL) cooled to −5° C. was added 2-chloro-5-(hydroxymethyl)benzene-1-sulfonyl chloride (1.25 g, 5.1 mmol) as a solution in tetrahydrofuran (2.5 mL) dropwise so as to maintain the temperature below 0° C. The reaction was stirred until TLC indicated substantially complete consumption of starting material (approximately 30 minutes). The reaction was diluted with dichloromethane (50 mL) and the organic portion was washed with water (1 mL) before being separated and dried over sodium sulfate, filtered and concentrated under reduced pressure. Trituration with n-pentane provided the N-hydroxy-5-methylfuran-2-sulfonamide as an off-white solid (0.37 g, 30% yield). ¹H NMR (300 MHz, DMSO) δ 9.74 (2H, q, 3.0 Hz), 7.98 (1H, d, 1.4 Hz), 7.60 (2H, dt, 8.2, 5.0 Hz), 5.51 (1H, s), 4.57 (2H, s).

Example 23: 1-Acetyl-5-chloro-N-hydroxy-2,3-dihydro-1H-indole-6-sulfonamide (11)

1-(5-Chloro-2,3-dihydro-1H-indol-1-yl)ethan-1-one

To a solution of 5-chloro-2,3-dihydro-1H-indole (6.0 g, 39 mmol) in acetic acid (60 mL) was added acetyl chloride (18.4 g, 23 mmol). The reaction was heated to 80° C. until consumption of the starting material was substantially complete (c.a. 1 h) and the solvents removed under reduced pressure. The organic portion was diluted into ethyl acetate (200 mL) and washed with sodium bicarbonate solution (2×100 mL). The combined organics were dried over sodium sulfate, filtered and concentrated under reduced pressure to provide 1-(5-chloro-2,3-dihydro-1H-indol-1-yl)ethan-1-one as a brown solid (7.1 g, 93% yield). ¹H NMR (400 MHz, DMSO) δ 8.00 (1H, d, 8.6 Hz), 7.28 (1H, s), 7.18 (12H, dd, 8.6, 2.0 Hz), 4.10 (2H, t, 8.6 Hz), 3.13 (2H, t, 8.6 Hz), 2.14 (3H, s).

1-Acetyl-5-chloro-2,3-dihydro-1H-indole-6-sulfonyl chloride 1-(5-chloro-2,3-dihydro-1H-indol-1-yl)ethan-1-one (7 g, 36 mmol) and chlorosulfonic acid (16.68 g, 143 mmol) were heated to 70° C. for 18 hours. The reaction was quenched by addition to ice and the resulting solid obtained was extracted into ethyl acetate (250 mL). The resulting solution was washed with water (2×100 mL) and the organic portion was dried over sodium sulfate, filtered and concentrated under reduced pressure to provide the acetyl-5-chloro-2,3-dihydro-1H-indole-6-sulfonyl chloride. The product was chromatographed with a silica gel column eluting with 40-50% ethyl acetate:hexane to provide 1-acetyl-5-chloro-2,3-dihydro-1H-indole-6-sulfonyl chloride as a off white solid (7.2 g, 68.4% yield). ¹H NMR (400 MHz, DMSO) δ 8.56 (1H, s), 7.19 (1H, s), 4.09 (2H, t, 8.6 Hz), 3.10 (2H, t, 8.5 Hz), 2.14 (3H, s).

1-Acetyl-5-chloro-N-hydroxy-2,3-dihydro-1H-indole-6-sulfonamide

To a solution of hydroxylamine (1.8 mL of a 50% aqueous solution; 61.1 mmol) in tetrahydrofuran (40 mL) and water (5 mL) cooled to −5° C. was added 1-acetyl-5-chloro-2,3-dihydro-1H-indole-6-sulfonyl chloride (4.0 g, 13.6 mmol) as a solution in tetrahydrofuran (10 mL) dropwise so as to maintain the temperature below 0° C. The reaction was stirred for 30 minutes, and TLC indicated substantially complete consumption of starting material. The reaction was diluted with water (5 mL) and the resulting solid collected under vacuum and washed further with water (2×10 mL) before drying under vacuum to provide 1-acetyl-5-chloro-N-hydroxy-2,3-dihydro-1H-indole-6-sulfonamide as a white solid (3.0 g, 76% yield). ¹H NMR (400 MHz, DMSO) δ 9.65 (1H, s), 9.55 (1H, s), 8.72 (1H, s), 7.68 (1H, s), 4.15 (2H, t, 8.6 Hz), 3.22 (2H, t, 8.5 Hz), 2.17 (3H, s); predicted [M−H]⁻=289.005; observed [M−H]⁻=289.0059.

Example 24: 4,5-Dichloro-N-hydroxythiophene-2-sulfonamide (12)

To a solution of hydroxylamine (0.655 mL of a 50% aqueous solution; 10.0 mmol) in tetrahydrofuran (6 mL) and water (1 mL) cooled to −5° C. was added 4,5-dichlorothiophene-2-sulfonyl chloride (1.0 g, 4.0 mmol) as a solution in tetrahydrofuran (1 mL) dropwise so as to maintain the temperature below 0° C. The reaction was stirred until TLC indicated substantially complete consumption of starting material (approximately 10 minutes). The reaction was diluted with diethyl ether (20 mL) and the organic portion was washed with citric acid solution (2×1 mL) before being separated and dried over sodium sulfate, filtered and concentrated under reduced pressure. Trituration with diethyl ether:heptane provided 4,5-dichloro-N-hydroxythiophene-2-sulfonamide as a-white solid (0.35 g, 38% yield). ¹H NMR (250 MHz, DMSO-d₆) δ 10.06 (1H, d 2.9 Hz), 10.00 (1H, d, 2.7 Hz), 7.73 (1H, s); predicted [M−H]⁻=245.8853; observed [M−H]⁻=245.8845.

Example 25: N-Hydroxy-6-methoxy-1-benzofuran-2-sulfonamide (13)

2-(2-Formyl-5-methoxyphenoxy)acetic acid

An aqueous solution of sodium hydroxide (20 mL, 5.2 g, 131 mmol) was added to a mixture of 2-hydroxy-4-methoxybenzaldehyde (10 g, 65 mmol), chloroacetic acid (6.2 g, 65 mmol) and water (80 mL). The mixture was stirred slowly before heating under reflux for 16 hours after which time the reaction mixture was allowed to cool to a temperature of about 25° C. where upon the reaction mixture was acidified with concentrated HCl to pH 3. The resulting acidic solution was extracted into ethyl acetate (3×50 mL) before being dried over sodium sulfate and concentrated under reduced pressure to provide the desired compound as a brown oil which was used directly in the next step (11.5 g, 83% yield). LC-MS $t_R$=0.75 min, [M+H]⁺=211.29

6-Methoxy-1-benzofuran

Sodium acetate (21.0 g, 254 mmol) was added to a mixture of 2-(2-formyl-5-methoxyphenoxy)acetic acid (11.4 g, 54 mmol) in acetic anhydride (75 mL) and acetic acid (75 mL) and the reaction was heated to 140° C. for 18 hours. The reaction mixture was allowed to cool at a temperature of about 25° C. before addition of water (100 mL) and the resulting aqueous solution was extracted with ethyl acetate (3×20 mL). The combined organic phases were washed with saturated sodium bicarbonate solution (3×30 mL), dried over sodium sulfate and concentrated under reduced pressure to provide the compound as a brown oil. The oil was chromatographed with a silica gel column eluting with 0.5% ethyl acetate in hexane to provide pale yellow oil (1.6 g, 20%) which was confirmed by $^1$H NMR. $^1$H NMR (400 MHz, CDCl$_3$) δ 7.53 (1H, t, 3.3 Hz) 7.45 (1H, d, 8.5 Hz), 7.04 (1H, d, 2.0 Hz), 6.88 (1H, dd, 8.5, 2.3 Hz), 6.70 (1H, dd, 2.2, 0.9 Hz), 3.86 (3H, s).

6-Methoxy-1-benzofuran-2-sulfonyl chloride

To a solution of 6-methoxy-1-benzofuran (1.6 g, 10.8 mmol) in THF (20 mL) at −78° C. was added n-BuLi (2.5 M solution in hexanes, 4.8 mL, 11.8 mmol) drop wise and stirring was continued at this temperature for 1 hour. Sulfur dioxide gas was bubbled into the reaction mixture maintaining the temperature of −50° C. for 1 hour and stirring was continued at this temperature for a further 1 hour. To this solution was added N-chlorosuccinamide (2.2 g, 16 mmol) and the reaction mixture was warmed from at −20° C. to a temperature of about 25° C. over 18 hours. The reaction mixture was quenched with water (25 mL) and the organics extracted into ethyl acetate (2×20 mL), dried over sodium sulfate, filtered and concentrated under reduced pressure. The sulfonyl chloride was chromatographed with a silica gel column eluting with 2% ethyl acetate in hexane to provide a green solid (0.8 g, 30% yield). $^1$H NMR (400 MHz, CDCl$_3$) δ 7.61 (1H, d, 8.8 Hz), 7.59 (1H, d, 0.9 Hz), 7.09 (1H, d, 2.1 Hz), 7.05 (1H, dd, 8.8, 2.2 Hz), 3.91 (s, 3H).

N-Hydroxy-6-methoxy-1-benzofuran-2-sulfonamide

To a solution of aqueous hydroxylamine (1.6 mL of a 50% solution, 33.0 mmol) in THF (18 mL) was added 6-methoxy-1-benzofuran-2-sulfonyl chloride solution (2.3 g, 9.3 mmol) in THF (6 mL) drop wise at 0° C. The reaction was stirred for 30 minutes, and TLC indicated substantially complete consumption of the starting material. The reaction mixture was diluted with diethyl ether (50 mL) and washed with water (2×15 mL), dried over sodium sulfate and concentrated under reduced pressure to provide the compound which was tritiated using 5% DCM pentane yielding the desired product as an off white solid (0.9 g, 40% yield). $^1$H NMR (400 MHz, DMSO) δ 10.13 (1H, d, 2.2 Hz), 9.80 (1H, d, 1.9 Hz), 7.69 (1H, d, 8.7 Hz), 7.63 (1H, d, 0.9 Hz), 7.32 (1H, d, 2.0 Hz), 7.03 (1H, dd, 8.7, 2.2 Hz), 3.85 (3H, s).

Example 26:
2-Fluoro-N-hydroxy-4-methylbenzene-1-sulfonamide (14)

To a solution of hydroxylamine (1.5 mL of a 50% aqueous solution; 23.9 mmol) in tetrahydrofuran (12 mL) and water (2 mL) cooled to −10° C. was added 2-fluoro-4-methylbenzene-1-sulfonyl chloride (2.0 g, 9.6 mmol) portion wise so as to maintain the temperature below 0° C. The reaction was stirred for 5 minutes, after which time LC-MS indicated complete consumption of starting material. The reaction was diluted with diethyl ether (30 mL) and the organic portion was washed with 10% citric acid solution (10 mL) before being separated and dried over magnesium sulfate, filtered and concentrated under reduced pressure. Trituration with heptanes:diethyl ether provided the N-hydroxy-sulfonamide as an off-white solid (1.06 g, 58% yield). $^1$H NMR (500 MHz, DMSO-d$_6$) δ 9.67 (2H, s), 7.69 (1H, t, 7.8 Hz), 7.29 (1H, d, 11.5 Hz), 7.23 (1H, d, 8.0 Hz), 2.40 (3H, s); predicted [M−H]$^-$=204.0131; observed [M−H]$^-$=204.0175.

Example 27:
N-Hydroxy-2,1,3-benzothiadiazole-5-sulfonamide (15)

To a solution of aqueous hydroxylamine (0.7 mL of a 50% solution, 10.65 mmol) in tetrahydrofuran (6 mL) and water (1 mL) cooled to −5° C. was slowly added 2,1,3-benzothiadiazole-5-sulfonyl chloride (1.0 g, 4.3 mmol) maintaining a reaction temperature of less than 10° C. The reaction was maintained at this temperature until complete consumption of the sulfonyl chloride was observed by LC-MS (about 5 min.), after which time the reaction was diluted with ethyl acetate (20 mL) and the organic portion was separated, washed with water (2×5 mL), dried over sodium sulfate, filtered and concentrated under reduced pressure to provide the N-hydroxysulfonamide as an orange solid, further washing with sodium bicarbonate solution (10 mL) was required to remove sulfinic acid impurities. Trituration was carried out using heptanes:DCM (9:1, v:v) to provide the title compound as a orange solid (0.53 g, 54% yield). $^1$H NMR (500 MHz, DMSO-d$_6$) δ 9.94 (1H, d, 3.2 Hz), 9.84 (1H, d, 3.2 Hz), 8.62-8.53 (1H, m), 8.42-8.32 (1H, m), 8.04 (1H, dd, 9.2, 1.7 Hz).

Example 28:
N-Hydroxy-4-methanesulfonylthiophene-2-sulfonamide (16)

3-(Methylsulfanyl)thiophene

To a solution of 3-bromothiophene (3.3 g, 0.02 mol) in heptane (30 mL) at −40° C. was added a solution of n-butyllithium (8.5 mL of a 2.5M solution in hexanes) dropwise. Tetrahydrofuran (3 mL) was added to the flask and the 3-lithiothiophene precipitated as a white solid and the reaction mixture was warmed to a temperature of about 25° C. Methyl disulfide (1.97 mL, 0.02 mol) was added dropwise to the resulting solution and the reaction mixture was stirred for 1 hour at a temperature of about 25° C. Water (10 mL) was added to the flask, the organic layer separated, dried over sodium sulfate, filtered and concentrated under reduced pressure to provide 3-(methylsulfanyl)thiophene as a colorless oil (2.6 g, 98% yield). $^1$H NMR (500 MHz, chloroform-d) δ ppm 7.34 (1H, dd, 3.0 Hz), 7.01 (1H, dd, J=5.0, 1.3 Hz), 6.99 (1H, dd, 1.3 Hz), 2.49 (3H, s).

3-Methanesulfonylthiophene

To a solution of 3-(methylsulfanyl)thiophene (2.6 g, 19.96 mmol) in acetic acid (20 mL) was added hydrogen peroxide (4.53 mL of a 30% aqueous solution, 39.93 mmol). The reaction was heated to reflux for 3 hours and allowed to cool to a temperature of about 25° C. for 18 hours before the acetic acid was removed under reduced pressure. The resulting organics were dissolved in ethyl acetate (30 mL) and the whole was washed with saturated sodium bicarbonate solution (2×10 mL). The organic layer was dried over sodium sulfate, filtered and concentrated under reduced pressure to provide a yellow oil which solidified on standing and was used directly in the next step (2.2 g, 67.9% yield). $^1$H NMR (500 MHz, chloroform-d) δ ppm 8.11 (1H, dd, J=3.1, 1.2 Hz), 7.49 (1H, dd, J=5.1, 3.1 Hz), 7.43 (1H, dd, J=5.2, 1.3 Hz), 3.11 (3H, s).

4-Methanesulfonylthiophene-2-sulfonyl chloride

Chlorosulfonic acid (8.11 mL, 0.12 mol) was added to 3-methanesulfonylthiophene (2.2 g, 13.56 mmol) and the suspension was heated to 90° C. for 1 hour. The solution was allowed to cool to a temperature of about 25° C. and poured onto ice (100 mL). The sulfonyl chloride was extracted into dichloromethane (3×50 mL) dried over sodium sulfate, filtered and concentrated under reduced pressure to provide the title compound as a fawn solid (3.16 g, 89% yield). $^1$H NMR (500 MHz, chloroform-d) δ ppm 8.50 (1H, d, J=1.6 Hz), 8.17 (1H, d, J=1.6 Hz), 3.19 (3H, s).

N-Hydroxy-4-methanesulfonylthiophene-2-sulfonamide

To a solution of aqueous hydroxylamine (2.03 mL of a 50% aqueous solution, 30.68 mmol) in tetrahydrofuran (12 mL) and water (3 mL) cooled to −5° C. was slowly added 4-methanesulfonylthiophene-2-sulfonyl chloride (3.2 g, 12.27 mmol) maintaining a reaction temperature of less than 10° C. The reaction was maintained at this temperature until substantially complete consumption of the sulfonyl chloride was observed by TLC (about 15 min.), after which time the reaction was diluted with diethyl ether (25 mL) and the organic portion was separated, washed with water (2×10 mL), dried over sodium sulfate, filtered and concentrated under reduced pressure to provide the N-hydroxysulfonamide as an off white solid. Trituration was carried out using diethyl ether to provide the title compound as an off white solid (1.34 g, 42.4% yield). LC-MS $t_R$=0.91 min, [M−H]$^-$=256; $^1$H NMR (500 MHz, DMSO-d$_6$) δ ppm 10.02 (1H, d, J=3.0 Hz), 9.96 (1H, d, J=3.2 Hz), 8.73 (1H, d, J=1.6 Hz), 7.98 (1H, d, J=1.6 Hz), 3.33 (3H, s).

Example 29: 5-Bromo-N-hydroxy-2-methoxybenzene-1-sulfonamide (17)

To a solution of aqueous hydroxylamine (2.89 mL of a 50% solution, 43.78 mmol) in tetrahydrofuran (30 mL) and water (5 mL) cooled to −5° C. was slowly added 5-bromo-2-methoxybenzene-1-sulfonyl chloride (5 g, 17.51 mmol) maintaining a reaction temperature of less than 10° C. The reaction was maintained at this temperature until complete consumption of the sulfonyl chloride was observed by LC-MS (about 5 min), after which time the reaction was diluted with dichloromethane (50 mL) and the organic portion was separated, washed with water (2×10 mL), dried over sodium sulfate, filtered and concentrated under reduced pressure to provide the N-hydroxysulfonamide as an off white solid. Trituration was carried out using heptanes:DCM (1:1, v:v) to provide the title compound as an off white solid (2.94 g, 60% yield). LC-MS $t_R$=1.66 min, [M−H]$^-$=281; $^1$H NMR (500 MHz, DMSO-d$_6$) δ 9.68 (s, 1H), 9.39-9.17 (m, 1H), 7.85 (dd, J=8.9, 2.6 Hz, 1H), 7.80 (d, J=2.5 Hz, 1H), 7.24 (d, J=8.9 Hz, 1H), 3.90 (s, 3H).

Example 30: 4-Chloro-N-hydroxy-2,5-dimethylbenzene-1-sulfonamide (18)

To a solution of aqueous hydroxylamine (3.45 mL of a 50% solution, 52.28 mmol) in tetrahydrofuran (30 mL) and water (5 mL) cooled to −5° C. was slowly added 4-chloro-2,5-dimethylbenzene-1-sulfonyl chloride (5 g, 20.91 mmol) maintaining a reaction temperature of less than 10° C. The reaction was maintained at this temperature until complete consumption of the sulfonyl chloride was observed by LC-MS (about 5 min), after which time the reaction was diluted with dichloromethane (50 mL) and the organic portion was separated, washed with water (2×10 mL), dried over sodium sulfate, filtered and concentrated under reduced pressure to provide the N-hydroxysulfonamide as an off white solid. Trituration was carried out using heptanes:DCM (1:1, v:v) to provide the title compound as a white solid (3.26 g, 66% yield). LC-MS $t_R$=1.86 min, [M−H]$^-$=234; $^1$H NMR (500 MHz, DMSO-d$_6$) δ 9.59 (s, 2H), 7.78 (s, 1H), 7.52 (s, 1H), 2.55 (s, 3H), 2.36 (s, 3H).

Example 31: N,N-Diethyl-5-(hydroxysulfamoyl)thiophene-2-carboxamide (19)

N,N-Diethylthiophene-2-carboxamide

To a solution of diethylamine (4.9 g, 68.2 mmol) in DCM (100 mL) was sequentially added triethylamine (6.9 g, 68.2 mmol) and thiophene-2-carbonyl chloride (10 g, 68.2 mmol) and the resulting solution was stirred for 8 hours at a temperature of about 25° C. The reaction mixture was diluted with DCM (50 mL) and washed with water (2×50 mL) and the organic phase was dried over sodium sulfate, filtered and concentrated under reduced pressure to provide the product as a brown liquid (11.0 g, 87% yield). $^1$H NMR (400 MHz, CDCl$_3$) δ 7.42 (1H, dd, 5.0, 1.1 Hz), 7.32 (1H, dd, 3.7, 1.1 Hz), 7.04 (1H, dd, 5.0, 3.6 Hz), 3.54 (4H, q, 7.1 Hz), 1.26 (6H, t, 7.1 Hz).

5-(Diethylcarbamoyl)thiophene-2-sulfonyl chloride

To an ice cold solution of N,N-diethylthiophene-2-carboxamide (15.0 g, 81.8 mmol) was added chlorosulfonic acid (38.2 g, 327 mmol) drop wise, and the resulting solution was stirred at 0° C. for 30 minutes before being heated to 80° C. for 12 hours. The reaction mixture was quenched by addition to ice and the resulting acidic solution was extracted into DCM (20 mL), dried over sodium sulfate filtered and concentrated under reduced pressure to give the sulfonyl chloride as a mixture of isomers. The desired compound was obtained by chromatographing with a silica gel column eluting with 18% EtOAc:hexane (1.9 g, 8% yield). $^1$H NMR (400 MHz, CDCl$_3$) δ 7.79 (1H, d, 4.1 Hz), 7.28 (1H, t, 3.6 Hz), 3.53 (4H, q, 7.1 Hz), 1.28 (6H, t, 7.1 Hz).

N,N-Diethyl-5-(hydroxysulfamoyl)thiophene-2-carboxamide

A solution of 5-(diethylcarbamoyl)thiophene-2-sulfonyl chloride (1.8 g, 6.3 mmol) in THF (20 mL) was added to a solution of aqueous hydroxylamine (0.5 g, 15.8 mmol) in water (5 mL) and THF (20 mL), maintaining a temperature of −10° C. to −5° C. The resulting reaction was stirred at this temperature for 40 minutes after which time the reaction was seen to be substantially complete by TLC. The reaction was poured into ethyl acetate (50 mL) and washed with water (20 mL). The organic layer was dried over sodium sulfate, filtered and concentrated under reduced pressure to give the title compound as an off white solid (1.9 g). The desired N-hydroxysulfonamide was isolated by trituration with DCM:n-pentane (2:8; v:v) to provide a white solid (1.0 g, 56% yield). $^1$H NMR (360 MHz, DMSO-d$_6$) δ 9.90 (1H, d, 3.2 Hz) 9.85 (1H, d, 3.2 Hz) 7.59 (1H, d, 4.1 Hz) 7.45 (1H, d, 4.1 Hz) 3.45 (4H, q, 6.8 Hz) 1.16 (6H, t, 6.4 Hz); predicted [M−H]$^-$=277.0317; observed [M−H]$^-$=277.0316.

Example 32: 5-Fluoro-N-hydroxy-2-methylbenzene-1-sulfonamide (20)

To a solution of aqueous hydroxylamine (1.5 mL of a 50% solution, 23.9 mmol) in tetrahydrofuran (10 mL) and water (2 mL) cooled to −5° C. was slowly added a solution of 5-fluoro-2-methylbenzene-1-sulfonyl chloride (2.0 g, 9.6 mmol) in tetrahydrofuran (2 mL) maintaining a reaction temperature of less than 10° C. The reaction was maintained at this temperature until complete consumption of the sulfonyl chloride was observed by LC-MS (about 10 min), after which time the reaction was diluted with diethyl ether (30 mL) and the organic portion was separated and washed with 1M citric acid solution (10 mL), dried over magnesium sulfate, filtered and concentrated under reduced pressure to provide the N-hydroxysulfonamide as an off white solid (0.64 g, 32.1% yield). $^1$H NMR (250 MHz, DMSO-$d_6$) δ ppm 9.77 (1H, m), 9.72 (1H, m), 7.59 (1H, dd, 8.7, 2.0 Hz), 7.49 (1H, m), 7.46 (1H, m), 2.58 (1H, d, 0.8 Hz); predicted [M−H]$^−$=204.0131; observed [M−H]$^−$=204.0129.

Example 33: N-Hydroxy-5-(morpholine-4-carbonyl)thiophene-2-sulfonamide (21)

4-[(Thiophen-2-yl)carbonyl]morpholine

To a solution of morpholine (3.3 mL, 37 mmol) and diisopropylethylamine (6.5 mL, 37 mmol) in dichloromethane (50 mL) cooled to 0° C. was added thiophene-2-carbonyl chloride (5 g, 34 mmol) dropwise. The reaction mixture was stirred for 18 hours at a temperature of about 25° C. before quenching by the addition of 1N HCl solution (20 mL). The organic portion was washed with water (10 mL) and dried over sodium sulfate, filtered and concentrated under reduced pressure to provide the title compound (7.01 g, 65% yield). $^1$H NMR (400 MHz, DMSO-$d_6$) δ ppm 7.76 (1H, dd, 5.0, 1.1 Hz), 7.42 (1H, dd, 3.7, 1.2 Hz), 7.12 (1H, dd, 4.9, 3.7 Hz), 3.53-3.71 (8H, m).

5-[(Morpholin-4-yl)carbonyl]thiophene-2-sulfonyl chloride

Chlorosulfonic acid (45.57 mL, 684.4 mmol) was added to 4-[(thiophen-2-yl)carbonyl]morpholine (13.5 g, 68.44 mmol) and the suspension was heated to 100° C. for 2 hours. The solution was allowed to cool to a temperature of about 25° C. and poured onto ice (500 mL). The sulfonyl chloride was extracted into dichloromethane (3×100 mL) dried over sodium sulfate, filtered and concentrated under reduced pressure to provide the title compound as a mixture of isomers (16.5 g) which were separated by silica gel column eluting with 0-50% ethyl acetate:heptanes gradient (4.15 g, 20.5% yield). $^1$H NMR (250 MHz, DMSO-$d_6$) δ ppm 7.19 (1H, d, J=3.7 Hz), 7.07 (1H, d, J=3.8 Hz), 3.62 (8H, s). The other isomer (5-(morpholine-4-carbonyl)thiophene-3-sulfonyl chloride) was isolated for use in the synthesis of the corresponding N-hydroxysulfonamide (1.4 g, 6.5% yield). $^1$H NMR (500 MHz, chloroform-d) δ ppm 8.35 (1H, d, J=1.4 Hz), 7.63 (1H, d, J=1.3 Hz), 3.78 (8H, s).

N-Hydroxy-5-[(morpholin-4-yl) carbonyl]thiophene-2-sulfonamide

To a solution of aqueous hydroxylamine (1.12 mL of a 50% solution, 16.91 mmol) in tetrahydrofuran (2 mL) and water (2 mL) cooled to −5° C. was slowly added a solution of 5-[(morpholin-4-yl)carbonyl]thiophene-2-sulfonyl chloride (2 g, 6.76 mmol) in tetrahydrofuran (10 mL) maintaining a reaction temperature of less than 10° C. The reaction was maintained at this temperature until complete consumption of the sulfonyl chloride was observed by LC-MS (about 10 min), after which time the reaction was diluted with diethyl ether (30 mL) and the organic portion was separated and washed with water (10 mL), dried over sodium sulfate, filtered and concentrated under reduced pressure to provide the N-hydroxysulfonamide as an off white solid. Trituration was carried out using heptane to provide the title compound as a white solid (0.24 g, 12.4% yield). LC-MS $t_R$=1.11 min, [M+H]$^+$=293; $^1$H NMR (500 MHz, DMSO-$d_6$) δ ppm 9.90 (1H, s), 9.85 (1H, s), 7.60 (1H, d, J=3.9 Hz), 7.48 (1H, d, J=3.9 Hz), 3.63 (8H, s).

Example 34: 5-(hydroxysulfamoyl)-N-(propan-2-yl)thiophene-2-carboxamide (22)

N-(Propan-2-yl)thiophene-2-carboxamide

To a solution of isopropylamine (3.2 mL, 37 mmol) and diisopropylethylamine (5.3 mL, 37 mmol) in dichloromethane (50 mL) cooled to 0° C. was added thiophene-2-carbonyl chloride (5 g, 34 mmol) dropwise. The reaction mixture was stirred for 18 hours at a temperature of about 25° C. before quenching by the addition of 1N HCl solution. The organic portion was washed with water and dried over sodium sulfate, filtered and concentrated under reduced pressure to provide the title compound (5.78 g, 99% yield).

5-[(Propan-2-yl)carbamoyl]thiophene-2-sulfonyl chloride

Chlorosulfonic acid (23 mL, 337 mmol) was added to N-(propan-2-yl)thiophene-2-carboxamide (5.7 g, 33.7 mmol) and the suspension was heated to 100° C. for 90 minutes. The solution was allowed to cool to a temperature of about 25° C. and poured onto ice (300 mL). The sulfonyl chloride was extracted into dichloromethane (3×100 mL) dried over sodium sulfate, filtered and concentrated under reduced pressure to provide the title compound as a mixture of isomers which were separated by silica gel column eluting with 0-30% ethyl acetate:heptanes gradient (1.6 g, 17.7% yield). $^1$H NMR (500 MHz, DMSO-$d_6$) δ ppm 7.97 (1H, d, 6.7 Hz), 7.30 (1H, d, 3.8 Hz), 6.83 (1H, d, 3.8 Hz), 3.71-3.82 (1H, m), 0.90 (6H, d, 6.7 Hz). The other isomer (5-[(propan-2-yl)carbamoyl]thiophene-3-sulfonyl chloride) was isolated from this synthesis and used to make the corresponding N-hydroxysulfonamide (2.3 g, 25.5% yield). $^1$H NMR (500 MHz, DMSO-$d_6$) δ ppm 8.36 (1H, d, 7.8 Hz), 7.91 (1H, d, 1.2 Hz), 7.64 (1H, d, 1.2 Hz), 4.01 (1H, sept., 6.8 Hz), 1.13 (6H, d, 6.6 Hz).

5-(Hydroxysulfamoyl)-N-(propan-2-yl)thiophene-2-carboxamide

To a solution of aqueous hydroxylamine (0.99 mL of a 50% solution, 15 mmol) in tetrahydrofuran (10 mL) and water (1.6 mL) cooled to −5° C. was slowly added 5-[(propan-2-yl)carbamoyl]thiophene-2-sulfonyl chloride (1.6 g, 5.98 mmol) portionwise maintaining a reaction temperature of less than 10° C. The reaction was maintained at this temperature until complete consumption of the sulfonyl chloride was observed by LC-MS (about 10 min), after which time the reaction was diluted with diethyl ether (30 mL) and the organic portion was separated and washed with water (10 mL), dried over sodium sulfate, filtered and concentrated under reduced pressure to provide the N-hydroxysulfonamide as a white solid (0.7 g, 44% yield). $^1$H NMR (500 MHz, DMSO-d$_6$) δ ppm 9.86 (1H, br. s.), 9.80 (1H, s), 8.57 (1H, d, 7.8 Hz), 7.81 (1H, d, 4.0 Hz), 7.63 (1H, d, 4.1 Hz), 3.95-4.21 (1H, m), 1.16 (6H, d, 6.6 Hz); predicted [M–H]$^-$=263.0160; observed [M–H]$^-$=263.0161.

Example 35:
N-Hydroxy-5-methanesulfonylthiophene-2-sulfonamide (23)

5-Methanesulfonylthiophene-2-sulfonyl chloride

Chlorosulfonic acid (14.4 mL, 215 mmol) was added to 2-methanesulfonylthiophene (5.0 g, 30.8 mmol) and the reaction was heated to 90° C. for 1 hour. The resulting colored solution was poured onto ice and the organic portion extracted into DCM (2×30 mL), dried over sodium sulfate, filtered and concentrated under reduced pressure to provide the desired sulfonyl chloride as a mixture with the undesired 2,4 isomer and the mixture was used directly in the synthesis of the corresponding N-hydroxysulfonamide (4.6 g, 26% yield). LC-MS t$_R$=1.92 min; [M–Cl+OH+H]$^+$=240.80; $^1$H NMR (250 MHz, DMSO-d$_6$) δ 7.57 (1H, d, 3.8 Hz), 7.18 (1H, d, 3.8 Hz), 3.31 (3H, s).

N-Hydroxy-5-methanesulfonylthiophene-2-sulfonamide

To a solution of aqueous hydroxylamine (1.6 mL of a 50% aqueous solution, 24 mmol) in THF (10 mL) and water (2 mL) at –10° C. was added 5-methanesulfonylthiophene-2-sulfonyl chloride (1.3 g, 4.8 mmol) portion wise maintaining and internal temperature of –5° C. Stirring was continued at low temperature until complete consumption of the sulfonyl chloride was observed by LC-MS. DCM (20 mL) was added and the reaction was washed with water (5 mL). The organics were dried over sodium sulfate, filtered and concentrated under reduced pressure to provide the desired N-hydroxysulfonamide as a mixture with the undesired 2,4 isomer as an off white solid. Separation of the two isomers was achieved by acidic reverse phase preparative HPLC yielding the desired 2,5-isomer (0.5 g, 41% yield). $^1$H NMR (500 MHz, DMSO-d$_6$) δ 10.09 (2H, s), 7.91 (1H, d, 4.0 Hz), 7.75 (1H, d, 4.0 Hz), 3.48 (s, 3H).

Example 36:
N-Hydroxy-2,1,3-benzothiadiazole-4-sulfonamide (24)

To a solution of aqueous hydroxylamine (0.7 mL of a 50% solution, 10.65 mmol) in tetrahydrofuran (6 mL) and water (1 mL) cooled to –5° C. was slowly added 2,1,3-benzothiadiazole-4-sulfonyl chloride (1.0 g, 4.3 mmol) maintaining a reaction temperature of less than 10° C. The reaction was maintained at this temperature until complete consumption of the sulfonyl chloride was observed by LC-MS (about 5 min), after which time the reaction was diluted with dichloromethane (20 mL) and the organic portion was separated, washed with water (2×5 mL), dried over sodium sulfate, filtered and concentrated under reduced pressure to provide the N-hydroxysulfonamide as a yellow solid which was triturated with heptane and dried under reduced pressure (0.59 g, 59.9% yield). LC-MS t$_R$=1.26 min, [M–H]$^-$=230; $^1$H NMR (500 MHz, DMSO-d$_6$) δ 9.73 (s, 2H), 8.45 (dd, J=8.8, 0.9 Hz, 1H), 8.28 (dd, 0.9 Hz, 1H), 7.92 (dd, J=8.8, 7.1 Hz, 1H); predicted [M–H]$^-$=229.9694; observed [M–H]$^-$=229.9687.

Example 37:
N-Hydroxy-2-methoxybenzene-1-sulfonamide (25)

To a solution of hydroxylamine HCl (1.31 g, 18.9 mmol) in water (1.6 mL) cooled to 0° C. was added a solution of potassium carbonate (2.62 g, 18.9 mmol) in water (2.4 mL) dropwise maintaining an internal reaction temperature between 5° C. and 15° C. The reaction mixture was stirred for 15 minutes, whereupon tetrahydrofuran (8 mL) and methanol (2.0 mL) were added. 2-methoxybenzene-1-sulfonyl chloride (1.96 g, 9.48 mmol) was added portionwise maintaining a temperature below 15° C. and the reaction mixture was stirred at 5° C. until substantially complete consumption of the sulfonyl chloride was observed by TLC. The resulting suspension was concentrated under reduced pressure to remove any volatiles and the aqueous suspension was extracted with diethyl ether (2×50 mL). The organic portion was dried over magnesium sulfate, filtered and concentrated under reduced pressure to provide the N-hydroxy sulfonamide as a white solid (0.4 g, 21% yield). $^1$H NMR (400 MHz, DMSO-d$_6$) δ ppm 9.53 (1H, d, J=3.4 Hz), 8.99 (1H, d, J=3.4 Hz), 7.76 (1H, dd, 1.7 Hz), 7.62-7.67 (1H, m), 7.23 (1H, d, J=8.3 Hz), 7.11 (1H, t, J=7.6 Hz), 3.89 (3H, s); predicted [M–H]$^-$=202.0174; observed [M–H]$^-$=202.0155.

Example 38: N-Hydroxypyridine-3-sulfonamide (26)

To a solution of aqueous hydroxylamine (11.07 mL of a 50% solution, 167.5 mmol) in tetrahydrofuran (40 mL) cooled to –15° C. was slowly added a suspension of pyridine-3-sulfonyl chloride (11.9 g, 67 mmol) in THF (30 mL) and the temperature was remained below 2° C.-3° C. throughout the addition and stirring was continued for an additional 10 minutes, after which time LC-MS showed complete consumption of the sulfonyl chloride. Dichloromethane (50 mL) and water (25 mL) were added and the mixture was shaken, the two layers were separated and the aqueous layer was further extracted with dichloromethane (1x 50 mL). The combined organic layers were dried over magnesium sulfate and concentrated to give a solid which was insoluble in dichloromethane and was triturated with dichloromethane:heptane (1:1 v:v) to give the title compound as a white solid (3.47 g, 29.7% yield). $^1$H NMR (500 MHz, DMSO-d$_6$) δ ppm 9.85 (1H, d, J=2.8 Hz), 9.80 (1H, s), 8.95 (1H, d, J=2.2 Hz), 8.87 (1H, dd, J=4.8, 1.5 Hz), 8.20 (1H, dt, 1.9 Hz), 7.69 (1H, dd, J=8.0, 4.9 Hz), predicted [M+H]$^+$=175.0177; observed [M+H]$^+$=175.0172.

Example 39:
N-Hydroxy-3,5-dimethyl-1,2-oxazole-4-sulfonamide (27)

To a solution of aqueous hydroxylamine (22.79 mL of a 50% solution, 0.35 mol) in tetrahydrofuran (160 mL) and water (27 mL) cooled to –5° C. was slowly added dimethyl-1,2-oxazole-4-sulfonyl chloride (27 g, 138.02 mmol) portionwise maintaining a reaction temperature of less than 10° C. The reaction was maintained at this temperature until complete consumption of the sulfonyl chloride was observed by LC-MS (about 10 min), after which time the reaction was diluted with dichloromethane (250 mL) and the organic portion was separated, washed with water (2×30 mL), dried over sodium sulfate, filtered and concentrated under reduced pressure to provide the N-hydroxysulfonamide as a white solid. Trituration was carried out using heptanes to provide the title compound as a white solid (16.16 g, 60.9% yield). LC-MS $t_R$=1.08 min, [M+H]$^+$=193; $^1$H NMR (500 MHz, DMSO-$d_6$) δ 9.79 (d, J=2.8 Hz, 1H), 9.64 (d, J=2.8 Hz, 1H), 2.60 (s, 3H), 2.35 (s, 3H).

Example 40: N-Hydroxy-5-(morpholine-4-carbonyl)thiophene-3-sulfonamide (28)

5-(Morpholine-4-carbonyl)thiophene-3-sulfonyl chloride

To 4-(thiophene-2-carbonyl)morpholine (15 g, 76.04 mmol) was added chlorosulfonic acid (35.44 g, 304.18 mmol) dropwise at −5 to 0° C. under a nitrogen atmosphere. The temperature was maintained at 0° C. for 30 min before stirring at a temperature of about 25° C. for 1 hour. No reaction was observed and the temperature was increased to 80° C. for another 12 hours. The resulting slurry was poured onto ice water (500 mL) and extracted into dichloromethane (30 mL) before being dried over sodium sulfate and concentrated under reduced pressure to give the compound as a mixture of isomers. The sulfonyl chloride was chromatographed with a silica gel column eluting with EtOAc:hexane (30% EtOAc) to provide the title compound as a colorless oil (3.0 g, 13.34% yield). LC-MS $t_R$=1.18 min, [M+H]$^+$= 293; $^1$H NMR (400 MHz, CDCl$_3$) δ 8.35 (d, J=1.3 Hz, 1H), 7.62 (d, J=1.4 Hz, 1H), 4.12 (d, J=7.1 Hz, 1H), 3.78 (s, 8H), 2.09 (s, 1H), 2.05 (s, 1H), 1.26 (t, J=7.1 Hz, 1H).

Example 41: 1-N-Hydroxy-2-N-(propan-2-yl)benzene-1,2-disulfonamide (29)

2-Fluoro-N-(propan-2-yl)benzene-1-sulfonamide

A solution of 2-fluorobenzenesulfonyl chloride (3.6 mL, 27.4 mmol) in DCM (50 mL) was cooled at 0° C. and propan-2-amine (3.5 mL, 41.2 mmol) was added followed by pyridine (3.3 mL, 41.2 mmol). The reaction was left to warm to a temperature of about 25° C. and stirring was continued for 1 hour. The reaction was quenched by the addition of 1M sodium hydroxide solution (10 mL) and the resulting organic portion was washed with water (10 mL), 1M aqueous HCl (10 mL) and brine (10 mL) before being dried over magnesium sulfate, filtered and the filtrate was concentrated under reduced pressure to give an oil that solidified upon standing (4.95 g, 83% yield). $^1$H NMR (250 MHz, chloroform-d) δ 7.91 (1H, td, 7.6, 1.8 Hz), 7.64-7.48 (1H, m), 7.26 (2H, m), 4.65 (1H, d, 6.5 Hz), 3.63-3.40 (1H, m, 6.7 Hz), 1.10 (6H, d, 6.5 Hz).

2-(Benzylsulfanyl)-N-(propan-2-yl)benzene-1-sulfonamide

To a solution of phenylmethanethiol (648 μL, 5.52 mmol) in DMSO (8 mL) was added NaOH (0.28 g, 6.9 mmol) and the reaction was left to stir for 20 minutes (until NaOH pellet dissolved). 2-Fluoro-N-(propan-2-yl)benzene-1-sulfonamide (645 μL, 4.6 mmol) was added and the reaction mixture was heated at 75° C. for 18 hours. The reaction was allowed to cool to a temperature of about 25° C. and water (1 mL) was added. The reaction was subsequently acidified with concentrated HCl before extraction of the organic portion into ethyl acetate (2×10 mL). The combined organics were washed with water (5 mL) and brine (5 mL) before being dried over magnesium sulfate, filtered and concentrated under reduced pressure to give an oil which was chromatographed with a silica gel column eluting with a 7-50% ethyl acetate:heptanes gradient to provide the desired compound as a yellow oil which solidified on standing and was subsequently triturated with heptanes to provide an off white solid (1.1 g 71% yield). $^1$H NMR (250 MHz, chloroform-d) δ 8.14-8.00 (1H, m), 7.45-7.23 (8H, m), 5.35 (1H, d, 7.2 Hz), 4.24 (2H, s), 3.37 (1H, sept., 6.6 Hz), 0.98 (6H, d, 6.5 Hz)

2-[(Propan-2-yl)sulfamoyl]benzene-1-sulfonyl chloride

A solution of 2-(benzylsulfanyl)-N-(propan-2-yl)benzene-1-sulfonamide (1.5 g, 4.67 mmol) in acetonitrile (46 mL), acetic acid (1.8 mL) and water (1.2 mL) was cooled at 0° C. (external) and 1,3-dichloro-5,5-dimethylimidazolidine-2,4-dione (1.84 g, 9.33 mmol) was added in one portion and the reaction was stirred for 1 hour at 0° C. The reaction was diluted with DCM (50 mL) and the organic portion was washed with aqueous saturated sodium bicarbonate solution (10 mL) and brine (20 mL) before being dried over sodium sulfate, filtered and concentrated under reduced pressure to provide a colorless oil which was chromatographed with a silica gel column eluting with a 5-40% heptane:EtOAc gradient to provide the title compound as a white solid (0.8 g, 52% yield). $^1$H NMR (250 MHz, chloroform-d) δ 8.36 (2H, dt, 7.9, 1.5 Hz), 7.95-7.77 (2H, m), 5.50 (1H, d, 7.3 Hz), 3.66-3.42 (1H, m), 1.06 (6H, d, 6.6 Hz).

1-N-Hydroxy-2-N-(propan-2-yl)benzene-1,2-disulfonamide

To a solution of aqueous hydroxylamine (0.8 mL of a 50% solution, 11.7 mmol) was added THF (6 mL) and water (1.5 mL) and the solution was cooled to −10° C. To this cold solution was added drop wise a solution of 2-[(propan-2-yl)sulfamoyl]benzene-1-sulfonyl chloride (1.4 g, 4.7 mmol) in THF (3 mL) while the temperature remained below 2-3° C. throughout the addition. The reaction mixture was stirred at 0° C. for 10 minutes whereupon LC-MS showed complete consumption of the sulfonyl chloride. The reaction was diluted with DCM (10 mL) and was washed with water (2 mL). The aqueous layer was further extracted into DCM (10 mL) and the organic layers were combined and dried over magnesium sulfate, filtered and concentrated under reduced pressure to give an oil. This oil was dissolved in a minimum amount of DCM and then heptane was added at which time a white solid precipitated. The precipitated solid was collected by filtration, washed with heptane and dried under reduced pressure to provide 1-N-hydroxy-2-N-(propan-2-yl)benzene-1,2-disulfonamide as a white solid (0.6 g, 42% yield). $^1$H NMR (250 MHz, DMSO-$d_6$) δ 10.06 (1H, d, 3.4 Hz), 9.09 (1H, d, 3.5 Hz), 8.25-8.08 (2H, m), 8.01-7.78 (2H, m), 7.02 (1H, d, 7.5 Hz), 3.41 (1H, dd, 13.5, 6.8 Hz), 0.98 (6H, d, 6.5 Hz).

Example 42: 5-Chloro-N-hydroxy-1,3-dimethyl-1H-pyrazole-4-sulfonamide (30)

To a solution of aqueous hydroxylamine (1.4 mL of a 50% solution, 0.02 mol) in tetrahydrofuran (12 mL) and water (2 mL) cooled to −5° C. was slowly added 5-chloro-1,3-dimethyl-1H-pyrazole-4-sulfonyl chloride (2 g, 8.7 mmol) maintaining a reaction temperature of less than 10° C. The reaction was maintained at this temperature until substantially complete consumption of the sulfonyl chloride was observed by TLC (about 5 min), after which time the reaction was diluted with dichloromethane (20 mL) and the organic portion was separated, washed with water (2×5 mL), dried over sodium sulfate, filtered and concentrated under reduced pressure. The solid was isolated by trituration from heptanes:diethyl ether (1:1 v:v) to provide the N-hydroxysulfonamide as a white solid (1.16 g, 58% yield). $^1$H NMR (500 MHz, DMSO-d$_6$) δ ppm 9.56 (1H, d, 2.1 Hz), 9.39 (1H, d, 2.3 Hz), 3.77 (3H, s), 2.30 (3H, s), predicted [M–H]$^-$= 223.9897; observed [M–H]$^-$=223.9893.

Example 43:
N-Hydroxy-1-methyl-1H-pyrazole-4-sulfonamide (31)

To a solution of aqueous hydroxylamine (0.91 mL of a 50% solution, 13.84 mmol) in tetrahydrofuran (3 mL) and water (1 mL) cooled to −5° C. was slowly added 1-methyl-1H-pyrazole-4-sulfonyl chloride (1 g, 5.54 mmol) maintaining a reaction temperature of less than 10° C. The reaction was maintained at this temperature until substantially complete consumption of the sulfonyl chloride was observed by TLC (about 5 min), after which time the reaction was diluted with dichloromethane (10 mL) followed by (200 mL due to low solubility) and the organic portion was separated, washed with water (2×5 mL), dried over sodium sulfate, filtered and concentrated under reduced pressure to provide the N-hydroxysulfonamide as a white solid (641 mg, 65% yield). LC-MS t$_R$=0.38 min, [M+H]$^+$=179; $^1$H NMR (500 MHz, DMSO-d$_6$) δ 9.52 (s, 1H), 9.26 (s, 1H), 8.26 (s, 1H), 7.72 (s, 1H), 3.89 (s, 3H).

Example 44: N-Hydroxypyridine-2-sulfonamide (32)

A solution of potassium carbonate (6.2 g, 45.0 mmol) in water (4.8 mL) was added drop wise to a solution of hydroxylamine hydrochloride (3.11 g, 45.0 mmol) in water (7.2 mL) at 0° C. maintaining an internal reaction temperature between 5° C. and 15° C. Tetrahydrofuran (24 mL) and methanol (6 mL) were added, followed by pyridine-2-sulfonyl chloride (4.0 g, 21.5 mmol) portion wise maintaining a temperature below 15° C. and the reaction mixture was stirred at a temperature of about 25° C. until substantially complete consumption of the sulfonyl chloride was observed by TLC. The resulting suspension was concentrated to remove any volatiles and the aqueous suspension was diluted with diethyl ether (50 mL) and the reaction was washed with water (10 mL). The organics were dried over sodium sulfate, filtered and concentrated under reduced pressure. Recrystallization of the desired compound was achieved from diethyl ether provide the expected product as a white solid (1.2 g, 31% yield). $^1$H NMR (400 MHz, DMSO-d$_6$) δ ppm 9.98 (1H, d, 2.9 Hz), 9.60 (1H, d, 2.9 Hz), 8.78 (1H, ddd, 4.6, 1.7, 1.0 Hz), 8.10 (1H, dd, 7.6, 1.7 Hz), 8.01 (1H, dt, 7.8, 1.0 Hz), 7.71 (1H, ddd, 7.6, 4.6, 1.2 Hz); predicted [M–H]$^-$=173.0021; observed [M–H]$^-$=173.0001.

Example 45:
3-Bromo-N-hydroxypyridine-2-sulfonamide (33)

3-Bromo-2-mercaptopyridine

To a solution of 2-chloro-3-bromopyridine (0.5 g, 2.5 mmol) in ethanol (5 mL) and water (1 mL) in a pressure tube was added sodium hydrogen sulfide (0.73 g, 13 mmol). The reaction was heated to 140° C. for 18 hours after which time no starting material remained. The product was taken up in ethyl acetate (10 mL) and was washed with a solution of 10% potassium carbonate solution (5 mL). The resulting aqueous extract was acidified to pH 5 with 6N hydrochloric acid and extracted with ethyl acetate (2×25 mL). The organic phase was died over sodium sulfate, filtered and concentrated under reduced pressure (0.41 g, 84% yield). $^1$H NMR (400 MHz, DMSO-d$_6$) δ ppm 8.05 (1H, dd, 7.5, 1.6 Hz), 7.75 (1H, d, 5.1 Hz), 6.66 (1H, dd, 7.6, 6.1 Hz).

3-Bromopyridine-2-sulfonyl chloride

To a solution of 2-mercapto-3-bromo-pyridine (5.3 g, 27.5 mmol) in concentrated hydrochloric acid (20 mL) cooled to 0° C. was added chlorine gas at a constant rate until substantially complete saturation was achieved. Upon reaction completion the sulfonyl chloride was added to ice water and the resulting aqueous phase extracted with dichloromethane (3×100 mL). The combined organics were dried over sodium sulfate, filtered and concentrated under reduced pressure. The sulfonyl chloride was used directly in the synthesis of the corresponding N-hydroxysulfonamide.

3-Bromo-N-hydroxypyridine-2-sulfonamide

A solution of potassium carbonate (3.21 g, 23.3 mmol) in water (3.6 mL) was added drop wise to a solution of hydroxylamine hydrochloride (1.61 g, 23.3 mmol) in water (2.4 mL) at 0° C. maintaining an internal reaction temperature between 5° C. and 15° C. Tetrahydrofuran (12 mL) and methanol (3 mL) were added, followed by 3-bromopyridine-2-sulfonyl chloride (3.0 g, 11.65 mmol) portion wise maintaining a temperature below 15° C. and the reaction mixture was stirred at a temperature of about 25° C. until substantially complete consumption of the sulfonyl chloride was observed by TLC. The resulting suspension was concentrated to remove any volatiles and the aqueous suspension was diluted with diethyl ether (50 mL) and the reaction was washed with water (10 mL). The aqueous portion was re-extracted with diethyl ether (2×15 mL) and the combined organics were dried over sodium sulfate, filtered and concentrated under reduced pressure. The N-hydroxysulfonamide was chromatographed with a silica gel column eluting with a heptanes:ethyl acetate gradient to provide the expected product as a white solid (0.4 g, 5% yield). $^1$H NMR (400 MHz, DMSO-d$_6$) δ ppm 10.34 (1H, d, 2.9 Hz), 9.62 (1H, d, 2.9 Hz), 8.71 (1H, dd, 4.5, 1.3 Hz), 8.37 (1H, dd, 8.2, 1.3 Hz), 7.62 (1H, dd, 8.1, 4.4 Hz); predicted [M–H]$^-$=250.9126; observed [M–H]$^-$=250.9135.

Example 46:
4-N-Hydroxythiophene-2,4-disulfonamide (34)

4-N-Hydroxythiophene-2,4-di sulfonamide was synthesized from 5-sulfamoylthiophene-3-sulfonyl chloride (1 g, 3.8 mmol) according to the herein-described methods for the synthesis of N-hydroxysulfonamides (0.25 g, 26 5 yield). $^1$H NMR (250 MHz, DMSO-d$_6$) δ 10.05 (s, 2H), 9.99 (s, 1H), 9.80 (s, 1H), 8.60 (1H, d, J 1.5 Hz), 7.83 (1H, d, 1.5 Hz).

Example 47: N-Hydroxy-4-(morpholine-4-carbonyl) thiophene-2-sulfonamide (35)

To a solution of aqueous hydroxylamine (0.3 mL of a 50% solution, 4.2 mmol) was added THF (3 mL) and water (0.5 mL) and the solution was cooled to −10° C. To this cold solution was added 4-(morpholine-4-carbonyl)thiophene-2-sulfonyl chloride (0.5 g, 1.7 mmol) portion wise while the temperature remained below 2-3° C. throughout the addition. The reaction mixture was stirred at 0° C. for 10 minutes whereupon LC-MS showed complete consumption of the sulfonyl chloride. The reaction was diluted with DCM (10 mL) and was washed with water (2 mL). The aqueous layer was further extracted into DCM (10 mL) and the organic layers were combined and dried over sodium sulfate, filtered and concentrated under reduced pressure. The compound was triturated with diethyl ether to provide the desired compound as a white solid (0.2 g, 40% yield). $^1$H NMR (500 MHz, DMSO-$d_6$) δ ppm 9.88 (1H, d, 2.9 Hz), 9.80 (1H, d, 2.9 Hz), 8.22 (1H, s), 7.67 (1H, s), 3.44-3.71 (8H, m); predicted [M−H]$^-$=291.0109; observed [M−H]$^-$=291.0110.

Example 48: N-Hydroxy-5-[5-(trifluoromethyl)-1,2-oxazol-3-yl]thiophene-2-sulfonamide (36)

N-Hydroxy-5-[5-(trifluoromethyl)-1,2-oxazol-3-yl]thiophene-2-sulfonamide was synthesized from 5-[5-(trifluoromethyl)-1,2-oxazol-3-yl]thiophene-2-sulfonyl chloride (1 g, 3.2 mmol) according to the herein-described methods for the synthesis of N-hydroxysulfonamides and was triturated from diethyl ether to provide the desired compound as a white solid (0.7 g, 71% yield). $^1$H NMR (500 MHz, DMSO-$d_6$) δ ppm 9.98 (1H, s), 9.95 (1H, br. s.), 8.17 (1H, s), 7.93 (1H, d, 4.0 Hz), 7.78 (1H, d, 3.8 Hz); predicted [M−H]$^-$=312.9565; observed [M−H]$^-$=312.9564.

Example 49: 6-Chloro-N-hydroxy-7H,7aH-imidazo[2,1-b][1,3]thiazole-5-sulfonamide (37)

6-Chloro-N-hydroxy-7H,7aH-imidazo[2,1-b][1,3]thiazole-5-sulfonamide was synthesized from 6-chloro-7H,7aH-imidazo[2,1-b][1,3]thiazole-5-sulfonyl chloride (0.1 g, 0.4 mmol) according to the herein-described methods for the synthesis of N-hydroxysulfonamides and was triturated from diethyl ether to provide the desired compound as a white solid (0.03 g, 30% yield), $^1$H NMR (500 MHz, DMSO-$d_6$) δ ppm 10.02 (1H, br. s.), 9.84 (1H, s), 7.88 (1H, d, 4.6 Hz), 7.61 (1H, d, 4.4 Hz).

Example 50: N-Hydroxy-5-(1,2-oxazol-5-yl)thiophene-2-sulfonamide (38)

N-Hydroxy-5-(1,2-oxazol-5-yl)thiophene-2-sulfonamide was synthesized from 5-(1,2-oxazol-5-yl)thiophene-2-sulfonyl chloride (5.0 g, 20 mmol) according to the herein-described methods for the synthesis of N-hydroxysulfonamides and was triturated with heptanes to provide the desired compound as a white solid (2.6 g, 53% yield). $^1$H NMR (500 MHz, DMSO-$d_6$) δ ppm 9.96 (1H, s), 9.92 (1H, br. s.), 8.74 (1H, s), 7.79 (1H, d, 3.8 Hz), 7.73 (1H, d, 4.0 Hz), 7.13 (1H, s); predicted [M−H]$^-$=244.9691; observed [M−H]$^-$=244.9702.

Example 51: 4-Fluoro-N-hydroxy-2-methylbenzene-1-sulfonamide (39)

4-Fluoro-N-hydroxy-2-methylbenzene-1-sulfonamide was synthesized from 4-fluoro-2-methylbenzene-1-sulfonyl chloride (1.0 g, 4.8 mmol) according to the herein-described methods for the synthesis of N-hydroxysulfonamides and was triturated with heptanes to provide the desired compound as a white solid (0.65 g, 65% yield). $^1$H NMR (500 MHz, DMSO-$d_6$) δ 9.60 (1H, s), 9.59 (1H, s), 7.89 (1H, dd, 8.7, 6.0 Hz), 7.28-7.33 (1H, m), 7.26 (1H, t, 8.5 Hz), 2.60 (3H, s); predicted [M−H]$^-$=204.0131; observed [M−H]$^-$=204.0138.

Example 52: N-Hydroxy-5-(1,3-oxazol-5-yl)thiophene-2-sulfonamide (40)

N-Hydroxy-5-(1,3-oxazol-5-yl)thiophene-2-sulfonamide was prepared from 5-(1,3-oxazol-5-yl)-2-thiophenesulfonyl chloride according to the herein-described methods for the synthesis of N-hydroxysulfonamides (0.02 g, 1%). $^1$H NMR (500 MHz, DMSO-$d_6$) δ ppm 9.91 (1H, s), 9.82 (1H, br. s.), 8.51 (1H, s), 7.77 (1H, s), 7.66 (1H, d, 3.7 Hz), 7.56 (1H, d, 3.5 Hz).

Example 53: N-Hydroxy-2,5-dimethylthiophene-3-sulfonamide (41)

N-Hydroxy-2,5-dimethylthiophene-3-sulfonamide was prepared from 2,5-dimethyl-3-thiophenesulfonyl chloride (2.0 g, 9.5 mmol) according to the herein-described methods for the synthesis of N-hydroxysulfonamides and was triturated with heptanes to provide the desired compound as a yellow solid (0.5 g, 25%). $^1$H NMR (500 MHz, DMSO-$d_6$) δ ppm 9.53 (1H, d, 3.1 Hz), 9.39 (1H, d, 3.1 Hz), 6.89 (1H, s), 2.57 (3H, s), 2.38 (3H, s); predicted [M+H]$^+$=208.0102; observed [M+H]$^+$=208.0374.

Example 54: Methyl 5-(hydroxysulfamoyl)-4-methylthiophene-2-carboxylate (42)

Methyl 5-(hydroxysulfamoyl)-4-methylthiophene-2-carboxylate was prepared from methyl 5-(chlorosulfonyl)-4-methyl-2-thiophenecarboxylate (2.0 g, 7.9 mmol) according to the herein-described methods for the synthesis of N-hydroxysulfonamides and was triturated with diethyl ether: heptanes to provide the desired compound as a white solid (0.96 g, 49%). $^1$H NMR (500 MHz, DMSO-$d_6$) 9.91 (1H, s), 9.89 (1H, br. s.), 7.74 (1H, s), 3.85 (3H, s), 2.44 (3H, s); predicted [M−H]$^-$=249.9844; observed [M−H]$^-$=249.9832.

Example 55: 5-(Benzenesulfonyl)-N-hydroxythiophene-2-sulfonamide (43)

5-(Benzenesulfonyl)-N-hydroxythiophene-2-sulfonamide was synthesized from 5-(benzenesulfonyl)thiophene-2-sulfonyl chloride (2.5 g, 7.7 mmol) according to the herein-described methods for the synthesis of N-hydroxysulfonamides and was chromatographed with a silica gel column eluting with a heptanes:ethyl acetate gradient followed by trituration with heptanes to provide the desired compound as a white solid (1.0 g, 40% yield). $^1$H NMR (500 MHz, DMSO-$d_6$) δ ppm 10.12 (1H, d, 2.9 Hz), 10.05 (1H, d, 2.9 Hz), 8.06 (2H, d, 8.2 Hz), 7.94 (1H, d, 4.0 Hz), 7.77 (1H, d, 7.3 Hz), 7.64-7.73 (3H, m); predicted [M−H]$^-$=317.9565; observed [M−H]$^-$=317.9550.

Example 56: N-Hydroxy-5-(1,2-oxazol-3-yl)thiophene-2-sulfonamide (44)

N-Hydroxy-5-(1,2-oxazol-3-yl)thiophene-2-sulfonamide was synthesized from 5-(1,2-oxazol-3-yl)thiophene-2-sulfonyl chloride (0.25 g, 1.0 mmol) according to the herein-described methods for the synthesis of N-hydroxysulfonamides to provide the desired compound as a white solid (0.18 g, 71% yield). $^1$H NMR (500 MHz, DMSO-$d_6$) δ ppm 9.95 (1H, d, 2.4 Hz), 9.91 (1H, d, 2.7 Hz), 8.75 (1H, s), 7.79 (1H, d, 4.0 Hz), 7.73 (1H, d, 3.8 Hz), 7.14 (1H, s); predicted [M−H]$^-$=244.9691; observed [M−H]$^-$=244.9693.

Example 57:
5-Bromo-N-hydroxythiophene-2-sulfonamide (45)

5-Bromo-N-hydroxythiophene-2-sulfonamide was prepared from 5-bromothiophene sulfonyl chloride (2.0 g, 7.6 mmol) according to the herein-described methods for the synthesis of N-hydroxysulfonamides and was triturated from diethyl ether to provide the desired compound as a white solid (1.2 g, 60%). $^1$H NMR (500 MHz, DMSO-$d_6$) δ ppm 9.88 (1H, s), 9.80 (1H, br. s.), 7.49 (1H, d, 4.0 Hz), 7.40 (1H, d, 3.9 Hz); predicted [M−H]$^-$=255.8738; observed [M−H]$^-$=255.8727.

Example 58:
3,5-Dibromo-N-hydroxythiophene-2-sulfonamide (46)

3,5-Dibromothiophene-2-sulfonyl chloride

To a solution of 2,4-dibromothiophene (2.0 g, 8.2 mmol) in DCM (10 mL) cooled to 0° C. was added chlorosulfonic acid (2.9 g, 24 mmol) drop wise. Stirring was continued for an additional 3 hours after which time the reaction was added to ice and the organic portion extracted into DCM (3×50 mL), dried over sodium sulfate, filtered and concentrated under reduced pressure to provide the desired sulfonyl chloride which was used directly in the synthesis of the corresponding N-hydroxysulfonamide (1.8 g, 63% yield); $^1$H NMR (500 MHz, DMSO-$d_6$) δ ppm 7.15 (1H, s).

3,5-Dibromo-N-hydroxythiophene-2-sulfonamide 3,5-Dibromo-N-hydroxythiophene-2-sulfonamide was prepared from 3,5-dibromothiophene-2-sulfonyl chloride (1.8 g, 5.2 mmol) according to the herein-described methods for the synthesis of N-hydroxysulfonamides and was chromatographed with a silica gel column eluting with heptanes:ethyl acetate (1:1 v:v) followed by trituration from diethyl ether:heptane to provide the desired compound as a white solid (0.7 g, 40% yield). $^1$H NMR (500 MHz, DMSO-$d_6$) δ ppm 10.02 (1H, d, 2.9 Hz), 9.93 (1H, d, 2.9 Hz), 7.59 (1H, s); predicted [M−H]$^-$=333.7843; observed [M−H]$^-$=333.7949.

Example 59:
5-Chloro-N-hydroxy-4-nitrothiophene-2-sulfonamide (47)

5-Chloro-N-hydroxy-4-nitrothiophene-2-sulfonamide was prepared from 5-chloro-4-nitrothiophene-2-sulfonyl chloride (2.0 g, 7.6 mmol) according to the herein-described methods for the synthesis of N-hydroxysulfonamides and was chromatographed with a silica gel column eluting with heptanes:ethyl acetate (1:7 v:v) to provide the desired compound as an orange solid (0.95 g, 48% yield). $^1$H NMR (500 MHz, DMSO-$d_6$) δ ppm 10.19 (1H, d, 3.6 Hz), 8.05 (1H, s); predicted [M−H]$^-$=256.9094; observed [M−H]$^-$=256.9087.

Example 60:
3-Chloro-N-hydroxythiophene-2-sulfonamide (48)

3 Chloro-thiophene-2-sulfonyl chloride

To a solution of 3-chlorothiophene (20 g, 0.17 mol) in DCM (40 mL) cooled to 0° C. was added chlorosulfonic acid (34 mL, 0.51 mol) and stirring was continued for 2 hours; after which time the reaction mixture was poured onto ice and the resulting solution was extracted into DCM (3×50 mL), dried over sodium sulfate, filtered and concentrated under reduced pressure to provide the desired compound which was used directly in the next step (3.5 g, 20%). $^1$H NMR (500 MHz, chloroform-d) δ ppm 7.75 (1H, d, 5.3 Hz), 7.15 (1H, d, 5.3 Hz).

3-Chloro-N-hydroxythiophene-2-sulfonamide

3-Chloro-N-hydroxythiophene-2-sulfonamide was prepared from 3-chlorothiophene-2-sulfonyl chloride (3.0 g, 13.8 mmol) according to the herein-described methods for the synthesis of N-hydroxysulfonamides and re-crystallization from 5% ethyl acetate:heptanes to provide the desired compound as a white solid (1.39 g, 46% yield). $^1$H NMR (500 MHz, DMSO-$d_6$) δ ppm 9.95 (1H, s.), 9.90 (1H, br. s.), 8.16 (1H, d, 5.4 Hz), 7.35 (1H, d, 5.2 Hz); predicted [M−H]$^-$=211.9243; observed [M−H]$^-$=211.9241.

Example 61:
N-Hydroxy-2,5-dimethylbenzene-1-sulfonamide (49)

N-Hydroxy-2,5-dimethylbenzene-1-sulfonamide was prepared from 2,5-dimethylbenzene-1-sulfonyl chloride (1.0 g, 4.9 mmol) according to the herein-described methods for the synthesis of N-hydroxysulfonamides to provide the desired compound as a white solid (0.6 g, 60% yield). $^1$H NMR (250 MHz, DMSO-$d_6$) δ ppm 9.48-9.54 (2H, m), 7.66 (1H, d, 1.2 Hz), 7.34-7.40 (1H, m), 7.25-7.31 (1H, m), 2.54 (3H, s), 2.34 (3H, s); predicted [M−H]$^-$=200.0381; observed [M−H]$^-$=200.0382.

Example 62: 5-Chloro-N-hydroxy-2,1,3-benzoxadiazole-4-sulfonamide (50)

5-Chloro-N-hydroxy-2,1,3-benzoxadiazole-4-sulfonamide was prepared from 5-chloro-2,1,3-benzoxadiazole-4-sulfonyl chloride (1 g, 3.9 mmol) according to the herein-described methods for the synthesis of N-hydroxysulfonamides and was chromatographed with a silica gel column eluting with heptanes:ethyl acetate (1:1 v:v) to provide the desired compound as an off white solid (0.04 g, 5% yield). $^1$H NMR (250 MHz, DMSO-$d_6$) δ ppm 10.19 (1H, d, 2.9 Hz), 9.95 (1H, d, 2.9 Hz), 8.45 (1H, d, 9.4 Hz), 7.82 (1H, d, 9.4 Hz).

Example 63: 4-(Benzenesulfonyl)-N-hydroxythiophene-2-sulfonamide (51)

4-(Benzenesulfonyl)-N-hydroxythiophene-2-sulfonamide was prepared from 4-(benzenesulfonyl)thiophene-2-sulfonyl chloride (1.0 g, 3.1 mmol) according to the herein-described methods for the synthesis of N-hydroxysulfonamides and was chromatographed with a silica gel column eluting with 30% ethyl acetate:heptanes to provide the desired compound as an off white solid (0.51 g, 51% yield). $^1$H NMR (250 MHz, DMSO-d$_6$) δ ppm 10.05 (1H, br. s.), 9.44 (1H, s), 8.84 (1H, s), 8.09 (1H, m,), 8.00 (1H, m,), 7.87 (1H, m,), 7.71 (3H, m,); predicted [M−H]$^−$=317.9565; observed [M−H]$^−$=317.9602.

Example 64:
N-Hydroxy-3,4-dimethoxybenzene-1-sulfonamide (52)

N-Hydroxy-3,4-dimethoxybenzene-1-sulfonamide was synthesized from 3,4-dimethoxybenzene-1-sulfonyl chloride (2 g, 8.46 mmol) according to the herein-described methods for the synthesis of N-hydroxysulfonamides and was triturated with diethyl ether:heptanes (0.3 g, 15% yield). $^1$H NMR (500 MHz, DMSO-d$_6$) δ ppm 9.48 (1H, d, 3.5 Hz), 9.40 (1H, d, 3.5 Hz), 7.42 (1H, dd, 8.4 Hz, 2.1 Hz), 7.33 (1H, d, 2.0 Hz), 7.16 (1H, d, 8.5 Hz), 3.85 (1H, s), 3.81 (1H, s,); predicted [M−H]$^−$=232.028; observed [M−H]$^−$=232.0285.

Example 65:
N-Hydroxy-2,3,5,6-tetramethylbenzene-1-sulfonamide (53)

N-Hydroxy-2,3,5,6-tetramethylbenzene-1-sulfonamide was prepared from 2,3,5,6-tetramethylbenzene-1-sulfonyl chloride (2 g, 8.6 mmol) according to the herein-described methods for the synthesis of N-hydroxysulfonamides to provide the desired compound as a white solid (0.7 g, 34% yield). $^1$H NMR (250 MHz, DMSO-d$_6$) δ ppm 9.52 (1H, br. s), 9.36 (1H, s), 7.30 (1H, s), 2.50 (6H, s), 2.27 (6H, s); predicted [M−H]$^−$=228.0694; observed [M−H]$^−$=228.074.

Example 66: N-Hydroxy-3,5-bis(trifluoromethyl)benzene-1-sulfonamide (54)

N-Hydroxy-3,5-bis(trifluoromethyl)benzene-1-sulfonamide was prepared from 3,5-bis(trifluoromethyl)benzene-1-sulfonyl chloride according to the herein-described methods for the synthesis of N-hydroxysulfonamides and was triturated with diethyl ether:heptane to provide the desired compound as a white solid (0.48 g, 24% yield). $^1$H NMR (250 MHz, DMSO-d$_6$) δ ppm 9.99 (2H, s), 8.58 (1H, s), 8.37 (2H, s); predicted [M−H]$^−$=307.9816; observed [M−H]$^−$=307.9823.

Example 67: Methyl 4-chloro-3-(hydroxysulfamoyl)benzoate (55)

Methyl 4-chloro-3-(chlorosulfonyl)benzoate

To 4-chloro-3-(chlorosulfonyl)benzoyl chloride (2 g, 7.3 mmol) was added MeOH (20 mL) with stirring. After 10 minutes the reaction was concentrated under reduced pressure and used directly in the synthesis of the corresponding N-hydroxysulfonamide (1.9 g, 96% yield). $^1$H NMR (500 MHz, chloroform-d) δ 8.79 (1H, d, J 2.0 Hz), 8.30 (1H, dd, 8.3, 2.0 Hz), 7.74 (1H, d, 8.3 Hz), 3.99 (3H, s).

Methyl 4-chloro-3-(hydroxysulfamoyl) benzoate

Methyl 4-chloro-3-(hydroxysulfamoyl)benzoate was synthesized from methyl 4-chloro-3-(chlorosulfonyl)benzoate (0.7 g, 2.6 mmol) according to the herein-described methods for the synthesis of N-hydroxysulfonamides (0.3 g, 45% yield). $^1$H NMR (250 MHz, DMSO-d$_6$) δ ppm 10.05 (1H, br. s.), 9.90 (1H, s), 8.50 (1H, d, 2.1 Hz), 8.18 (1H, dd, 8.4, 2.1 Hz), 7.85 (1H, d, 8.2 Hz), 3.90 (3H, s); predicted [M−H]$^−$=263.9733; observed [M−H]$^−$=263.973.

Example 68:
2-Fluoro-N-hydroxy-5-methylbenzene-1-sulfonamide (56)

2-Fluoro-N-hydroxy-5-methylbenzene-1-sulfonamide was prepared from 2-fluoro-5-methylbenzene-1-sulfonyl chloride (1 g, 4.8 mmol) according to the herein-described methods for the synthesis of N-hydroxysulfonamides (0.19 g, 20% yield). $^1$H NMR (500 MHz, DMSO-d$_6$) δ ppm 9.71 (2H, s), 7.61 (1H, dd, 6.6, 1.7 Hz), 7.54 (1H, dt, 8.2, 2.3 Hz), 7.33 (1H, dd, 10.0, 8.6 Hz), 2.36 (3H, s); predicted [M−H]$^−$=204.0131; observed [M−H]$^−$=204.0121.

Example 69: 4-Chloro-N-(3-chloropropyl)-3-(hydroxysulfamoyl)-benzamide (57)

2-Chloro-5-[(3-chloropropyl)carbamoyl]benzene-1-sulfonyl chloride

To a solution of 4-chloro-3-(chlorosulfonyl)benzoyl chloride (1.5 g, 5.51 mmol) in chlorobenzene (20 mL) was added azetidine hydrochloride (0.54 g, 5.79 mmol) and the reaction was heated to 130° C. for 18 hours after which time LC-MS showed no starting material remaining. The reaction mixture was concentrated under reduced pressure and triturated using diethyl ether to provide the desired product as an off white solid which was used directly in the synthesis of the corresponding N-hydroxysulfonamide (1 g, 55% yield).

4-Chloro-N-(3-chloropropyl)-3-(hydroxysulfamoyl)-benzamide

4-Chloro-N-(3-chloropropyl)-3-(hydroxysulfamoyl)-benzamide was prepared from 2-chloro-5-[(3-chloropropyl)carbamoyl]benzene-1-sulfonyl chloride (1 g, 3.4 mmol) according to the herein-described methods for the synthesis of N-hydroxysulfonamides and was triturated with diethyl ether to provide the desired compound as a white solid (0.13 g, 14% yield). $^1$H NMR (500 MHz, DMSO-d$_6$) δ ppm 9.88 (1H, d, 2.7 Hz), 9.81 (1H, d, 2.9 Hz), 8.86 (1H, t, 5.4 Hz), 8.45 (1H, d, 2.0 Hz), 8.11 (1H, dd, 8.4, 2.0 Hz), 7.81 (1H, d, 8.4 Hz), 3.70 (2H, t, 6.5 Hz), 3.40 (2H, q, 6.5 Hz), 1.91-2.06 (2H, m).

Example 70: 2-Chloro-N-hydroxy-5-[4-(hydroxyimino)piperidine-1-carbonyl]benzene-1-sulfonamide (58)

2-Chloro-5-(4-oxopiperidine-1-carbonyl)benzene-1-sulfonyl chloride

To a solution of 4-chloro-3-(chlorosulfonyl)benzoyl chloride (1.0 g, 3.7 mmol) in chlorobenzene (15 mL) was added 4-piperidinone hydrochloride (0.59 g, 3.9 mmol) and the reaction was heated to 130° C. for 18 hours after which time LC-MS showed no starting material remaining. The reaction mixture was concentrated under reduced pressure and taken up in DCM (50 mL), washed with water (2×10 mL) before being dried over magnesium sulfate, filtered and concentrated under reduced pressure to provide the product which was triturated with diethyl ether to provide the desired compound as a off white solid (0.27 g, 22% yield). $^1$H NMR (500 MHz, DMSO-d$_6$) δ ppm 7.96 (1H, d, 1.6 Hz), 7.51-7.40 (2H, m), 3.74-3.56 (4H, m) 2.55-2.27 (4H, m).

2-Chloro-N-hydroxy-5-[4-(hydroxyimino)piperidine-1-carbonyl]benzene-1-sulfonamide 2-Chloro-N-hydroxy-5-[4-(hydroxyimino)piperidine-1-carbonyl]benzene-1-sulfonamide was synthesized from 2-chloro-5-(4-oxopiperidine-1-carbonyl)benzene-1-sulfonyl chloride (0.27 g, 0.82 mmol) according to the herein-described methods for the synthesis of N-hydroxysulfonamides and was triturated with heptanes:diethyl ether to provide the desired compound as a white solid (0.05 g, 16% yield). $^1$H NMR (500 MHz, DMSO-d$_6$) δ ppm 9.98 (1H, m), 9.86 (1H, m), 7.95 (1H, m), 7.71 (2H, m), 3.59 (2H, m), 3.29 (2H, m), 3.16 (2H, m), 2.95 (2H, m).

Example 71: 4-Chloro-3-(hydroxysulfamoyl)-N-(2-methoxyethyl)-N-methylbenzamide (59)

2-Chloro-5-[(2-methoxyethyl)(methyl)carbamoyl]benzene-1-sulfonyl chloride

To a solution of 4-chloro-3-(chlorosulfonyl)benzoyl chloride (2.0 g, 3.7 mmol) in chlorobenzene (25 mL) was added 2-(methoxyethyl)methylamine hydrochloride (0.48 g, 3.9 mmol) and the reaction was heated to 130° C. for 18 hours after which time LC-MS showed no starting material remaining. The reaction mixture was concentrated under reduced pressure and used directly in the synthesis of the corresponding N-hydroxysulfonamide (2 g, 75% yield).

4-Chloro-3-(hydroxysulfamoyl)-N-(2-methoxyethyl)-N-methylbenzamide

4-Chloro-3-(hydroxysulfamoyl)-N-(2-methoxyethyl)-N-methylbenzamide was synthesized from 2-chloro-5-[(2-methoxyethyl)(methyl)carbamoyl]benzene-1-sulfonyl chloride (2 g, 6.1 mmol) according to the herein-described methods for the synthesis of N-hydroxysulfonamides and was triturated with diethyl ether followed by silica gel column eluting with ethyl acetate:heptanes (1:1 v:v) to provide the desired compound as an off white solid (0.17 g, 9% yield). $^1$H NMR (500 MHz, DMSO-d$_6$) δ ppm 9.98 (1H, m), 9.86 (1H, m), 7.95 (1H, m), 7.71 (2H, m), 3.59 (2H, m), 3.29 (2H, m), 3.16 (2H, m), 2.95 (3H, m).

Example 72: 2-Hydroxy-5-(hydroxysulfamoyl)benzoic acid (60)

2-Hydroxy-5-(hydroxysulfamoyl)benzoic acid was prepared from 5-(chlorosulfonyl)-2-hydroxybenzoic acid (1 g, 4.2 mmol) according to the herein-described methods for the synthesis of N-hydroxysulfonamides and was isolated as a white solid (0.4 g, 41% yield). $^1$H NMR (500 MHz, DMSO-d$_6$) δ ppm 10.75 (1H, br. s.), 10.66 (1H, s), 9.39 (1H, d, 2.1 Hz), 9.04 (1H, dd, 8.8, 2.2 Hz), 8.31 (1H, d, 5.0 Hz); predicted [M−H]$^−$=231.9916; observed [M−H]$^−$=231.9907.

Example 73: N-Hydroxy-4-methyl-3,4-dihydro-2H-1,4-benzoxazine-7-sulfonamide (61)

N-Hydroxy-4-methyl-3,4-dihydro-2H-1,4-benzoxazine-7-sulfonamide was prepared from 4-methyl-3,4-dihydro-2H-1,4-benzoxazine-7-sulfonyl chloride (0.9 g, 3.8 mmol) according to the herein-described methods for the synthesis of N-hydroxysulfonamides and was triturated with heptanes: ethyl acetate to provide the desired product as an off white solid (0.35 g, 38% yield). $^1$H NMR (500 MHz, DMSO-d$_6$) δ ppm 9.40 (1H, br. s.), 9.32 (1H, s), 7.00-7.12 (2H, m), 6.83 (1H, d, 8.9 Hz), 4.20-4.36 (2H, m), 3.24-3.35 (2H, m), 2.87 (3H, s); predicted [M+H]$^+$=245.0595; observed [M+H]$^+$=245.0589.

Example 74: 2-Chloro-N,4-dihydroxybenzene-1-sulfonamide (62)

2-Chloro-4-hydroxybenzene-1-sulfonyl chloride

To a solution of 2-chloro-4-hydroxyaniline (5.0 g, 35 mmol) in acetic acid (30 mL) and HCl (7 mL) cooled to 0° C. was added sodium nitrite (2.65 g, 38.5 mmol) portion wise maintaining an internal temperature <5° C. The reaction mixture was allowed to stir at 0° C. for 1 hour. Simultaneously, CuCl$_2$.H$_2$O (5.98 g, 34.8 mmol) was suspended in AcOH:water (20 mL:10 mL) at 0° C. and stirred at 0° C. until all CuCl$_2$ was in solution. SO$_2$ gas was condensed into a flask at −78° C. via the aid of a cold finger and the diazo compound and CuCl$_2$ solution added and the reaction warmed to 0° C. The reaction was allowed to warm to a temperature of about 25° C. over 18 hours and was quenched by addition to ice and extracted into diethyl ether (3×100 mL). The organics were dried over sodium sulfate, filtered and concentrated under reduced pressure to provide the title compound as a yellow oil which was used directly in the next step.

2-Chloro-N,4-dihydroxybenzene-1-sulfonamide

2-Chloro-N,4-dihydroxybenzene-1-sulfonamide was prepared from 2-chloro-4-hydroxybenzene-1-sulfonyl chloride according to the herein-described methods for the synthesis of N-hydroxysulfonamides and was chromatographed with a silica gel column eluting with 1% MeOH:DCM to provide the desired compound as a white solid (0.3 g, 15% yield). $^1$H NMR (250 MHz, DMSO-d$_6$) δ ppm 10.93 (1H, s), 9.58 (1H, d, 3.0 Hz), 9.42 (1H, d, 3.0 Hz), 7.80 (1H, d, 8.7 Hz), 6.97 (1H, d, 2.4 Hz), 6.89 (1H, dd, 8.7, 2.4 Hz) predicted [M−H]$^−$=221.9628; observed [M−H]$^−$=221.9621.

Example 75: 3,5-Dichloro-N,4-dihydroxybenzene-1-sulfonamide (63)

3,5-Dichloro-N,4-dihydroxybenzene-1-sulfonamide was prepared from 3,5-dichloro-4-hydroxybenzene-1-sulfonyl chloride (1 g, 3.8 mmol) according to the herein-described methods for the synthesis of N-hydroxysulfonamides to provide the desired compound as a white solid (0.05 g, 5% yield). $^1$H NMR (250 MHz, DMSO-d$_6$) δ ppm 9.60 (1H, br. s.), 9.43 (1H, s), 7.64 (2H, s).

Example 76: 4-Chloro-2-hydroxy-5-(hydroxysulfamoyl)-N,N-dimethylbenzamide (64)

2-Chloro-5-(dimethylcarbamoyl)-4-hydroxybenzene-1-sulfonyl chloride

To a solution of 5-(chlorosulfonyl)-2-hydroxybenzoic acid (1 g, 4.2 mmol) in toluene (20 mL) was added thionyl chloride (0.62 mL, 8.4 mmol) and the reaction was heated to reflux for 1 hour or until no further starting material was evident by TLC. The reaction was concentrated under reduced pressure and used directly in the synthesis of the amide (1 g, 82% yield). To a solution of 4-chloro-5-(chlorosulfonyl)-2-hydroxybenzoyl chloride (1 g, 3.5 mmol) in chlorobenzene (25 mL) was added dimethylamine hydrochloride (0.31 g, 3.9 mmol) and the reaction was heated to 130° C. for 18 hours after which time LC-MS showed no starting material remaining. The reaction mixture was concentrated under reduced pressure and used directly in the synthesis of the corresponding N-hydroxysulfonamide (2.9 g, quantitative yield); LC-MS $t_R$=1.75 min, $[M+H]^+$=264.

4-Chloro-2-hydroxy-5-(hydroxysulfamoyl)-N,N-dimethylbenzamide

4-Chloro-2-hydroxy-5-(hydroxysulfamoyl)-N,N-dimethylbenzamide was prepared from 2-Chloro-5-(dimethylcarbamoyl)-4-hydroxybenzene-1-sulfonyl chloride (2.9 g, 9.7 mmol) according to the herein-described methods for the synthesis of N-hydroxysulfonamides and was chromatographed with a silica gel column eluting with 10% MeOH in DCM followed by trituration from DCM to provide the desired compound as an off white solid (0.38 g, 13% yield). $^1$H NMR (500 MHz, DMSO-$d_6$) δ ppm 11.42 (1H, br. s.), 9.67 (1H, d, 2.7 Hz), 9.60 (1H, d, 2.9 Hz), 7.68 (1H, s), 7.06 (1H, s), 2.96 (3H, br. s.), 2.81 (3H, br. s.); predicted $[M-H]^-$=292.9999; observed $[M-H]^-$=293.0003.

Example 77: 5-Chloro-N-hydroxy-1-methyl-2,3-dihydro-1H-indole-6-sulfonamide (65)

5-Chloro-1-methyl-2,3-dihydro-1H-indole

To a solution of 5-chloro-2,3-dihydro-1H-indole (3.0 g, 19.5 mmol) in DMF (60 mL) was added dimethylcarbonate (5.27 g, 58.6 mmol) and potassium carbonate (1.35 g, 9.75 mmol). The reaction was heated to reflux for 18 hours, after which time no starting material was evident by LC-MS. The reaction mixture was allowed to cool to a temperature of about 25° C. and the product isolated by extraction into diethyl ether (250 mL). The organic portion was washed with water (2×100 mL) and the organics dried over magnesium sulfate, filtered and concentrated under reduced pressure to provide the title compound as a white solid (2.4 g, 71% yield). $^1$H NMR (500 MHz, DMSO-$d_6$) δ ppm 7.67 (1H, br. s.), 7.27 (1H, s), 7.20 (1H, d, 8.7 Hz), 3.97 (2H, t, 8.7 Hz), 3.74 (3H, br. s.), 3.09 (2H, t, 8.7 Hz).

5-Chloro-1-methyl-2,3-dihydro-1H-indole-6-sulfonyl chloride

5-Chloro-1-methyl-2,3-dihydro-1H-indole (0.6 g, 3.6 mmol) and chlorosulfonic acid (1.7 g, 14.3 mmol) were heated in a sealed tube to 70° C. for 18 hours. The reaction was quenched by pouring onto ice and the resulting solid was dried under reduced pressure then chromatographed with silica gel column eluting with 20% heptane:ethyl acetate to provide the title compound as a white solid (0.37 g, 38% yield). $^1$H NMR (250 MHz, DMSO-$d_6$) δ ppm 8.23 (1H, br. s.), 7.19 (1H, s), 3.97 (2H, t, 8.7 Hz), 3.75 (3H, s), 3.07 (2H, t, 8.6 Hz).

5-Chloro-N-hydroxy-1-methyl-2,3-dihydro-1H-indole-6-sulfonamide

5-Chloro-N-hydroxy-1-methyl-2,3-dihydro-1H-indole-6-sulfonamide was prepared from 5-chloro-1-methyl-2,3-dihydro-1H-indole-6-sulfonyl chloride (0.35 g, 1.3 mmol) according to the herein-described methods for the synthesis of N-hydroxysulfonamides (0.19 g, 55% yield). $^1$H NMR (250 MHz, DMSO-$d_6$) δ ppm 9.54-9.72 (2H, m), 8.33 (1H, br. s.), 7.51 (1H, s), 4.03 (2H, t, 8.8 Hz), 3.76 (3H, s), 3.18 (2H, t, 8.5 Hz).

Example 78: 2-Chloro-N,5-dihydroxybenzene-1-sulfonamide (66)

2-Chloro-N,5-dihydroxybenzene-1-sulfonamide was prepared from 2-chloro-5-hydroxy benzene-1-sulfonyl chloride (2.32 g, 10 mmol) according to the herein-described methods for the synthesis of N-hydroxysulfonamides and was chromatographed with a neutral reverse phase preparative HPLC to provide the desired compound as a white solid (0.05 g, 3% yield). $^1$H NMR (250 MHz, DMSO-$d_6$) δ ppm 9.74 (2H, s), 7.31-7.53 (2H, m), 7.04 (1H, d, 8.7, 2.9 Hz).

Example 79: 5-Bromo-N-hydroxy-1-methyl-2,3-dihydro-1H-indole-6-sulfonamide (67)

5-Bromo-1-methyl-2,3-dihydro-1H-indole

5-Bromo-1-methyl-2,3-dihydro-1H-indole was synthesized using the method described for the synthesis of 5-chloro-1-methyl-2,3-dihydro-1H-indole (1.1 g, 54% yield). $^1$H NMR (250 MHz, DMSO-$d_6$) δ ppm 7.60 (1H, br. s.), 7.40 (1H, d, 0.9 Hz), 7.28-7.37 (1H, m), 3.96 (2H, t, 8.7 Hz), 3.74 (3H, s), 3.10 (2H, t, 8.7 Hz).

5-Bromo-1-methyl-2,3-dihydro-1H-indole-6-sulfonyl chloride

5-Bromo-1-methyl-2,3-dihydro-1H-indole-6-sulfonyl chloride was synthesized using the method described for the synthesis of 5-chloro-1-methyl-2,3-dihydro-1H-indole-6-sulfonyl chloride (0.29 g, 34% yield). $^1$H NMR (500 MHz, DMSO-$d_6$) δ ppm 8.30 (1H, br. s.), 7.37 (1H, s), 3.96 (2H, t, 8.7 Hz), 3.74 (3H, br. s.), 3.07 (2H, t, 8.7 Hz).

5-Bromo-N-hydroxy-1-methyl-2,3-dihydro-1H-indole-6-sulfonamide

5-Bromo-N-hydroxy-1-methyl-2,3-dihydro-1H-indole-6-sulfonamide was prepared from bromo-1-methyl-2,3-dihydro-1H-indole-6-sulfonyl chloride (0.29 g, 0.94 mmol) according to the herein-described methods for the synthesis of N-hydroxysulfonamides (0.24 g, 82% yield). $^1$H NMR (250 MHz, DMSO-$d_6$) δ ppm 9.54-9.74 (2H, m), 8.38 (1H, br. s.), 7.68 (1H, s), 4.02 (2H, t, 8.7 Hz), 3.76 (3H, s), 3.18 (2H, t, 8.6 Hz).

Example 80: 2-Chloro-N-hydroxy-5-(methoxymethyl)benzene-1-sulfonamide (68)

1-Chloro-4-(methoxymethyl)-2-nitrobenzene

1-Chloro-4-(methoxymethyl)-2-nitrobenzene was synthesized according to the method detailed in Buenzli et al., *J. Amer. Chem. Soc.* 120:12274-12288 (1998). To a solution of KOH (5.98 g, 106 mmol) in DMSO (50 mL) was added 4-chloro-3-nitrobenzyl alcohol (5.0 g, 26.6 mmol) and methyl iodide (4 mL, 64 mmol). Stirring was continued for 1 hour after which time water (60 mL) was added and the reaction was extracted into DCM (3×50 mL), washed with water and dried over sodium sulfate, filtered and concentrated under reduced pressure (4.7 g, 88% yield). $^1$H NMR (250 MHz, chloroform-d) δ ppm 7.86 (1H, d, 1.4 Hz), 7.40-7.61 (2H, m), 4.49 (2H, s), 3.44 (3H, s).

2-Chloro-5-(methoxymethyl) benzene-1-sulfonyl chloride

To a solution of 1-chloro-4-(methoxymethyl)-2-nitrobenzene (2.7 g, 13.4 mmol) in EtOH (14 mL) and water (2 mL) was added iron (1.94 g, 34.8 mmol) and HCl (5 drops). The reaction was heated to 80° C. for 1 hour. The cooled reaction mixture was filtered through CELITE, washed with EtOAc (50 mL) and concentrated under reduced pressure and used directly in the next step. To a solution of 2-chloro-5-(methoxymethyl)aniline (4.19 g, 24.5 mmol) in acetic acid (25 mL) and HCl (6 mL) cooled to 0° C. was added sodium nitrite (1.85 g, 26.9 mmol) portion wise maintaining an internal temperature <5° C. The reaction mixture was allowed to stir at 0° C. for 1 hour. Simultaneously, $CuCl_2.H_2O$ (4.16 g, 24.5 mmol) was suspended in AcOH: water (25 mL:10 mL) at 0° C. and stirred at 0° C. until all $CuCl_2$ was in solution. $SO_2$ gas was condensed into a flask at −78° C. via the aid of a cold finger and the diazo compound and $CuCl_2$ solution added and the reaction warmed to 0° C. The reaction was allowed to warm to a temperature of about 25° C. over 2 hours. The reaction was quenched by addition to ice and extracted into DCM (3×50 mL). The organics were dried over sodium sulfate, filtered and concentrated under reduced pressure to provide the title compound as a yellow oil (5.1 g, 81% yield). $^1$H NMR (250 MHz, DMSO-$d_6$) δ ppm 7.82 (1H, d, 2.0 Hz), 7.30-7.48 (2H, m), 4.38 (2H, s), 3.27 (3H, s).

2-Chloro-N-hydroxy-5-(methoxymethyl)benzene-1-sulfonamide

1-Chloro-4-(methoxymethyl)-2-nitrobenzene was prepared from 2-chloro-5-(methoxymethyl) benzene-1-sulfonyl chloride (1 g, 3.9 mmol) according to herein-described methods for the synthesis of N-hydroxysulfonamides (0.55 g, 56% yield). $^1$H NMR (250 MHz, DMSO-$d_6$) δ ppm 9.69-9.89 (2H, m), 7.93 (1H, d, 1.7 Hz), 7.68 (1H, d, 8.1 Hz), 7.60 (1H, dd, 8.2, 2.0 Hz), 4.49 (2H, s), 3.33 (3H, s); predicted [M−H]$^-$=249.9941; observed [M−H]$^-$=249.9945.

Example 81: Methyl 5-(hydroxysulfamoyl)furan-2-carboxylate (69)

Methyl 5-(hydroxysulfamoyl)furan-2-carboxylate was prepared from methyl 5-(chlorosulfonyl)furan-2-carboxylate (1.0 g, 4.5 mmol) according to the herein-described methods for the synthesis of N-hydroxysulfonamides and was chromatographed with a silica gel column eluting with heptanes:ethyl acetate (4:1 v:v) followed by trituration from heptane to provide the desired compound as a yellow solid (0.46 g, 47% yield). $^1$H NMR (500 MHz, DMSO-$d_6$) δ ppm 10.28 (1H, d, 2.8 Hz), 9.89 (1H, d, 2.8 Hz), 7.48 (1H, d, 3.8 Hz), 7.36 (1H, d, 3.6 Hz), 3.87 (3H, s).

Example 82: N-Hydroxy-2,5-dimethylfuran-3-sulfonamide (70)

N-Hydroxy-2,5-dimethylfuran-3-sulfonamide was prepared from 2,5-dimethylfuran-3-sulfonyl chloride (0.5 g, 2.6 mmol) according to the herein-described methods for the synthesis of N-hydroxysulfonamides and was triturated with DCM:heptane to provide the desired compound as a white solid (0.34 g, 69% yield). $^1$H NMR (CDCl$_3$, 500 MHz) δ ppm 6.65 (1H, d, 3.7 Hz), 6.20 (1H, s), 6.13 (1H, s), 2.54 (3H, s), 2.28 (3H, s).

Example 83: N-Hydroxy-8-oxatricyclo[7.4.0.0]trideca-1(9), 2(7), 3,5,10,12-hexaene-4-sulfonamide (71)

N-Hydroxy-8-oxatricyclo[7.4.0.0]trideca-1(9), 2(7), 3,5,10,12-hexaene-4-sulfonamide was synthesized from 8-oxatricyclo[7.4.0.0$^{2,7}$]trideca-1(9), 2,4,6,10,12-hexaene-4-sulfonyl chloride (1.0 g, 3.75 mmol) according to the herein-described methods for the synthesis of N-hydroxysulfonamides and was triturated with diethyl ether to provide the desired compound as a white solid (0.46 g, 48% yield). $^1$H NMR (500 MHz, DMSO-$d_6$) δ ppm 9.66 (1H, d, 3.3 Hz), 9.62 (1H, d, 3.3 Hz), 8.67 (1H, d, 1.7 Hz), 8.35 (1H, d, 7.7 Hz), 7.93-8.02 (2H, m), 7.80 (1H, d, 8.4 Hz), 7.58-7.65 (1H, m), 7.49 (1H, t, 7.5 Hz).

Example 84: 2-(Ethanesulfonyl)-N-hydroxybenzene-1-sulfonamide (72)

1-Chloro-2-(ethylsulfanyl)benzene

To a solution of sodium methoxide (5.6 g, 103.7 mmol) in MeOH (100 mL) was added 2-chlorobenzene-1-thiol (10.0 g, 69.1 mmol) in MeOH (50 mL). The reaction was cooled to 0° C. and a solution of iodoethane (5.8 mL, 72.6 mmol) in MeOH (50 mL) was added dropwise. The reaction was stirred for 18 hours at a temperature of about 25° C. where upon LC-MS showed no starting material present. The solvent was removed and the reaction quenched by the addition of water (100 mL). The organics were extracted into DCM (3×200 mL), combined, dried over sodium sulfate, filtered and concentrated under reduced pressure to provide the desired compound as a clear oil (11.5 g, 96% yield). $^1$H NMR (CDCl$_3$, 500 MHz) δ ppm 7.36 (1H, dd, 7.9, 1.2 Hz), 7.28-7.19 (2H, m), 7.13-7.07 (1H, m), 2.97 (2H, q, 7.4 Hz), 1.37 (3H, t, 7.4 Hz).

1-Chloro-2-(ethanesulfonyl) benzene

A solution of 1-chloro-2-(ethylsulfanyl)benzene (11.5 g, 66.6 mmol) in DCM (230 mL) was added over 1 hour to a 0-5° C. solution of 10% sulfuric acid (345 mL) with simultaneous addition of potassium permanganate solid (35.8 g, 0.23 mol) in portions. The resulting reaction mixture was allowed to warm to a temperature of about 25° C. and stirring was continued for 1 hour, after which time LC-MS showed the reaction to be complete. Sodium bisulfate (65 g) was added to the reaction mixture slowly until all color had disappeared from the reaction and a clear, colorless solution was observed and the organic phase separated. The aqueous phase was re-extracted into DCM (3×100 mL) and the combined organic portion was dried over sodium sulfate, filtered and concentrated under reduced pressure to provide the desired compound as a clear, colorless oil which was used directly in the next step (14.0 g, 99.99% yield). $^1$H NMR (CDCl$_3$, 500 MHz) δ ppm 8.13 (1H, dd, 8.0, 1.1 Hz), 7.62-7.54 (2H, m), 7.48 (1H, ddd, 8.6, 6.6, 2.1 Hz), 3.44 (2H, q, 7.5 Hz), 1.27 (3H, t, 7.5 Hz).

1-(Benzylsulfanyl)-2-(ethanesulfonyl)benzene

To a solution of 1-chloro-2-(ethanesulfonyl)benzene (14.0 g, 68.4 mmol) in DMSO (70 mL) was added (benzylsulfanyl)methanimidamide HCl (14.56 g, 71.8 mmol) was added and the reaction mixture was cooled to 10° C. NaOH (6.84 g, 171.0 mmol) was added to the reaction mixture and the reaction was heated to 75° C. for 18 hours and allowed to cool to a temperature of about 25° C. where stirring was continued for an additional 72 hours. The reaction was quenched by the addition of water (50 mL) and the resulting aqueous solution extracted into DCM (4×100 mL). The combined organics were washed with brine solution (50 mL), dried over sodium sulfate, filtered and concentrated under reduced pressure to provide the product as a yellow oil which was chromatographed with a silica gel column eluting with 50-100% DCM acetate:heptanes gradient to provide the desired compound as a yellow oil (3.25 g, 16% yield). $^1$H NMR (CDCl$_3$, 500 MHz) δ ppm 8.06-8.00 (1H, m), 7.54-7.45 (2H, m), 7.35 (1H, ddd, 8.5, 6.8, 1.9 Hz), 7.32-7.21 (5H, m), 4.23 (2H, s), 3.37 (2H, d, 7.4 Hz), 1.11 (3H, t, 7.4 Hz).

2-(Ethanesulfonyl)benzene-1-sulfonyl chloride

Chlorine gas was bubbled through a solution of 1-(benzylsulfanyl)-2-(ethanesulfonyl)benzene (3.25 g, 11.1 mmol) in acetic acid (110 mL) and water (10 mL) maintaining an internal temperature of <10° C. for 1 hour. Upon complete addition of the chlorine gas the sulfonyl chloride was extracted into DCM (100 mL) and was washed with water (100 mL) and 2.5% w:v NaOH solution (50 mL). The organic portion was dried over sodium sulfate, filtered and concentrated under reduced pressure. The resulting solid was triturated with heptanes to provide the desired compound as a white solid (2.7 g, 89% yield). $^1$H NMR (CDCl$_3$, 500 MHz) δ ppm 8.44 (1H, dd, 7.8, 1.3 Hz), 8.40 (1H, dd, 7.7, 1.4 Hz), 7.97 (2H, dtd, 22.4, 7.6, 1.3 Hz), 3.61 (2H, q, 7.5 Hz), 1.36 (3H, t, 7.5 Hz).

2-(Ethanesulfonyl)-N-hydroxybenzene-1-sulfonamide 2-(Ethanesulfonyl)-N-hydroxybenzene-1-sulfonamide was synthesized from 2-(ethanesulfonyl)benzene-1-sulfonyl chloride (1.0 g, 3.7 mmol) according to the herein-described methods for the synthesis of N-hydroxysulfonamides and was triturated with heptanes to provide the desired compound as a white solid (0.8 g, 83% yield). $^1$H NMR (DMSO, 500 MHz) δ ppm 10.12 (1H, d, 3.5 Hz), 8.96 (1H, d, 3.5 Hz), 8.26-8.19 (2H, m), 8.08-7.99 (2H, m), 3.65 (2H, q, 7.4 Hz), 1.17 (3H, t, 7.4 Hz).

Example 85: N-Hydroxy-2-(propane-2-sulfonyl) benzene-1-sulfonamide (73)

1-Chloro-2-(propan-2-ylsulfanyl)benzene

To a solution of sodium methoxide (5.6 g, 103.7 mmol) in MeOH (100 mL) was added 2-chlorobenzene-1-thiol (10.0 g, 69.1 mmol) in MeOH (50 mL). The reaction was cooled to 0° C. and a solution of 2-iodopropane (7.26 mL, 72.6 mmol) in MeOH (50 mL) was added dropwise. The reaction was stirred for 18 hours at a temperature of about 25° C. where upon LC-MS showed starting material still present. An additional portion of 2-iodopropane (3 mL, 30 mmol) and sodium methoxide (3 g, 29 mmol) was added and stirring continued for a further 18 hours until complete consumption of the starting material was observed by LC-MS. The solvent was removed and the reaction quenched by the addition of water (100 mL). The organics were extracted into DCM (3×200 mL), combined, dried over sodium sulfate, filtered and concentrated under reduced pressure to provide the desired compound as a clear oil (12.8 g, 99% yield). $^1$H NMR (CDCl$_3$, 500 MHz) δ ppm 7.39 (2H, d, 7.9 Hz), 7.21 (1H, td, 7.6, 1.4 Hz), 7.14 (1H, td, 7.7, 1.6 Hz), 3.50 (1H, hept, 6.7 Hz), 1.34 (6H, d, 6.7 Hz).

1-Chloro-2-(propane-2-sulfonyl) benzene

A solution of 1-chloro-2-(propan-2-ylsulfanyl)benzene (12.8 g, 68.3 mmol) in DCM (230 mL) was added over 1 hour to a 0-5° C. solution of 10% sulfuric acid (380 mL) with simultaneous addition of potassium permanganate solid (36.7 g, 0.23 mol) in portions. The resulting reaction mixture was allowed to warm to a temperature of about 25° C. and stirring was continued for 1 hour after which time, LC-MS showed the reaction to be complete. Sodium bisulfate (60 g) was added to the reaction mixture slowly until all color had disappeared from the reaction and a clear, colorless solution was observed and the organic phase separated. The aqueous phase was re-extracted into DCM (3×100 mL) and the combined organic portion was dried over sodium sulfate, filtered and concentrated under reduced pressure to provide the desired compound as a clear, colorless oil (13.7 g, 92% yield). $^1$H NMR (CDCl$_3$, 250 MHz) δ ppm 8.17-8.06 (1H, m), 7.62-7.52 (2H, m), 7.46 (1H, ddd, 8.7, 5.5, 3.2 Hz), 3.80 (1H, hept, 6.9 Hz), 1.32 (6H, dd, 6.9, 0.9 Hz).

1-(Benzylsulfanyl)-2-(propane-2-sulfonyl) benzene

To a solution of 1-chloro-2-(propane-2-sulfonyl)benzene (13.7 g, 62.6 mmol) in DMSO (70 mL) was added (benzylsulfanyl)methanimidamide HCl (13.3 g, 65.8 mmol) was added and the reaction mixture was cooled to 10° C. NaOH (6.3 g, 156.6 mmol) was added to the reaction mixture and the reaction was heated to 75° C. for 18 hours. The reaction was quenched by the addition of water (50 mL) and the resulting aqueous solution extracted into DCM (4×100 mL). The combined organics were washed with brine solution (50 mL), dried over sodium sulfate, filtered and concentrated under reduced pressure to provide the product as a yellow oil which was chromatographed with a silica gel column eluting with 50-100% DCM acetate:heptanes gradient to provide the desired compound as a yellow oil (4.7 g, 20% yield). $^1$H NMR (CDCl$_3$, 500 MHz) δ ppm 8.03-7.98 (1H, m), 7.50-7.45 (2H, m), 7.36-7.21 (6H, m), 4.23 (2H, s), 3.82 (1H, dt, 13.7, 6.9 Hz), 1.19 (6H, d, 6.9 Hz).

2-(Propane-2-sulfonyl) benzene-1-sulfonyl chloride

Chlorine gas was bubbled through a solution of 1-(benzylsulfanyl)-2-(propane-2-sulfonyl)benzene (4.1 g, 13.4 mmol) in acetic acid (140 mL) and water (12 mL) maintaining an internal temperature of <10° C. for 1 hour. Upon complete addition of the chlorine gas the sulfonyl chloride was extracted into DCM (100 mL) and was washed with water (100 mL) and 2.5% w:v NaOH solution (50 mL). The organic portion was dried over sodium sulfate, filtered and concentrated under reduced pressure. The resulting solid was triturated with heptanes to provide the desired compound as a white solid (2.9 g, 77% yield). $^1$H NMR (CDCl$_3$, 500 MHz) δ ppm 8.42 (1H, dd, 7.8, 1.4 Hz), 8.34 (1H, dd, 7.6, 1.6 Hz), 7.93 (2H, dtd, 20.1, 7.5, 1.4 Hz), 4.05 (1H, hept, 6.8 Hz), 1.35 (6H, d, 6.9 Hz).

N-Hydroxy-2-(propane-2-sulfonyl)benzene-1-sulfonamide

N-Hydroxy-2-(propane-2-sulfonyl)benzene-1-sulfonamide was prepared from 2-(propane-2-sulfonyl)benzene-1- sulfonyl chloride (1.0 g, 3.5 mmol) according to the herein-described methods for the synthesis of N-hydroxy-sulfonamides and was triturated with heptanes to provide the desired compound as a white solid (0.84 g, 85% yield). $^1$H NMR (DMSO, 500 MHz) δ ppm 10.11 (1H, d, 3.5 Hz), 8.93 (1H, d, 3.5 Hz), 8.26-8.22 (1H, m), 8.22-8.17 (1H, m), 8.06-7.99 (2H, m), 4.09 (1H, hept, 6.9 Hz), 1.22 (6H, d, 6.8 Hz).

Example 86: 4-Acetyl-N-hydroxy-3,4-dihydro-2H-1,4-benzoxazine-6-sulfonamide (74)

4-Acetyl-N-hydroxy-3,4-dihydro-2H-1,4-benzoxazine-6-sulfonamide was prepared from 4-acetyl-3,4-dihydro-2H-1,4-benzoxazine-6-sulfonyl chloride (0.72 g, 2.6 mmol) according to the herein-described methods for the synthesis of N-hydroxysulfonamides and was triturated with diethyl ether to provide the desired compound as a white solid (0.70 g, 59% yield). $^1$H NMR (500 MHz, DMSO-$d_6$) δ ppm 9.50 (1H, br. s.), 9.43 (1H, br. s.), 7.47 (1H, d, 8.4 Hz), 7.09 (1H, d, 8.5 Hz), 4.36 (2H, t, 4.3 Hz), 3.89 (2H, t, 4.4 Hz), 2.27 (3H, s).

Example 87: Methyl 5-(hydroxysulfamoyl)-1-methyl-1H-pyrrole-2-carboxylate (75)

Methyl 5-(hydroxysulfamoyl)-1-methyl-1H-pyrrole-2-carboxylate was prepared from methyl 5-(chlorosulfonyl)-1-methyl-1H-pyrrole-2-carboxylate (0.46 g, 1.9 mmol) according to the herein-described methods for the synthesis of N-hydroxysulfonamides and was triturated with diethyl ether to provide the desired compound as a white solid (0.09 g, 19% yield). $^1$H NMR (500 MHz, DMSO-$d_6$) δ ppm 9.47 (1H, d, 3.3 Hz), 9.21 (1H, d, 3.5 Hz), 7.70 (1H, d, 1.6 Hz), 7.06 (1H, d, 1.9 Hz), 3.91 (3H, s), 3.78 (3H, s).

Example 88: N-[5-(Hydroxysulfamoyl)-1,3-thiazol-2-yl]acetamide (76)

N-[5-(Hydroxysulfamoyl)-1,3-thiazol-2-yl]acetamide was prepared from 2-(acetylamino)-1,3-thiazole-5-sulfonyl chloride (0.28 g, 1.3 mmol) according to the herein-described methods for the synthesis of N-hydroxysulfona-mides and was triturated with diethyl ether to provide the desired compound as a white solid (0.12 g, 42% yield). $^1$H NMR (500 MHz, DMSO-$d_6$) δ ppm 9.80 (1H, d, 3.2 Hz), 9.65 (1H, d, 3.3 Hz), 7.94 (1H, s), 2.20 (3H, s).

Example 89: N-Hydroxy-2,5-dimethyl-4-(morpho-line-4-carbonyl)furan-3-sulfonamide (77)

4-(2,5-Dimethylfuran-3-carbonyl)morpholine

To a solution of diisopropylethylamine (3.8 mL, 21.5 mmol) and morpholine (1.79 g, 20.5 mmol) in DCM (30 mL) cooled to 0° C. was added 2,5 dimethyl-furan-3-carbonyl chloride (3.1 g, 19.6 mmol) and the resulting solution was warmed to a temperature of about 25° C. for 6 hours. The reaction was quenched by the addition of 1N HCl (20 mL) and the organic portion was extracted into DCM (50 mL), dried over sodium sulfate, filtered and concentrated under reduced pressure to provide the desired compound as a brown oil (4.41 g, quantitative yield). $^1$H NMR (500 MHz, DMSO-$d_6$) δ ppm 6.09 (1H, s), 3.40-3.63 (8H, m), 2.25 (3H, s), 2.21 (3H, s).

2,5-Dimethyl-4-(morpholine-4-carbonyl)furan-3-sulfonyl chloride 4-(2,5-Dimethylfuran-3-carbonyl)morpholine (2.0 g, 9.6 mmol) was added to chlorosulfonic acid (6.4 mL, 95 mmol) and the reaction heated to 90° C. for 1 hour after which time LC-MS showed complete consumption of the starting material. The brown solution was poured onto ice and the organic portion extracted into DCM (2×50 mL), dried over sodium sulfate, filtered and concentrated under reduced pressure to provide the desired compound as a brown solid which was used directly in the synthesis of the corresponding N-hydroxysulfonamide (2.29 g, 78% yield). $^1$H NMR (500 MHz, DMSO-$d_6$) δ ppm 3.03-3.85 (8H, m), 2.31 (3H, s), 2.07 (3H, s).

N-Hydroxy-2,5-dimethyl-4-(morpholine-4-carbonyl)furan-3-sulfonamide

N-Hydroxy-2,5-dimethyl-4-(morpholine-4-carbonyl)furan-3-sulfonamide was prepared from 2,5-dimethyl-4-(morpholine-4-carbonyl)furan-3-sulfonyl chloride (2.3 g, 7.4 mmol) according to the herein-described methods for the synthesis of N-hydroxysulfonamides and was triturated with DCM to provide the desired compound as an off white solid (1.3 g, 56% yield). $^1$H NMR (500 MHz, DMSO-$d_6$) δ ppm 9.71 (1H, d, 3.5 Hz), 8.64 (1H, d, 3.6 Hz), 3.62-3.78 (2H, m), 3.42-3.62 (4H, m), 3.36-3.42 (2H, m), 2.47 (3H, s), 2.22 (3H, s).

Example 90: Ethyl 5-(hydroxysulfamoyl)furan-3-carboxylate (78)

Ethyl 5-(hydroxysulfamoyl)furan-3-carboxylate was prepared from ethyl 5-(chlorosulfonyl)furan-3-carboxylate (0.3 g, 1.4 mmol) according to the herein-described methods for the synthesis of N-hydroxysulfonamides and was triturated with heptane to provide the desired compound as an off white solid (0.2 g, 60% yield). $^1$H NMR (500 MHz, DMSO-$d_6$) δ ppm 10.14 (1H, br. s.), 9.88 (1H, s), 8.76 (1H, d, 0.8 Hz), 7.38 (1H, d, 0.8 Hz), 4.28 (2H, q, 7.1 Hz), 1.21-1.35 (3H, t, 7.1 Hz).

Example 91: 5-Chlorothiophene-2-sulfonamido oxane-4-carboxylate (79)

[(tert-Butoxy)carbonyl]amino oxane-4-carboxylate

To a solution of tetrahydro-2H-pyran-4-carboxylic acid (5.0 g, 38.42 mmol) in DCM (200 mL) was added EDCI (5.96 g, 38.42 mmol). The reaction was stirred at a temperature of about 25° C. for 10 minutes and BOC hydroxylamine (5.12 g, 38.42 mmol) was added and stirring was continued for 18 hours. The reaction mixture was diluted with DCM (50 mL) and washed with water (2×20 mL) and brine (1×20 mL), dried over magnesium sulfate, filtered and concentrated to give [(tert-butoxy)carbonyl]amino oxane-4-carboxylate as a light orange oil (6.93 g, 74% yield). $^1$H NMR (250 MHz, chloroform-d) δ ppm 8.00 (1H, br. s.), 3.98 (2H, td, 3.7, 11.7 Hz), 3.60-3.32 (2H, m), 2.86-2.64 (1H, m), 1.79 (4H, s), 1.48 (9H, s).

N-[(tert-Butoxy)carbonyl]5-chlorothiophene-2-sulfonamido oxane-4-carboxylate

To a solution of [(tert-butoxy)carbonyl]amino oxane-4-carboxylate (2 g, 8.15 mmol) in DCM (100 mL) was added 5-chlorothiophene-2-sulfonyl chloride (1.09 mL, 8.15 mmol) and triethylamine (1.7 mL, 12.23 mmol), followed by the addition of DMAP (149 mg, 1.22 mmol). The reaction mixture was stirred at a temperature of about 25° C. for 1 hour and then water was added (10 mL). The mixture was shaken, the 2 layers were separated and the organic layer was washed with aqueous 0.1M HCl (1×10 mL), water (1×10 mL) and brine (1×10 mL), dried over magnesium sulfate, filtered and concentrated under reduced pressure to give an oil. The product was chromatographed with a silica gel column eluting with heptane:EtOAc 30%-40% to give N-[(tert-butoxy)carbonyl]5-chlorothiophene-2-sulfonamido oxane-4-carboxylate (0.92 g, 27% yield). $^1$H NMR (500 MHz, chloroform-d) δ ppm 7.65 (1H, d, 4.3 Hz), 7.00 (1H, d, 4.1 Hz), 4.01 (2H, td, 3.6, 11.7 Hz), 3.55-3.46 (2H, m), 2.84 (1H, tt, 5.1, 9.8 Hz), 2.00-1.87 (4H, m), 1.49 (9H, s).

5-Chlorothiophene-2-sulfonamido oxane-4-carboxylate

To a solution of N-[(tert-butoxy)carbonyl]5-chlorothiophene-2-sulfonamido oxane-4-carboxylate (0.86 g, 2.0 mmol) in DCM (8 mL) was added trifluoroacetic acid (2.24 mL, 30.3 mmol) and the reaction mixture was stirred at a temperature of about 25° C. for 1 hour. The solvents were evaporated to give a yellow oil which was chromatographed with a silica gel column eluting with heptanes:EtOAc 20%-50% to give 5-chlorothiophene-2-sulfonamido oxane-4-carboxylate as a white solid (0.53 g, 80% yield). $^1$H NMR (500 MHz, DMSO-$d_6$) δ ppm 11.52 (1H, br. s.), 7.68 (1H, d, 4.1 Hz), 7.39 (1H, d, 4.1 Hz), 3.80 (2H, td, 3.5, 11.3 Hz), 3.41-3.30 (2H, m), 2.78 (1H, tt, 4.1, 11.1 Hz), 1.73 (2H, dd, 2.1, 12.8 Hz), 1.62-1.49 (2H, m).

Example 92: N-Hydroxy-2-(oxan-4-ylmethanesulfonyl)benzene-1-sulfonamide (80)

4-[(2-Fluorobenzenesulfonyl)methyl]oxane

To a solution of 4-(iodomethyl)oxane (1.0 g, 4.4 mmol) and 2-fluorobenzene-1-thiol (0.57 g, 4.4 mmol) in DMF (10 mL) was added potassium carbonate (0.79 g, 5.7 mmol) and the reaction mixture was stirred at a temperature of about 25° C. for 18 hours. The reaction was quenched by the addition of water (20 mL) and the organic portion extracted into DCM (50 mL). The organics were washed with water (10 mL) before being dried over sodium sulfate, filtered and concentrated under reduced pressure. The product was chromatographed with a silica gel column eluting with 100-70% heptanes:ethyl acetate to provide the desired compound as a clear, colorless oil (0.9 g, 92% yield). $^1$H NMR (500 MHz, chloroform-d) δ ppm 7.37 (1H, td, 7.6, 1.7 Hz), 7.18-7.25 (1H, m), 6.99-7.17 (2H, m), 3.85-4.04 (2H, m), 3.35 (2H, td, 11.8, 2.0 Hz), 2.84 (2H, d, 6.9 Hz), 1.77-1.87 (2H, m), 1.65-1.77 (1H, m), 1.36 (2H, qd, 12.3, 4.4 Hz).

4-{[2-(Benzylsulfanyl)benzenesulfonyl]methyl}oxane

To a solution of 4-[(2-fluorobenzenesulfonyl)methyl] oxane (1.0 g, 3.9 mmol) in DMSO (20 mL) was added benzyl carbamimidothioate hydrochloride (0.84 g, 4.2 mmol) and the mixture was cooled during the addition of NaOH (0.4 g, 9.8 mmol) so the internal temperature was kept below 15° C.-20° C. The reaction mixture was heated at 75° C. for 2 hours after which time LC-MS shows complete consumption of the starting material. The reaction was allowed to cool to a temperature of about 25° C. and quenched by the addition of 1N HCl solution (5 mL). The formed emulsion was extracted with ethyl acetate (2×50 mL) and the resulting organic layer was dried over sodium sulfate, filtered and concentrated under reduced pressure. The oil was chromatographed with a silica gel column eluting with 20-40% heptanes:ethyl acetate to provide the desired compound as a yellow oil (1.2 g, 87% yield). $^1$H NMR (250 MHz, DMSO-$d_6$) δ ppm 7.78-7.95 (2H, m), 7.67 (1H, td, 7.7, 1.5 Hz), 7.14-7.49 (6H, m), 4.40 (2H, s), 3.71 (2H, dt, 9.7, 1.9 Hz), 3.30 (2H, d, 6.4 Hz), 3.17 (2H, td, 11.6, 2.1 Hz), 1.79-1.97 (1H, m), 1.48 (2H, dd, 13.0, 1.9 Hz), 1.06-1.30 (2H, m).

2-(Oxan-4-ylmethanesulfonyl)benzene-1-sulfonyl chloride

Chlorine gas was bubbled through a solution of 4-{[2-(benzylsulfanyl)benzenesulfonyl] methyl}oxane (1 g, 2.8 mmol) in acetic acid (35 mL) and water (3 mL) maintaining an internal temperature of <10° C. for 1 hour. Upon complete addition of the chlorine gas the sulfonyl chloride was extracted into DCM (150 mL) and was washed with water (150 mL) and 2.5% w:v NaOH solution (50 mL). The organic portion was dried over sodium sulfate, filtered and concentrated under reduced pressure and chromatographed with a silica gel column eluting with 80% ethyl acetate: heptane to provide the desired compound as an oil which was used directly in the synthesis of the corresponding N-hydroxysulfonamide (0.9 g, 96% yield). $^1$H NMR (500 MHz, chloroform-d) δ ppm 8.40 (2H, ddd, 7.6, 5.9, 1.4 Hz), 7.88-8.05 (2H, m), 3.87-4.03 (2H, m), 3.38-3.51 (3H, m), 2.99 (1H, br. s.), 2.41-2.64 (1H, m), 1.80-1.91 (2H, m), 1.43-1.63 (2H, m).

N-Hydroxy-2-(oxan-4-ylmethanesulfonyl)benzene-1-sulfonamide

N-Hydroxy-2-(oxan-4-ylmethanesulfonyl)benzene-1-sulfonamide was prepared from 2-(oxan-4-ylmethanesulfonyl)benzene-1-sulfonyl chloride (0.72 g, 2.1 mmol) according to the herein-described methods for the synthesis of N-hydroxysulfonamides and was chromatographed with a silica gel column eluting with heptanes:ethyl acetate (1:1 v:v) to provide the desired compound as a white solid (0.37 g, 52% yield). $^1$H NMR (500 MHz, DMSO-$d_6$) δ ppm 10.11 (1H, d, 3.5 Hz), 8.98 (1H, d, 3.5 Hz), 8.23-8.28 (1H, m), 8.17-8.22 (1H, m), 7.99-8.04 (2H, m), 3.74-3.81 (2H, m), 3.62 (2H, d, 6.5 Hz), 3.29 (2H, td, 11.6, 2.0 Hz), 2.11-2.23 (1H, m), 1.66 (2H, dd, 13.1, 1.9 Hz), 1.28-1.40 (2H, m).

Example 93: N-Hydroxy-3-methyl-1-benzofuran-2-sulfonamide (81)

Ethyl 2-(2-acetylphenoxy)acetate

To a solution of 1-(2-hydroxyphenyl)ethan-1-one (7.5 g, 0.06 mol) in dimethyl formamide (75 mL) was added potassium carbonate (22.8 g, 0.17 mol) at a temperature of about 25° C. The reaction mixture was stirred for 10 minutes before the addition of ethyl bromoacetate (9.2 mL, 0.08 mol) and stirring was continued for a further 5 hours at a temperature of about 25° C. After completion of reaction, observed by TLC, the reaction was diluted with ethyl acetate (150 mL) and water (150 mL), the organic portion was separated, and the aqueous portion was further extracted with ethyl acetate (2×150 mL). The combined organic layers were washed with water (2×150 mL), dried over sodium sulfate, filtered and concentrated under reduced pressure to provide the O-alkylated product as an colorless oil. The product was chromatographed with a silica gel column eluting with 5-8% ethyl acetate:hexane to give ethyl 2-(2-acetylphenoxy)acetate as an off white solid (10.5 g, 86% yield). $^1$H NMR (400 MHz, CDCl$_3$) δ ppm 7.78-7.74 (1H, m), 7.47-7.41 (1H, m), 7.08-7.02 (1H, m), 6.85-6.80 (1H, m), 4.72 (2H, s), 4.28 (2H, q, 7.1 Hz), 2.72 (3H, s), 1.30 (3H, t, 7.1 Hz).

2-(2-Acetylphenoxy)acetic acid

To a solution of ethyl 2-(2-acetylphenoxy) acetate (8 g, 0.04 mol) in ethanol:water (80 mL:8 mL) was added lithium hydroxide hydrate (1:1:1) (4.5 g, 0.11 mol) at 0° C. The reaction mixture was stirred at a temperature of about 25° C. for 18 hours and after completion of reaction (observed by TLC), the reaction mixture was concentrated under reduced pressure. The product was taken into water (350 mL) and extracted with diethyl ether (2×150 mL). The aqueous extract was then acidified using 1N HCl (pH of about 2-3) at 0° C. and extracted into dichloromethane (4×300 mL). The combined organic layers were washed with water (150 mL), dried over sodium sulfate, filtered and concentrated under reduced pressure to provide the acid product as an off white solid. Trituration with pentane provided the product compound as an off white solid (6.7 g, 95.8% yield). $^1$H NMR (400 MHz, DMSO) δ ppm 13.16 (1H, s), 7.60-7.55 (1H, m), 7.54-7.49 (1H, m), 7.12-7.07 (1H, m), 7.07-7.02 (1H, m), 4.85 (2H, s), 2.62 (3H, s).

3-Methyl-1-benzofuran

To a solution of 2-(2-acetylphenoxy)acetic acid (8 g, 0.041 mol) in acetic anhydride (48 mL) was added sodium acetate (20.3 g, 0.25 mol) at a temperature of about 25° C. The reaction mixture was stirred at reflux (140° C.) for 18 hours. Upon reaction completion (checked by TLC), the reaction mixture was poured onto ice-cold water (400 mL) and extracted into ethyl acetate (3×400 mL). The combined organic layer was washed with water (400 mL), dried over sodium sulfate, filtered and concentrated under reduced pressure to provide cyclized product as a red oil which was chromatographed with a silica gel column eluting with hexane to provide the cyclized compound as a colorless liquid (2.6 g, 48% yield). $^1$H NMR (400 MHz, CDCl$_3$) δ ppm 7.55-7.51 (1H, m), 7.48-7.44 (1H, m), 7.42-7.39 (1H, m), 7.32-7.27 (1H, m), 7.27-7.22 (1H, m), 2.26 (3H, d, 1.3 Hz).

3-Methyl-1-benzofuran-2-sulfonyl chloride

To a solution of 3-methyl-1-benzofuran (2.6 g, 17.7 mmol) in diethyl ether (50 mL) cooled to −78° C. was added n-BuLi (8.7 mL of a 2.5M solution in hexanes, 21.64 mmol) dropwise. The reaction was stirred for 1 hour before SO$_2$ gas was bubbled through the reaction and stirring continued at −50° C. for an additional 1 hour. The reaction was allowed to warm to −20° C. and NCS (3.42 g, 25.58 mmol) was added portion wise and stirring was continued for 18 hours at a temperature of about 25° C. After substantially complete consumption of the starting material was observed by TLC, water (40 mL) was added and the organic portion was extracted into ethyl acetate (3×20 mL), dried over sodium sulfate, filtered and concentrated under reduced pressure. The product was chromatographed with a silica gel column eluting with 0.5% ethyl acetate in hexane to provide the desired compound as a yellow solid (2.5 g, 55% yield). $^1$H NMR (300 MHz, CDCl$_3$) δ ppm 7.72 (1H, dd, 7.9, 0.9 Hz), 7.64-7.58 (2H, m), 7.43 (1H, dd, 8.1, 4.2 Hz), 2.65 (3H, s).

N-Hydroxy-3-methyl-1-benzofuran-2-sulfonamide

N-Hydroxy-3-methyl-1-benzofuran-2-sulfonamide was prepared from 3-methyl-1-benzofuran-2-sulfonyl chloride (1.5 g, 6.5 mmol) according to the herein-described methods for the synthesis of N-hydroxysulfonamides and was triturated with 5% DCM:pentane to provide the desired compound as a white solid (0.74 g, 50% yield). $^1$H NMR (400 MHz, DMSO) δ ppm 10.11 (1H, d, 3.0 Hz), 9.79 (1H, d, 3.0 Hz), 7.81 (1H, ddd, 7.9, 1.1, 0.7 Hz), 7.70-7.66 (1H, m), 7.55 (1H, ddd, 8.4, 7.2, 1.3 Hz), 7.41 (1H, td, 7.6, 0.9 Hz), 2.50 (3H, s).

Example 94: N-Hydroxy-5-(piperidine-1-carbonyl)furan-2-sulfonamide (82)

5-(Piperidine-1-carbonyl)furan-2-sulfonyl chloride

Sulfur trioxide pyridine complex (2.66 g, 16.74 mmol) and 1,2 dichloroethane (20 mL) were heated with (furan-2-carbonyl) piperidine (2 g, 11.16 mmol) in a sealed tube at 140° C. for 22 hours, after which time the reaction mixture was allowed to cool to a temperature of about 25° C. and the mixture concentrated under reduced pressure to provide a slurry. The residue was treated with a solution of sodium carbonate (1.7 g, 16.74 mmol) in water (20 mL) and the resulting mixture was evaporated to dryness. The solid was stirred with dichloromethane (20 mL) before refluxing in ethanol (10 mL) for 30 min and the filtrate was concentrated under reduced pressure to provide 1.2 g of the sodium salt. The sodium salt was dissolved in methanol (10 mL) and the resulting solution was treated with charcoal and filtered through CELITE. The filtrate was concentrated under reduced pressure to provide 5-(piperidine-1-carbonyl)furan-2-sulfonic acid as the sodium salt (950 mg). The sodium salt was mixed with dichloromethane (10 mL) at 0° C. and slowly added to phosphorous oxychloride (2 mL). Phosphorus pentachloride (2.32 g, 16.74 mmol) was then added portion wise to the reaction mixture at 0° C. and the reaction mixture was allowed to warm to a temperature of about 25° C. and stirred for a further 2 hours at that temperature. The reaction mixture was diluted with dichloromethane (30 mL) and water (20 mL), and the organic portion was separated and dried over sodium sulfate, filtered and concentrated under reduced pressure to provide 5-(piperidine-1-carbonyl)furan-2-sulfonyl chloride (0.6 g, 19% yield).

N-Hydroxy-5-(piperidine-1-carbonyl)furan-2-sulfonamide

To a solution of aqueous hydroxylamine (0.3 mL of a 50% aqueous solution, 4.95 mmol) in tetrahydrofuran (7 mL) and water (3 mL) cooled to −5° C. was slowly added a solution of 5-(piperidine-1-carbonyl)furan-2-sulfonyl chloride (550 mg, 1.98 mmol) in THF (3 mL), maintaining a reaction temperature of less than 10° C. The reaction was maintained at this temperature until substantially complete consumption of the sulfonyl chloride was observed by TLC (about 30 min), after which time the reaction was diluted with dichloromethane (20 mL) and the organic portion was separated, washed with water (2×10 mL), dried over sodium sulfate, filtered and concentrated under reduced pressure to provide the N-hydroxy-5-(piperidine-1-carbonyl)furan-2-sulfonamide as an yellow solid. Trituration was carried out using DCM:pentane (1:1 v:v) followed by dichloromethane (2×1 mL) to provide the title compound as an off white solid (0.3 g, 55% yield). $^1$H NMR (400 MHz, DMSO) δ ppm 10.13 (s, $^1$H), 9.84 (s, 1H), 7.31 (d, 1H), 7.09 (d, 1H), 3.58 (s, 4H), 1.74-1.45 (m, 6H)

Example 95:
N-Hydroxy-5-methanesulfonylthiophene-2-sulfonamide (83)

5-Methanesulfonylthiophene-2-sulfonyl chloride

2-Methanesulfonylthiophene (5 g, 30.82 mmol) was added to chlorosulfonic acid (14.37 mL, 215.74 mmol) and the resulting solution was heated to 90° C. for 1 h after which time the solution was cooled to a temperature of about 25° C. before being poured onto ice (250 mL). The resulting suspension was extracted into dichloromethane (3×100 mL) and the combined organic portion was dried over sodium sulfate, filtered and concentrated under reduced pressure to provide the desired compound as a fawn solid which existed as a mixture with the corresponding 1,4 isomer and was used as such directly in the synthesis the corresponding N-hydroxysulfonamide (4.6 g, 39% yield as a 1:1 mixture with the 2,4 isomer). $^1$H NMR (500 MHz, DMSO-$d_6$) δ 7.59 (d, J=3.8 Hz, 1H), 7.20 (d, J=3.8 Hz, 1H), 3.33 (s, 3H).

N-Hydroxy-5-methanesulfonylthiophene-2-sulfonamide

To a solution of aqueous hydroxylamine (158 mL of a 50% solution, 23.97 mmol) in tetrahydrofuran (15 mL) and water (2.5 mL) cooled to −5° C. was slowly a 1:1 mixture of 5-methanesulfonylthiophene-2-sulfonyl chloride and 5-methanesulfonylthiophene-3-sulfonyl chloride (2.5 g, 9.58 mmol) maintaining a reaction temperature of less than 10° C. The reaction was maintained at this temperature until complete consumption of the sulfonyl chloride was observed by LC-MS (about 5 min), after which time the reaction was diluted with dichloromethane (20 mL) and the organic portion was separated, washed with water (2×5 mL), dried over sodium sulfate, filtered and concentrated under reduced pressure to provide the N-hydroxysulfonamide as a 1:1 mixture with the corresponding 2,4 isomer as a by-product. The compound was then chromatographed by acidic HPLC which fully separated the 2 isomers (0.58 g, 46% yield). $^1$H NMR (500 MHz, DMSO-$d_6$) of title compound: δ 10.09 (s, 2H), 7.91 (d, J=4.0 Hz, 1H), 7.75 (d, J=4.0 Hz, 1H), 3.48 (s, 3H). $^1$H NMR (500 MHz, DMSO-$d_6$) of 2,4 isomer: $^1$H NMR (500 MHz, DMSO-$d_6$) δ 9.84 (s, 1H), 9.77 (s, 1H), 8.65 (d, J=1.6 Hz, 1H), 7.99 (d, J=1.6 Hz, 1H), 3.46 (s, 4H).

Example 96: Preparation of
N-Hydroxy-5-methylthiophene-2-sulfonamide (84)

5-Methylthiophene-2-sulfonyl chloride

5-Methylthiophene-2-sulfonyl chloride was synthesized according to the methods disclosed in Sone et al., *Bull. Chem. Soc. Japan* 58:1063-1064 (1985). Freshly distilled sulfuryl chloride (74.9 mL, 0.93 mol) was added drop wise with stirring to ice cold DMF (71.5 mL, 0.93 mol) maintaining a temperature below 25° C. The hygroscopic solid complex which formed after 10 minutes was held at the same temperature for an additional 30 minutes. 2-methyl thiophene (70 g, 0.71 mol) was added to the complex and the mixture was heated at 98° C. for 1 hour. The viscous brown mixture was cooled, poured into ice-water and extracted into diethyl ether (2×1 L). The organic layer was washed successively with water (500 mL), 5% $NaHCO_3$ solution (200 mL) and water (500 mL) before being dried over sodium sulfate, filtered and concentrated under reduced pressure to provide the sulfonyl chloride as a dark brown liquid. The sulfonyl chloride was chromatographed by CC eluting with 0-30% EtOAc:heptane (110 g, 78% yield). $^1$H NMR (400 MHz, $CDCl_3$) δ ppm 7.69 (1H, d, J=3.9 Hz), 6.88-6.83 (1H, m), 2.60 (3H, d, J=0.8 Hz).

N-Hydroxy-5-methylthiophene-2-sulfonamide

To a solution of aqueous hydroxylamine (8.4 mL of a 50% aqueous solution, 50.9 mmol) in THF (60 mL) and water (10 mL) cooled to −5° C. was slowly added 5-methylthiophene-2-sulfonyl chloride (10 g, 50.9 mmol) maintaining a reaction temperature of less than 10° C. The reaction was maintained at this temperature until complete consumption of the sulfonyl chloride was observed by LC-MS (about 5 min), after which time the reaction was diluted with DCM (100 mL) and the organic portion was separated and washed with water (2×25 mL). The aqueous extracts were combined and rewashed with DCM (2×75 mL). All of the organic portions were combined, dried over sodium sulfate, filtered and concentrated under reduced pressure to provide the N-hydroxysulfonamide as a beige solid. Trituration with heptanes provided the title compound as a beige solid (6.1 g, 61.8% yield). LC-MS $t_R$=1.1 min; HRMS: theoretical ($C_5H_7NO_3S_2$)=191.9789, measured=191.9781; $^1$H NMR (500 MHz, DMSO-$d_6$) δ ppm 9.71 (1H, d, J=3.3 Hz), 9.58 (1H, d, J=3.5 Hz), 7.46 (1H, d, J=3.8 Hz), 6.95 (1H, dd, 1.0 Hz), 2.53 (3H, s).

Example 97:
N-Hydroxy-1-methyl-1H-pyrazole-3-sulfonamide (85)

To a solution of aqueous hydroxylamine (7.32 mL of a 50% solution, 110.73 mmol) in tetrahydrofuran (48 mL) and water (8 mL) cooled to −5° C. was slowly added 1-methyl-1H-pyrazole-3-sulfonyl chloride (8 g, 44.29 mmol) maintaining a reaction temperature of less than 10° C. The reaction was maintained at this temperature until substantially complete consumption of the sulfonyl chloride was observed by TLC (about 5 min), after which time the reaction was diluted with dichloromethane (50 mL) and the organic portion was separated, washed with water (2×10 mL), dried over sodium sulfate, filtered and concentrated under reduced pressure to provide the N-hydroxysulfonamide as an off white solid. Trituration was carried out using heptanes:DCM (1:1, v:v) to provide the title compound as an off white solid (4.3 g, 55% yield). LC-MS $t_R$=0.41 min, $[M+H]^+$=179. $^1$H NMR (250 MHz, DMSO-$d_6$) δ ppm 9.62 (d, J=3.2 Hz, 1H), 9.51 (d, J=3.2 Hz, 1H), 7.89 (d, J=2.3 Hz, 1H), 6.68 (d, J=2.3 Hz, 1H), 3.93 (s, 3H).

Example 98: Preparation of
3-Chloro-4-fluoro-N-hydroxybenzene-1-sulfonamide (87)

To a solution of hydroxylamine (1.3 mL of a 50% aqueous solution; 21.8 mmol) in THF (12 mL) and water (2 mL) cooled to 0° C. was added 3-chloro-4-fluorobenzene-1-sulfonyl chloride (2 g, 8.7 mmol) portionwise so as to maintain the temperature below 10° C. The reaction was stirred for 20 minutes, after which time LC-MS showed complete consumption of the sulfonyl chloride. The reaction was diluted with diethyl ether (2×50 mL) and the organic portion was separated and washed with 5% citric acid solution (10 mL) and water (10 mL). The organic portion was dried over sodium sulfate, filtered and concentrated under reduced pressure. The product was triturated with diethyl ether:heptane to provide the title compound as a white solid (1.14 g, 58% yield). LC-MS $t_R$=1.54 min; HRMS: theoretical ($C_6H_5ClFNO_3S$)=223.9584, measured=223.963; $^1$H NMR (500 MHz, DMSO-$d_6$) δ ppm 9.79 (1H, d, 3.2 Hz), 9.73 (1H, d, 3.2, Hz), 7.98 (1H, dd, 6.87 Hz, 2.29, Hz), 7.85 (1H, m).

Example 99:
1-N,3-N-dihydroxybenzene-1,3-disulfonamide (88)

To a solution of aqueous hydroxylamine (2.4 mL of a 50% solution, 36.35 mmol) in tetrahydrofuran (12 mL) and water (2 mL) cooled to −5° C. was slowly added benzene-1,3-disulfonyl dichloride (2 g, 7.27 mmol), maintaining a reaction temperature of less than 10° C. The reaction was maintained at this temperature until substantially complete consumption of the sulfonyl chloride was observed by TLC (about 5 min), after which time the reaction was diluted with ethyl acetate (25 mL) and the organic portion was separated, washed with water (2×10 mL), and ammonium chloride (25 mL), dried over sodium sulfate, filtered and concentrated under reduced pressure to provide the N-hydroxysulfonamide as a white solid. Trituration was carried out using heptane to provide the title compound as a white solid (0.567 g, 29% yield). Concentration to 1/3 volume of the filtrate provided a second batch of the N-hydroxysulfonamide (0.327 g, 17% yield) LC-MS $t_R$=0.87 min; $^1$H NMR (500 MHz, DMSO-$d_6$) δ 9.88 (s, 2H), 9.82 (s, 2H), 8.28 (t, J=1.7 Hz, 1H), 8.14 (dd, 1.8 Hz, 2H), 7.91 (t, J=7.9 Hz, 1H).

Example 100:
3-Bromo-N-hydroxybenzene-1-sulfonamide (89)

To a solution of hydroxylamine HCl (1.62 g, 23.48 mmol) in water (2.4 mL) cooled to 0° C. was added a solution of potassium carbonate (3.24 g, 23.48 mmol) in water (3.6 mL) dropwise maintaining an internal reaction temperature between 5° C. and 15° C. The reaction mixture was stirred for 15 minutes, whereupon tetrahydrofuran (12 mL) and methanol (3.0 mL) were added. 3-Bromobenzene sulfonyl chloride (3.0 g, 11.74 mmol) was added portionwise maintaining a temperature below 15° C. and the reaction mixture was then stirred at a temperature of about 25° C. until substantially complete consumption of the sulfonyl chloride was observed by TLC. The resulting suspension was concentrated under reduced pressure to remove any volatiles and the aqueous suspension was extracted with diethyl ether (2×50 mL). The organic portion was dried over magnesium sulfate, filtered and concentrated under reduced pressure to provide the N-hydroxy sulfonamide as a white solid (1.8 g, 61% yield). $^1$H NMR (400 MHz, DMSO-$d_6$) δ ppm 9.75 (1H, d, J=8.1 Hz), 9.77 (1H, s), 7.92 (1H, d, J=8.1 Hz), 7.95 (1H, t, J=1.7 Hz), 7.84 (1H, d, J=7.8 Hz), 7.60 (1H, t, J=7.9 Hz); predicted [M−H]$^-$=249.9174; observed [M−H]$^-$=249.9163.

Example 101: Preparation of N-Hydroxy-3-(trifluoromethoxy)benzene-1-sulfonamide (92)

To a solution of hydroxylamine (6.4 mL of a 50% aqueous solution; 95.9 mmol) in THF (60 mL) and water (10 mL) cooled to 0° C. was added 3-(trifluoromethoxy)benzene-1-sulfonyl chloride (10 g, 38.4 mmol) portionwise so as to maintain the temperature below 10° C. The reaction was stirred for 20 minutes, after which time LC-MS showed complete consumption of the sulfonyl chloride. The reaction was diluted with DCM (2×50 mL) and the organic portion was separated and washed with ammonium chloride solution (10 mL) and water (10 mL). The organic portion was dried over sodium sulfate, filtered and concentrated under reduced pressure. The product was triturated with heptane to provide the title compound as a white solid (6.77 g, 66.6% yield). LC-MS $t_R$=1.67 min; HRMS: theoretical ($C_7H_6F_3NO_4S$)= 255.9891, measured=255.9903; $^1$H NMR (250 MHz, DMSO-$d_6$) δ ppm 9.82 (2H, s), 7.89 (1H, dt, J=7.3, 1.7 Hz), 7.84-7.70 (3H, m).

Example 102:
N-Hydroxy-4-methanesulfonylbenzene-1-sulfonamide (93)

To a solution of aqueous hydroxylamine (6.48 mL of a 50% solution, 98.15 mmol) in tetrahydrofuran (60 mL) and water (10 mL) cooled to −5° C. was slowly added 4-methanesulfonylbenzene-1-sulfonyl chloride (10 g, 39.26 mmol) as a suspension in tetrahydrofuran (20 mL) maintaining a reaction temperature of less than 10° C. The reaction was maintained at this temperature until complete consumption of the sulfonyl chloride was observed by LC-MS (about 10 min), after which time the reaction was diluted with dichloromethane (150 mL) and the organic portion was separated, washed with water (2×25 mL), dried over sodium sulfate, filtered and concentrated under reduced pressure to provide the N-hydroxysulfonamide as an off white solid. Trituration was carried out using heptanes:DCM (9:1 v:v) to provide the title compound as an off white solid (5.46 g, 55.4% yield). LC-MS $t_R$=0.89 min, [M−H]$^-$=250; $^1$H NMR (500 MHz, DMSO-$d_6$) δ ppm 9.89 (1H, d, J=2.4 Hz), 9.85 (1H, d, J=2.4 Hz), 8.19 (2H, d, J=8.4 Hz), 8.08 (2H, d, J=8.4 Hz), 3.32 (3H, s).

It will be apparent to those in the art that specific embodiments of the disclosed subject matter may be directed to one or more of the above- and below-indicated embodiments While the invention has been disclosed in some detail by way of illustration and example for purposes of clarity of understanding, it is apparent to those in the art that various changes may be made and equivalents may be substituted without departing from the true spirit and scope of the invention. Therefore, the description and examples should not be construed as limiting the scope of the invention.

All references, publications, patents, and patent applications disclosed herein are hereby incorporated by reference in their entirety.

What is claimed is:
1. A method of treating heart failure, comprising intravenously administering to a human patient a nitroxyl donor composition comprising a compound of the formula (1):

(1)

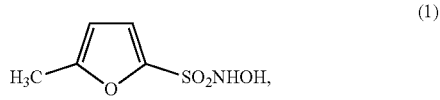

wherein said composition is administered at a pH of from about 5 to about 6.5 and at a dose of about 1 µg/kg/min to about 30 µg/kg/min.

2. The method of claim 1, wherein the composition is administered at a pH of from about 5.5 to about 6.

3. The method of claim 1, wherein the composition is administered at a pH of about 6.

4. The method of claim 1, wherein the composition further comprises a stabilizing agent.

5. The method of claim 4, wherein the stabilizing agent is a cyclodextrin.

6. The method of claim 5, wherein the cyclodextrin is a β-cyclodextrin.

7. A method of treating acute decompensated heart failure, comprising intravenously administering to a human patient a nitroxyl donor composition comprising a compound of the formula (1):

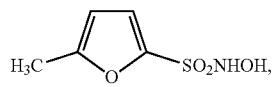

wherein said composition is administered at a pH of from about 5 to about 6.5 and at a dose of about 1 µg/kg/min to about 30 µg/kg/min.

8. The method of claim 7, wherein the composition is administered at a pH of from about 5.5 to about 6.

9. The method of claim 7, wherein the composition is administered at a pH of about 6.

10. The method of claim 7, wherein the composition further comprises a stabilizing agent.

11. The method of claim 10, wherein the stabilizing agent is a cyclodextrin.

12. The method of claim 11, wherein the cyclodextrin is a β-cyclodextrin.

13. The method of claim 1, wherein the composition is administered at a dose of at least 2.5 µg/kg/min.

14. The method of claim 1, wherein the composition is administered in an amount of at least 5 µg/kg/min.

15. The method of claim 1, wherein the composition is administered at a dose of at least 7.5 µg/kg/min.

16. The method of claim 1, wherein the composition is administered at a dose of at least 12 µg/kg/min.

17. The method of claim 1, wherein the composition is administered at a dose of at least 15 µg/kg/min.

18. The method of claim 7, wherein the composition is administered at a dose of at least 2.5 µg/kg/min.

19. The method of claim 7, wherein the composition is administered in an amount of at least 5 µg/kg/min.

20. The method of claim 7, wherein the composition is administered at a dose of at least 7.5 µg/kg/min.

21. The method of claim 7, wherein the composition is administered at a dose of at least 12 µg/kg/min.

22. The method of claim 7, wherein the composition is administered at a dose of at least 15 µg/kg/min.

* * * * *